United States Patent
Huang et al.

(10) Patent No.: US 10,844,415 B2
(45) Date of Patent: Nov. 24, 2020

(54) SPINOSAD HETEROLOGOUS EXPRESSION STRAIN AND CONSTRUCTION METHOD THEREOF AND USE

(71) Applicant: ZHEJIANG HISUN PHARMACEUTICAL CO., LTD, Zhejiang (CN)

(72) Inventors: Jun Huang, Zhejiang (CN); Zhen Yu, Zhejiang (CN); Meihong Li, Zhejiang (CN); Linghui Zheng, Zhejiang (CN); Na Li, Zhejiang (CN); Haibin Wang, Zhejiang (CN); Hua Bai, Zhejiang (CN)

(73) Assignee: Zhejiang Hisun Pharmaceutical Co., LTD., Zhejiang (CN)

( * ) Notice: Subject to any disclaimer, the term of this patent is extended or adjusted under 35 U.S.C. 154(b) by 0 days.

(21) Appl. No.: 15/526,075

(22) PCT Filed: Nov. 14, 2014

(86) PCT No.: PCT/CN2014/091118
§ 371 (c)(1),
(2) Date: May 11, 2017

(87) PCT Pub. No.: WO2016/074221
PCT Pub. Date: May 19, 2016

(65) Prior Publication Data
US 2018/0016610 A1    Jan. 18, 2018

(51) Int. Cl.
*C12N 9/22* (2006.01)
*C12P 19/62* (2006.01)
*C12N 15/74* (2006.01)

(52) U.S. Cl.
CPC .............. *C12P 19/62* (2013.01); *C12N 15/74* (2013.01)

(58) Field of Classification Search
None
See application file for complete search history.

(56) References Cited

FOREIGN PATENT DOCUMENTS

| CN | 1298447 | 6/2001 |
|---|---|---|
| CN | 103740631 | 4/2014 |
| JP | 2005520500 A | 7/2005 |
| WO | 9946387 A1 | 9/1999 |
| WO | 9905283 A2 | 8/2001 |
| WO | 0179520 | 10/2001 |
| WO | 03070908 A2 | 8/2003 |

OTHER PUBLICATIONS

Summers et al. (Microbiol., 1997, vol. 143, pp. 3251-3262).*
Huang et al., High Level Spinosad Production in teh Heterologous Host Saccharopolyspora erythraea, Applied and Environmental Microbiology, 2016, vol. 52, No. 18, pp. 5603-5611.
Martin et al., Heterologous expression in Saccharopolyspora erythraea of a pentaketide synthase derived from the spinosyn polyketide synthase; The Journals, The Royal Society of Chemistry 2003, 4-pages.
Waldron et al., Cloning and analysis of the spinosad biosynthetic gene cluster of Saccharopolyspora spinosa; Chemistry & Biology; 2001, pp. 487-499.
Wu et al., Screening and breeding of high producing strains of spinosad by protoplast fusion; 2012, 5-pages (english abstract).
Wu Ping et al., Screening and Breeding of High Producing Strains of Spinosad by Protoplast Fusion, Science and Technology of Cereals, Oils and Foods, 2012,20 (3): 46-49.
Gust B, et al., Redirect Technology: PCR-targeting system in Streptomyces coelicolor. Norwich: John Innes Center. 2002: pp. 13-35.
Waldron C. et al., Cloning and analysis of the spinosad biosynthetic gene cluster of Saccharopolyspora spinosa, Chemistry & Biology, Mar. 30, 2001, pp. 487-499.
Ping et al., Screening and breeding of high producing strains of spinosad by protoplast fusion; 2012, 03-0046-04.
Su Jianya et al., Biosynthesis of Spinosad, China Biotechnology, Mar. 20, 2012, vol. 23, No. 5 (english abstract).

* cited by examiner

*Primary Examiner* — Hope A Robinson
(74) *Attorney, Agent, or Firm* — Stinson LLP

(57) ABSTRACT

The invention provides a construction method of spinosad heterologous expression strain, a spinosad heterologous expression strain obtained by the method and use thereof in preparing spinosad. The method utilizes a plurality of homologous recombination to replace the erythromycin synthetic gene cluster of *Saccharopolyspora erythraea* with the spinosad synthetic gene cluster and the rhamnose synthetic gene cluster, such that the *Saccharopolyspora erythraea* produces spinosad.

12 Claims, 14 Drawing Sheets
Specification includes a Sequence Listing.

SPINOSAD HETEROLOGOUS EXPRESSION STRAIN AND CONSTRUCTION METHOD THEREOF AND USE

This application claims priority to International Application Number PCT/CN2014/091118, filed on 14 Nov. 2014, which is hereby incorporated by reference in its entirety.

FIELD OF THE INVENTION

The present invention belongs to the field of biotechnology, relates to spinosad heterologous expression; and more particularly, relates to a spinosad heterologous expression strain and a construction method thereof and use.

BACKGROUND OF THE INVENTION

Spinosad is a macrolide compound, which has both the safety of biological pesticides and the fast-acting property of chemical pesticides, and won the American "Presidential Green Chemistry Challenge Award" in June 1999. In nature, spinosad is fermented from *Saccharopolyspora spinosa*, and its biosynthesis mainly includes two aspects: one is a glycone, which is synthesized by polyketide synthase (PKS); the second is the addition and modification of rhamnose and forosamine, which are carried out by the relevant synthetases and modification enzymes respectively (see SU Jianya et al., Biosynthesis of Spinosad, CHINA BIOTECHNOLOGY, Vol. 23, No. 5). Except the rhamnose synthetic gene, the other related spinosad biosynthetic genes in *Saccharopolyspora spinosa* are clustered in a DNA fragment (GenBank AY007564) of about 80 kb.

*Saccharopolyspora spinosa* is a naturally spinosad producing strain, but its yield is not high. Moreover, the genetic manipulation of *Saccharopolyspora spinosa* is relatively difficult, and the transformation space is limited, so that it is difficult to obtain the strain with a good production performance. In the prior art, someone conducts interspecific fusion of *Saccharopolyspora spinosa* and *Saccharopolyspora erythraea* via a method of biparental inactivation to screen and breed high producing strains of spinosad (WU Ping et al., Screening and Breeding of High Producing Strains of Spinosad by Protoplast Fusion, SCIENCE AND TECHNOLOGY OF CEREALS, OILS AND FOODS, 2012, 20 (3): 46-49). However, after the protoplast fusion, the intricate recombination occurs between two parental genomes, which results in a complex genetic background and instable genetic feature of the strains screened finally, and is not beneficial for further genetic modification.

SUMMARY OF THE INVENTION

The present invention aims at providing a construction method of spinosad expression strain and obtaining a spinosad heterologous expression strain, in order to solve the problems of unclear genetic background and instable genetic feature of the above-mentioned recombinant expression strain.

In a first aspect, the present invention provides a construction method of spinosad heterologous expression strain, wherein the erythromycin synthetic gene cluster in *Saccharopolyspora erythraea* is replaced with the spinosad synthetic gene cluster and rhamnose synthetic gene cluster of *Saccharopolyspora spinosa*; preferably, the method utilizes a plurality of homologous recombination to replace the erythromycin synthetic gene cluster in *Saccharopolyspora erythraea* with the spinosad synthetic gene cluster and the rhamnose synthetic gene cluster of *Saccharopolyspora spinosa*.

Further preferably, the method comprises the following steps:

(1) obtaining a plurality of nucleic acid fragments covering the spinosad synthetic gene cluster sequence and its upstream and downstream sequences of *Saccharopolyspora spinosa*, the adjacent nucleic acid fragments possess overlapping sequences; (2) using a mode of homologous recombination to successively ligate the plurality of nucleic acid fragments obtained in step (1) into the genome of *Saccharopolyspora erythraea*, thereby replacing the erythromycin synthetic gene cluster in *Saccharopolyspora erythraea* with the spinosad synthetic gene cluster sequence and its upstream and downstream sequences of *Saccharopolyspora spinosa*, to obtain a recombinant strain; and (3) obtaining the nucleic acid fragment of rhamnose synthetic gene cluster of *Saccharopolyspora spinosa*, and using a mode of homologous recombination to replace the downstream sequence of spinosad synthetic gene cluster of the recombinant strain obtained in step (2) with the nucleic acid fragment of rhamnose synthetic gene cluster, to obtain the spinosad heterologous expression strain.

Preferably, in step (2), the plurality of nucleic acid fragments are respectively constructed as plasmids, and then recombined with the *Saccharopolyspora erythraea* through homologous crossover. Wherein, according to the 5'-3'(from 5' to 3') sequence of the plurality of nucleic acid fragments, except the plasmid containing the last nucleic acid fragment, each of the others include a 5' homologous arm, the nucleic acid fragments obtained in step (1), and a resistance gene cassette necessary for conjugation that are connected in sequence, wherein the 5' homologous arm of each plasmid is homologous to the upstream sequence of the erythromycin synthetic gene cluster of *Saccharopolyspora erythraea*. The plasmid containing the last nucleic acid fragment comprises a resistance gene cassette, a 5' homologous arm, the last nucleic acid fragment and a 3' homologous arm that are connected in sequence, wherein the 3' homologous arm is homologous to the downstream sequence of the erythromycin synthetic gene cluster of *Saccharopolyspora erythraea*. Further preferably, firstly, homologous recombination occurs between the plasmid containing the last nucleic acid fragment and the initial *Saccharopolyspora erythraea*, and then homologous recombination between the plasmids containing other nucleic acid fragments and the *Saccharopolyspora erythraea* obtained in last step occurs in sequence. Preferably, the initial *Saccharopolyspora erythraea* is ATCC11635.

Further preferably, cosmid supercos-1 is used as the initial plasmid in step (2); and preferably, the resistance gene cassette comprises an aac(3)IV+oriT sequence.

Further preferably, the plasmid constructing process in step (2) is as follows: firstly, the upstream and downstream nucleic acid fragments (about 3 kb, respectively) of the erythromycin synthetic gene cluster of *Saccharopolyspora erythraea* are inserted into cosmid supercos-1, as the 5' homologous arm and the 3' homologous arm respectively, to obtain a modified cosmid eryUD-cos2; Then, the nucleic acid fragment obtained in step (1) is inserted between the two homologous arms of the cosmid eryUD-cos2. For the resistance gene cassette, in the plasmid containing the last nucleic acid fragment, it is inserted in the upstream of the 5' homologous arm, while in other plasmids, it is introduced by replacing the 3' homologous arm. Further preferably, replacement of the 3' homologous arm of other plasmids with the resistance gene cassette is achieved through homologous recombination.

Further preferably, the sequence of the 5' homologous arm is shown in SEQ ID NO: 46, and the sequence of the 3' homologous arm is shown in SEQ ID NO: 47.

Preferably, in step (3), the rhamnose synthetic gene cluster is constructed into a plasmid for homologous recombination, the plasmid is then homologously recombined with the recombinant strain obtained in step (2), the plasmid comprises two homologous arms between which is the rhamnose synthetic gene cluster, and both of these two homologous arms are homologous to the downstream sequence of the spinosad synthetic gene cluster respectively. Preferably, the sequences of these two homologous arms are SEQ ID NO: 49 and SEQ ID NO: 48 respectively.

Preferably, in step (1), the plurality of nucleic acid fragments are at least 3 nucleic acid fragments, preferably 3, 4, 5, 6 or 7 nucleic acid fragments, each nucleic acid fragment has a size of 25-40 kb; further preferably, the plurality of nucleic acid fragments are 4 nucleic acid fragments, the sequences of which are shown in SEQ ID NOS: 17-20, respectively.

Preferably, in step (1), the genomic DNA of *Saccharopolyspora spinosa* is digested with Sau3AI to construct a genomic library and screen the plurality of nucleic acid fragments covering the spinosad synthetic gene cluster sequence and its upstream and downstream sequences by polymerase chain reaction (PCR).

In a second aspect, the present invention provides a spinosad heterologous expression strain constructed by the method of the present invention, wherein the expression strain is *Saccharopolyspora erythraea*, in which the erythromycin synthetic gene cluster is replaced by the spinosad synthetic gene cluster and the rhamnose synthetic gene cluster of *Saccharopolyspora spinosa*. Preferably, the expression strain is a genetically engineered strain ES05.

In a third aspect, the present invention provides the use of the spinosad heterologous expression strain of the present invention in the preparation of spinosad.

In a fourth aspect, the present invention provides a method of producing spinosad, wherein the method uses the spinosad heterologous expression strain constructed by the present invention.

In the present invention, the erythromycin biosynthetic gene cluster (32 kb, GenBank AY661566.1) of the erythromycin producing strain *Saccharopolyspora erythraea* is replaced by the spinosad biosynthetic gene cluster (80 kb, GenBank AY007564) of *Saccharopolyspora spinosa*, and the rhamnose biosynthetic gene cluster (total four genes: gdh+ kre, GenBank AF355468.1; gtt, GenBank AF355467.1; epi, GenBank AF355466.1) is inserted, such that the *Saccharopolyspora erythraea* produces spinosad. The obtained genetically engineered strain has clear genetic background, the sequence information of the entire genome is quite definite. Therefore, the gene at any position can be modified precisely, so as to facilitate conducting genetic manipulation and strain breeding. The *Saccharopolyspora erythraea* itself has the potential of modification, so that the obtained recombinant strain also has the potential of modification, which is superior to the original spinosad producing strain *Saccharopolyspora spinosa*, and the fermentation time of the obtained recombinant strain is short, so that it is not easy to be infected, is more beneficial to the production of the spinosad, reduces costs, guarantees the quality, and is suitable for large-scale production in industry.

DETAILED DESCRIPTION OF THE INVENTION

Figure 1:
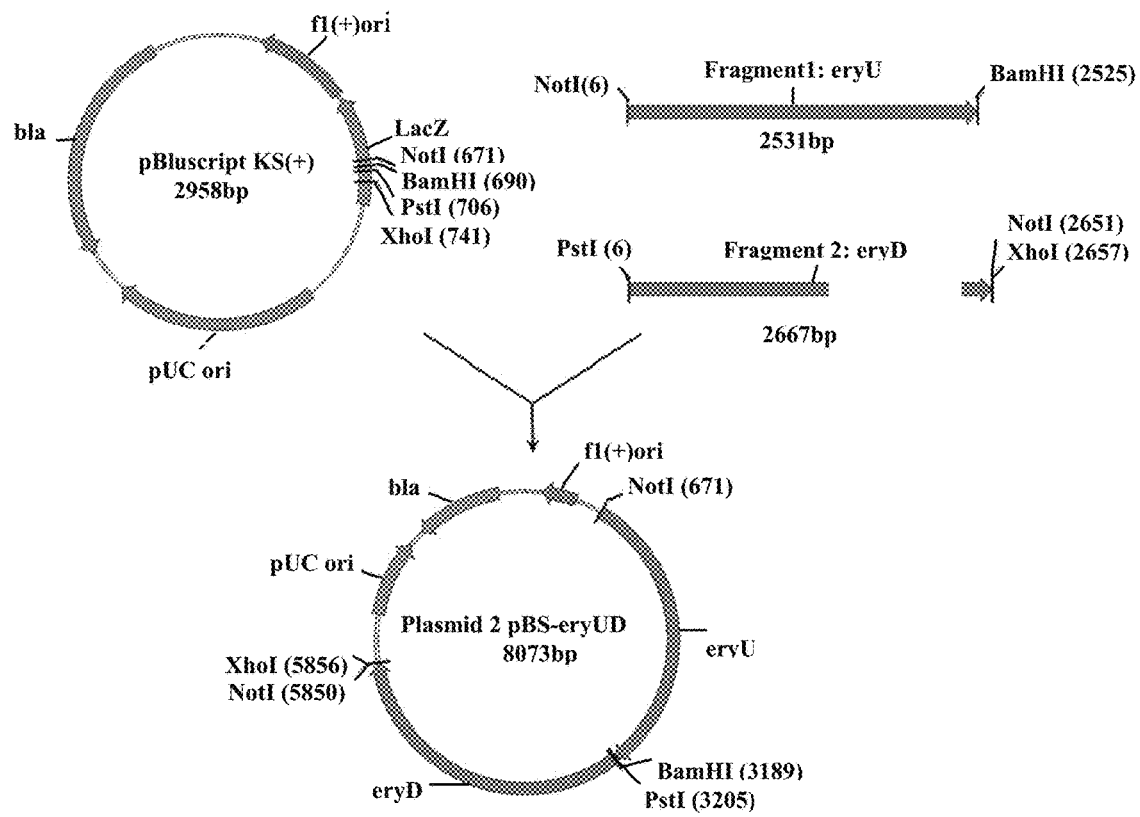
FIG. 1 is a construction process of plasmid pBS-eryUD.

The present invention will be described hereinafter with reference to the specific embodiments, but the content of the present invention is not limited to this.

A spinosad heterologous expression strain construction method of the present invention may be described into the following steps:

(1) modifying an original cosmid: i.e., inserting upstream and downstream fragments (about 3 kb, respectively) of erythromycin synthetic gene cluster of *Saccharopolyspora erythraea* at both sides of a cloning site BamHI of cosmid supercos-1 respectively, to obtain a modified cosmid eryUD-cos2. The erythromycin synthetic gene cluster in chromosomes of *Saccharopolyspora erythraea* can be directly replaced with the cloned target fragments through the two homologous fragments.

(2) cloning a spinosad synthetic gene cluster fragment of *Saccharopolyspora spinosa*: performing partial enzyme digestion on genomic DNA of *Saccharopolyspora spinosa* with Sau3AI, so as to distribute most of the fragments after enzyme digestion in a range of 25-40 kb, then taking the modified cosmid eryUD-cos2 as a carrier, utilizing a packaging kit Gigapack® III XL Packaging Extract for packaging, constructing a *Saccharopolyspora spinosa* genomic library, and screening library plasmids containing the spinosad synthetic gene cluster fragments via PCR.

(3) sequencing the screened genomic library to determine a relative position of the DNA fragment contained therein in the spinosad biosynthetic gene cluster: selecting four library plasmids which have the foreign fragments with the same insertion direction, can completely cover the spinosad biosynthetic gene cluster and have an enough long overlapping portion with each other for transferring the gene cluster.

(4) trimming library plasmids: using PCR targeting method, replacing unnecessary homologous arm fragments on the spinosad synthetic gene cluster fragment with an apramycin resistance gene cassette aac(3)IV+oriT, so that the homologous arm is as long as the homologous arm designed in eryUD-cos2 and has necessary elements for conjugation. The resistance gene cassette subjected to PCR targeting is located outside the two homologous arms, and will be lost when the target fragment is transferred to the *Saccharopolyspora erythraea* chromosome by homologous double crossover, so that the resistance gene cassette can be reused in the next round of trimming and DNA fragment transferring.

(5) transforming the four trimmed library plasmids into *Saccharopolyspora erythraea* through conjugation in a sequence of the contained DNA fragments, and achieving the transfer of the gene fragments through screening strains of double crossover. After four-step transfer, the spinosad synthetic gene cluster of 80 kb is successfully transferred to the position where the erythromycin synthetic gene cluster is originally located on the *Saccharopolyspora erythraea* chromosome. The fragments of about 10 kb at the upstream and downstream of the spinosad synthetic gene cluster are transferred simultaneously, these fragments can be used as target sites for subsequent genetic manipulation, and are respectively called as "operational area 1" and "operational area 2" respectively.

(6) cloning and ligating the rhamnose synthetic gene cluster including gtt, epi, gdh and kre genes onto a carrier, and inserting the cluster into the above-mentioned "operational region 2" via a homologous double crossover method to complete the whole recombination process, and obtain the spinosad heterologous expression strain.

The following methods will be used in the following embodiments, which are particularly as follows:
Method 1: Ligation Reaction of DNA A foreign fragment and a linearized carrier were prepared at a molar ratio of 3:1 to 9:1, wherein the total volume was 3 μl. 3 μl of solution I (TaKaRa, Item No. D6020A) was added, and a water bath was kept at 16° C. for 30 min or longer.

Method 2: *Escherichia coli* Transformation ($CaCl_2$) Method) (Molecular Cloning: A Laboratory Manual, Third Edition; Beijing Science Press, 2002:93-99)

1) a single colony of *Escherichia coli* was inoculated into 3 ml of LB medium (if the *Escherichia coli* carried a resistance gene, then corresponding antibiotics were added) at 37° C. (BW25113 at 30° C.), and cultured for 14-18 h at 220 rpm;

2) the mixture was transferred to a LB medium at 1% inoculation quantity (if necessary, corresponding antibiotics were added, wherein the final concentrations of various antibiotics were as follows: the final concentration of ampicillin (Ap) was 100 μg/mL, the final concentrations of both kanamycin (Km) and apramycin (Am) were 50 μg/mL, and the final concentration of chloramphenicol (Cm) was 25 μg/mL), at 37° C. (BW 25113 at 30° C.), and then the mixture was cultured at 220 rpm until OD600 was between 0.4 and 0.6;

3) the strain was collected by centrifuging, suspended with 100 mM of sterile $CaCl_2$ (equal volume), and placed on ice for 20 min;

4) the strain was collected by centrifuging, suspended with 100 mM of $CaCl_2$/15% (W/V) glycerol (1/10 volume), and subpackaged in a 1.5 ml centrifuge tube with 100 μl/tube to obtain competent cells;

5) one tube of competent cells was taken, added with DNA (plasmid or ligation product, with a volume not exceeding 10 μl), gently blended, and placed on ice for 30 min;

6) the mixture was immediately placed on ice for 1-2 min after subjecting to water bath at 42° C. for 90 sec;

7) 900 μl of LB medium was added, and a water bath was kept at 37° C. for 45-60 min; and 8) the strain solution (50 μl was taken for plasmid transformation; for ligation product transformation, then most of supernatant was removed after centrifuging, and the strain was suspended with the residual solution) was coated on an LB plate containing the corresponding antibiotics for screening, cultured at 37° C. (BW25113 at 30° C.) for 14-18 h to grow transformants.

Method 3: PCR Amplification

A reaction solution was prepared according to a following proportion: 25 μl of 2×PrimeSTAR GC buffer solution ($Mg^{2+}$ Plus); 4 μl of dNTP mixture (2.5 mM each); 1 μl of upstream primer (25 μM); 1 μl of downstream primer (25 μM); 18 μl of dd$H_2O$; 0.5 μl of template DNA; and 0.5 μl of PrimeSTAR® HS DNA polymerase; Reaction procedure: 95° C.×5 min; (98° C.×10 sec, 68° C.×1 min/1 kb target fragment length)×25 cycles; 72° C.×2 min, 16° C.×1 min.

Method 4: Recovery of DNA

A PCR product recovery kit (item No.: W5202) and a gel recovery kit (Item No.: W5203) of Shanghai Huashun Biotechnology Co., Ltd. was used for recovering.

1) in case of recovering DNA from a solution, 5 times by volume of PB buffer solution was added in the solution, blended and absorbed to an adsorption column; in case of recovering from electrophoretic gel, 3 times by weight (calculated by that 100l was equivalent to 100 mg) of Si buffer solution was added to the sliced gel, and subjected to a water bath at 50° C. to melt the gel and absorbed to the absorption column;

2) centrifugation with 9000 ref was performed for 30 sec;

3) the liquid in recovery tube was poured, 500 μl of W1 buffer solution was added, and centrifuged with 9000 rcf for 30 sec;

4) step 3) was repeated and the liquid in the recovery tube was poured;

5) the adsorption column was transferred to a clean 1.5 ml centrifuge tube, 30 μl of T1 buffer solution was added to the center of the column, and placed at a room temperature for 5 min; and 6) centrifugation with 9000 rcf was performed for 1 min to obtain the recovered DNA.

Method 5: Filling-in of Cohesive End of DNA Fragment and 5' Phosphorylation

A following reaction solution was prepared: 4.2 μl of purified DNA fragment, 0.5 μl of BKL buffer solution, and 0.25 μl of BKL enzyme mixture, were then subjected to a water bath at 37° C. for 30 min or longer, then transferred to a water bath at 70° C. for 5 min to inactivate the enzyme mixture.

Method 6: Dephosphorylation of DNA Fragments after Linearization by Endonuclease Digestion 1 µl of FastAP (Fermentas, Item No. EF0651) was directly added into an endonuclease digestion reaction solution, and subjected to a water bath at 37° C. for 30 min.

Method 7: Conjugation Method of *Escherichia coli-Saccharopolyspora erythraea*

1) competent cells of *Escherichia coli* ET12567 (pUZ8002) (Gust B, Kieser T, Chater K F. REDIRECT Technology: PCR-targeting system in *Streptomyces coelicolor*. Norwich: John Innes Center. 2002: 13-35) were prepared according to the method 2, and then Km and Cm were added in the medium during culturing;

2) 5 µl of plasmid used for conjugation was taken and transformed into ET12567 (pUZ8002) competent cells according to the method 2, and coated on an LB plate containing Km, Cm and Am after transformation;

3) one transformant was picked up, and cultured in 3 ml of LB liquid medium containing Km, Cm and Am at 37° C. for 14-18 h under 220 rpm;

4) the mixture was transferred to 30 ml of LB liquid medium containing Km, Cm and Am at 1% inoculation amount, and cultured at 37° C. under 220 rpm until OD600 was between 0.4 and 0.6;

5) the strain was collected by centrifuging, washed with an LB liquid medium for twice, suspended in 2 ml of LB liquid medium, and then placed at room temperature for use;

6) At the same time of performing step 5), the *Saccharopolyspora erythraea* spore solution containing $10^6$-$10^8$ cells and suspended in 500 µl of 2×YT medium (1.6% tryptone, 1.0% yeast extract, and 0.5% NaCl) was thermally shocked at 50° C. for 10 min, and then cooled at a room temperature;

7) 500 µl of strain solution in step 5) was mixed with the spore solution subjected to thermal shock in step 6), centrifuged with 9000 rcf for 1 min, then about 800 µl of supernatant was discarded, and the strain was suspended with the residual solution, coated on an MS (2% soybean cake powder, 2% mannitol, and 1.5% agar powder) plate (the plate was previously blown up for 1 h in a sterile environment to partially dehydrate), and cultured at 34° C. for 14-18 h;

8) 1 ml of sterile water containing 1.25 mg of Am and 0.5 mg of nalidixic acid (Nal) was covered on the plate, and continuously cultured at 34° C.; and 9) the transformant was grown after 6-7 d.

Method 8: Preparation of Plasmid DNA Via Alkaline Lysis 1) a single colony was inoculated in 3 ml (if necessary, a larger volume could be used) of LB liquid medium, appropriate antibiotics were added, and then subjected to shake cultivation at 37° C. for 14-18 h;

2) 1.5 ml (5 ml was taken in case of preparing a low copy number plasmid) was taken and centrifuged for 30 sec under 12000 r/min;

3) the supernatant was completely absorbed, and the strain was suspended in 100 µl of pre-cooled solution I (50 mmol/L glucose, 25 mmol/L Tris-HCl, 10 mmo/L EDTA, and pH 8.0);

4) 200 µl of freshly prepared solution II (NaOH 0.2 mol/L, SDS 1%) was added, quickly reversed for 5 times, and placed on ice for 3 min;

5) 150 µl of pre-cooled solution III (60 ml of 5 mol/L potassium acetate, 11.5 ml of glacial acetic acid, and 28.5 ml of water) was added to blend up and down quickly, and placed on ice for 3 min;

6) centrifuged for 5 min under 12000 r/min; then the supernatant was transferred to another centrifuge tube, equal amount of phenol-chloroform-isoamyl alcohol (BioFlux, Item No.: BSA03M1) was added to vibrate and blend;

7) centrifuged for 5 min under 12000 r/min; then the supernatant was carefully transferred to another centrifuge tube, double volume of ice-cold anhydrous ethanol was added, and placed at a room temperature for 2 min;

8) centrifuged for 5 min under 12000 r/min; then the supernatant was poured, and the precipitate was washed twice by 70% ice-precooled alcohol; and 9) the precipitate was dried, dissolved in 20-50 µl of TE (pH 8.0), and stored at −20° C.

Method 9: PCR Detection

A following reaction solution is prepared: 25 µl of 2×GC I buffer solution (TaKaRa, Item No. DRR20GCI); 4 µl of 2.5 mM dNTP; 1 µl of primer 1 (25 µM); 1 µl of primer 2 (25 µM); 1 µl (10-100 ng) of template DNA; and 32.5 µl of $H_2O$.

If the PCR product was less than 3 kb in size, 0.5 µl of rTaq DNA polymerase (TaKaRa, Item No. R001) was added; and If the PCR product was greater than 3 kb in size, 0.5 µl of LA Taq DNA polymerase (TaKaRa, Item No. DRR002B) was added.

Procedure: 94° C.×5 min, (95° C.×30 sec, (Tm-5°) C×15 sec, 72° C.×1 min/kbp)×30 circles, 72° C.×2 min, 16° C.×1 sec.

Method 10: Extraction of Total DNA of Actinomycete 1) actinomycete spores or hyphae were taken and inoculated in 30 ml of TSB medium (Item No. 211825, BD, USA), and cultured at 28° C. for 40 h under 200 rpm;

2) the strain was collected by centrifuging, washed with sterile water for twice, suspended in 4 ml of lysozyme solution (10 mM Tris-HCl, pH7.0, 10.3% sucrose, and 4 mg/ml lysozyme), and then subjected to a water bath at 37° C. for 4 hr;

3) 400 µl of 10% SDS solution and 15 µl of 20 mg/ml of proteinase K (TaKaRa, Item No. D9033) solution were added, and continuously subjected to a water bath at 37° C. for 30 min;

4) the mixture was extracted twice with an equal volume of phenol-chloroform-isoamyl alcohol (BioFlux, Item No. BSA03M1), and 2.5 ml of supernatant was taken;

5) 250 µl of 3M NaAc solution (pH 5.3) and 3 ml of isopropanol were added, a white flocculent precipitate was picked out in a new 2.5 ml centrifuge tube after reversing for several times; and dried at a room temperature for 1 h after washing twice with 70% ethanol; and 6) 2 ml of 2 mM Tris-HCl solution (pH 8.0) was used to dissolve the precipitate, and then 2 µl of 20 mg/ml RNA enzyme was added.

Unless otherwise specified, the specific experimental methods used in the present invention are all conventional methods known in the research field, for instance:

1. single enzyme digestion of endonuclease is operated according to the product manual;

2. the plasmids are extracted by alkaline lysis, and see method 8 for details; and 3. ordinary Taq DNA polymerase is used for the PCR detection, and see method 9 for details.

In addition, for the convenience of description, the following description actually includes the contents as follows:

1. when constructing plasmids, the "ligate to obtain the plasmid" is a continuous operation process, which includes the operation contents of the following several aspects: (1) ligation reaction of DNA fragment (see method 1); (2) transforming the ligation reaction product into *Escherichia coli* DH5α (see method 2); (3) picking out the transformant to extract the plasmids; (4) performing the enzyme digestion of the plasmids with endonuclease to test whether the fragment size of the digested product thereof is consistent with an expected size;

2. "PCR amplification": unless otherwise specified, it refers to using PrimeSTAR® HS DNA polymerase and GC buffer solution for amplification, and see method 3 for details;

3. "recovering": using a PCR product recovery kit to recover from a solution, and using a gel recovery kit to recover from the electrophoretic gel; and see method 4 for the specific operation.

Unless otherwise specified, all the reagents used in the following examples can be purchased from chemical or biological reagent stores or suppliers; and the instruments used are also conventional instruments in the art.

Example 1: Modification of Cosmid Carrier

Step (1) and step (2) aimed at cloning an upstream fragment and a downstream fragment (i.e., two homologous arms for double crossover, including a 5' homologous arm and a 3' homologous arm) of the erythromycin biosynthetic gene cluster into the vector pBluscript KS (+)(GenBank: X52331.1) sequentially, introducing a BamHI site between the two homologous arms, and respectively introducing a NotI site at the 5'-end of the upstream fragment and the 3'-end of the downstream fragment, so as to use the NotI to cut off the fragment containing the two homologous arms. The construction process was as shown in FIG. 1:

(1) the *Saccharopolyspora erythraea* (ATCC 11635) genome (see method 10 for the extraction of the genome DNA) was used as a template, euF (SEQ ID NO: 1, introducing the NotI site at the 5' end)/euR (SEQ ID NO: 2, introducing the BamHI site at the 5' end) were taken as primers, and a 2511 bp fragment 1:eryU (SEQ ID NO: 46, containing a restriction digestion site and a protective base sequence, so that the size was 2531 bp) at the upstream of the erythromycin biosynthetic gene cluster was amplified by PCR. The PCR product was recovered and subjected to enzyme digestion with NotI (TaKaRa) for 1 h; the enzyme-digested product was then recovered and subjected to enzyme digestion with BamHI(TaKaRa) for 1 h to obtain a double enzyme-digested product; the vector pBluscript KS (+) was also subjected to enzyme digestion with NotI and BamHI and recovered, then ligated with the above PCR product after double digestion, and a recombinant plasmid 1:pBS-eryU was obtained after screening and testing.

(2) Then the genomic DNA of erythromycin producing strain was taken as a template again, and a 2642 bp fragment 2:eryD (SEQ ID NO: 47, containing an restriction digestion site and a protective base sequence, so that the size was 2667 bp) from the downstream of the erythromycin biosynthetic gene cluster was amplified by PCR using edF (SEQ ID NO: 3, introducing Pst I site at the 5' end)/edR (SEQ ID NO: 4, introducing NotI and XhoI sites at the 3' end) as a primer pair. After recovering, the PCR product as well as the recombinant plasmid 1: pBS-eryU was subjected to double enzyme digestion with XhoI and PstI: 5 µl of 10×H buffer solution; 25 µl of PCR product (or plasmid 1: pBS-eryU); 18 µl of ddH$_2$O; 1 µl of PstI (TaKaRa, Item No. 1073A); and p µl of XhoI (TaKaRa, Item No. 1094A). The mixtures were subjected to a water bath at 37° C. for 1 h, then the products were recovered respectively, and ligated to obtain a recombinant plasmid 2: pBS-eryUD through screening and identification.

Figure 2:
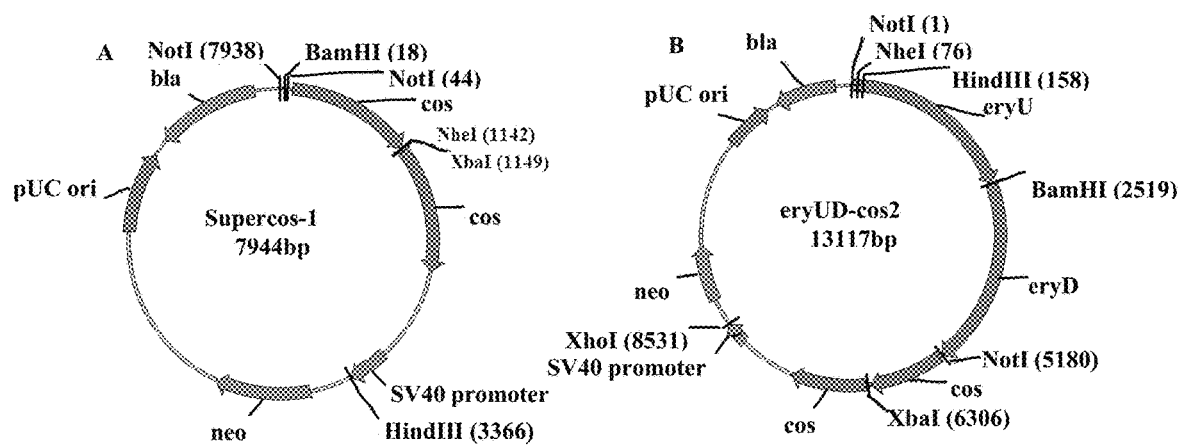
FIG. 2 is a plasmid profile of plasmids Supercos-1 (A) and eryUD-cos2 (B)

(3) The recombinant plasmid 2 pBS-eryUD was subjected to restriction digestion with NotI, and a 5179 bp fragment containing two homologous arms (i.e., the fragment 1:eryU and the fragment 2:eryU) was recovered via gel cutting, and then ligated with a dephosphorylated cosmid supercos-1 (Stratagene, Item No. 251301, see FIG. 2A for profile) digested with NotI. Finally, cosmid EryUD-Cos2 (see FIG. 2B for profile) was obtained through PCR and enzyme digestion detection.

Example 2: Extraction of Total DNA of Spinosad Producing Strain

The spore solution of the spinosad producing strain *Saccharopolyspora spinosa* (NRRL 18538) from a cryogenic vial was taken and inoculated in 30 ml of TSB medium, and the total DNA was extracted according to method 10.

Example 3: Construction of Spinosad Producing Strain Genomic Library (1) Test for Partial Enzyme Digestion Condition of Total DNA of Spinosad Producing Strain:

A following reaction solution was prepared: 100 µl of the total DNA of spinosad producing strain prepared in example 2; 15 µl of 10×H buffer solution; and 35 µl of ddH$_2$O.

Figure 3:
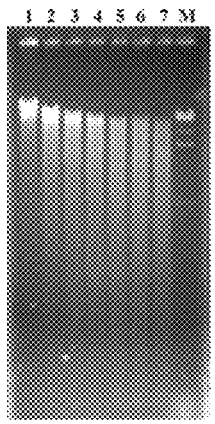
FIG. 3 is an enzyme digestion result of genomic DNA of a spinosad producing strain, wherein various lanes respectively represent: 1. genomic DNA without enzyme digestion; 2. enzyme digestion for 5 min: 3. enzyme digestion for 8 min: 4. enzyme digestion for 11 min; 5. enzyme digestion for 14 min; 6. enzyme digestion for 17 min; 7. enzyme digestion for 20 min; and M, k/Hind III.

After the solution was subjected to a water bath at 37° C. for 5 min, 0.25u of Sau3AI (Takara Biological Engineering (Dalian) Co., Ltd., Item No. D1082A, diluted with an enzyme stock solution to a target concentration) was added, and then the mixture was subjected to a water bath at 37° C. again. From the 5$^{th}$ minute, 25 µl of reactant was taken to terminate reaction in 5 µl of 6× loading buffer solution (Takara Biological Engineering (Dalian) Co., Ltd., Item No. D604) every 3 min. An electrophoretic result (FIG. 3) showed that when the reaction time was 5-8 min, the digested fragments of the total DNA of the spinosad producing strain were relatively concentrated around 30 kb.

(2) Partial Enzyme Digestion of Total DNA of Spinosad Producing Strain:

A following reaction solution was prepared: 1000 µl of total DNA of spinosad producing strain; 150 µl of 10×H buffer solution; and 350 µl of ddH$_2$O.

Figure 4:
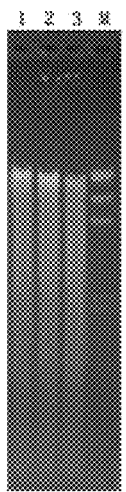
FIG. 4 is an enzyme digestion result of genomic DNA of a spinosad producing strain, wherein various lanes respectively represent: 1. enzyme digestion for 5 min; 2. enzyme digestion for 6 min; 3. enzyme digestion for 7 min; and M, k/Hind III.

After the solution was subjected to a water bath at 37° C. for 5 min, 0.25u of Sau3AI was added, and then the mixture was subjected to a water bath at 37° C. again. 500 µl of the reaction solution was respectively taken when the reaction was conducted for 5 min, 6 min and 7 min, and an equal volume of phenol-chloroform-isoamyl alcohol was added to extract, and then 5 µl of the mixture was taken for electrophoretic test. The result showed that when the reaction time was 5 min and 6 min, the digested fragments of the total DNA of the spinosad producing strain were relatively concentrated around 25-40 kb. The result was shown in FIG. 4.

Two tubes with the reaction time of 5 min and the reaction time of 6 min were combined, then 100 µl of 3 mol/L NaAc solution (pH 5.3) and 1.1 ml of isopropanol were added, and a white flocculent precipitate was picked out in a new 2.5 ml centrifuge tube after reversing for several times. The precipitate was washed twice with 70% ethanol, dried at room temperature for 30 min, and dissolved in 100 µl of 2 mmol/L Tris-HCl solution (pH 8.0).

(3) Dephosphorylation of the Partial Enzyme-Digested Product of the Total DNA of Spinosad Producing Strain:

A following reaction solution was prepared: 100 μl of the partial enzyme-digested product of the total DNA of the spinosad producing strain; 11.5 μl of FastAP buffer solution; and 3 μl of FastAP.

After the solution was subjected to a water bath at 37° C. for 50 min, an equal volume of phenol-chloroform-isoamyl alcohol was added to extract; 90 μl of supernatant was taken, 9 μl of 3 mol/L NaAc solution (pH 5.3) and 200 μl of anhydrous ethanol were added, the supernatant was removed through centrifuging, then the precipitate was washed twice with 70% ethanol, and dried at room temperature for 30 min; the precipitate was dissolved with 50 μl of 2 mmol/L Tris-HCl solution (pH 8.0) to obtain the dephosphorylated partial enzyme-digested product of the total DNA of the spinosad producing strain.

(4) Enzyme Digestion and Dephosphorylation of Cosmid EryUD-Cos2:

A following reaction solution was prepared: 5 μl of cosmid EryUD-Cos2; 1 μl of 10×H buffer solution; 37 μl of ddH$_2$O; and 3 μl of Xho I.

After the solution was subjected to a water bath at 37° C. for 2 h, 1 μl of FastAP was added and subjected to a water bath at 37° C. for 30 min; an equal volume of phenol-chloroform-isoamyl alcohol was added to extract; 80 μl of supernatant was taken, 8 μl of 3M NaAc solution (pH 5.3) and 180 μl of anhydrous ethanol were added, then the supernatant was removed by centrifuging; the precipitate was washed twice with 70% ethanol, and dried at the room temperature for 30 min; then the precipitate was dissolved with 50 μl of 2 mM Tris-HCl solution (pH 8.0) to obtain a 5'-dephosphorylated linearized cosmid EryUD-Cos2.

A following reaction solution was prepared: 50 μl of 5'-dephosphorylated linearized cosmid EryUD-Cos2; 10 μl of 10×BamH I buffer solution; 37 μl of ddH$_2$O; and 3 μl of BamH I.

After the solution was subjected to a water bath at 37° C. for 2 h, an equal volume of phenol-chloroform-isoamyl alcohol was added to extract; 80 μl of supernatant was taken, 8 μl of 3 mol/L NaAc solution (pH 5.3) and 180 μl of anhydrous ethanol were added, then the supernatant was removed by centrifuging; the precipitate was washed twice with 70% ethanol, and dried at the room temperature for 30 min; then the precipitate was dissolved with 30 μl of 2 mM Tris-HCl solution (pH 8.0) to obtain Xho I and BamH I double enzyme-digested cosmid EryUD-Cos2.

(5) Ligation of Spinosad Producing Strain Genomic Library:

A following reaction solution was prepared: 3 μl of dephosphorylated partial enzyme-digested product of the total DNA of the spinosad producing strain; 1 μl of the XhoI and BamHI double enzyme-digested cosmid EryUD-Cos2; 3 μl of 10×T4 ligase buffer solution; 21 μl of ddH$_2$O; and 2 μl of T4 ligase (TaKaRa, Item No. D2011A).

After the solution was subjected to a water bath at 16° C. overnight, 3 μl of 3 mol/L NaAc solution (pH 5.3) and 180 μl of absolute ethanol were added, then the supernatant was removed by centrifuging, the precipitate was washed twice with 70% ethanol, and dried at the room temperature for 30 min; then the precipitate was dissolved with 5 μl of ddH$_2$O to obtain the ligation product.

(6) Packaging and Transfection of Spinosad Producing Strain Genomic Library:

The packaging kit was a Gigapack® III XL packaging system (Stratagene Inc., Item No.: 200201), which was operated by the following steps:

a) one pack (one centrifuge tube) of the kit was taken out and held in hand until the reagent in the tube was melted;

b) 4 μl of ligation product obtained from step 5) was added, gently stirred and mixed, and quickly centrifuged for 3-5 s in a centrifuge to ensure that all the solution was at the bottom of the centrifuge tube;

c) after reacting at 22° C. for 2 h, 500 μl of SM buffer solution was added (each 1000 g containing the following substances: 5.8 g of NaCl, 2.0 g of MgSO$_4$.7H$_2$O, 50 ml of 1 M Tris-HCl (pH 7.5), and 5.0 ml of 2% (W/V) gelatin);

d) 20 μl of chloroform was added, gently mixed, and quickly centrifuged for 5-10 s, and saved in a refrigerator at 4° C. for use;

e) *Escherichia coli* DH10B was picked out from a glycerol coexisting tube in the kit to streak on an LB medium, and cultured at 37° C. for 14-18 h to grow out single colonies;

f) one single colony was picked out and inoculated in 3 ml of LB medium containing 10 mM MgSO$_4$ and 0.2% (w/v) maltose, subjected to shaking culture at 37° C. for 4-6 h under 220 rpm until OD600 was between 0.6 and 0.8;

g) 1.5 ml of strain solution was taken, and centrifuged at 500 g for 10 min to collect the strain, and the precipitate was suspended with sterile 10 mM MgSO$_4$, and diluted until OD600=0.5, to obtain competent cells;

h) 5 μl of the packaged product obtained in d) was taken, diluted to 50 μl by an SM buffer solution, then 1 μl of the mixture was taken and added into 200 μl of the competent cells, and cultured at 37° C. for 15 min;

i) then 1 ml of LB medium was added and mixed evenly, and the mixture was evenly spread on ten LB plates containing 100 μg/ml ampicillin, and cultured at 37° C. for about 16 h, wherein the number of transformants on each plate was 300-400.

(7) Screening of Spinosad Producing Strain Genomic Library Plasmid:

an LB medium containing 100 μg/ml Cb was subpackaged into fifteen 96-well plates with 150 μl/well, the 15 plates were numbered from 1# to 15# respectively, one of the above-mentioned transformants was picked via a toothpick to each well respectively for inoculation, and then cultured at 37° C.×220 rpm for about 16 h.

10 μl of the strain solution in each of the 12 wells in the above-mentioned 96-well plates was mixed into new 96-well plates (numbered as 16# and 17#, respectively), with the rules as follows:

Longitudinal direction of 16#96-well plate: wells A1-A12 in the 1#96-well plate were mixed into a well A1 of the 16#96-well plate, wells B1-B12 were mixed into a well B1 of the 16#96-well plate, and so on, wells H1-H12 were mixed into a well H1 of the 16#96-well plate.

Figure 5:
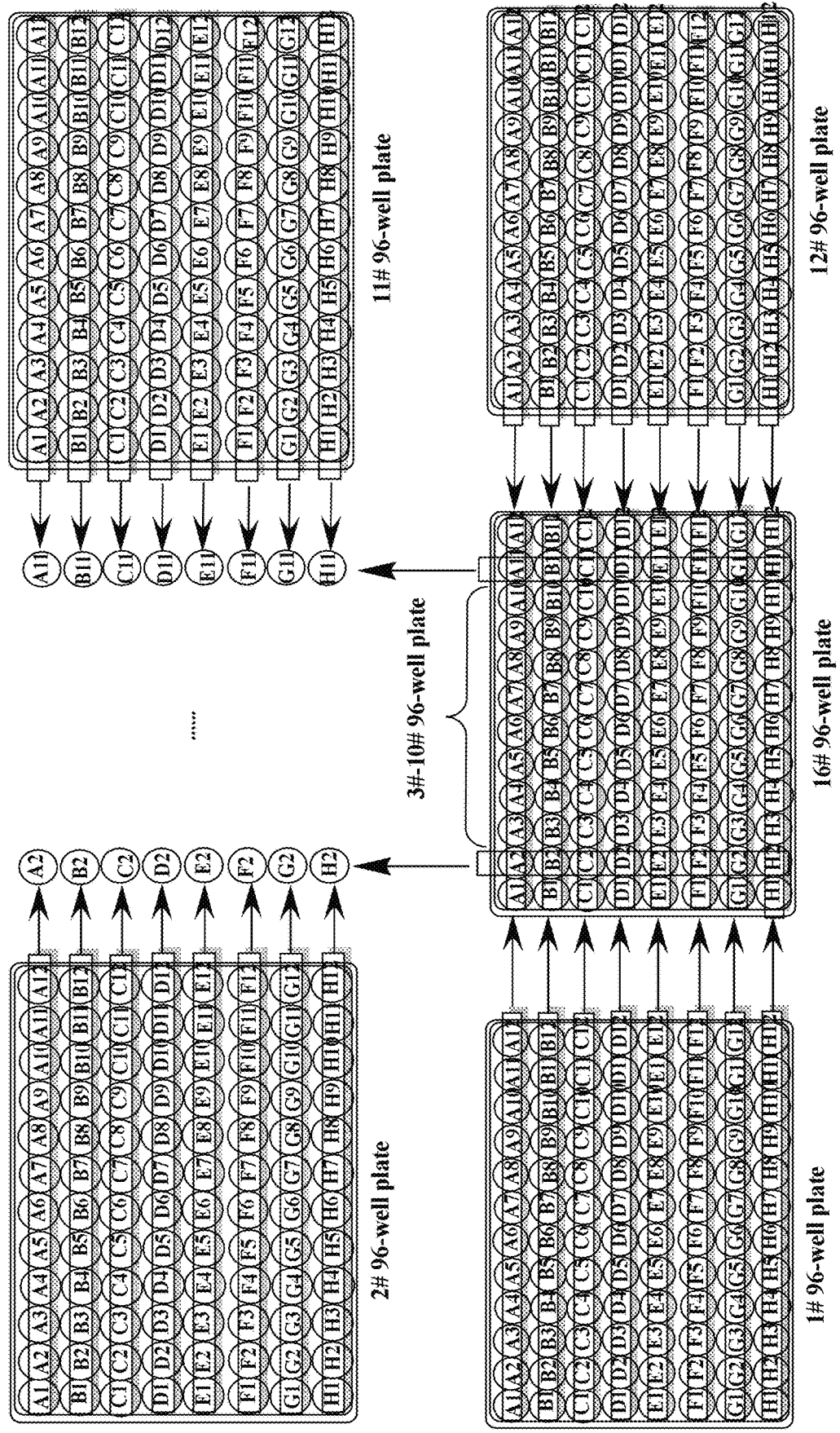
FIG. 5 is a flow diagram of screening a genomic plasmid library using a 96-well plate.

Transverse direction of the 16#96-well plate: wells A1-A12 in the 1#96-well plate were mixed into the well A1 of the 16#96-well plate, wells A1-A12 in the 2#96-well plate were mixed into a well A2 of the 16#96-well plate, and so on, wells A1-A12 in the 12#96-well plate were mixed into a well A12 of the 16#96-well plate. See FIG. 5 for the details.

Similarly, longitudinal direction of 17#96-well plate: wells A1-A12 in the 13#96-well plate were mixed into a well A1 of the 17#96-well plate, wells B1-B12 were mixed into a well B1 of the 17#96-well plate, and wells H1-H12 were mixed into a well H1 of the 17#96-well plate.

Transverse direction of the 17#96-well plate: wells A1-A12 in the 13#96-well plate were mixed into a well A1 of the 17#96-well plate (re-numbered as A13), wells A1-A12 in the 14#96-well plate were mixed into a well A2 of the 17#96-well plate (re-numbered as A14), and wells A1-A12 in the 15#96-well plate were mixed into a well A3 of the 17#96-well plate (re-numbered as A15).

Figure 6:
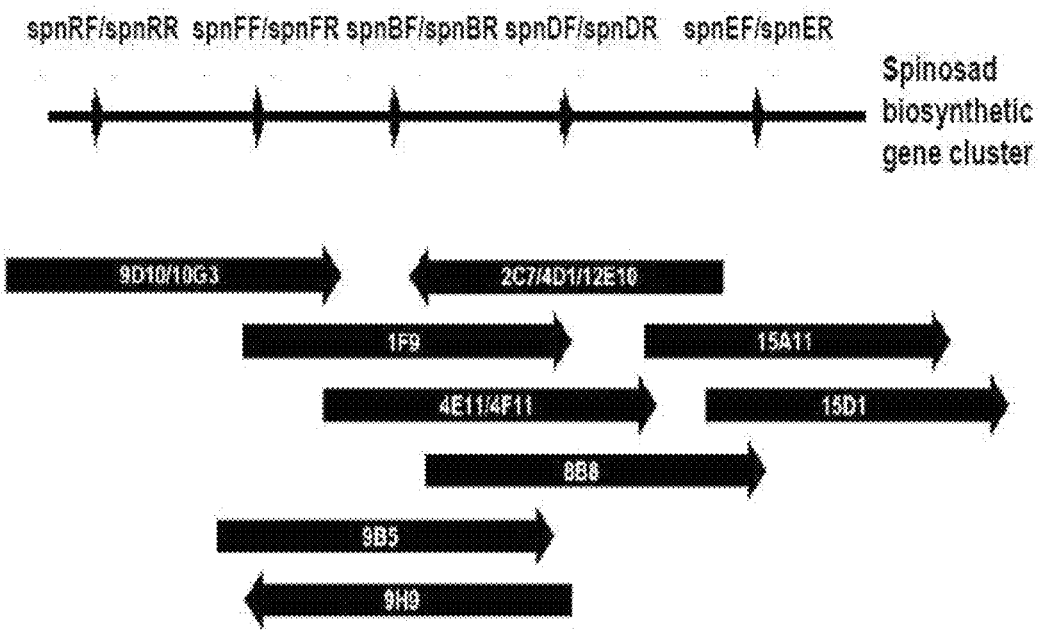
FIG. 6 is a schematic diagram of each gene position in the spinosad synthetic gene cluster and each genomic plasmid library position.

(8) PCR Screening of Spinosad Producing Strain Special Genomic Library:

a) PCR was used to detect whether the library plasmid contains partial fragments (the relative positions on the spinosad biosynthetic gene cluster were 4168-5330, 20151-21020 and 34049-34639 respectively) contained in the three genes of spnR, spnF and spnB, wherein the relative positions of the three fragments on the spinosad biosynthetic gene cluster were shown in FIG. 6 (arrows on the spinosad biosynthetic gene cluster indicated the positions of the fragments namely). The sizes of PCR products of the partial fragments of the three genes were 1163 bp (spnR), 870 bp (spnF) and 591 bp (spnB) respectively. Primer sequences used for the PCR amplification of the three genes were as follows respectively:

spnR primers: spnRF(SEQ ID NO: 5) and spnRR(SEQ ID NO: 6);

spnF primers: spnFF(SEQ ID NO: 7) and spnFR(SEQ ID NO: 8); and spnB primers: spnBF(SEQ ID NO: 9) and spnBR(SEQ ID NO: 10).

A following reaction solution was prepared:

750 µl of 2×GC I buffer solution; 120 µl of 2.5 mM dNTP; 15 µl of spnRF(25 µM); 15 µl of spnRR(25 µM); 15 µl of spnFF(25 µM); 15 µl of spnFR(25 µM); 15 µl of spnBF (25 µM); 15 µl of spnBR (25 µM); 535 µl of ddH$_2$O; and 7.5 µl of rTaq, (TaKaRa, Item No. DR001A).

The solution was subpackaged with 10 µl/tube, 0.5 µl of the strain solution in each well of the 16# and 17#96-well plate was added respectively, and 0.2 µl of the total DNA of the spinosad producing strain was used as control. The PCR reaction procedure was as follows: 95° C.×10 min, (94° C.×30 sec, 55° C.×30 sec, 72° C.×1 min 10 sec)×35 cycles, 72° C.×1 min, 16° C.×1 sec.

PCR results were tested by electrophoresis, and the results were shown in FIGS. 7A-7F.

Figure 7A:
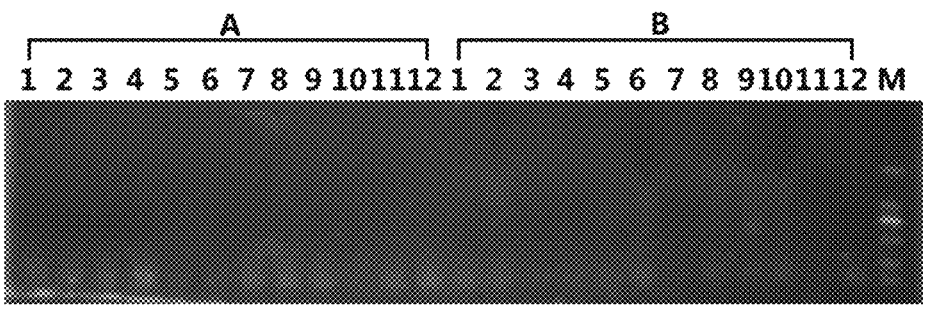
FIGS. 7A-7F are PCR electrophoretic results of screening a plasmid library containing spnR, spnF and spnB.
Figure 7B:
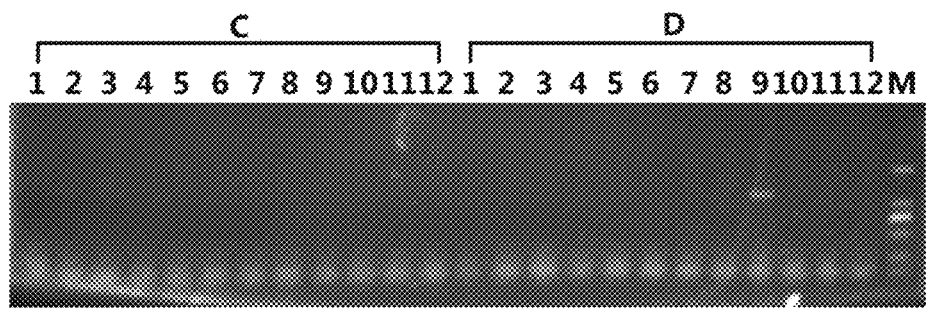
Figure 7C:
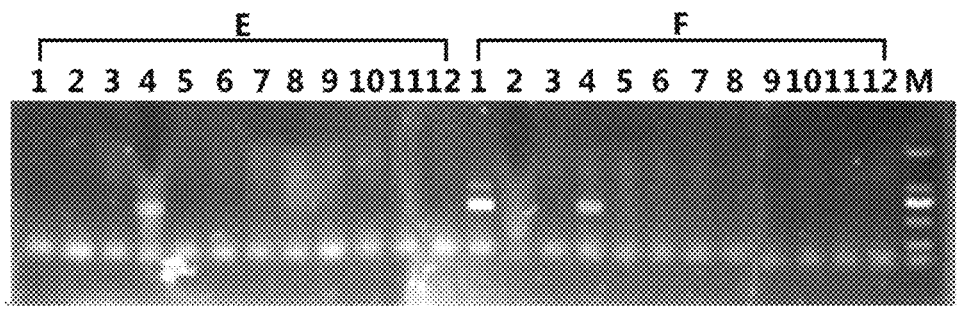
Figure 7D:
Figure 7E:
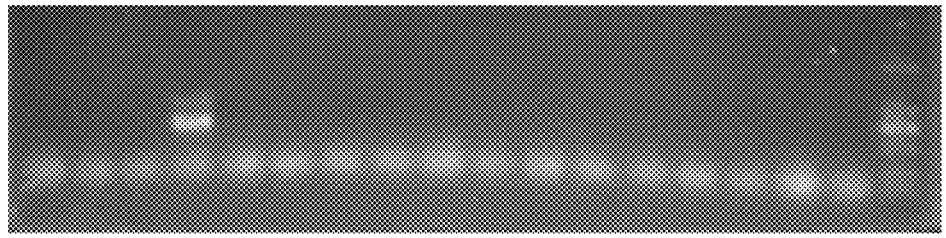
Figure 7F:
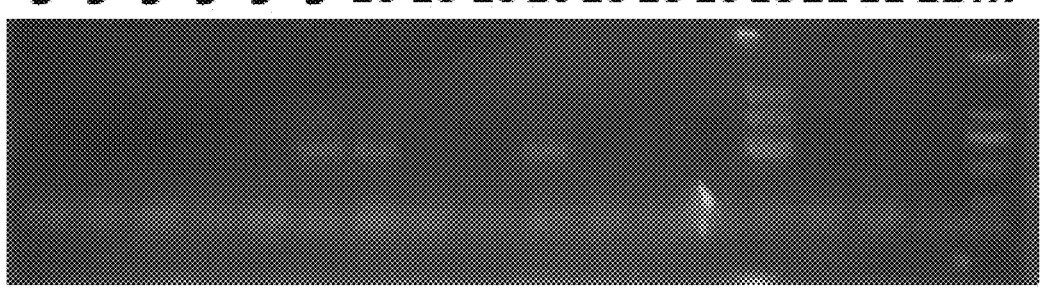

The results of FIGS. 7A-7C showed that: B9, D9, E4, F1 and F4 had target bands, i.e. the strain solutions of F1-F12 (denoted as 1F1-1F12) of the 1#96-well plate, E1-E12 (denoted as 4E1-4E12) and F1-F12 (denoted as 4F1-4F12) of the 4#96-well plate, B1-B12 (denoted as 9B1-9B12) and D1-D12 (denoted as 9D1-9D12) of the 9#96-well plates had the corresponding target genes, and the above five were denoted as the first group. The results of FIGS. 7D-7F showed that: H5, E7, H9, A10, D10, G10 and H10 had target bands, i.e., the strain solutions of H1-H12 (denoted as 5H1-5H12) of the 5#96-well plate, E1-E12 (denoted as 7E1-7E12) of the 7#96-well plate, H1-H12 (denoted as 9H1-9H12) of the 9#96-well plate, A1-A12 (denoted as 10A1-10A12), D1-D12 (denoted as 10D1-10D12), G1-G12 (denoted as 10G1-10G12) and H1-H12 (denoted as 10H-10H12) of the 10#96-well plate had the corresponding target genes, and the above seven were denoted as the second group.

Figure 8A:
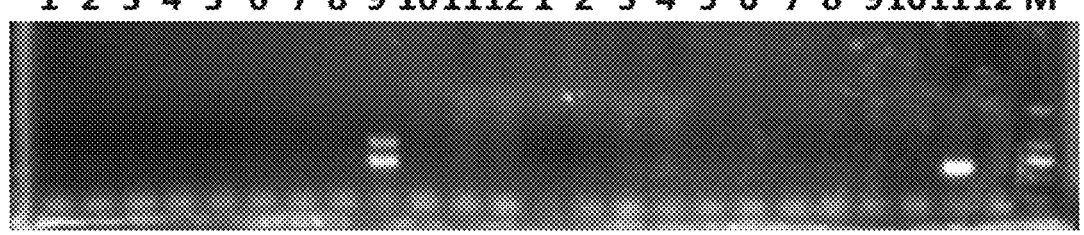
FIGS. 8A-8F are PCR electrophoretic results of further screening the positive results obtained in FIGS. 7A-7F.
Figure 8B:
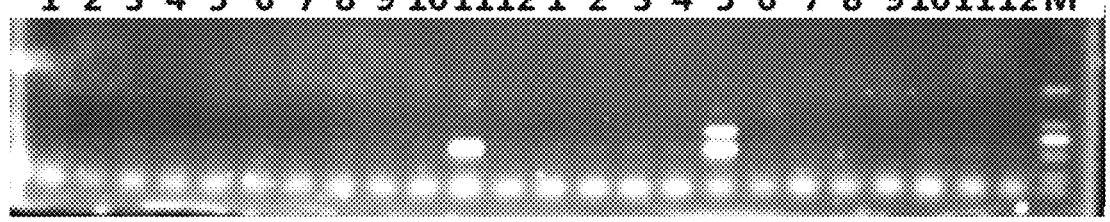
Figure 8C:
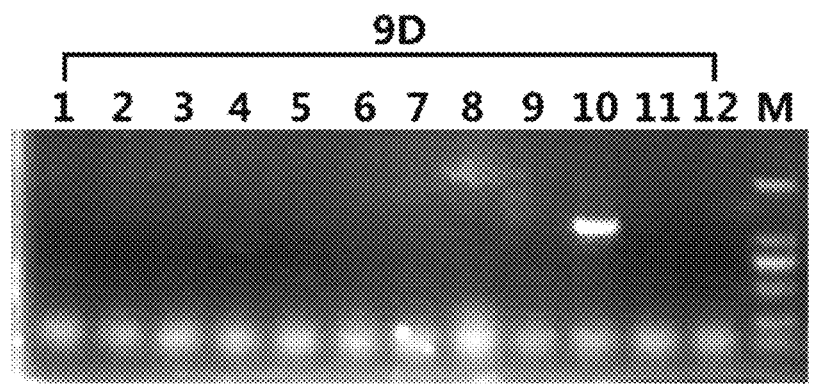
Figure 8D:
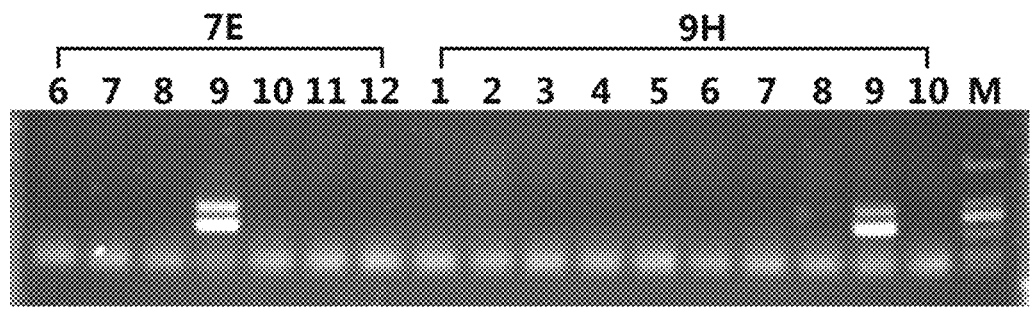
Figure 8E:
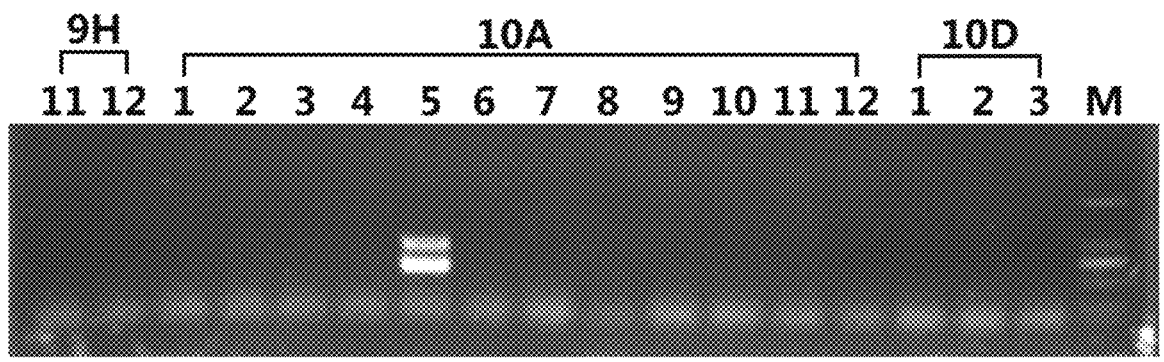
Figure 8F:
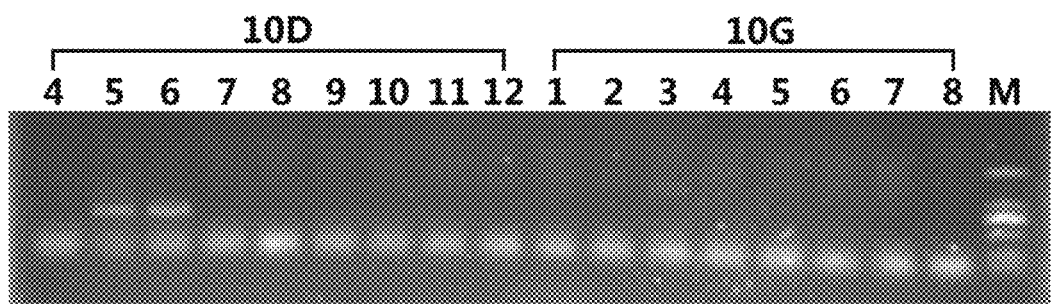
Figure 9A:
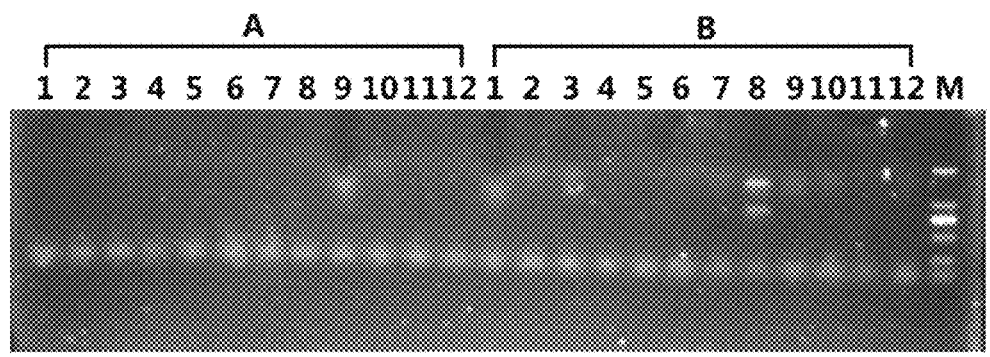
FIGS. 9A-9D are PCR electrophoretic results of screening a plasmid library containing spnD and spnE.
Figure 9B:
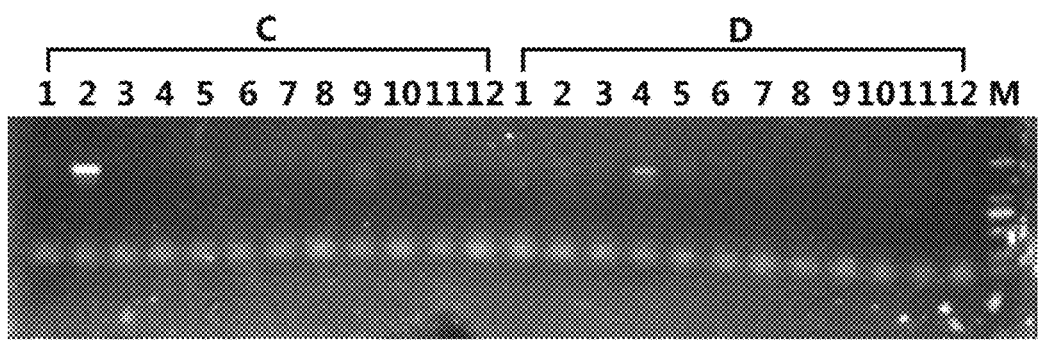
Figure 9C:
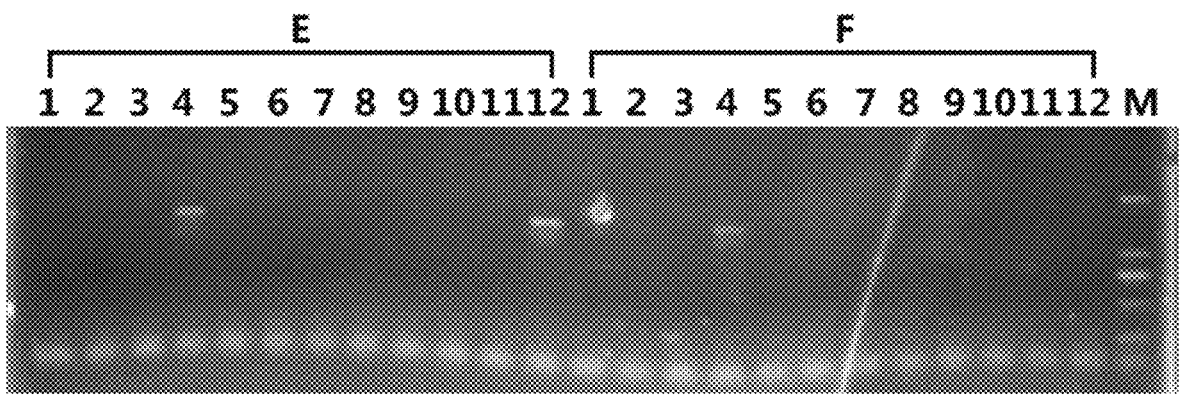
Figure 9D:
Figure 10A:
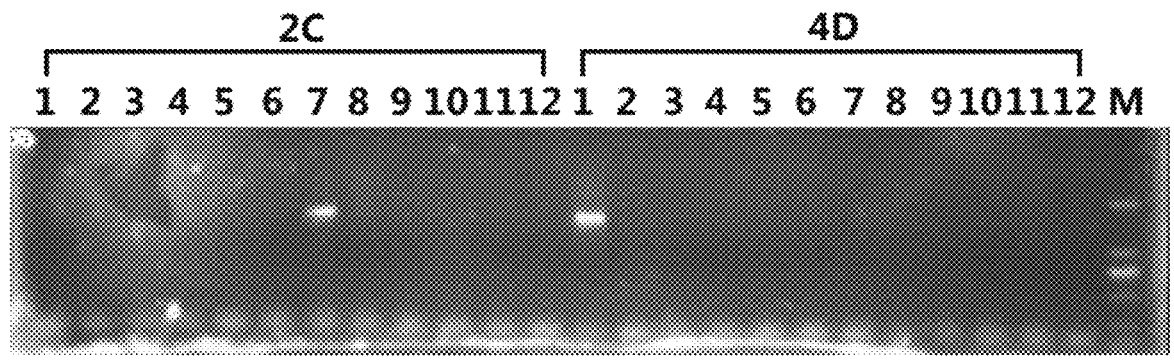
FIGS. 10A-10D are PCR electrophoretic results of further screening the positive results obtained in FIGS. 9A-9D.
Figure 10B:
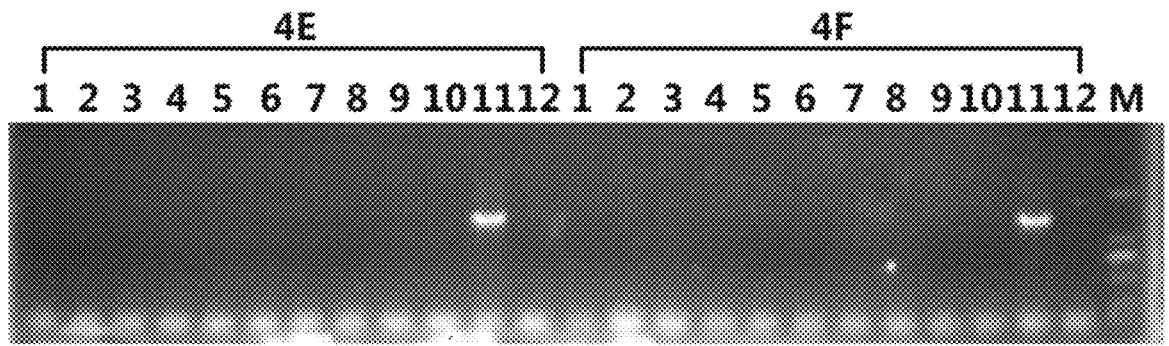
Figure 10C:
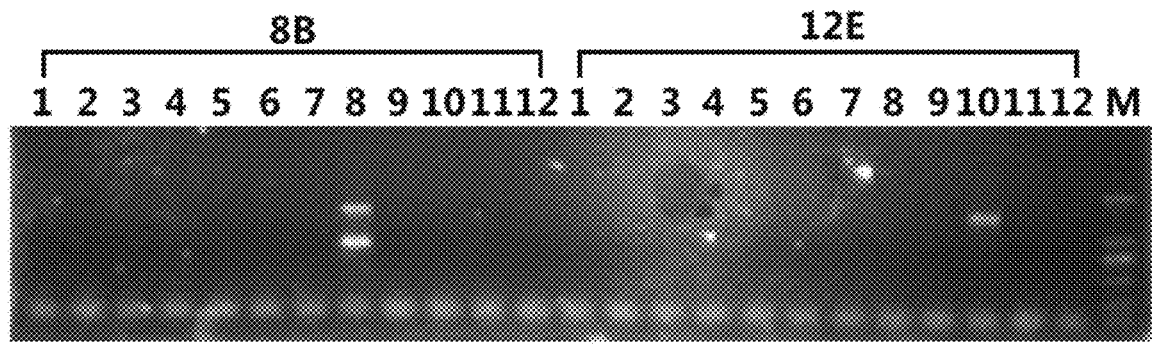
Figure 10D:
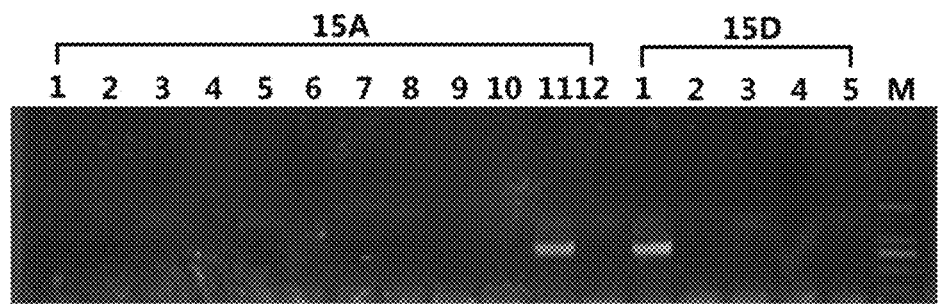

60 strain solutions of the first group and 84 strain solutions of the second group were subjected to PCR detection separately and respectively, with a formulation the same as above. The results were shown in FIGS. 8A-8F (FIGS. 8A-8C were referred to as the first group, and FIGS. 8D-8F were referred to as the second group):

The results of the first group showed that: 1F9, 4E11, 4F11, 9B5 and 9D10 had corresponding target fragments respectively; while the results of the second group showed that: 7E9, 9H9, 10A5, 10D5, 10D6 and 10G3 had corresponding target fragments respectively. After re-culturing the above-mentioned strain solutions to extract the plasmids, the plasmids were named by the above-mentioned numbers respectively, and the samples were sent for sequencing. Sequencing primers were: cosF: SEQ ID NO: 11; and cosR: SEQ ID NO: 12.

b) PCR was used to detect whether the library plasmid contains partial fragments (the relative positions on the spinosad biosynthetic gene cluster were 50305-51725 and 69264-70076 respectively) of the two genes of spnD and spnE, the relative positions of the two fragments on the spinosad biosynthetic gene cluster were shown in FIG. 6, and the sizes of PCR products of the two fragments were 1421 bp and 813 bp respectively; and primer sequences used were as follows:

spnD primers: spnDF(SEQ ID NO: 13), and spnDR(SEQ ID NO: 14); and spnE primers: spnEF(SEQ ID NO: 15), and spnER(SEQ ID NO: 16).

A following reaction solution was prepared:

750 µl of 2×GC I buffer solution; 120 µl of 2.5 mM dNTP; 15 µl of spnDF(25 µM); 15 µl of spnDR(25 µM); 15 µl of spnEF(25 µM); 15 µl of spnER(25 µM)l; 580 µl of ddH$_2$O; and 7.5 µl of rTaq.

The solution was subpackaged with 10 µl/tube, 0.5 µl of the strain solution in each well of the 16# and 17#96-well plate was added respectively, and 0.2 µl of the total DNA of spinosad producing strain was used as control. The PCR reaction procedure was as follows: 95° C.×10 min, (94° C.×30 sec, 55° C.×30 sec, 72° C.×1 min 30 sec)×35 cycles, 72° C.×1 min, 16° C.×1 sec.

PCR products were tested by electrophoresis, and the results were shown in FIGS. 9A-9D.

The result showed that: B8, C2, D4, E4, E12, F4, A15 and D15 had the corresponding target bands, i.e., the strain solution of B1-B12 (denoted as 8B1-8B12) of the 8#96-well plate, C1-C12 (denoted as 2C1-2C12) of the 2#96-well plate, D1-D12 (denoted as 4D1-4D12), E1-E12 (denoted as 4E1-4E12) and F1-F12 (denoted as 4F1-4F12) of the 4#96-well plate, E1-E12 (denoted as 12E1-12E12) of the 12#96-well plate, A1-A12 (denoted as 15A1-15A12) and D1-D12 (denoted as 15D1-15D12) of the 15#96-well plate had the corresponding target genes. The above-mentioned 96 strain solutions were picked up to perform separate PCR detection respectively, with a formulation the same as above. The results were shown in FIGS. 10A-10D:

The results showed that the strain solutions of 2C7, 4D1, 4E11, 4F11, 8B8, 12E10, 15A11 and 15D1 had the corresponding target genes. After re-culturing the above-mentioned strain solutions to extract the plasmids, the plasmids were named by the above-mentioned numbers respectively, and the samples were sent for sequencing. The sequencing primers were cosF and cosR as well.

The sequencing results showed that: 9D10 and 10G3 had exactly the same sequence, 2C7, 4D1 and 12E10 had exactly the same sequence, and 4E11 and 4F11 had exactly the same sequence. The fragments carried by 2C7/4D1/12E10 and 9H9 were reverse, while the rest were all forward.

The relative positions of the spinosad biosynthetic gene cluster fragments contained in each library plasmid were shown in the following table. It is given that the sequence position published by GenBank AY007564.1 was 1-80161, and partial sequences of all 9D10, 10G3, and 15A11 and 15D1 were located outside the scope. According to an additional sequencing result of 10G3 (SEQ ID NO: 17) and 15D1(SEQ ID NO: 20), the sequences before position 1 were set to be minus, and the sequences after position 80161 were counted sequentially.

TABLE 1

Starting Position and Insertion Direction of Fragments Carried by Various Plasmids

| Name of plasmid | Starting position | End position | Direction of inserted fragment |
|---|---|---|---|
| 1F9 | 18952 | 51269 | Forward |
| 2C7 | 66097 | 35230 | Reverse |
| 4D1 | 66097 | 35230 | Reverse |
| 4E11 | 26937 | 59590 | Forward |
| 4F11 | 26937 | 59590 | Forward |
| 8B8 | 36931 | 70419 | Forward |
| 9B5 | 16413 | 49516 | Forward |
| 9D10 | −10753 | 22293 | Forward |
| 9H9 | 51269 | 18952 | Reverse |
| 10G3 | −10753 | 22293 | Forward |
| 12E10 | 66097 | 35230 | Reverse |
| 15D1 | 64384 | 91447 | Forward |
| 15A11 | 58537 | 89670 | Forward |

The positions of the fragments carried by various plasmids relative to the spinosad biosynthetic gene cluster were shown in FIG. 6.

Wherein, the fragments carried by the four plasmids 10G3, 9B5, 8B8 and 15D1 were able to cover the complete spinosad biosynthetic gene cluster and upstream and downstream sequences thereof. The sequences of the fragments carried by the four plasmids were as follows:

DNA fragment sequence carried by 10G3: SEQ ID NO: 17;
DNA fragment sequence carried by 9B5: SEQ ID NO: 18;
DNA fragment sequence carried by 8B8: SEQ ID NO: 19; and
DNA fragment sequence carried by 15D1: SEQ ID NO: 20.

Figure 11:
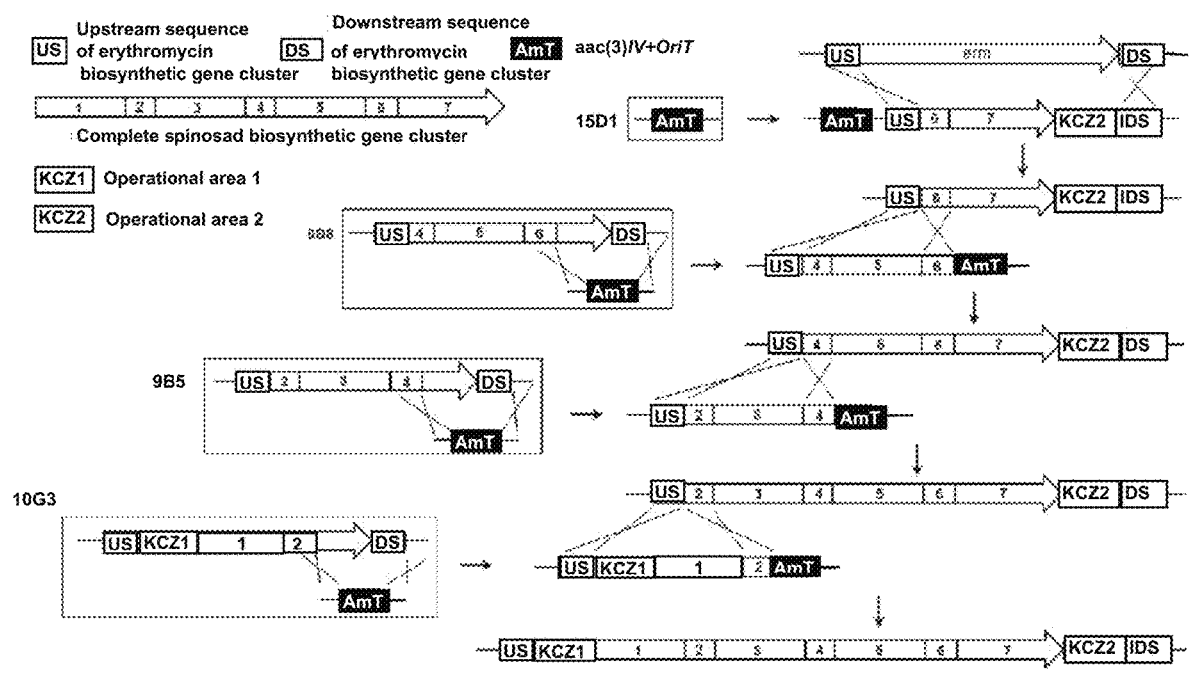
FIG. 11 is a schematic diagram showing a fragment modification and homologous recombination process of the spinosad synthetic gene cluster.

After trimming, the library plasmids 15D1, 8B8, 9B5 and 10G3 were integrated into the position of erythromycin synthetic gene cluster of *Saccharopolyspora erythraea* by homologous double crossover in sequence. FIG. 11 was a schematic diagram of the whole process, wherein "US" was an upstream fragment eryU of the erythromycin synthetic gene cluster, and "DS" was a downstream fragment eryD of the erythromycin synthetic gene cluster. How to modify the various plasmids and perform the homologous recombination will be introduced in details hereinafter.

Example 4: Modification of Library Plasmid 15D1

Figure 12:
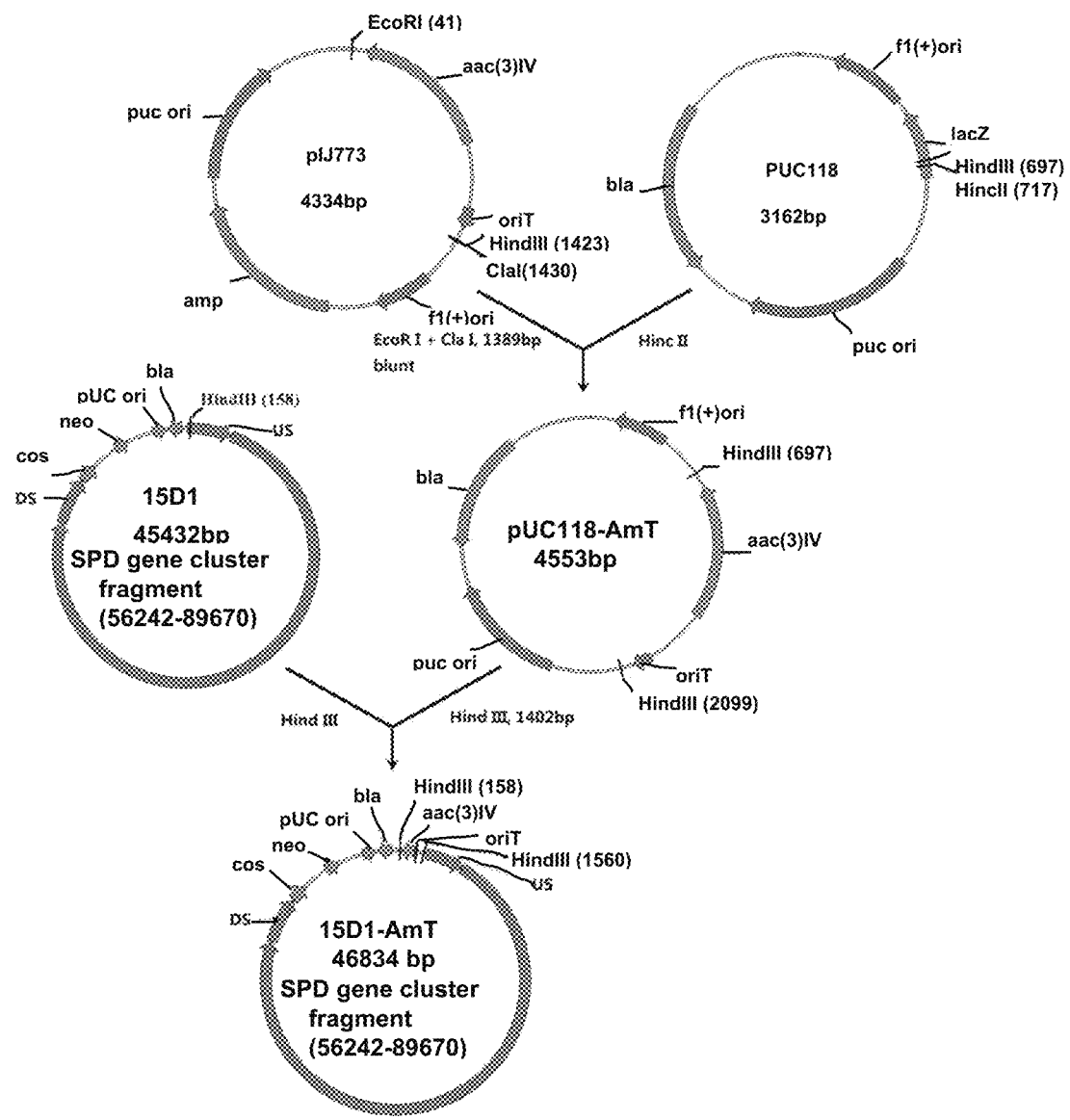
FIG. 12 is a construction process of a plasmid 15D1-AmT.

The example aimed at inserting a resistance fragment containing an aac(3)IV gene (apramycin resistance gene) and oriT (conjugative origin, essential element for conjugation) into the HindIII site of the library plasmid 15D1, to enable the modified plasmid to be used for conjugation. The example was carried out in two steps: cutting off the resistance gene cassette from plasmid pIJ773 with ClaI and EcoRI, and ligating the resistance gene cassette to the HincII site of vector pUC118 (TaKaRa, Item No. D3322) after end blunting (SEQ ID NO: 65). Because the cut resistance fragment had a HindIII site at the end near ClaI, while the vector pUC118 also had one HindIII site, thereby screening a transformant with a correct insertion direction, and the resistance fragment could be cut off with HindIII; the second step was to insert the resistance fragment cut with HindIII into the HindIII site of 15D1. Because the resistance fragment only functioned for screening and conjugation, the insertion direction thereof did not affect the result of subsequent experiment. Therefore, there was no need to determine the insertion direction thereof. A specific operation was as follows (as shown in FIG. 12):

A following reaction solution was prepared: 20 µl of pIJ773; 5 µl of 10×H buffer solution; 23 µl of ddH$_2$O; 1 µl of Cla I(TaKaRa, Item No. D1034A); and 1 µl of EcoR I(TaKaRa, Item No. D1040A).

After the solution was subjected to a water bath at 37° C. for 1 h, a 1389 bp fragment containing the aac(3)IV gene and oriT was recovered by electrophoresis. After end blunting with a BKL kit, the fragment was ligated with pUC118/Hinc II, BAP (TaKaRa, Item No. D3322) for transformation. Transformants were picked out for extracting the plasmids, HindIII was used for enzyme digestion, and the recombinant plasmids with an enzyme-digested result of 3502 bp+1402b were screened. A 1402 bp fragment containing the aac(3)IV gene and oriT was recovered by electrophoresis, and was ligated with the dephosphorylated plasmid 15D1 digested with HindIII to obtain the recombinant plasmid 15D1-AmT.

Example 5: Migration of the First Fragment of Spinosad Biosynthetic Gene Cluster into *Saccharopolyspora erythraea*

The recombinant plasmid 15D1-AmT was transformed into *Saccharopolyspora erythraea* (ATCC 11635) by conjugation (see the method 7). After the transformants were subcultured twice, apramycin sensitive colonies were screened. Genomic DNA was extracted (according to the method 10, but the volume of TSB was changed to 3 ml, the volumes of other reagents were correspondingly reduced as well except that the volume was still 500 µl during washing with 70% ethanol, similarly hereinafter), and primers spnEF (SEQ ID NO: 15)/spnER (SEQ ID NO: 16) and primers ery1F (SEQ ID NO: 21)/ery1R (SEQ ID NO: 22) were used for PCR detection respectively. Sequences inside the DNA fragment carried by the library plasmid 15D1 were amplified by primers spnEF/spnER, while sequences inside the erythromycin synthetic gene cluster were amplified by the primers ery1F/ery1R. Therefore, the spnEF/spnER could amplify the target bands, while the ery1F/ery1R could not amplify the target bands, which indicated that the erythromycin synthetic gene cluster had been replaced with the DNA fragment carried by the library plasmid 15D1, and was the target strain. A genetically engineered strain ES01 was obtained by screening.

The following examples 6, 8 and 10 aimed at utilizing the resistance gene cassette aac(3)IV+oriT (the resistance gene cassette was amplified by PCR from plasmid pIJ773, the 14-1382 site of SEQ ID NO: 65) to replace the DS on corresponding library plasmid and partial sequence of the 3' end of the carried genomic fragment. It was mainly divided into two steps: forward and reverse primers with lengths of 59 nt and 58 nt were firstly designed respectively, wherein 39 nt of the 5' ends of the primers were served as homologous arms respectively, while 20 nt (forward primer, SEQ ID NO: 63) and 19 nt (reverse primer, SEQ ID NO: 64) of the 3' ends were matched with the primer sequences on the resistance gene cassette. The resistance gene cassette was amplified from pIJ773 by PCR. The homologous arms with a length of 39 bp were introduced by the PCR product at both ends of the resistance gene cassette respectively. These two homologous arms were located at two sides of the fragment to be replaced on the library plasmid respectively; and then the PCR product was transformed into *Escherichia* coli BW25113 (pIJ790) containing the library plasmid, and the target sequence was replaced with the resistance gene cassette using the recombinant system in the *Escherichia coli*. See table 2 for the relevant information of the primers used in various examples and the replaced fragments.

TABLE 2

Relevant Information of Library Plasmids Modified in Examples 6, 8 and 10

|  | Examples | | |
|---|---|---|---|
|  | 6 | 8 | 10 |
| Modified library plasmid | 8B8 | 9B5 | 10G3 |
| Fragment* contained in the library plasmid | 36931~70419 | 16413~49516 | −10753~22293 |
| 39 bp upstream homologous arm* | 69981~70019 | 42561~42599 | 19524~19562 |
| 39 bp downstream homologous arm* | Located on a cos site at downstream of DS, 5' end of 39 bp of SEQ ID NO. 24 | Located on a cos site at downstream of DS, 5' end of 39 bp of SEQ ID NO. 28 | Located on a cos site at downstream of DS, 5' end of 39 bp of SEQ ID NO. 28 |
| Replaced fragment* | 70020~70419 + DS | 42600~49516 + DS | 19563~22293 + DS |
| Contained fragment after modification | 36931~70019 | 16413~42599 | −10753~19562 |

*refers to the relative position on the spinosad biosynthetic gene cluster

Example 6: Modification of Library Plasmid 8B8

(1) The library plasmid 8B8 was transformed into BW25113 (pIJ790) competent cells according to method 2;

(2) one transformant of BW25113 (pIJ790, 8B8) was picked out and inoculated into a 3 ml LB medium containing Cm, and cultured at 30° C. for 14-18 h under 220 rpm;

(3) then the transformant was transferred to 30 ml of SOB medium (2.0% tryptone, 0.5% yeast extract, 0.05% NaCl, 1M of 2.5 ml/L KCl; and 2.5M of 4 ml/L MgCl$_2$ after sterilization) containing Km, Cm, Ap and 300 µl of 1M L-arabinose with 1% inoculation amount, and cultured at 30° C. under 220 rpm until OD600 was between 0.4 and 0.6;

(4) the strain was collected by centrifuging at 4° C. and washed twice with 10% glycerol, and then suspended in 100 µl of 10% glycerol to obtain electroporation-competent cells;

(5) a plasmid pIJ773 was taken as a template to amplify the aac(3)IV+oriT resistance gene cassette by PCR, and homologous arms with a length of 39 bp for homologous crossover were added at both ends of the resistance gene cassette.

Reaction system: 25 µl of 5×PrimeSTAR buffer solution (Mg$^{2+}$ Plus); 4 µl of dNTP mixture (each 2.5 mM); 1 µl of primer 8BA-L(SEQ ID NO: 23, 25 µM); 1 µl of primer 8BA-R (SEQ ID NO: 24, 25 µM); 18 µl of ddH$_2$O; 0.5 µl of plasmid pIJ773; and 0.5 µl of PrimeSTAR® HS DNA polymerase Reaction program: 95° C.×5 min; (98° C.×10 sec, 50° C.×10 sec, 72° C.×90 sec)×10 cycles; 72° C.×2 min, 16° C.×1 min. (98° C.×10 sec, 68° C.×90 sec)×15 cycles; 72° C.×1 min, 16° C.×1 min.

After electrophoresis of the PCR product, a target fragment about 1.4 kb was recovered by cutting gel.

(6) 3 µl of the resistance fragment obtained in step (5) was taken and added to 50 µl of the BW25113 (pIJ790/8B8) electroporation-competent cells obtained in step (4), which were completely transferred to a 2 mm electrotransformation cup (BioRad). The parameters of electric shock were 2500V, 25 µF, 200Ω. After the electric shock, 1 ml of SOC medium (adding 2 ml of 1 mol/L glucose in per 100 ml of SOB medium) was rapidly added and completely transferred to a 1.5 ml centrifuge tube.

(7) After a water bath at 37° C. for 1 h, 900 µl of the supernatant was removed by centrifuging, the precipitate was suspended in the remaining medium, completely spread on an LB solid medium containing Am, and cultured at 37° C. for 16 h.

(8) Transformants with large size were picked out and added in 3 ml of LB liquid medium containing Am, cultured at 37° C. for 6 h under 200 rpm, then plasmids were extracted, and primers 8BD-L (SEQ ID NO: 25)/8BD-R (SEQ ID NO: 26) were utilized for PCR detection (the extension time in the PCR reaction procedure was 4 min). The primers 8BD-L and 8BD-R were located at the two sides of the sequence to be replaced on the library plasmid 8B8 respectively. If the replacement was successful, the PCR product of plasmid should be a target band of 1963 bp; if the replacement was unsuccessful, the PCR product was 3957 bp. After screening, the recombinant plasmid 8B8-AmT was obtained.

Example 7: Migration of the Second Fragment of Spinosad Biosynthetic Gene Cluster into *Saccharopolyspora erythraea*

The recombinant plasmid 8B8-AmT was transformed into the genetically engineered strain ES01 obtained in the example 5 by conjugation. After the transformants were subcultured twice, apramycin sensitive colonies were screened. The total DNA was extracted, and primers 8BD-L (SEQ ID NO: 25)/8BD-R (SEQ ID NO: 26) were used for PCR detection. The principle was the same as that in step (8) of example 6, and the PCR product of target strain was only a band with 1963 bp. A genetically engineered strain ES02 was obtained by screening.

Example 8: Modification of Library Plasmid 9B5

The target and method were similar to the library plasmid 8B8 of example 6, and primers for amplifying the resistance gene cassette were 9B5-L (SEQ ID NO: 27)/9B5-R (SEQ ID NO: 28). Primers 95A-L (SEQ ID NO: 29)/95A-R (SEQ ID NO: 30) were utilized for plasmid PCR detection to screen the plasmids through which a 1881 bp band can be amplified, and a recombinant plasmid 9B5-AmT was obtained.

Example 9: Migration of the Third Fragment of Spinosad Biosynthetic Gene Cluster into *Saccharopolyspora erythraea*

The recombinant plasmid 9B5-AmT was transformed into the genetically engineered strain ES02 obtained in example 7 by conjugation. After the transformants were subcultured twice, apramycin sensitive colonies were screened. The total DNA was extracted, and primers 95A-L (SEQ ID NO: 29)/95A-R (SEQ ID NO: 30) were used for the PCR detection, and the PCR product of target strain was only a 1881 bp band. A genetically engineered strain ES03 was obtained by screening.

Example 10: Modification of Library Plasmid 10G3

The aim and method were similar to modification of library plasmid 8B8 in example 6, and primers for amplifying the resistance gene cassette were 10G3-L (SEQ ID NO: 31)/9B5-R (SEQ ID NO: 28). Primers 10G-L (SEQ ID NO: 32)/10G-R (SEQ ID NO: 33) were utilized for the PCR detection to screen the plasmids through which 1676 bp target band can be amplified, and a recombinant plasmid 10G3-AmT was obtained.

Example 11: Migration of the Fourth Fragment of Spinosad Biosynthetic Gene Cluster into *Saccharopolyspora erythraea*

The recombinant plasmid 10G3-AmT was transformed into the genetically engineered strain ES03 obtained in example 9 by conjugation. After the transformants were subcultured twice, apramycin sensitive colonies were screened. The total DNA was extracted, and primers 10G-L/10g-R was used for the PCR detection, and the PCR product of target strain was only a 1676 bp band. A genetically engineered strain ES04 was obtained by screening.

Example 12: Construction of Recombinant Plasmid Containing Rhamnose Synthetic Gene Cluster of *Saccharopolyspora spinosa*

The example aimed at gathering the four rhamnose synthetic genes together between the upstream and downstream homologous arms, thereby inserting the four genes into the chromosome of the genetically engineered strain ES04 obtained in example 11 via homologous double crossover. In the chromosome of the genetically engineered strain ES4, a 80 kb spinosad biosynthetic gene cluster was inserted into the position of the erythromycin synthetic gene cluster through the previous examples, and the erythromycin synthetic gene cluster was deleted simultaneously; however, two fragments derived from the *Saccharopolyspora spinosa* and are uncorrelated with the spinosad biosynthesis were also introduced simultaneously, which were called as "operational areas" (as shown in FIG. 11, KCZ1 and KCZ2). While two homologous arms were selected in one of the "operational areas" in this example, so that the four inserted genes would not damage the spinosad biosynthetic gene cluster. Therefore, the example includes the following several steps:

(1) cloning the upstream and downstream homologous arms from "operational area 2" and inserting the arms into a vector pUAmT14 in sequence; and (2) cloning the four rhamnose synthetic genes respectively, and inserting the genes between the two homologous arms in sequence.

Figure 13:
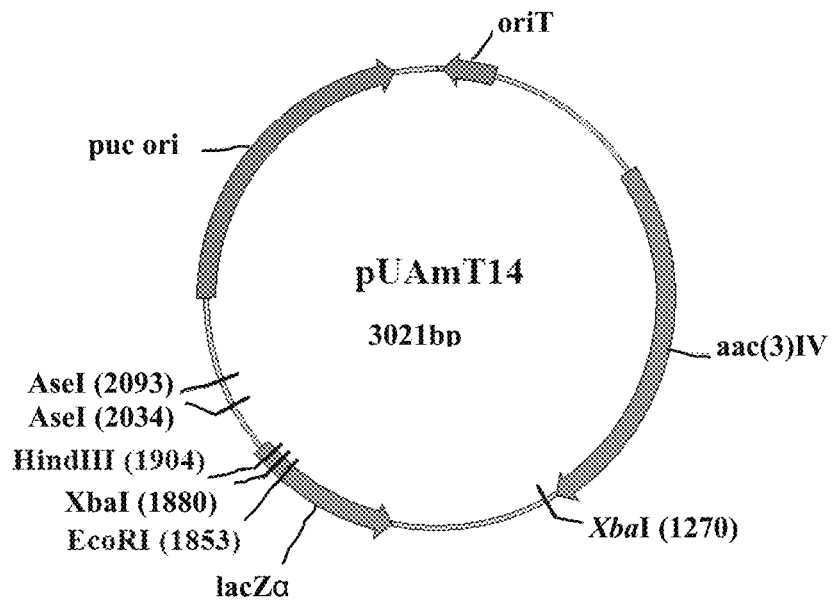
FIG. 13 is a profile of plasmid pUAmT14.

Since this example relates to one vector and five fragments (two homologous arms, wherein four rhamnose synthetic genes were distributed in three fragments), only an XbaI site was selected for cloning during cloning the second homologous arm and the three gene fragments in order to facilitate the operation. The following was a solution designed based on the following conditions;

(1) there was no XbaI site in both the 2 homologous arms and 4 rhamnose synthetic genes; while there were two XbaI sites in the vector pUAmT14 (FIG. 13), but only one XbaI site was remained after the first step of digestion;

(2) the endonuclease XbaI was an enzyme that was affected by methylation. When the two bases behind the recognition site TCTAGA were TC, plasmids extracted from a host strain with a methylation function, such as DH5α, could not be cut off by XbaI, since PCR product was not methylated, the enzyme digestion would not be affected no matter what sequence the bases behind the recognition site was when the PCR product was directly digested.

Therefore, the specific solution was as follows.

(1) The downstream homologous arm was firstly cloned into an AseI-HindIII site of vector pUAmT14. Double enzyme digestion ensured that the insertion direction of the fragment was correct, and the XbaI site was located at the upstream of the downstream homologous arm.

(2) The XbaI site affected by methylation was introduced at the 5' end of the upstream homologous arm obtained by PCR amplification, while the XbaI site not affected by methylation was introduced at the 3' end. When the fragment was subjected to enzyme digestion with XbaI and inserted into the XbaI site of the plasmid obtained in the previous step, only the XbaI site between the upstream homologous arm and the downstream homologous arm in the plasmid extracted from DH5α was able to be cut off, and the other XbaI site was unable to be cut off due to the effect of methylation. This could ensure that all the following rhamnose gene fragments were inserted between the two homologous arms.

(3) The three rhamnose gene fragments were inserted into the XbaI site by the same method.

The specific implementation process is as follows:

(1) Insertion of Downstream Homologous Arm:

The library plasmid 15D1 was taken as a template, and primers 005DF (SEQ ID NO: 34, introducing the Hind III site at the 5' end)/006DR (SEQ ID NO: 35, introducing the Ase I site at the 5' end) were used for PCR amplification, to obtain a downstream homologous arm fragment 5: D PCR (SEQ ID NO: 48). The fragment 5 was recovered, and subjected to AseI+HindIII double enzyme digestion together with the vector pUAmT14:

Reaction system: 20 μl of fragment 5 (or carrier pUAmT14); 5 μl of 10×Tango buffer solution; 23 μl of ddH$_2$O; 1 μl of AseI (Fermentas, Item No. ER0911); and 1 μl of EcoRI (Fermentas, Item No. ER0501).

After performing a water bath at 37° C. for 1 h, the products were directly recovered respectively and ligated to obtain a recombinant plasmid pAT-D.

(2) Insertion of Upstream Homologous Arm:

The library plasmid 15D1 was taken as a template, and primers 007UF (SEQ ID NO: 36, introducing an XbaI site affected by methylation at the 5' end)/008UR (SEQ ID NO: 37, introducing an XbaI site not affected by methylation at the 5' end) were used for PCR amplification, to obtain an upstream homologous arm fragment 6: U PCR (SEQ ID NO: 49). The fragment 6 was subjected to enzyme digestion with XbaI and ligated with the dephosphorylated plasmid pAT-D digested with XbaI and transformed. The plasmids of transformants were extracted, and primers 009F (SEQ ID NO: 44)/010R (SEQ ID NO: 45) were used for PCR detection. The forward primer 009F was located at the upstream homologous arm, and the reverse primer 010R was located at the downstream homologous arm. If the insertion direction of the upstream homologous arm was correct, the PCR product should be 170 bp; while if the insertion direction is wrong, no PCR product would be obtained. A recombinant plasmid pAT-DU was obtained by screening.

(3) Insertion of Gtt Gene Between the Upstream Homologous Arm and the Downstream Homologous Arm:

The total DNA of *Saccharopolyspora spinosa* was taken as a template, and primers gttF (SEQ ID NO: 38, introducing an XbaI site not affected by methylation at the 5' end)/gttR (SEQ ID NO: 39, introducing an XbaI site affected by methylation at the 5' end) were used for PCR amplification, to obtain a fragment 7: gtt PCR (SEQ ID NO: 50) containing gtt gene. The fragment 7 was subjected to enzyme digestion with XbaI, and was ligated with the dephosphorylated plasmid pAT-DU digested with XbaI to obtain a recombinant plasmid pAT-DgU.

(4) Insertion of Epi Gene Between the Upstream Homologous Arm and the Downstream Homologous Arm:

The total DNA of *Saccharopolyspora spinosa* was taken as a template, and primers epiF (SEQ ID NO: 40, introducing an XbaI site not affected by methylation at the 5' end)/epiR (SEQ ID NO: 41, introducing an XbaI site affected by methylation at the 5' end) were used for PCR amplification, to obtain a fragment 8:epi PCR(SEQ ID NO: 51) containing epi gene. The fragment 8 was subjected to enzyme digestion with XbaI, and was ligated with the dephosphorylated plasmid pAT-DgU digested with XbaI to obtain a recombinant plasmid pAT-DgeU.

Figure 14:
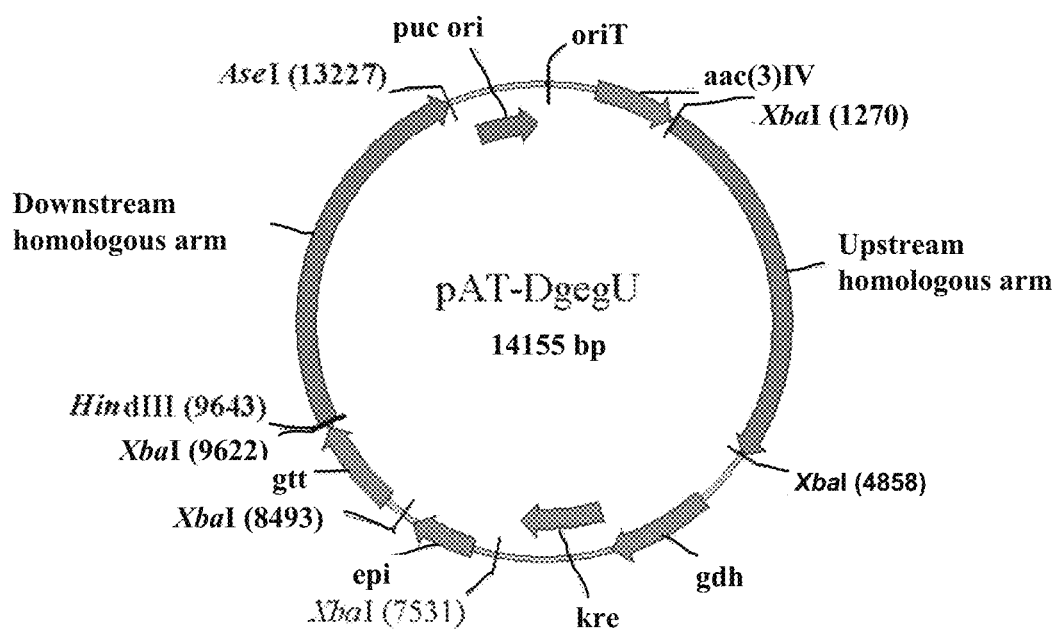
FIG. 14 is a profile of plasmid pAT-DgegU.

(5) Insertion of Gdh and Kre Genes Between the Upstream Homologous Arm and the Downstream Homologous Arm:

The total DNA of *Saccharopolyspora spinosa* was taken as a template, and primers gdhF (SEQ ID NO: 42, introducing an XbaI site not affected by methylation at the 5' end)/gdhR (SEQ ID NO: 43, introducing an XbaI site not affected by methylation at the 5' end) were used for PCR amplification, to obtain a fragment 9: gdh PCR(SEQ ID NO: 2) containing gdh+kre genes. The fragment 9 was subjected to enzyme digestion with XbaI, and was ligated with the dephosphorylated plasmid pAT-DgeU digested with XbaI to obtain a recombinant plasmid pAT-DgegU, wherein the plasmid profile was shown in FIG. 14.

Since the sequence and direction of the four rhamnose synthetic genes would not affect the synthesis of rhamnose, it was only needed to confirm that the genes were inserted in steps (3)-(5), and did not need to determine the direction and sequence of insertion. Through sequencing detection, the plasmid pAT-DgegU includes four rhamnose synthetic genes.

Example 13: Transfer of Rhamnose Synthetic Gene Cluster of *Saccharopolyspora spinosa* into *Saccharopolyspora erythraea*

The recombinant plasmid pAT-DgegU was transformed into the genetically engineered strain ES04 obtained in example 11 by conjugation. After the transformants were subcultured twice, apramycin sensitive colonies were screened. The total DNA was extracted, and primers 009F (SEQ ID NO: 44)/010R(SEQ ID NO: 45) were used for PCR detection. The primers 009F and 010R were located on the upstream homologous arm and the downstream homologous arm respectively. If the four rhamnose synthetic genes were successfully inserted, the PCR product should be 4931 bp; if the four rhamnose synthetic genes were not successfully inserted, the PCR product should be 1322 bp. A genetically engineered strain ES05 was obtained by screening.

Figure 16:
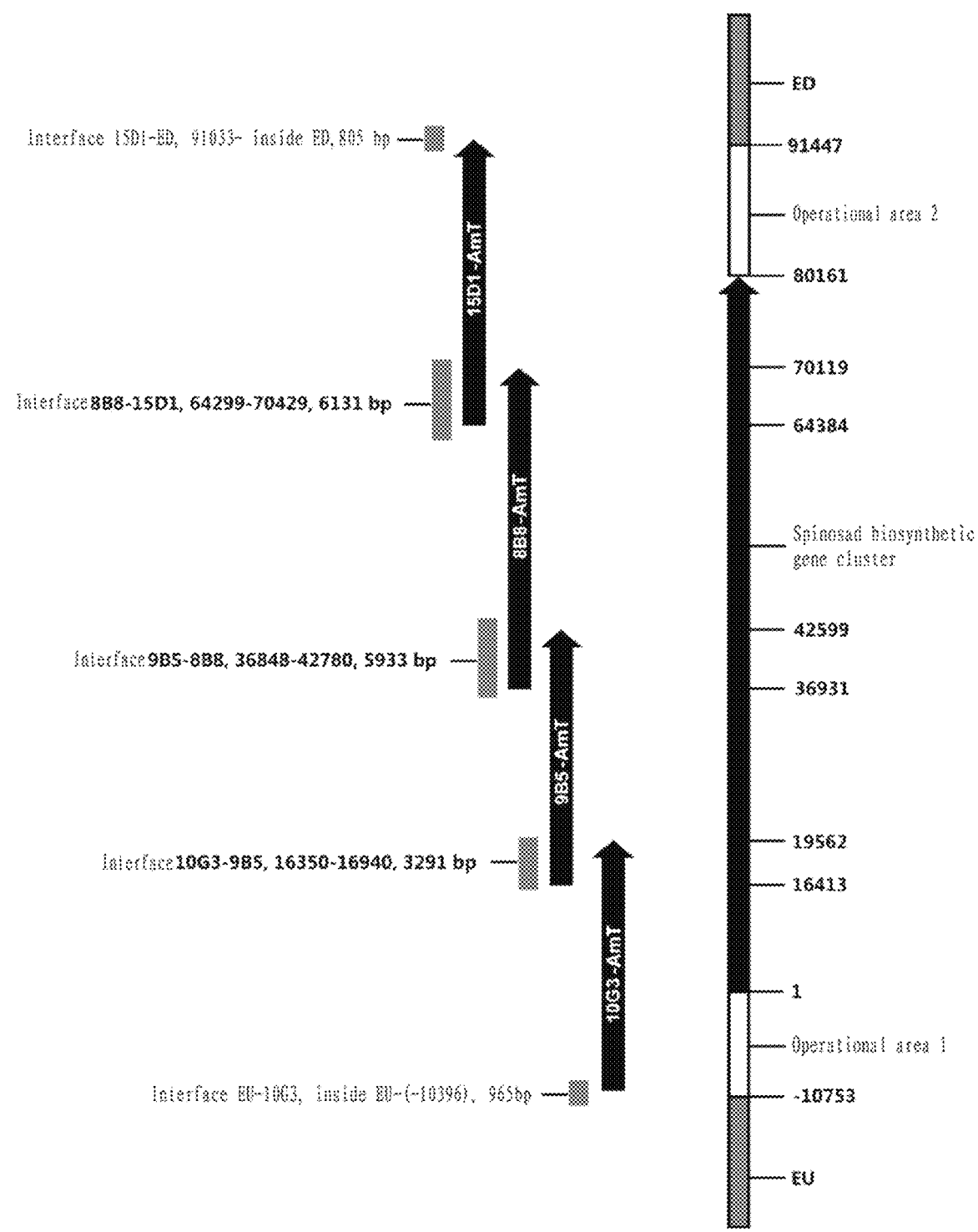
FIG. 16 is a schematic diagram of PCR detection of overlapping portions of various fragments.

Sequencing was performed for interface portions among various library plasmids of the spinosad synthetic gene cluster in the genetically engineered strain ES05. The relative positions of various interfaces were shown in FIG. 16, and the results were shown in Table 3. The sequencing results were consistent with expected results, which indicated that the spinosad synthetic gene cluster was already transferred into the genetically engineered strain, and the sequence order was consistent with the sequence order of the spinosad synthetic gene cluster in the *Saccharopolyspora spinosa*.

TABLE 3

| | Sequencing Result of Interface Portions between Library Plasmids | | | | |
|---|---|---|---|---|---|
| Interface situation | EU-10G3 | 10G3-9B5 | 9B5-8B8 | 8B8-15D1 | 15D1-ED |
| Position[1] of overlapping portion | −10753 | 16413-19512 | 36931-42599 | 64384-70119 | 91447 |
| Primer | U10G3F: (SEQ ID NO.53) | 10G39B5F: (SEQ ID NO.55) | 9B58B8F: (SEQ ID NO.57) | 8B815D1F: (SEQ ID NO.59) | 15D1DF: (SEQ ID NO.61) |
| | U10G3R: (SEQ ID NO.54) | 10G39B5R: (SEQ ID NO.56) | 9B58B8R: (SEQ ID NO.58) | 8B815D1R: (SEQ ID NO.60) | 15D1DR: (SEQ ID NO.62) |
| Size of PCR product | 965 bp | 3291 bp | 5933 bp | 6131 bp | 805 bp |
| Position of PCR product | Inside EU-(−10396) | 16350-19640 | 36848-42780 | 64299-70429 | 91033- Inside ED |
| Sequencing result [2] | Consistent | Consistent | Consistent | Consistent | Consistent |

[1]"position" refers to the relative position on the spinosad biosynthetic gene cluster. Since there was no overlapping portion between EU-10G3 and 15D1-ED, only the position ligated to the *Saccharopolyspora erythraea* chromosome was shown;

[2] "consistent" refers to being consistent with the expected results.

Sequencing was further performed for the spinosad synthetic gene cluster and the rhamnose synthetic gene cluster inserted into the genetically engineered bacterium ES05, the results were completely consistent with the expected sequence, which indicated that the genetically engineered strain with a clear genetic background could be obtained.

Example 14: Fermentation of Genetically Engineered Strain ES05

Figure 15A:
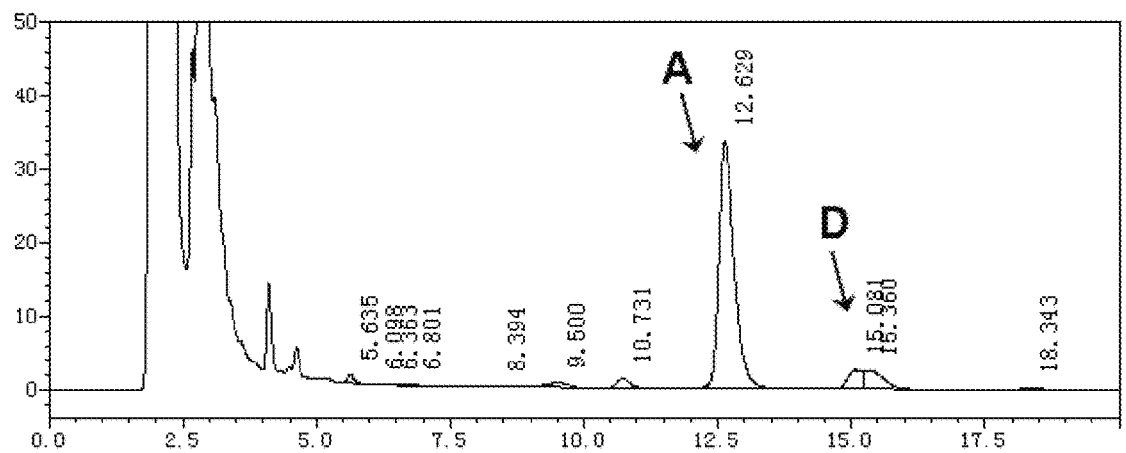
FIGS. 15A-15C are HPLC profiles of three strain fermentation.
Figure 15B:
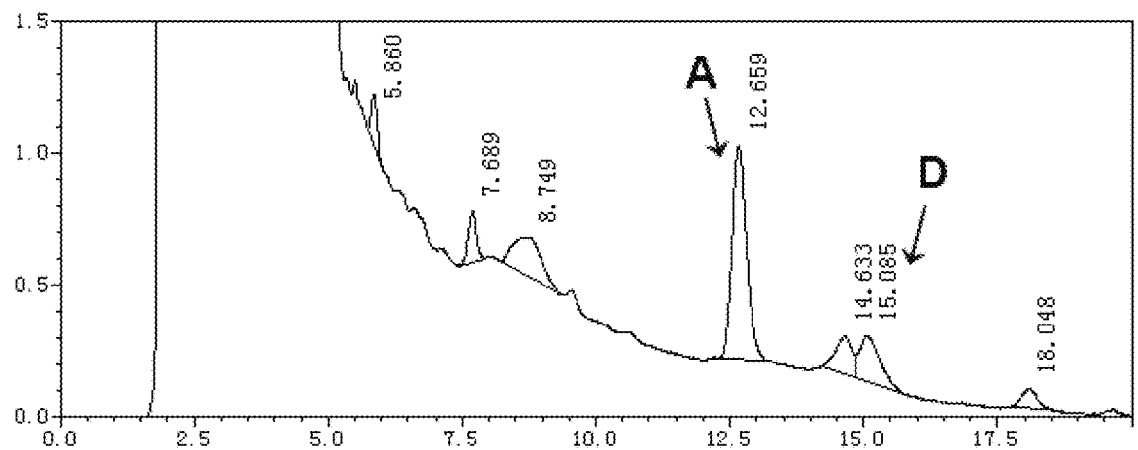
Figure 15C:
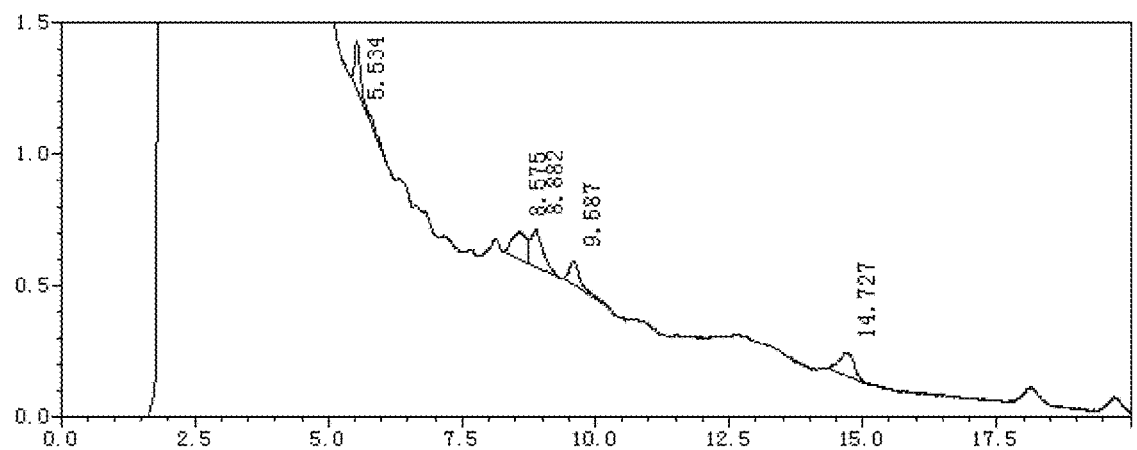

A colony block of ES05 was cultured in a seed medium (3.0% starch, 2.5% soybean cake powder, 0.5% peptone, 3.0% dextrin, 1.0% glucose, 0.4% sodium chloride, pH 7.5) at 34° C. for 48 h under 200 rpm, and transferred to fermentation medium (3.0% soybean cake powder, 4.0% corn starch, 3.0% dextrin, 0.2% ammonium sulfate, 0.6% calcium sulfate, 1.0% glucose, 0.04% potassium dihydrogenphosphate, pH 6.8) in 10% inoculation amount, and cultured at 34° C. for 7-8 d under 200 rpm. 1 ml of fermentation liquor was taken, and soaked in 4 ml of anhydrous ethanol, subjected to ultrasound for 1 h, then filtered. The filtrate was subject to HPLC detection, with conditions as follows: C18 column, a mobile phase of an aqueous solution of methanol:acetonitrile:0.05% ammonium acetate (1800:1800:400), a flow rate of 1 ml/min, and a 250 nm detection wavelength. The spinosad producing strain *Saccharopolyspora spinosa* was taken as positive control, and the *Saccharopolyspora erythraea* was taken as negative control. The results were shown in FIGS. 15A-15C: both the positive control (FIG. 15A) and the genetically engineered strain ES05 (FIG. 15B) obtained in the present invention were able to produce the spinosad components A and D, while the negative control (FIG. 15C) was unable to product the spinosads A and D.

The invention claimed is:

1. A method to construct a spinosad heterologous expression strain, the method comprising:
    replacing the erythromycin synthetic gene cluster in *Saccharopolyspora erythraea* with a spinosad synthetic gene cluster and rhamnose synthetic gene cluster of *Saccharopolyspora spinosa* by:
    obtaining nucleic acid fragments possessing overlapping sequences, wherein, the fragments are four nucleic acid fragments set forth in SEQ ID NOs: 17-20;
    ligating the nucleic acid fragments obtained with homologous recombination into the genome of *Saccharopolyspora erythraea*, thereby replacing the erythromycin synthetic gene cluster in *Saccharopolyspora erythraea* with the nucleic acid fragments to obtain a recombinant strain;
    obtaining the nucleic acid fragment of the rhamnose synthetic gene cluster of *Saccharopolyspora spinosa*, and replacing the downstream sequence of spinosad synthetic gene cluster of the recombinant strain obtained with the nucleic acid fragment of rhamnose synthetic gene cluster using a mode of homologous recombination to obtain the spinosad heterologous expression strain.

2. The method of claim 1, wherein the nucleic acid fragments are constructed as plasmids, and homologous recombination occurs between the plasmids and the genome of *Saccharopolyspora erythraea*, wherein the nucleic acid fragments are in a sequence order of 5' to 3', except the plasmid containing the last nucleic acid fragment, all other plasmids comprise a 5' homologous arm, the nucleic acid fragments obtained and a resistance gene cassette that are connected in sequence, and wherein the 5' homologous arm of each plasmid is homologous to the upstream sequence of the erythromycin synthetic gene cluster of *Saccharopolyspora erythraea*; the plasmid containing the last nucleic acid fragment comprises a resistant gene cassette, a 5' homologous arm, the last nucleic acid fragment and a 3' homologous arm that are connected in sequence, and wherein the 3' homologous arm is homologous to the downstream sequence of the erythromycin synthetic gene cluster of *Saccharopolyspora erythraea*.

3. The method of claim 2, wherein a cosmid supercos-1 is used as an initial plasmid, and the resistance gene cassette comprises an aac(3)IV+oriT sequence, and wherein the aac(3)IV+oriT sequence is the 14-1382 site of SEQ ID NO: 65.

4. The method of claim 2, wherein the plasmid is constructed by: inserting the upstream and downstream nucleic acid fragments of the erythromycin synthetic gene cluster of *Saccharopolyspora erythraea* into the cosmid supercos-1 to serve as the 5' homologous arm and the 3' homologous arm respectively to obtain a modified cosmid eryUD-cos2; and then inserting the nucleic acid fragments obtained between the two homologous arms of the cosmid eryUD-cos2; introducing a resistance gene cassette at the upstream of the 5' homologous arm of the plasmid containing the last nucleic acid fragment; and replacing the 3' homologous arms of other plasmids with a resistance gene cassette in other plasmids.

5. The method of claim 4, wherein, the 3' homologous arms of other plasmids are replaced with the resistance gene cassette via homologous recombination.

6. The method of claim 5, wherein, the sequence of the 5' homologous arm comprises SEQ ID NO: 46, and the sequence of the 3' homologous arm comprises SEQ ID NO: 47.

7. The method of claim 2, wherein homologous recombination occurs between the plasmid containing the last nucleic acid fragment and the initial *Saccharopolyspora erythraea*, and then homologous recombination occurs between the plasmids containing other nucleic acid fragments and the *Saccharopolyspora erythraea* obtained through homologous recombination in sequence.

8. The method of claim 7, wherein the initial *Saccharopolyspora erythraea* is ATCC11635, and wherein ATCC11635 is obtained from American Type Culture Collection.

9. The method of claim 1, wherein the rhamnose synthetic gene cluster is constructed as a plasmid for homologous recombination, homologous recombination occurs between the plasmid and the recombinant strain obtained, the plasmid comprises two homologous arms and the rhamnose synthetic gene cluster located between these two homologous arms, and both of the two homologous arms are homologous to the downstream sequence of the spinosad synthetic gene cluster respectively.

10. The method of claim 9, wherein the sequences of these two homologous arms are SEQ ID NO: 49 and SEQ ID NO: 48.

11. A spinosad heterologous expression strain obtained by the method of claim 1.

12. The spinosad heterologous expression strain of claim 11, wherein the expression strain is a genetically engineered strain ES05.

* * * * *

```
                         SEQUENCE LISTING

<160> NUMBER OF SEQ ID NOS: 65

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
taagcggccg caacccgccc tcgtacatcc ctgctc                             36

<210> SEQ ID NO 2
<211> LENGTH: 34
<212> TYPE: DNA
<213> ORGANISM: Artificial Sequence
<220> FEATURE:
<223> OTHER INFORMATION: Synthetic

<400> SEQUENCE: 2
taaggatcca cgcgtccccc tactcgacga ccac                               34

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
taactgcagc cacgaccgat cgcgccggg                                     29

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
taactcgagc ggccgcgctc atctcgccgc cgacc                              35

<210> SEQ ID NO 5
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 5
tcactttcgg agtggtgatc tttgg                                          25

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gcaacgtgat caacctgcac ca                                             22

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
agagatcagg cataccggtg ttgc                                           24

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aacgtcatcg aattgcggcg                                                20

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
aagctggtgc tcaccatgcc tc                                             22

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggtgctggcc atgccatgtt                                                20

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ccacagtagg tagccgccgt tg                                             22

<210> SEQ ID NO 12
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 12
ggtaagggtc gccgttgctg c                                                21

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
gagtgccgaa gaggatcttg ttgc                                             24

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
acatcaatgc atctgcctgg gc                                               22

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tgcgttgggc tcgatggaac                                                  20

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
aggaaagtcc tgtccaactt cgcc                                             24

<210> SEQ ID NO 17
<211> LENGTH: 33046
<212> TYPE: DNA
<213> ORGANISM: Saccharopolyspora spinosa

<400> SEQUENCE: 17
gatcgcaatg ttgcacctgc acaagaagct ccgcgcacaa ggcgagtacc cggacgaacc       60
ccggagaccg cactagtggc cacgaggacg atcggcgaac ccgccaacgc gctgaactct      120
gcgatccggc cacaccgcct tgaacattgc tttcaaccac tgggttgacg gatgggcaac      180
atacgcctac ggttctttca accaaggagt tgaaactggg aagatgacca cggacccgct      240
gtcccgagcc ttcgccgccc tcgcggatcc gaccggcgc gacatggtcg cccggctctc       300
ggaaggcgac gcgaccgtga gccagctggc cgagccgtat gggatcacgc tgcaggccgt      360
ctacaagcac ctgcgggtgc tcgaggacgc cgggctcgtc agccgaccac gagggccgca      420
```

```
gccacggtcg gcacgcttgg aggcccaggc cttcgacctc ttggacacct ggatcgagcg      480
ccaccggagt cgcgtcgagc agcgctaccg ccgccttgac gccgtcctgg cggagatgga      540
ggaagaaacg catgaaaagg atcacagaaa cgagcatcga agccgacccg aggctgccgg      600
tcatccggac gactcgtgac ttcgcggcaa ggcccgagca actgttccgc gcccacaccg      660
aacccgcgtt gttcgctcag tgggtgggcc ccaacgccac gaccacccgg atcgagcgct      720
gggacgcgtc caccggcggc agctggcggt acgtttcggt gcacgacgga acggagtact      780
ggttccacgg ctgcttccac gaggtgcggc cggaccgaat cgtgcagacc ttcacgttcg      840
agggcgatcc cgacggagtc gcgctggaga cgctgtggtt cgaggatctg ggcgacggcc      900
gcacgcggct gcggacgcag tcgctggtcg acagcttcga aagccgcgat gcgtggctgc      960
acagcggcat ggaggtcggt gtcaacgagg gctacgcgaa gctggagagg atgctcatcg     1020
atggcgctgc ctgagcgccc ggccgaacgg caccgccagg ttgccgggct gttcaccgac     1080
aaggtccgcc ggaccggtc ctgggacgcg ccatccccgg tcgccggctg gaccgcccgc      1140
gacgtcgtgc gccacctgac cgaatggttc cccgggttcc ttgccgccgg cgccggcatc     1200
gaactgcccc gcggaccatc agtggacgag aacccggtcg ctgcatggca agttcactgc     1260
gacggcgtgc aggcggtgct ggacgatccg gacacgcgc accgggaact caccaacccg      1320
cacctcggca acctgcccct gcaaaccgcg atcgaccagt tctacaccgc tgacgtgttc     1380
atgcacacct gggatctcgc cagggctacc ggccaggacg accggctgga ccccgacttc     1440
tgcgctcagc tcctcggcgg gatggagcag atggaacaga tcctccgctc ctccggccag     1500
ttcggcgccc gggtcgaggt tcccggcgat gcggacaccc aggccaaact gctcggtttc     1560
atcggccggg atccgtactg gccggggcgg tgagccggac ggcccgacct cctagccggg     1620 tgtgccggt gcgttcgcca tgccgcgcct acgcgtgccg cgtctacgaa ccttgatcgg       1680
cctatcgatc atcatgcgtt cgcagcccac ccaccatccg ggccgcattg gagtgtgggc     1740
gatcggtgcc gaggtgctgc acgacggcag cggcgtcgag acggccgacg acatcgcggc     1800
cgcactgggc accgccatcg gcccggtcgg ccctacctgt tctacctcgg cctgctcggc     1860
ggcctagacg acggtcaccg gctcgatctt cgcgctgagc aagatgaccg ccgaggcatt     1920
gcacgtcgtc cgtccacacc ggaccaggag atccgacggc gacccgggca aggacgcgtt     1980
ctaccaggtc atgatcgtcc ggggccgccc agcagccgga ggcggatggc tagtgcgcga     2040
gtcgaacctc ggacccagct gatcagcgag cagtgccatt cgcgcactcc ggcctcatgt     2100 cccctgcgg aacaggaagg tcaggtcttc gccggtggaa cgggtgaatt cctcgccctc      2160
ctggagcatg cgcagacgaa ccgcgagatc ggccgcaaag acatccacag tggactcgat     2220 aagcgtggc tacgtgtgtg ccgcgtcccg cccgcgcaac cacccgttga cccacacgca      2280
ggccgcgatt gggagcgcag gccaccagaa cagtccgatc agcaggtacc cgaccgccca     2340
ggtggcctgg ttcgccgcgg tgtcgaacgc ctcgcgggcg gcccgcagct ccgcgcggga     2400
ggtgtcgtcg aggatcagcc acaaccgggg ccaccaagat tcgacgtccg cctcgtactg     2460
gtggtggacc cgggtatccg ccgcggcgat ccggtcaccg atgaaggtcg gccggaccgg     2520
cgtcgccagg gaaatacggt tgcgccgcct ggcgaagcgg tgcttggttg cctcatccac     2580
ggcttcagcg gaggcgtcgt ccgccgcgcg ccatctgcgc tctcgacgtg ctcgcagctt     2640
ctccccggct gcggacaccc aggacgatcg cgcatccacc cagacaccta gccacagccg     2700
ctgggttcgt gcggtgaggc cacgcacgat cagccccgcg atcgtggagg cgagcagtac     2760
cgcgccgacc accagcaact gggccatcgg cggtcggcgt cccagcgcgc tggaccaggc     2820
```

-continued

```
atcggcacga cgcagcagtt cgttccagtc gagtgcgtgc gagtggccga gcatgccggc    2880
caccagcgcc gtggccacca gcagcaagcc gggcagcacc agcagggaga accacttctc    2940
cgcgaacttg cggcccagct cgttgaagaa ggcgttcacc cgcgtgtccg gcgcagcggc    3000
cggtccagca accagcactc gggcaccggt ccgcctggcg tgcgccgcac ctggcggtca    3060
caccgtccgt tcgggcagct gtagctttcg gccgccgaac gggaaccgag gcccggcaca    3120
atcatgtgat cggtcgatcg ctgcccttcg aacacgtcgc gcgggatgcc cagcctcggc    3180
agctgatcca ccacgagagc accttctctg atcttgcgga gcacgtcgtc gagaaccggg    3240
gaaacctgct gctggcgcgc gaactgcgag agtttcggca gcgcttcgca aaacccggcg    3300
aggttgttgt ccagatgcac ggttccatct tccacatctc gatcgcactg ctgcgcgaaa    3360
tgccggtatc gtaaccagaa ctgcccaacg ggcgaccgtg tcgcaccatc gcgaggtgag    3420
ctcgtcaggt acatgggcat catcccgatg agccggagtt ctcatggcgc aaccggatcc    3480
gcaccgccac cgcgacctgg cggcgtccgc agtggccctg cgggcgcggt acgagcagac    3540
cggtgacgcc accgcgctgg gcaaggcgat cagcacgctg gcagacgccg tcaggttggc    3600
cgagcacgga gaaccgatgc ttgccgcgat gctcgccgaa ctgggttacg tgctgcgact    3660
ggaattcgag cgagtgcgcg acgtgaccgc gatcgacgag gcgatcgcgg tcgggcgccg    3720
tgccgccgag ctctgcccgt ccagttctcc gcagcgcgcc ggaatcctga gctacctagc    3780
gggcagtctc ttgtcggcgt cagcagtgcg caaggatccc gcgctggtgg ccgaggccgt    3840
tcgcgatgca cgcgaggcgg tcgcgacgac ccggcaggac gacccgctgc gcgcgggacg    3900
gctgggcgac ctcgccctgg cattgctcgc gcagcgccac gtcacaggcg atcaggacgc    3960
ccgaggcgag atcgtggaga tgttgcgcga ggccattgcc ggcactggaa ccgacgatcc    4020
gagccgcagc tggctgctga ccaacctggg gtacgcgctc gttctccccg gtgggaacga    4080
ccttgcgggt gcacggctgt ccgaggcggt tcggtgttc gaggaggcgg tcgccgcaac    4140
acccccggag cacgccaact acgggaggtc ccagtacgga ctgggcacgg tgctccggat    4200
gcgctggcag cacacccacg agcgagcgct gctggaccgt gcgatcgatg ccgtgcgtgc    4260
cgcggtggcg tcggtgcccg ctgaccacgg ttcgccccgc gcctggcttt ccgaactcgc    4320
gaagctgctg gctgtccgca cctcgtggtg gccgcgggca gacctcgtcg aggaggcggt    4380
cgccgtctac cgccgcctgc tggagctgga tcccgagaac gtcaccgacc ggctgggcct    4440
cgcggaagca ctccttgctc gtttcgcctc ctgcaccctc gatctgcggc tggtaaacga    4500
agccctcgac cacgttcgcg tcgccctcgg cgccgacatg ccggacgagc aagttcgggt    4560
gctggcgcgg tcggtggagg gagagtgcct cgagcagctt gccacggccc agcaagacct    4620
cgacctgtgc gagcaggcgg tggacgcgct gcggacagtc ctgcgggatt ccgcgagcc    4680 cccgggcgtc gaggcgggac tgtggttgag gctcagcatg gcgctgagga cacggcacgt    4740
attgaccggg gaaggggatcc aggaggcggt ggaagcggct cggcgggcag tcgcactcgg    4800
cgaagacgcg ctggacaccc ggcatggatc cgcgcagcat gccttgcggc tgtcgaccct    4860
ggccaacctg ctgttgcggg ccgccgacga agaccgcgcc gacctggacg aggccgagcg    4920
ggtcgggcgt cgggccgtgc gcgagtgccc gcctgacgat ctcatgcgtt ctcgggtcct    4980
cttcgagttc agcgagatcc tcctggcgcg cgaacgccgt tctggtgatc cggcagagct    5040
ggacgaggcg atcgatctga tgcgggaggc cgaagccgta ccggtgaagg tccccgagca    5100
caccctgcac atgtcggctc tggcaagcgc gttgatcgcg cgctaccagc gtttcgcgga    5160
```

```
cctgcgcacg ctcgaggaag ccatcgcggt cgggcgcgcg gcggtcgacg cgcttcccgc    5220
gtccaacccg gagcgcgtca accaactcgc gagactggtc ggctaccctct acgagcacta   5280 cctgcgctcc gccgaggaat ccagcatcac cgaagccatc gagaccagcc ggcacctgat    5340
cgccgcgact ccgccgaacc accccgagct cggacggcga cttgcgaaca tggccctgat    5400
gctgcgcgcc cggtggttca tcgacaccgg gcagcctgac gatctgcggg cggcgctcga    5460
cgtacaccgg caggcggccg atgcgctgcc cgacggccat cccgtccgcg ggcgcgcgtt    5520
gagcaaccgg agcctggccc tgctcgacga ctaccaggag accgggcgcg agcagagcat    5580
cgtcgaagcc gtggacaatg cgcggcaggc ggtggcggcc actccgccgg ccatcccga    5640 ccgggccgac accctgggcg ttctcggtca tgcactgggc tcgttgttcg aacggaccgg    5700
cgccatcgga catgcgctgg aagccatccg ggtgacccag gtcgccacgt cgatcacgac    5760
ggcccagccg tcaaaacgtt tcaagaacgc cgagctcttg ggaaggctag tactccagcc    5820
gcacttggtg atcttcgccg cggagggata ccgggaggca gtcggcctgt ttccgttgct    5880
tgcgccccgc aacctgcacc gcatggacct ggagcaccag gtggccagcg ctgggcgggt    5940
agcatccgac gccgccgcga gtgcgctgtg ggccggcctc gacgccgagg cgttcgagct    6000
cctggagcag gggcgcgggg tcctgttgtc gcgcgttctc gacagccgcg acgagctggc    6060
ggaactgcgc gtgaagcacc cggaactcgc cggcgaatgg gaggaactga ggaacgaact    6120
ggacgcgacg accgggttcg gcgaaatacc gcctgccgct gggacttcgg ggatgccgga    6180
ctcggatcgg cgccatcggc tgggccggcg tcgcgaccaa ctgctcgtgc ggatcaggga    6240
cgtgccgggg ttcgtggact tcctccgacc tgccagcctg gcggcgatgc tccccgccgc    6300
cgaggccggg ccggtggtca cgatcaacgt cagcgcgtgg cgttgcgacg cgctggtgct    6360
caccgggggc gaaacccgga tcatgcggct gcccgacctg agcacgacgg aactggacga    6420
gcggatcccg gtgttccagg aagcgttggt cagcacgcat tccggcgact cgccgagcg    6480 agcgacggca caggtcgtgg tccggcggac gctgagctgg ctgtgggacg tggtagccgg    6540
cccggtgctg gaagtcctcg ggtacacagc cgcgcccgtc gaaggcgcgc cctggcccag    6600
ggtctggtgg tccccgaccg gcctgctcaa cttcctcccg ctgcacgccg ccggccggtt    6660
cccgggcgaa ccgggcgaac cggtgcggga agatgccgcc gtgctggacc gcgtcgtgtc    6720
gtcctacaca ccgacgatcc gcgcgctctc ccatgcccgc tcccggcctg ctgcgccgca    6780
tcagcggcta ctggcggcgg cgatgcccgt gacacgaggg cagcacccgc tgccctacgc    6840
gcgggccgag gtgaggatc tggcccagca acgcggcgac gtgtcactcc tcatcgaaga    6900
ggaagcgacg cacgacaccg tgatagccgc cctccgccac tcgagctggg cgcacttcgc    6960
ctgccacgcg cacagcgatc cggtcagccc ttcgaagagc catctgctgc tgcacgacag    7020
cccgctgagc gtcatcgaga tcagtcggct caggttgcag gacgccgaac tggcgtacct    7080
ttccgcgtgt tcgaccgcgc gcggaagcac ccgcctcgcc gatgaggcga tccacatcgc    7140
ctcggcgttc cagttggcgg gctaccggaa tgtggtcgga tcgctctggt cggtggcgga    7200
cagcactgcg gcgaaggtgg ccaagggctt ctaccaccgg ctgaccagcg gcctgccacc    7260
tgccgtcgcg ctgcatgcgg tgatccgggg actgcgggac gaggagccgt tgaccccgtc    7320
ggcatgggcc ggctacgtcc acgccggccc atagcccggg caatggcagc gagatgatct    7380
gcggtgaacc tcgaccgacg ggccatccg ccaccactgt ccacatcaga cggctacgcc    7440
ggaactgcgc tccataggtc gcgatcccgg cagcgcgcag cagcctccgg ggggccgcag    7500
gtccggaccg caccgacatc agccgccgcc gtcaggtgcc gggggcgcgg aagtcgaccg    7560
```

```
ccttccgcac agcctcgtcg atgtcctcgg ggcggagcag cggcaccgcc ctggacgtca      7620
cggcgccggt ggcccgcacc gccatagccg tggcggccat cgaggcgtcg tcgggcacgt      7680
cgacaacgat gtagaaatca tggtcgccga aagcgaagta catcgactcg agcgttccgc      7740
cgcacgaccc gaggaccctc tcaacggcct cccgccgccc ggttccgccc tcggcgagca      7800
ctcccttcgt cccctcggcg gtgtagctgc cctgcaccaa gtacttcggc atgtcgctcc      7860
cccacttcac cgtgcggcca cccgcagccg cggttctgct cccaccctcg ggcactagag      7920
caggctgggc cattcgaaac agccgcccgg actactcatc cgcgggacaa gcggtcgcgg      7980
ccgcctacaa cgccagcagg tcacggccgc tacgcggctc gacgaacgat cagttaattc      8040
atccgatgat cgtccaggac cgaaaaattt tggcaatctt gaatagtcaa atgtaagtct      8100
tgcgatcacg catcgtcagc cacacctgcg ggagcacaaa cttcaagcag caagacggg      8160 accacccata cggccgccca agccgacccg aaaggcccat tgtgacatgc gaatcaacca      8220
gctactttca gtgggccgca accagtttct gcgtcgctac ctgcgatttt gataactgaa      8280
ctgcggtcta ttgcaactca cctttccctt ggaggattca ttgctgccca ttcggaacta      8340
cctcgctgct gccacggcgg ccgttcttat cggcggtgca ggcaccttgc tggcggcacc      8400
ggcttccgca tcgccgagcg cgatcagcca ttttgacgac ggaagtttcg aaacaccaac      8460
ggtagcagca aacacgttcc agaacatcac gatgggcag tctttcggac cgtggcgagt      8520
ggcgagtggg aatatcgacc tgatcggtgc agggtactgg caggctgccg agggtgacca      8580
gtccgtcgac ctcaacggca caactgcggg ggctgtttcc cagactttta ccacggtccc      8640
tggaacggga tacacggtga cgtattccct tgctggcaat cccggcggat cggcgatcct      8700
gaaaacgggc aaagtcctca tcgacgggca gaatttccaa gacttttcct tcgacacgac      8760
cggaaaaact acgaccaaca tgggctatgt gagacggcag gtgaccttcg tggccaccag      8820
tacatccacg acgttgacgt tcgccagcac caccccaac agtgcgtggg gaccggtgat      8880
cgacgacgtc acggtcaagt cctgcccgcc tcccccgtgt tgcgggtgat ccgggcgcgg      8940
tgatggcggg caacccggtc ggatcgccgg tgcggcctgc acagcacgcg caagttcttt      9000
aaaccggctg ttagggcggg tgtggggca gggccgtctc acaccgccg actctcgtcg      9060 cttttcagcg ccggagcgag agcctgcacc gtttccgatc gcctcggcgg ggggcgcggc      9120
gcggcaccgt ttttcggcag gccgggactg gccgtaccac tgcagaccgg caaaactcgc      9180
tcggatgatg acggcgaaga gcgtccggac ctgccagttc gggcgctctt cgctgttcag      9240
gagccgatcc tggctggtcg gcccgcgaaa ccgccgtcgg ccatccgtgg cggcgtgcgg      9300
acctgactca gctgttcacg ctgggggcga tgctggttac cttggtgttg gccattcctc      9360
aggccatcag cgtgcaagcc acgtgggtaa gcaggtcggc gtcgcgtatc ccgagtcact      9420
ggagtttcag tcctggttcc agcctgcttc ccggcgtcgg tcttttcga ctattcgatg      9480 gtttacgtct aagagaggaa ggcgaagcgc cttctggagg aatgcgtgga cagcttgatt      9540
ggagcggcgg catgtcggct gtagcggtgg gcaactgaat gccgacccag gcataggctc      9600
cccgagaggt ccgggggaaa tcagcagttc ttcgaccaaa ggaaagtgga ttcccaaggc      9660
cgaatacgac gagatcacca agaagatccc gattctgtgc atcgaagtgt tgccgatcca      9720
cccggggcca gagcgcttgg tgggactgat actccgcaac accttctggg gccgccgtcg      9780
atggtgcctc gtgggcggcg gagcccaaca cggcgaaccg ctgccgaacg ccgtctagcg      9840
gtcttcgatt gggcgcgggg tgaccgagtt tcactcgacc tcgacactgt gaatctgaag      9900
```

```
gaagtggcgg agtactttcc cgatcctgac accggcgagt tcttcgaccc ccgcaagcat    9960
gccgtcgctc tcacttacac ctgcgtcatg tcgggtgacc cgtgtcctcg tgggaaagcc   10020
atcgatttcc gctggtcctc gtcccgaccc gcttcccgag catgacgacc tcggtttcgg   10080
gcaaagcgtc ttgtaccgcg ccttctgact ggttgaccct cgatcaaacc accaagccga   10140
cccagcgata tgacggcttc cgcatctgcc ggccggtatc gggccctccg ggagatctgc   10200
ctgcagctgc gcgaacaaag ccctggatac agcgctgcgc tgagcgcttc agatgccctg   10260
acgaccgtgc tggtcgaggt agcgccgtag ggccgtgttg atggtggtgt ggtcggcgtc   10320
gggtctccgg tcaggccctc gatggtcgcg gtggtggtca tggcggtgtc ctcctggcgc   10380
tggtcggggt cgatgcagcg ggcccgaagg tctgcatgga cggtcggccg gctgacccgg   10440
gcgacgtcgg ccaacgcggc atccggattg ccaccagggg cctgaagtca tcgtgaagaa   10500
ggtttgaacc gacgttgggc atgcttcgtt gaagagggtg tgaaccgacg ttggggatgc   10560
ttcgttaaga gggtatgaag ccacgttgga catgcttcgt ctcgggaggg aagccgatgc   10620
ttgggagtgc tgacatgatg gcaaacgatc acgacacggt gctcgccacc atgaccttca   10680
acctggtagc cccggcggga gtgatcgcgc cagttggcgt gcagctgcgg tacgacagcc   10740
gcaatccgta cgagatctcc atgaagctca acgtaggcac ggacggtcag gtggactggg   10800
tgatcgcccg cgacctgctg gccgacgggc tgatcgccga ggcaggcgaa ggcgatgtgc   10860
ggatcggccc tcgacggggt tttccggggt tggtcgtgat cgagatgagc tcgccgtcgg   10920
ggcaggcctc cttcgaggtg aatgctgacc agcttgcgga cttcttgaac gacacctacg   10980
acgtggtcga acctggtgat gaacaccggt ggatgaacgt cgacgaggtg ctgagccagc   11040
tgctctcgcc aacctgtaat ggcccagctc tcccgaagcg ccgcacgcca aagcgctggc   11100
tgcgggacct ggcggcgctg aacaccgcca cgctgtgtct ccgagctcca gctggaccac   11160
gtcggtgccg tgcgcccggc tcggtcaggc cgaaggtgct gatcttctcc aggcgcgcca   11220
tcggcgcagg aagcgctgct tctgctcccg ccgcagtacc gtcgtgtcat ggccacggac   11280
agcttcgatt cctcgaagct acaggcggcc gtggcatcga gcgtcgcgtc gtgcgtctcg   11340
gaagtcagcc gagacgtcta cacgcacctg attaccgagg ctccgcagtt gcgagccgat   11400
gagatcgtcc tcagcattct acggacgagt gttgaggaaa atatcgccac attgccgcac   11460
gttctcgaat tcgagattcc gttgggatat tcgccgggtc ctgctgcggt gttggagtat   11520
ccgcgacgac tggcgaaaca tttccatcaa cgcgctgatc agggccaacc gcatcgggca   11580
cttccgcttc ctgtagtgat gcctcgacga gatccgccgc caatgcgccg acgaggccgt   11640
atccgcagcg accacgcaac gaatgctcgc aaccagcttc ggctacatcg accgcgtcac   11700
ggagcagatc gccgaaacct accagctcga acgggaccgc tggctcctgg cgacgggacg   11760
gccgtgaggt ctctgcggca tccgcatagc gtcttctccc gctgaggcac atgaggtgtt   11820
gcgcgcggtc gtttcggca gtcgcacggc attcgtccta gctgcgggca attgagggag   11880
cgaagattta gaggagtgtg gccacgcgga ccaagccggc gagtgctcgg gagcggctgt   11940
ggggcggcca ggcgatgact gtcgtcacgt ccggcgcgtc tagaaccggt acggcggcga   12000
ggccttcgag caggttgacg cgactggatt cgggcatgac cacggtagtg cggccgagtg   12060
cgatcatttg gaacagttgc gtctggttgc gtacttccac gccggggcca tctggataga   12120
cgccgtcggg gccgggccag cgcgcaagcg ggagatccgg cagtgagctg acatccgcca   12180
tccgtacatg gggctcgctg gcaagcgat gcgaggtcga aagaatggcg acttgttgct   12240
cggtgttcag aatttcgatg tcgagttcgg ccgtcgggtc gaagggttga tgcaacagcg   12300
```

```
ccacgtcggc cggccgtca tgcagcgttt tctggggctg ggattcgcag agcagcaggt    12360
cgacggccac ggctcccggc tcggcggcgt acgcgtcgag caacttcgcc agcagctcac    12420
cggaggcgcc ggccttggca gccaggacta gcgagggctg gctcgtcgcg gcacgctggg    12480
tgcgtcgctc ggctgctgcc agcgcgccga ggatcgcccg gccttcggtc agcagcattg    12540
ccccggcttc ggtgagcgag actttgcggc tggtgcgttg cagcaacacg actccgagtc    12600
gttgctcgag ctgggcgatc gtccgcgaca cggcggctg ggcgatgccc aggcgctggg     12660
cggcccggcc gaagtgcaac tcctcggcga ctgcaacgaa gtaccgcaac tcccgcgtct    12720
ccatccgtcg agcctaccgc tgattcatat cagctgggta tcggtgtgag acctagatgg    12780
tgttggttcc ccgccggttt cgggccacgc tagaaagcat gagcgaacag acgattgcac    12840
tggtcaccgg cgcaaacaag ggaatcggat acgagatcgc ggcccgggctc ggcgcgctgg   12900 ggtggagcgt cggaatcggg gcacgggacc accagcgcgg ggaggatgcc gtggcgaaat    12960
tgcgtgcgga cggcgtcgat gcgttcgcgg tatccctgga cgtgacagac gacgcgagcg    13020
tcgcggctgc tgcggctctg ctcgaggagc gcgccggccg gctcgatgtg ctggttaata    13080
acgccggcat cgccggggca tggccggagg agccctcgac cgtcacaccg gcgagcctcc    13140
gggcggtggt ggagaccaac gtgatcggcg tcgttcgggt taccaacgct atgctgccgt    13200
tgctacgccg ctccgagcgc ccgcggatcg tcaaccagtc cagccacgtc gcttccctga    13260
ccttgcaaac cacgccgggc gtcgacctcg gcgggatcag cggagcctac tcaccgtcga    13320
agacgttcct caacgcgatc accatccagt acgccaagga actcagcgat accaacatca    13380
aaatcaacaa cgcctgcccc ggctacgtcg cgaccgacct taacggcttc cacggaacca    13440
gcacgccggc agacggtgcc aggatcgcca ttcggctcgc cacgctgcca gacgacggcc    13500
cgaccggagg catgttcgac gacgccggga atgtgccctg gtgaggcgct cagtcggcga    13560
tggtgcaatc gaagtcggag aggctcgctg cgaccgggta cgccgaacaa cacctgttcc    13620
tgtgggtacg gatgtcggcc ttcgccgtct cggtcattga caacctgtac ttcgggcgcc    13680
gttaccgccg gtgcgccgcg gttgcctggc gacactgggc cagccgtggc tcaccggcgg    13740
cttaggtcag gcgtgggcgg ttgccagcat ggcgggtgcg gctttgcgta ggtcgggtag    13800
gcgcatccgg cgcgggagcc ggtcgagttc ttcgccgatg gccggtgctt tggggctgct    13860
caggagccga acacctccca gccgcaggtg ccgggctgaa ccgagtggtt ctcgtcggct    13920
cggatcacaa cgtctgccgg aacagctgcg gcgaggtggt cgcagattcg aggcgggatc    13980
gtcctcggcg accttgccga cgatcgcggc tagggcccag ggcttcgtcg acctggttgg    14040
cacctagatc acgacggtca aaacttgccg gcatcagaga cgatcgaagt gatcccgggt    14100
cacgtcggct tatcggtcga gtgagtcccg gggcctgccc agccaggtct tgcgtcgttg    14160
ttccgggctc agttgcggat tccgacgaac aggcctcggc cgttcggtgc tccaggaagg    14220
tattccgcgc ggatccctgc gtcttcgagc gcggcggtgt actcgtcctc agtgaacagc    14280
gagaggattt cgaactctgt gaagtcccgg atcccggtgg gttcggcgac tgtgtagcgg    14340
acggtcatcc ggctcgtacg gccctccagg accgagtgcg atagccggct gatcacccgc    14400
tcgccgtggt gcgcgacggc tccggtgacg aacccgtcga tgaacttgtc gggaaaccac    14460
cagggttcga tgaccgcgac tccaccaggg gccaggtgcc gggccatgtt ccgcgtcacg    14520
cgtcgcaggt cgtcaacggt ccgcatgtaa gccgcggtaa agcacaggca ggtgatgacg    14580
tcgaatggct cgccgaggtc gaaatcgcgg atgtcaccga tgtgaatcgg tacctcaggg    14640
```

```
actcgtctga tcgcgatctc ccgcatcgca tcggacagtt caagccccgc gaccttcgcg    14700
tattcggcac ggaatcgctc taggtgcgcc ccggtccacc aggcgacgtc gagtagggac    14760
tgtgcttcgg gcagcctggt gcgtacgagc tggactactt ccccggcctc ggctgcccag    14820
tcccggccac gcgcggagtg gatcgcgtcg tagatgtcgg catgatctgg gctgtatacc    14880
gaggaggttt ctgcgaatgt gtcgctcacg cgcgacatcc tcactttcgg agtggtgatc    14940
tttggctgat gtggtgttcg acggccttct ggaactcgtc agccaccgtg cgcacctcgg    15000
cgtcgtcaag gcttgggtgc agtggtagca ggagtgttct gcggcaggcg tcctccgcag    15060
aaggcagctt gcagtccgcg cggtagatgg ggaccttgtg caggggcggg tagcggtagc    15120
tcgtgtagat gccgcgttcc agcatttgct gcgccacctg gtcgcggatc tccggagcca    15180
gctggaccca gtagaagtag tgtgacgaga cgtgcccatc cggtagcgtc ggcggtagga    15240
ggacacccgg cacatcggaa agcaaccggt cgtactgcgt agcgatttct ctacgcctgt    15300
tgatgaattc tggcagtttg cgcagctgca cgctgccaag cgctgccgtc atgtcgttcc    15360
cgatcagccg ctggccgatg tcttcgacgc gaatatccca ccagcggttg gaagacttgg    15420
ccgaatcgaa tccgctcatc tgctcaagac cgtggtaggc gagtcgtctt gcgcggtgcg    15480
ccagctccgg atccgccgcg tagaacatgc ccccatcccc ggtgaccagg atcttcatcg    15540
catcgaaact ccacgtggcc aggtcaccaa aggttccgca agcggtgccg tgcacggacg    15600
atgccaccgc gcaggcggag tcctcgatga gcatgaggcc cttttcacgg cagaaatcgg    15660
cgatcgcggt gacttctccc ggcgatcctc catagtggag cagcaatacg gccttggtcg    15720
ccggcgtgat ggccctcgcc acatcatcca gcgtggggtt caacgtccgg gggtcgacgt    15780
cgcagaacac cgggcgggca ccggaggatg cgatggcgtt ggccgccgcc acgaagctta    15840
tcgaaggaag taccacgtcg tcgcctgggc cgaggtcgag cacctgcacg gtaaggaaca    15900
gcgcggcagt ccccgagttg aggaacacga cctgttcggg atccactccc aggtggtggg    15960
cgaattcggc ctcgaacgtc cgggtgcgcg gcccgagccc gatccagttg gaggcgaaca    16020
cctccgcgat cgcgtcgagt tcttcggtgc cgaggatcgg ctggtgcagg ttgatcacgt    16080
tgctgaaatc ctccgagatg ccgccatgct ggatgctagg aactcttggc cacgaattca    16140
gcgattgatt cgacgacgta gtcgatcatt tggtccgtta tgcctgggta gacgccgacc    16200
cagaaggttc ggtcggtgac gatgtcgctg ttggtgagcg cgtcggcgat ccggtaccgc    16260
acctgctcga aggccgggtg ccgggtgatg ttaccgccga acagcagtcg ggtgccgatg    16320
ttgcgggatt ccaggaagtt caccagggcg gcacgggtga acccggcgtc cgcactgatg    16380
gtgatcgcaa acccgaacca gctcgggtcg ctgtgcggtg tggctaccgg cagcagcagg    16440
cccggcaacc cggacagccc ttcgcgcaac cgtcgccagt tacggcggcg tgccgacccg    16500
aatgcggaaa tcttgctcaa ctggctcagc gcaagtgcgg cctgcaggtc ggtggtcttg    16560
aggttgtaac cgacgtggga gaacgtgtac ttgtggtcgt agcccggtgg aagggtaccg    16620
aggtggtagt cgaacctctt gcggcaggtg ttgtccacgc cgggctcgca ccagcaatcc    16680
cgtccccagt cacgcagcga ctcgatgatg cgagccaatt ccaggctgcc ggtcaacacg    16740
cagccaccct cgccgctggt gatgtgatgg gcaggataga agctgaccgt tgtcaggtcg    16800
ccgaaggttc cggtcagccg tccccggtag gtggatccca ccgcatcaca gttgtcttcg    16860
acgaggaaca gctcgtgttc ttttgcgatc tccgcgattt cgtcagcggc gaagggggttg    16920 cccagggtgt gcgccagcat gatggctcgc gtccgttccg tgacgcggc cttgatgcgg    16980 tctggcgttg cgttgtaggt gcccagttcc acgtcgacga ataccgggac gagtccgttt    17040
```

```
tggaccgccg gattgatcgt cgtggggaag ccgaccgccg cagtgatcac ttcgtcgccg   17100
ggccgcagtc gtgcctcgcc gagtttgggg gaggtaagcg aactcagtgc caggagattg   17160
gccgacgaac cggagttgac gagatgagcc ttgcggaggc cgaagaagcg ggcgaactcg   17220
ctctcgaatc gccgtgcatt cccgcccgcg gcgatccgga gctccagcgc ggcttccacc   17280
agtgccaccc ggtcgtcctc gtcgagcacg gcgcccgatg gccggatcgg cgtcgatcca   17340
gccacgaagg tcggggattc ctgttcgcgg tggtaatcgc gtacggatgc caatatccgg   17400
tccttggcat ccggcaccat ctcagtagcg gtagcgcaag tgtcgtcaca cgaagtcact   17460
ctggcgcgcc ctttccccag cgctctggtt ttccggctct gcatgcaggc gacgatcagt   17520
cttcgcgcct tgccttcagg agatgagcga tgcccgtggc gaatcgcgtt atgacgtccc   17580
agcgggacag tgtgctgtct cggcgcctta caccttcctg ccctggttcg atgcggtgcg   17640
ggacatcagg acagcggagc aaggagaagc gctcattgac tcagaaatcc tcgatctacc   17700
cggcacaccc gactcggtag agcccaggct agcgggaacg acctgctcgc gcttgtcaag   17760
atcgctacca tcacctggaa ggcctaagat ttggcttgcg aaagcggcgt ttcccggggg   17820
atatcagaga tttctgtgat tcttggcatg cttcccgggt gttcaattgc gatcggagag   17880
ttcatgcgtg tcctgttcac cccgctgccg gcgagttcgc acttcttcaa cctggtgccg   17940
ttggcgtggg cgttgcgtgc cgcggggcac gaggtccgtg tcgccatctg cccgaatatg   18000
gtgtcgatgg tcaccggagc aggactcacc gcggttcccg tcggcgacga gctcgacctc   18060
atctccttgg cggccaagaa cgaactcgtt tccggcagcg gggtctcgtt cgacgagaag   18120
gggcggcatc cggaactctt cgacgagctg ctgtcaatca actccggcag agacacggac   18180
gccgtggagc aactccacct tgtggatgac cgatcgctgg acgatctcat ggggttcgcc   18240
gagaaatggc agcctgatct cgttgtgtgg gacgctatgg tgtgttcggg gccagttgtg   18300
gcgcgagcgc tcggcgcacg acacgtgcgg atgctcgtcg ccctcgatgt gtcggggtgg   18360
ctgcggtccg gtttcctcga ataccaggaa tcgaagccgc ctgagcagcg cgtcgacccg   18420
ctcgggacgt ggctgggagc gaagctcgcc aagttcggag ccacgttcga tgaagagatc   18480
gtgacgggcc aagcgaccat agatccgatt ccatcctgga tgcgcctgcc tgtggacttg   18540
gactacatct cgatgcgttt cgtgccgtac aacggtccgg cggtgttgcc ggagtggttg   18600
cgcgaacgac cgacgaagcc gcgcgtctgc atcacgcgcg ggctgaccaa gcggcggctg   18660
agcagggtga ccgaacagta cggggagcaa agtgaccagg aacaagcaat ggtggaaagg   18720
ttgttgcgcg cgcggccag gctcgacgtc gaggtgatcg ccaccttgtc tgacgacgaa   18780
gtacgggaga tgggggagtt gccctcgaac gtccgggtcc acgaatacgt accgctcaac   18840
gaactgctgg agtcgtgttc agtgatcatc catcatggct cgacgacgac gcaggaaacc   18900
gccacggtca acggcgtacc gcagttgatt ctccctggga ccttctggga cgaatctcgt   18960
agggcggagc tcctagccga tcggggagcc ggtctggtcc tcgaccccgc gacgtttacc   19020
gaagacgacg tgcgaggtca gctggcccgc ctgctcgacg agccgtcgtt cgctgccaac   19080
gcggcgctga tccgccgtga aatcgaggaa agtcccagcc cgcacgacat cgttccacgt   19140
ctggaaaagc tagttgccga acgtgagaac cgccgcactg ggcagtctga tggccatccg   19200
tgagcaacgt gtggccggaa acatggacgc cggggtttgg caggtgttca tcgctgttgc   19260
gtcgactcgg attccgccgt gacgggacg atgccaggcg agtccgaag tcagattctt   19320 gtccagaatc gtccaatggg gtgttgatct ccccagaggt ttgcgctcca accgatttcc   19380
```

```
gacgaggatc gtggcgcccg ctgagcaacg actaccgtgc ggtcgagaca taccgctgtg    19440
cgccaggagc gaaggtgggt tgcccgatca ccgtgctggt ggtagatgcc gagccgaagg    19500
tcaccttgga tgaggcggaa gcctggcgag agcacaccga ggccgtggcc gacgtccgtg    19560
tcttctccgg cgggcatttc ttcatgaccg aacgccagga cgaggtgctc gcggtccttc    19620
cgggcggatc gcttcgatga tcctcgccag gccgctggac cagaccgcga cgcccctggg    19680
agccggcgtg cacatcgtca cggcagtgag ggattgggca tgagcagttc tgtcgaagct    19740
gaggcaagtg ctgctgcgcc gctcggcagc aacaacacgc ggcggttcgt cgactctgcg    19800
ctgagcgctt gcaatggcat gattccgacc acggagttcc actgctggct cgccgatcgg    19860
ctgggcgaga acagcttcga gaccaatcgc atcccgttcg accgcctgtc gaaatggaaa    19920
ttcgatgcca gcacggagaa cctggttcat gccgacggta ggttcttcac ggtagaaggc    19980
ctgcaggtcg agaccaacta tggcgcggca cccagctggc accagccgat catcaaccag    20040
gctgaagtag gtatcctcgg cattctcgtc aaggagatcg acggcgtgct gcactgcctc    20100
atgtcagcaa agatggaacc gggcaacgtc aacgtcctgc agctctcgcc gacggttcag    20160
gcaactcgga gcaactacac gcaggcacac cgtggcagcg ttccgcccta tgtggactac    20220
ttcctcgggc ggggccgcgg ccgcgtgctg gtagacgtgc tccagtctga acaggggtcc    20280
tggttctacc ggaagcgcaa ccggaacatg gtggtggaag tccaggagga agtgccagtc    20340
ctgccagact tctgctggtt gacgctcggc caggtgctgg ctctccttcg tcaggacaac    20400
atcgtcaaca tggacacccg gacggtgctg tcttgcatcc cgttccacga ttccgccacc    20460
ggacccgaac tagccgcctc ggaggagccc ttccgacagg cggtggccag gtcgctctcg    20520
cacggcatcg attcgtcgag tatctccgag gcggtcggtt ggttcgagga agccaaggcc    20580
cgctaccgct tgcgggcaac gcgcgttccg ctgagcaggg tcgacaagtg gtatcgcacc    20640
gataccgaga tcgcccacca ggacggcaag tacttcgcgg tgatcgcggt gtcggtgtcc    20700
gcgaccaatc gtgaggtcgc cagctggacg cagccgatga tcgaaccgcg agaacaaggt    20760
gagatcgcac tgttggtcaa gcggatcggc ggagtgctgc acggtttggt ccacgctcgg    20820
gtggaggctg ggtataagtg gactgcggaa atcgctccca cggtccagtg cagtgtggcc    20880
aactaccaaa gcaccccgtc gaacgactgg ccgccgttct tggacgacgt gctcaccgcc    20940
gatcccgaaa ccgtgcggta cgaatcgatc ctgtccgaag aaggcggtcg gttctaccag    21000
gcgcagaaca ggtaccggat catcgaggtg catgaggact tcgcggcacg acctcccagc    21060
gacttccggt ggatgacttt gggacagttg ggcgagctgc tccggagcac ccacttcttg    21120
aacatccagg cgcgcagctt ggtcgcctcc ctgcatagct tgtgggcgtt ggggcgatga    21180
ccagctcgat gcgaaagccg gtgcgcatcg gtgtgctcgg gtgcgcttcc ttcgcgtggc    21240
gacggatgct gcccgcgatg tgcgacgtgg ccgaaacaga ggtggtggcg gtggcgagcc    21300
gtgatccggc gaaagccgaa cggttcgcag cgcgattcga atgcgaggcg gtgctgggtt    21360
accagcggct cctggagcgg ccggacatcg atgccgtcta cgtgccgttg ccgcctggca    21420
tgcatgcaga gtggatcggc aaggcgcttg aggcagacaa acacgtgctt gcggagaaac    21480
cgctgacgac gacggcgtcc gacaccgctc gcctggtcgg gctggccagg aggaagaacc    21540
tgctgctgcg ggagaattac ctgttcctcc accacggccg gcacgacgtg gtccgcgacc    21600
tgctgcaatc cggggagatc ggtgagctcc gggagttcac cgccgtgttc ggaattccgc    21660
cgcttcccga cacggacatc cgctatcgca ccgaactcgg tggcggagcg ttgctggaca    21720
tcggtgtcta tcccgcccgt gccgctcggc actttctcct cggtccgctc acggttctcg    21780
```

```
gcgcaagctc gcacgaggcc caggagtcgg gcgtcgactt gtcgggcagc gtgctgctcc   21840
aatcggaagg tggcaccgtt gcccacctcg gatacggttt cgtgcaccac taccgcagcg   21900
cgtacgagct gtgggggagt cgtgggcgaa tcgtcgtcga ccgggcgttc acgccgcccg   21960
ccgagtggca ggccgtgatc cgaatcgagc ggaagggcgt tgtcgacgag ttgtccttgc   22020
cagcggaaga tcaggttcgc aaggcggtca ccgccttcgc acgcgacatc agagcaggga   22080
caggcgtgga cgaccctgcg gtggccgag attcgggcga atcgatgatc cagcaggccg    22140
cgctggtgga ggcgatcgt caggcccgtc ggtgcgggtc cacatagccg cccggcatcc    22200
gcgggtagta gttcgcctcg aagcctgacc gggcatccgg aagccagcgg ggaagccgct   22260
ggagaggctc accgccatcc gctcacctgg catctcgcgg accgctgatc gcggacggct   22320
cggagaagtg ctcgtcgaac cacgagacga ccactcgcga gctggccagg gcggcgggaa   22380
agtgagccaa tccggagagc ggatgccacc gcactggcgt acccgccgcg cggtagctgt   22440
cccggagtcg ctcgccgaat gcgaacggaa cgatctcgtc gtccgtgctg tggtagacga   22500
gcgtggggac caccgggcca ccgttcctac ctgcgacgct ttcggccagt cgtgcgcgcc   22560
atcgaggttc ctcgaaaagg ccggaagtgt cgaggaagtc gctcagctcg cggccgagga   22620
agcgggtgac gagctccggt gcaccgagct cgcgcacttg atcaacggcg gtacgacccg   22680
cttcggtgag aagctcgtcg aatggcagat cggggtaggc agcggcatgc ccgaccaggc   22740
cggccagcac cggcccggtg aacaccccgt catttcggtg gatgatgtcc agcagatcga   22800
tcggcaccgc acctgcggcc gcagcgcgga ttcgcagttc aggtgcgtag gtggggtgca   22860
gttcgccggc gaaggccgac gcttgcccac cctgcgcata gccccagatg ccgaccgggc   22920
agtcggtcgt caggccggag cccggtagcc gttgcgcagc gcgggcggca tcgagcatgg   22980
cgtgtccctg cgccctgccg acggtgtagg tgtgggttcc aggagtaccg aggccttcgt   23040
agtcggtgat gaccacggcc cacccgcggt cgagggccac ggcgatcagc tcggtctccg   23100
gctcggttcc ggttcgaagc aggtacgacg gggcaacttg gctaccgagg ccgtgggtgc   23160
ccactgcgaa agtgatgatg gggcgatctt cgcgcggcca cgggatgttc ggcaccagaa   23220
cggtgccgga gacggcgttc ggcatgccaa gggcggagtt ggaccggtag aggatttgcc   23280
aggccttggc tgcgacgggt tcgcccgtgc cgcgcagtgc cgagacgggc cgggccctga   23340
ggagcgtgcc cgggacaccc ggcggtagcg gcgtcggcgg tcggtagaag ggatcatccg   23400
cgggtgcccg cagatcgtcg ccgaccaggc tggcgtgctc ggaggccatc aggactgctt   23460
ctttcgagcc tgcaggagca tgaaacccat gctttcctcg tttctggcgt aatccggatg   23520
tttccggtat tccgcaaccg cggcgatcag ctgtgctggt cccggtccgt gcttcgccgc   23580
gatgtctccc aagtagcgtt gctggtaggt gccgacagcc gcaggctcga cgccggcgag   23640
ctcatcgagt ttccggagca actcgtcgac gtaccaggag accatgcacc tggtctgtgc   23700
cgtgaggtcg gtgacttcga gaatctcgaa cccggcttcg ctgaccagcg ccgtgaagct   23760
gttcaaggta tgggcggtcg tgcccgtcca aaccgccgcg tactcttccg ggagtcgaac   23820
ccgagtgatg atgtctccga ggacgaaccg gccgccgggt tccaggattc ggtggacctc   23880
gcggatcgcg gcggcctggt ccacgatctg cacgacggac tgcatcgccc atgcggcctc   23940
aaagaaaccg tccgggtagg gcagctgggc gccgtcgact agatcgaact caagactgcc   24000
ggccagtccg gtctcgttgg cgagcctggt ggcggcggcg agatgctggg cgttcacggt   24060
gattccggtg actcgaacgc cgctggcgca tgccgcacgg actacgggct gcccattgcc   24120
```

```
gcagcccagg tcgaacaggt gcgctccggg acggagcgcg gccttgtcga tgaacaggtc    24180
ggtcagttgg tcggcagcat ccgaccacgg tgtggcaccg gcatcctccc gatacccgcc    24240
cgcccagtaa ccgtggtgca ggggacgccc gtgcgccaac gcatcgaaga tggactccac    24300
ctgatccgcg gtcggaaatg cctgtgtgtt cgcccctctg ctgttcactc gtcctccgcg    24360
ctgttcacgt cggccaggtg caatatgtcg tccagactcc ttggcaccca agcaggaacg    24420
ccgccttcgg cgttgacgcc tttctccagg aacgcgatgt tgtggtaggt gtggaggccg    24480
accaaattgc gttccaggta gctcggctcg tacgagcccg catgcggctg ctcctcgtgc    24540
tgaacgcctt ccaacaggtt cttgagcagg ctgaccgtgg tgccgggtgc ggccgggcac    24600
tgcgcctgcc cgccgaatcc gggagcatag gtcgtccaca gatcctcgat cacgtatacg    24660
ccaccgctgc gcaaccgggg gaacagcgtt tccaggqatg tgcgcacgtg tccgttgatg    24720
tggctgccat cgtcgatgat gatgtcgaac ggtccgtact tgtcgtcaac ggcggccagc    24780
tcctcgggct tgctctggtc ggcgcggacg gtgcagagcc tctgctggtc gaggaaggac    24840
ttgtcgaaaa cgtccatccc gaacacgagg ccgcggtgga agtagcgctt ccacatcttc    24900
agggattcgc cgccgccacc gtcgaagttg tagccaccga caccgatctc caggatgcgc    24960
accgggcgat cacggaactc gccgaggtgt cgctcgtata gcggggtgaa ccagtgcagg    25020
ccgcccacct tgtccgtgcg gtagtgggag gcgagcaagt tgaggtcggg acgtcggtgc    25080
ccgcagccgg cgaccactgc ggagatggcc tggaagccat cggacagttc cgacggaccg    25140
ggtatcgaac cggatgtggt ggttcggagg aagttggtgc tccgggcgcc gacggccctg    25200
ggagctcctg ggccgaacaa ctcggcgatg agatcggtga gctcgtaacc gatccgcagc    25260
gggacgtctc cgaccggtcg ttgctcggcc ttgatcagct caccggactg tagcgtcagg    25320
acgaagtcaa cggtctcgcc tcggtgggtg atctggaccg cgacctcggt ccgttcgatg    25380
tcggggcccg gttccgcgcg gaagaggatc tcgtcgatca gcacgggtgc gatcctggcg    25440
agtccgagtt cggtggtcag gtcggccagg ctcgccgcac tggatccggc ggcgaggatg    25500
atgcgttcca cggtttcgat ctcgtgcgtt gtggacatcg tgatgagctc ctcatggctg    25560
accgggtgaa agccgtgccg gcggtttgat cgacaggccg tgctggaaga tgttctgcgg    25620
atcccaccgc gctttggccc gctgcagccg cgggtagttg tctttgtagt acaggtcgtg    25680
ccaggcaaca ccgqaqqtqt tccacaatgg atcggccaag tcggtgtccg ggtagttgat    25740
gtaggagccg tcgacacggg tacctggcac cggaactccg ccggtttcgg cgtacatctc    25800
gcggtagaaa ccgcgaatcc aggtcagatg ccgctcgtcc tcggcgggct ccgaccagtt    25860
cgtgacgaac agcgctttga gaaccgagtc gcgctgagcg agtgcggtgg ccgacggagc    25920
cacggcattc gccataccgc cgtaaccgag cagcaacagc gccgccgcag ggttgtcgta    25980
tccgtagacg gtcagccgcc ggtaaaccgt ggctagttga gcttcggaca gcccggtgcg    26040
caagtaggcg gctttgacct tggtccgttg catgcccggt tcgccgcctt cggcgatcgc    26100
cccggccacc tgggtcgatc gcaaccacgg cagggtttcc cgcagccctt cggctggagt    26160
cacgccgacc tgggcgttga tcgccgacag gtgttcggcc agggtgcgtt ccgcgttcgg    26220
atccgtgccg tccaggtgaa cgttcagcgt gacgtagcca gcttgccggt gtgcgcagac    26280
gagcgtgctg aacaacccga gttgcgtgga ttcaggcgcg ctgtgctgct cgtaccaatt    26340
gccgaagttc tgtaggagca cggcgaatga ctgctctgtc agttcgtgcc acggccagtg    26400
gaacgatcgg agcagcactg tcgcgggcgg ccgtggcagg agctctgcgg cgtcggtgct    26460
gaccacgtcc ggcgttcgga gccaaaacct ggtgacgatc ccgaagttgc cgccaccgcc    26520
```

```
accggtgtgc gcccaccaca agtcgtgacc ggcgcccgtg gagttccggt cggcctcgac  26580
gatgtgcact tcaccggcct ggtcgaccac gacgacctcg acgccttgaa ggtagtcgac  26640
gaccgaaccg aatcggcgcg acagcgggcc gtatcccccg ccgaggatgt gcccgcctgc  26700
gcccaccccg ggacatgcgc cggtcggat cgtcacgccc cagttcttga acagggttcg  26760
gtacacctgc ccgagggcgg cgcccgcctc gatcgcgaat gccccgcgcg tgctgtcgta  26820
gtacacgcgc ttgagctcgg agaggtcgac gagcactcgg atcgccgggt ccgcaacgag  26880
attctcgaag cagtgcccgc cgctgcggac ccctacccgc ctgccggtgc gcacggcgtc  26940
ggcgacggcg tgcacgacgt cttcggcgga gctggcgatg tggatgcgtt cgggttttcc  27000
ggtgaaacgg gggttgtgcc cgacgacgag gtccggataa cgaggatcgt cgggctcgac  27060
ggtgatctct gttcctgggg ttcgacgatt catgggtgcc gggtcatgga attcgggcac  27120
cgcccctcct tttctgactg gtccactttg ttcgcccgca gccgagatca tctacgcgtc  27180
cgggtgatta tctgtgtgtt tcagctcata cgtgaaaccc ggtcgcctcc gccggctcta  27240
ctttgtggat cgatatcgcg gtgcgcatgg tgccgtatgc gctggaaccg aaaaggtgat  27300
gacttaccat gagtgagatc gcagttgccc cctggtcggt ggtggagcgt ttgctgctcg  27360
cggcgggtgc gggcccggcg aagctccagg aagcagtgca ggtggccgga ctggacgcgg  27420
tggccgacgc catcgtcgac gaactcgtcg tacgctgcga tccgctgtcg ttggacgagt  27480
cggtgcgaat cggcctggag atcacttctg gcgctcagct ggtccggaga accgttgagc  27540
tcgatcacgc aggcctgcgg ctcgcggcgg tcgccgaagc agctgctgtt ctccggttcg  27600
acgcggtgga tctgctggaa gggctcttcg gcccggttga cggcaggcgg cacaacagcc  27660
gtgaagtccg ctggtcggac agcatgacgc agttctcgcc cgaccagggc ctcgccggcg  27720
cgcagcgcct gctggcgttc cggaacaggg tgtccaccgc ggtgcacgcc gtgctggccg  27780
cagccgccac caggcgcgcg gacctcggtg cgctggcagt ccgctacgga tccgacaaat  27840
gggcggacct gcactggtac accgaacact acgagcacca cttctcccga ttccaggatg  27900
ccccggtgcg agtgttggaa ataggaatcg gtggttatca cgcacccgaa ctcggtggtg  27960
cttcgctgcg catgtggcag cggtacttcc ggcgaggtct cgtttacggg ctggacattt  28020
tcgagaaagc cgggaacgaa gggcaccgag tgcgaaagct gcgaggtgac cagagcgatg  28080
cggaattcct ggaagacatg gtggcgaaga tcggcccgtt cgacattgtc atcgacgacg  28140
gcagccatgt caacgaccac gtcaagaaat ccttccaatc cctgtttccg cacgtccgcc  28200
caggtggttt gtacgtcatc gaggatctcc agacggcgta ctggcccggc tacggcggtc  28260
gcgatgggga acccgcggcc cagcgcacct cgatcgacat gctcaaagaa ctgatcgacg  28320
gcctgcatta tcaggagcgc gaatcgcggt cgggaccga gccctcctac acggaacgga  28380
acgtggcggc cctgcacttc taccacaacc tggtattcgt ggagaaaggg ctcaacgctg  28440
agactgccgc gccggggttc gtgccccggc aagcgctcgg cgtcgagggc ggctgagccg  28500
ttcaccagct gcggcgccag taggcgcccg tgccgtcgat gtcgtggatg ggttccgtga  28560
tcccgagttc cgcgcggaac cccttcaccg cgtcctggca ggacggcaga aaatagtcgt  28620
cgatgatgac gaatccgccc ggcgagagct tcgggtacag gttccgcaat gagtccattg  28680
tggattcgta gaggtcgccg tcgagtcgta gcacggcgag ttcctggatg ggggcggtgg  28740
gcaaggtgtc ccggaaccag ccggggagga acctgacctg ttcgtcgagc agcccgtagc  28800
gggcgaagtt ctgccggacg gtctcaagcg atacgccaag cacgtcgttg tactcgtgca  28860
```

-continued

```
gcgccatagc ctggtccgct tggtggtctt gcgcagagct ttccggcatt ccctggaagg    28920
aatccactac ccagacggta cgtccggtat ctccgaatgc ctggagaacc gcgcgcatga    28980
agatgcatgc gccgccccgc cagacaccgg tctcggcgaa atccccggga acaccgtctg    29040
cgagcacggc ttccacgcag tgctggaggt tgtccagccg ctccagaccg atcatcgtgt    29100
gcgcgacagt tggccagtcc gtgcctttgg cccgagcggc ctgcctgtag tcggtgttgt    29160
cctgccaggc gttcggatgc ggccgatcac tgtaaatcgt gttggtgagt accttcttga    29220
gcaggtccag gtacagcgcg ttctgggagg gcatcggttc tccggatcca gctgttctcg    29280
ggtgactagt tcatcaggca cggatggccg cagtgttctc cagtgtccgc accagcgcgg    29340
cgggatgggg catggccgtg atctcgtcgc tgagtttgat tgccgcagaa gcgaagccgg    29400
tgtcgccgag caccgttgcg attgagtcgg tgaactgttc gtggtcggac tgggcctgct    29460
catccggcaa gcagatgccc gccccggcag cggcgaggtt gcgcgcgtag tcgaactggt    29520
cgaagtactg gggaagcacg agttgcggga tgccgagtcg ggtcgcggtg aatgccgttc    29580
ccgagccgcc cgcgcagatg accagctcgc aggtacgcag gaacaggttg agcgggaccg    29640
attcggcgat ccgggcgttg tcgggtaggt cggtgagaag tgcccggtgc tcgggggggaa    29700 cggcgatcac ggcctcgacg ccgggcaact cggtggcagc cgctactgcg cgcagcagcg    29760
gagccggccc ggtggcgttc agcaccatgc ggcccatgca gatgcagacc gccgtgctg    29820 aggtgcgcgc cgcgccccat gccgggaatg cgccgcttcc gttgtacggc acgtactgga    29880
ccggtgcgcc ttgcggcgcg tcgcttgctt gcaggctcgg cggacaggga tcgaggatga    29940
gctcgggagt gggcaggccg gtcagtccgt ggtgccggca caccgggtca agcaactcgt    30000
gggctcgatc gctgaagggg cctgcggtgg ggtcgactcc ccagcggtgc agcacgaccg    30060
gcaggtcgag caatccgccg agcacccggc cgatcagcgc gcagacgtcg accaacagca    30120
ctgacggtcg ccaggcctcg gccagtcgaa ggtattcggg gagctgatcg agcgagcttt    30180
gcgcgacatt ggacgcggtc tgctcccaca gttgccggcc tgcctcggtg tcgcgctgac    30240
cgaacgccgg attgggaaag cgcagctgcg tggttccacc cgtatcgccg gtcctgtcgt    30300
tcccgcggat cccggccgtg gtgagacctg caccatgcgc ggtcgcctgc agctctggtg    30360
gtgcggcgat caggacctcg tgcccggatg cttgcagcgc ccagcacagc ggcaccattg    30420
ccatgagatg cgtcggatag ggcaagggaa cgacgagtac gcgcatactt cggaccccag    30480
tctctttccc ccgattagcg cagcagcccc tactcccatt ggccaggatt tggaaaatgc    30540
gctgcgtatg tcgatcgccg ttgacgtcca acggacttcc ggcggcaaca atagtgtgtc    30600
acggcaggaa tgtcacgcga ccatcgaaga tctttgggtc gccgcacctg gtttcacgcg    30660
aacgagtgaa atgcgcgagc tccgctcgat cggggtgggc cggacctgta cggtgatcac    30720
cgttggttct gcggggattc atggggaaga tttcgctgg ctgtttgcct cctggccgga    30780
tagttatagt cggtaccgcc gcatgcggcg gtaaccgcga attaactgac ggctagtttg    30840 ccgtctttc tctctgtgtg tttcctgctc ggttccagaa aattacgaga aggtgaacgt    30900
tgcagagatc aggcataccg gtgttgccag gtggcgcacc aacatcgcag caggttgggc    30960
agatgtatga cctggtcacg ccgttgctga actcggtcgc gggcggcccc tgcgccatcc    31020
accacggcta ctgggagaac gacgggcggg cttcctggca gcaggccgcc gaccggctca    31080
ccgaccttgt cgccgaacgg accgtgctcg atggcggcgt tcgactgctc gatgtggggt    31140
gcggtaccgg acaaccagcg ctgcgcgtcg cgcgcgacaa cgcgatccag atcaccggca    31200
tcaccgtcag ccaggtgcaa gtggccatcg ccgctgattg cgcacgcgaa cgcggactaa    31260
```

```
gccaccgggt ggacttctcg tgcgtcgatg ccatgtccct gccgtacccg gacaatgctt   31320
tcgacgccgc ctgggccatg cagtcgctgt tggagatgtc cgaaccggac cgtgccatcc   31380
gggaaatcct tcgagtactc aaacccggtg gcatcctcgg cgtcaccgag gtcgtcaaac   31440
gagaagcggg cggcgggatg ccggtgtccg ggacaggtg gccgaccggc cttcggatct    31500
gcctggctga gcaacttctg gaatcgctgc gtgcagcggg gttcgagatc ctcgattggg   31560
aggacgtgtc gtcgaggacc cggtacttca tgccgcagtt cgccgaagag ctcgctgcgc   31620
accagcacgg gatcgcggac aggtacgggc cggctgtcgc cggctgggcc gccgcggtct   31680
gcgattatga gaaatatgcc cacgacatgg gctatgcgat tctgacgcg cggaagccgg     31740 tcggctgagg gcgcgccgca attcgatgac gttcatgcgc cgtgtcggag aatcgccggt   31800
ggcggcgcca gcagaggctg aacttactgg tggtgtgtcc aggaatcgga ggggcagtac   31860
cgaatgagcg aagccgggaa cctgatagcc gtcatcggac tgtcctgccg cctaccccag   31920
gcgcctgacc cggcttcctt ctggcggttg ctgcgcaccg gaacggacgc catcaccacg   31980
gtcccggaag gcggtgggg cgacccgttg cctggtcggg atgcgcccaa gggcccggaa    32040
tggggtggtt tcctggctga tgtcgactgc ttcgatcccg agttcttcgg gatctcgccg  32100
cgagaagcgg caaccgtgga tccccagcag aggctggctc tggagctcgc ctgggaggca   32160
ctcgaagacg ccggtatccc cgccggcgag ctgcgcggta ctgccgccgg tgtgttcatg   32220
ggggcgatct ctgacgacta cgccgccctg ctgcgcgaga gcccgccgga agtggctgcg   32280
cagtaccgcc tcaccggcac ccatcgaagc ctgatcgcca accgcgtgtc ctatgtgctc   32340
ggcctgcgcg ggccaagcct gacggtggat tcaggtcagt cctcgtccct ggtcggcgtg   32400
catctcgcca gcgagagcct gcgacgggt gagtgcacga tcgcactcgc cggcggcgtg    32460
aacctcaacc tggccgccga gagcaacagc gctctgatgg acttcggcgc gctctccccg   32520
gacggtcgct gcttcacctt cgatgtgcgg gcgaacggtt acgtccgtgg tgagggcggc   32580
ggccttgtcg tgctgaagaa ggccgatcag gcgcacgccg atggcgaccg gatctactgc   32640
ctcatccgcg gcagcgcggt caacaacgat ggggcggtg ccgggctcac cgttccggcg    32700
gcggacgccc aggcggagct gctgcgccag gcataccgga acgcgggcgt cgacccggcc   32760
gccgtgcagt atgtcgagct ccacggcagc gcgaccaggg tcggggatcc cgtcgaagca   32820
gcagccctcg gagctgtcct gggggcggcg agacggcccg cgacgagct gcgtgtgggg    32880 tcggcgaaga ccaacgtcgg ccatctggaa gcagcggcgg gcgtcaccgg gttgctgaag   32940
accgcactca gcatctggca ccgcgaactg ccgccgagtc ttcatttcac cgcccccaac   33000
ccggaaatcc cgctggacga attgaaccta cgcgtccagc gtgatc                 33046
```

<210> SEQ ID NO 18
<211> LENGTH: 33104
<212> TYPE: DNA
<213> ORGANISM: Saccharopolyspora spinosa

<400> SEQUENCE: 18

```
gatcatctac gcgtccgggt gattatctgt gtgtttcagc tcatacgtga aacccggtcg     60
cctccgccgg ctctactttg tggatcgata tcgcggtgcg catggtgccg tatgcgctgg   120
aaccgaaaag gtgatgactt accatgagtg agatcgcagt tgcccctgg tcggtggtgg    180 agcgtttgct gctcgcggcg ggtgcgggcc cggcgaagct ccaggaagca gtgcaggtgg   240
ccggactgga cgcggtggcc gacgccatcg tcgacgaact cgtcgtacgc tgcgatccgc   300
```

```
tgtcgttgga cgagtcggtg cgaatcggcc tggagatcac ttctggcgct cagctggtcc    360
ggagaaccgt tgagctcgat cacgcaggcc tgcggctcgc ggcggtcgcc gaagcagctg    420
ctgttctccg gttcgacgcg gtggatctgc tggaagggct cttcggcccg gttgacggca    480
ggcggcacaa cagccgtgaa gtccgctggt cggacagcat gacgcagttc tcgcccgacc    540
agggcctcgc cggcgcgcag cgcctgctgg cgttccggaa cagggtgtcc accgcggtgc    600
acgccgtgct ggccgcagcc gccaccaggc gcgcggacct cggtgcgctg gcagtccgct    660
acggatccga caaatgggcg gacctgcact ggtacaccga acactacgag caccacttct    720
cccgattcca ggatgccccg gtgcgagtgt tggaaatagg aatcggtggt tatcacgcac    780
ccgaactcgg tggtgcttcg ctgcgcatgt ggcagcggta cttccggcga ggtctcgttt    840
acgggctgga cattttcgag aaagccggga acgaagggca ccgagtgcga aagctgcgag    900
gtgaccagag cgatgcggaa ttcctggaag acatggtggc gaagatcggc ccgttcgaca    960
ttgtcatcga cgacggcagc catgtcaacg accacgtcaa gaaatccttc caatccctgt   1020
ttccgcacgt ccgcccaggt ggtttgtacg tcatcgagga tctccagacg gcgtactggc   1080
ccggctacgg cggtcgcgat ggggaacccg cggcccagcg cacctcgatc gacatgctca   1140
aagaactgat cgacggcctg cattatcagg agcgcgaatc gcggtgcggg accgagccct   1200
cctacacgga acggaacgtg gcggccctgc acttctacca caacctggta ttcgtggaga   1260
aagggctcaa cgctgagact gccgcgccgg ggttcgtgcc ccggcaagcg ctcggcgtcg   1320
agggcggctg agccgttcac cagctgcggc gccagtaggc gcccgtgccg tcgatgtcgt   1380
ggatgggttc cgtgatcccg agttccgcgc ggaaccccct taccgcgtcc tggcaggacg   1440
gcagaaaata gtcgtcgatg atgacgaatc cgcccggcga gagcttcggg tacaggttcc   1500
gcaatgagtc cattgtggat tcgtagaggt cgccgtcgag tcgtagcacg gcgagttcct   1560
ggatgggggc ggtgggcaag gtgtcccgga accagccggg gaggaacctg acctgttcgt   1620
cgagcagccc gtagcgggcg aagttctgcc ggacggtctc aagcgatacg ccaagcacgt   1680
cgttgtactc gtgcagcgcc atagcctggt ccgcttggtg gtcttgcgca gagctttccg   1740
gcattccctg gaaggaatcc actacccaga cggtacgtcc ggtatctccg aatgcctgga   1800
gaaccgcgcg catgaagatg catgcgccgc cccgccagac accggtctcg gcgaaatccc   1860
cgggaacacc gtctgcgagc acggcttcca cgcagtgctg gaggttgtcc agccgctcca   1920
gaccgatcat cgtgtgcgcg acagttggcc agtccgtgcc tttggcccga gcggcctgcc   1980
tgtagtcggt gttgtcctgc caggcgttcg gatgcggccg atcactgtaa atcgtgttgg   2040
tgagtacctt cttgagcagg tccaggtaca gcgcgttctg ggagggcatc ggttctccgg   2100
atccagctgt tctcgggtga ctagttcatc aggcacggat ggccgcagtg ttctccagtg   2160
tccgcaccag cgcggcggga tggggcatgg ccgtgatctc gtcgctgagt ttgattgccg   2220
cagaagcgaa gccggtgtcg ccgagcaccg ttgcgattga gtcggtgaac tgttcgtggt   2280
cggactgggc ctgctcatcc ggcaagcaga tgcccgcccc ggcagcggcg aggttgcgcg   2340
cgtagtcgaa ctggtcgaag tactgggaa gcacgagttg cgggatgccg agtcgggtcg   2400
cggtgaatgc cgttcccgag ccgcccgcgc agatgaccag ctcgcaggta cgcaggaaca   2460
ggttgagcgg gaccgattcg gcgatccggg cgttgtcggg taggtcggtg agaagtgccc   2520
ggtgctcggg gggaacggcg atcacggcct cgacgccggg caactcggtg gcagccgcta   2580
ctgcgcgcag cagcggagcc ggcccggtgg cgttcagcac catgcggccc atgcagatgc   2640
agacccgccg tgctgaggtg cgcgccgcgc cccatgccgg gaatgcgccg cttccgttgt   2700
```

```
acggcacgta ctggaccggt gcgccttgcg gcgcgtcgct tgcttgcagg ctcggcggac    2760
agggatcgag gatgagctcg ggagtgggca ggccggtcag tccgtggtgc cggcacaccg    2820
ggtcaagcaa ctcgtgggct cgatcgctga aggggcctgc ggtggggtcg actccccagc    2880
ggtgcagcac gaccggcagg tcgagcaatc cgccgagcac ccggccgatc agcgcgcaga    2940
cgtcgaccaa cagcactgac ggtcgccagg cctcggccag tcgaaggtat tcggggagct    3000
gatcgagcga gctttgcgcg acattggacg cggtctgctc ccacagttgc cggcctgcct    3060
cggtgtcgcg ctgaccgaac gccggattgg gaaagcgcag ctgcgtggtt ccacccgtat    3120
cgccggtcct gtcgttcccg cggatcccgg ccgtggtgag acctgcacca tgcgcggtcg    3180
cctgcagctc tggtggtgcg gcgatcagga cctcgtgccc ggatgcttgc agcgcccagc    3240
acagcggcac cattgccatg agatgcgtcg gatagggcaa gggaacgacg agtacgcgca    3300
tacttcggac cccagtctct ttcccccgat tagcgcagca gcccctactc ccattggcca    3360
ggatttggaa aatgcgctgc gtatgtcgat cgccgttgac gtccaacgga cttccggcgg    3420
caacaatagt gtgtcacggc aggaatgtca cgcgaccatc gaagatcttt gggtcgccgc    3480
acctggtttc acgcgaacga gtgaaatgcg cgagctccgc tcgatcgggg tgggccggac    3540
ctgtacggtg atcaccgttg gttctgcggg gattcatggg gaagatttgc gctggctgtt    3600
tgcctcctgg ccggatagtt atagtcggta ccgccgcatg cggcggtaac cgcgaattaa    3660
ctgacggcta gtttgccgtc ttttctctct gtgtgtttcc tgctcggttc cagaaaatta    3720
cgagaaggtg aacgttgcag agatcaggca taccggtgtt gccaggtggc gcaccaacat    3780
cgcagcaggt tgggcagatg tatgacctgg tcacgccgtt gctgaactcg gtcgcgggcg    3840
gcccctgcgc catccaccac ggctactggg agaacgacgg gcgggcttcc tggcagcagg    3900
ccgccgaccg gctcaccgac cttgtcgccg aacggaccgt gctcgatggc ggcgttcgac    3960
tgctcgatgt ggggtgcggt accgacaaca cagcgctgcg cgtcgcgcgc gacaacgcga    4020
tccagatcac cggcatcacc gtcagccagg tgcaagtggc catcgccgct gattgcgcac    4080
gcgaacgcgg actaagccac cgggtggact tctcgtgcgt cgatgccatg tccctgccgt    4140
acccggacaa tgctttcgac gccgcctggg ccatgcagtc gctgttggag atgtccgaac    4200
cggaccgtgc catccgggaa atccttcgag tactcaaacc cggtggcatc ctcggcgtca    4260
ccgaggtcgt caaacgagaa gcgggcggcg ggatgccggt gtccggggac aggtggccga    4320
ccggccttcg gatctgcctg gctgagcaac ttctggaatc gctgcgtgca gcggggttcg    4380
agatcctcga ttgggaggac gtgtcgtcga ggacccggta cttcatgccg cagttcgccg    4440
aagagctcgc tgcgcaccag cacgggatcg cggacaggta cgggccggct gtcgccggct    4500
gggccgccgc ggtctgcgat tatgagaaat atgcccacga catgggctat gcgattctga    4560
cggcgcggaa gccggtcggc tgagggcgcg ccgcaattcg atgacgttca tgcgccgtgt    4620
cggagaatcg ccggtggcgg cgccagcaga ggctgaactt actggtggtg tgtccaggaa    4680 tcggagggc agtaccgaat gagcgaagcc gggaacctga tagccgtcat cggactgtcc    4740
tgccgcctac cccaggcgcc tgacccggct tccttctggc ggttgctgcg caccggaacg    4800
gacgccatca ccacggtccc ggaagggcgg tgggcgacc cgttgcctgg tcgggatgcg    4860
cccaagggcc cggaatgggg tggtttcctg gctgatgtcg actgcttcga tcccgagttc    4920
ttcgggatct cgccgcgaga agcggcaacc gtggatcccc agcagaggct ggctctggag    4980
ctcgcctggg aggcactcga agacgccggt atccccgccg gcgagctgcg cggtactgcc    5040
```

```
gccggtgtgt tcatgggggc gatctctgac gactacgccg ccctgctgcg cgagagcccg    5100
ccggaagtgg ctgcgcagta ccgcctcacc ggcacccatc gaagcctgat cgccaaccgc    5160
gtgtcctatg tgctcggcct gcgcgggcca agcctgacgg tggattcagg tcagtcctcg    5220
tccctggtcg gcgtgcatct cgccagcgag agcctgcgac ggggtgagtg cacgatcgca    5280
ctcgccggcg gcgtgaacct caacctggcc gccgagagca acagcgctct gatggacttc    5340
ggcgcgctct ccccggacgg tcgctgcttc accttcgatg tgcgggcgaa cggttacgtc    5400
cgtggtgagg gcggcggcct tgtcgtgctg aagaaggccg atcaggcgca cgccgatggc    5460
gaccggatct actgcctcat ccgcggcagc gcggtcaaca cgatgggggg cggtgccggg    5520
ctcaccgttc cggcggcgga cgcccaggcg gagctgctgc gccaggcata ccggaacgcg    5580
ggcgtcgacc cggccgccgt gcagtatgtc gagctccacg gcagcgcgac cagggtcggg    5640
gatcccgtcg aagcagcagc cctcggagct gtcctggggg cggcgagacg gcccggcgac    5700
gagctgcgtg tggggtcggc gaagaccaac gtcggccatc tggaagcagc ggcgggcgtc    5760
accgggttgc tgaagaccgc actcagcatc tggcaccgcg aactgccgcc gagtcttcat    5820
ttcaccgccc caacccggga aatcccgctg gacgaattga acctacgcgt ccagcgtgat    5880
ctgcggccgt ggccggagag cgaggggccg ctgctggccg cgtcagcgc cttcggaatg    5940
ggaggcacga actgccacct ggtgctctcc ggcacgtccc gggtggagcg acggcgcagt    6000
ggacccgctg aggcgaccat gccgtgggtc ttgtcggcca gaacaccggt cgcattgcgt    6060
gcgcaggcgg cgcgcttgca cacgcacctc aatacggccg gtcaaagtcc gttggacgtc    6120
gcctactcac tggcgaccac tcgatcccgc ctaccgcacc gggccgcgct ggtcgcggac    6180
gacgaaccga aactgctcgc cgggttgaag gccctcgctg acggcgacga cgcgcccacg    6240
ctgtgccacg cgcgcgactt cggcgagcgg gcagcggtct tcgtctttcc cggacagggc    6300
agccagtgga tcgggatggg taggcagctg ctcgaaacct ccgaggtttt cgcggcgtcg    6360
atgtcggact gcgccgacgc attggcgcca cacctggatt ggtccctgct ggatgtgctg    6420
cgcaacgcgg ccggcgctgc gcaccttgac cacgacgatg tcgtccagcc cgcgctgttc    6480
gccatcatgg tctcgctcgc ggagctctgg cgttcgtggg gcgtgcgtcc ggtggcggtc    6540
gtcgggcact cgcaggggga gatcgcggcg gcctgcgtcg ccggggcccct gtccgtccgc    6600
gatgccgcca gggtggtggc ggtgcgcagc aggcttctga cggcgctggc cggcagtggc    6660
gcgatggcct cgttgcagca tcccgccgaa gaggtgcggc aaatcctgtt gccctggcgc    6720
gatcggatcg gcgtggcggg ggtgaacgga ccgtcgtcga ccctggtgtc aggggaccgg    6780
gaggcgatgg cggaactgct ggccgagtgc gcagaccgag agctccggat cgccggatt    6840
cccgttgaat acgcctccca ttcgcctcac atcgaggttg tccgggatga gctgctgggg    6900
ctgttggcgc cggtcgaacc caggacggga agcatcccga tctattcgac gacgaccggg    6960
gacctgctgg accggccgat ggacgccgac tactggtacc gcaaccttcg tcaaccggtg    7020
ctgttcgaag cggccgtcga ggccctgttg aagcgggggt acgacgcatt catcgagatc    7080
agcccacacc cggtgctgac tgcgaacatc caggaaaccg ccgtgcgagc agggcgggag    7140
gtagtggcgc tcgggacact ccgccgcggc gaaggtggca tgcggcaggc gctgacgtcg    7200
ctggccagag cacacgtaca cggagtggcc gcggactggc acgcggtctt cgccggtacc    7260
ggggcgcagc gggtcgacct gccgacgtac gcctttcagc gacagcgcta ctggctggac    7320
gcgaagcttc ccgacgtcgc catgcccgag agcgacgtgt cgacgcgtt gcgggaaaag    7380
ctgcggtctt cgccgagggc ggacgtggac tcgacgaccc tcacgatgat ccgggcacag    7440
```

```
gcagccgtgg tcctcggcca ctccgatccg aaagaggtgg acccggatcg gacgttcaag    7500
gacctgggct tcgattcctc gatggtggtc gagctgtgcg accgcctaaa cgccgccaca    7560
ggtctgcgac tcgcaccgag cgtcgttttc gactgtccta cgccggacaa gctcgcccgc    7620
caggtacgga cgttgttgtt gggcgagccg gctcccatga cgtcacaccg gccggactcc    7680
gatgcggacg agcctatcgc cgtgatcggg atgggctgtc ggtttccggg tggggtgtcc    7740
tcgcccgagg agttgtggca gttggtcgcc gctgggcggg acgtcgtgtc cgagttcccg    7800
gctgaccgag gttgggacct ggagcgtgcg gggacatcgc acgtgcgcgc cggcgggttc    7860
ttgcatggcg ccccggattt tgaccccggg ttcttccgga tttcgccgcg cgaggcgttg    7920
gcgatggatc cacagcagcg gttgctgctg gaaatcgcct gggaagcagt cgaacgaggc    7980
gggatcaacc cgcagcacct gcacggaagt caaaccgggg tcttcgtcgg cgcgacctcc    8040
ctggactacg ggccacgcct gcacgaagcg tccgaggagg cggccgggta cgtgctcacc    8100
ggcagcacca cgagtgtggc gtcgggtcgg gttgcgtatt cgttcgggtt cgagggccct    8160
gcggtgacgg tggatacggc cgtgttcgtcg tcgttggtgg ccctgcattt ggcgtgtcag    8220
tcgttgcgtt cgggtgagtg tgatctggcg ttggccggtg gtgtgaccgt gatggccacg    8280
ccggggatgt tcgtggagtt ttcgcggcag cgtggtttgg cgccggatgg gcggtgcaag    8340
tcgttcgcgg aggccgccga cggcaccggc tggtccgagg gtgctggcct ggttctactg    8400
gagcggttgt cggatgcccg gcggaatggg catgaggtgc tggcggttgt tcgtggtagt    8460
gcggtgaatc aggacggtgc gtcgaatggt ttgaccgcgc cgaatggttc gtcgcagcag    8520
cgggtgattg cccaggcatt ggcgagtgcg gggttgtcgg tgtccgatgt ggatgctgtg    8580
gaggcgcatg ggacgggcac gcggcttggt gatccgatcg aggcgcaggc gctgatcgcc    8640
acctacggcc agggccggct tccggaacgg ccattgtggt tgggctcgat gaagtcgaac    8700
atcggtcacg cgcaggcagc tgcggggata ccggcgtca tgaagatggt gatggcgatg    8760
cggcacgggc agctaccgcg cacgttgcac gtggatgagc cgacttctgg ggtggattgg    8820
tcggcgggga cggttcaact ccttacgag aacacgccct ggcccgggag tggtcgtgtt    8880
cgtcgggtgg gggtgtcgtc gttcgggatc agtggtacta cgcgcacgt catcctcgaa    8940 cagcccccgg gagtgccgag tcagtctgcg gggccgggtt cgggctctgt cgtggatgtt    9000
ccggtggtgc cgtggatggt gtcgggcaaa acacccgaag cgctatccgc gcaggcaacg    9060
gcgttgatga cctatctgga cgagcgacct gatgtctcct cgctggatgt tgggtactcg    9120
ctggcgttga caacggtcggc gctggatgag cgagcggtgg tgctggggtc ggaccgtgaa    9180
acgttgttgt gcggtgtgaa agcgctgtct gccggtcatg aggcttctgg gttggtgacc    9240
ggatctgtgg gggctggggg ccgcatcggg tttgtgtttt ccggtcaggg tggtcagtgg    9300
ctggggatgg gccgggggct ttaccgggct tttccggtgt tcgctgctgc ctttgacgaa    9360 gcttgtccg agctggatgc gcatctgggc caggaaatcg gggttcggga ggtggtgtcc    9420
ggttcggatg cgcagttgct ggatcggacg ttgtgggcgc agtcgggttt gttcgcgttg    9480
caggtgggct tgctgaagtt gctggattcg tgggggggttc ggccgagtgt ggtgttgggg    9540
cattcggtgg gcgagttggc ggcggcgttc gcggcgggtt tggtgtcgtt gtcgggtgcg    9600
gctcggttgg tggcgggtcg tgcccggttg atgcaggcgt tgccgtctgg cggtgggatg    9660
ctggcggtgc ctgctggtga ggagctgttg tggtcgttgt tggccgatca gggtgatcgt    9720
gtggggatcg ccgcggtcaa cgctgcgggg tcggtggtgc tctctggtga tcgggatgtg    9780
```

```
ctcgatgacc ttgccggtcg gctggacggg caagggatcc ggtcgaggtg gttgcgggtg   9840
tcgcatgcgt ttcattcgta tcggatggat ccgatgctgg cggagttcgc cgaattggca   9900
cgaaccgtgg attaccggcg ttgtgaagtg ccgatcgtgt cgaccttgac cggagacctc   9960
gatgacgctg gcaggatgag cgggcccgac tactgggtgc gtcaggtgcg agagccggtc  10020
cgcttcgccg acggtgtcca ggcgctggtc gagcacgatg tggccaccgt tgtcgagctc  10080
ggtccggacg gggcgttgtc ggcgctgatc caggaatgtg tcgccgcatc cgatcacgcc  10140
gggcggctga gcgcggtccc ggcgatgcgc aggaaccagg acgaggcgca aaggtgatg  10200 acggccctgg cacacgtcca cgtacgtggt ggtgcggtgg actggcggtc gttcttcgcc  10260
ggtacaaggg cgaagcaaat cgagctgccc acctacgcct tccaacgaca gcggtactgg  10320
ctgaacgcgc tgcgtgaatc ttccgccggc gacatgggca ggcgtgtcga agcgaagttc  10380
tggggcgccg tcgagcacga agatgtggaa tcgcttgcac gcgtattggg cattgtggac  10440
gacggcgctg ctgtggattc cctgagaagc gcccttccgg tgttggccgg ttggcagcga  10500
acccgcacca ccgagtccat tatggatcag cggtgttacc gaattggctg gcggcaggta  10560
gccggactcc cgccgatggg aactgttttc ggtacctggc tggtcttcgc gcctcatggc  10620
tggtccagcg aaccggaggt ggtggactgc gttacgcac tgcgggcacg tggtgcctcg  10680
gtggtgttgg tggaagctga tcccgacccg acctccttcg gcgaccgggt acgaaccctg  10740
tgttcgggcc ttccggatct tgttggcgtg ttgtcaatgt tgtgcttgga agaatcggtc  10800
cttccgggat tttctgcggt gtcacggggt tttgcgttga ccgtggagtt ggtgcgggtt  10860
ttgcgggcag ctggtgcgac tgcccggttg tggttgctga cgtgtggtgg cgtgtcggtc  10920
ggagatgtac cggttcgtcc agcgcaggcc ctggcgtggg ggttggggcg tgttgtgggg  10980
ttggagcatc cggactggtg gggcggcttg atcgatattc cggtcttgtt cgacgaagac  11040
gctcaagagc ggttgtcgat tgtgctggca ggtctcgatg aggacgaggt cgcgatccgt  11100
cctgacggca tgttcgcgcg tcggttggta cgccacactg tctcagctga tgtgaagaag  11160
gcgtggcgcc ccaggggatc ggtgctggtg acgggcggca cgggtggttt ggggcgcac   11220 gttgctcgct ggctggccga cgccggagcc gaacatgtgg cgatggtgag tcgacgcggc  11280
gagcaggcac cgagtgctga aagttgcgg acggaactgg aggatctggg tacccgggtg   11340
tcgatcgtgt catgcgatgt gaccgatcgc gaggcgctcg ccgaagtgct gaaagccctt  11400
ccggctgaaa acccgttgac cgcggtagtg catgcggcag gcgtgatcga gactggtgat  11460
gcggcggcaa tgagcctggc tgatttcgat cacgtgttgt ccgcaaaggt ggccggtgcc  11520
gcgaatctgg atgccttgtt ggccgatgtg gaattggacg cgttcgtctt gttctcatcg  11580
gtgtcaggag tttggggcgc tgggggacac gggcgttacg cagcggcgaa tgcctatctg  11640
gatgcgctcg cggaacagcg tcggtcgcga gggctggtcg cgactgcggt ggcctggggg  11700
ccgtgggccg gcgagggcat ggcctccgga gaaacaggag accagctgcg ccgatacggc  11760
ctttccccaa tggctccgca gcacgccatc gccggaatcc ggcaggccgt ggaacaggac  11820
gaaatttccc tggtagtggc cgatgtcgat tgggcacgtt tcagcgcggg attgctggcg  11880
gctaggccgc ggccgctgct gaacgaactg gccgaggtca aggaactcct cgtcgatgcc  11940
cagcccgagg cgggagtcct tgccgacgcg tcgttggaat ggcggcagcg attgtccgcg  12000
gcaccgaggc cgacacagga acagctgatc ctgagctggt acgcggcga aaccgctctg   12060 gtgctgggac accccggggc agcggccgtt gcatcggaac gagccttcaa ggacagcgga  12120
ttcgactcgc aggccgcggt cgaactccgc gttcggctca atcgagctac cggcctccag  12180
```

-continued

```
ttgccatcga caattatctt cagccatccc acgcctgcgg aactggctgc ggagctgcgg    12240
gcgaggcttc ttcccgagtc cgcaggagca ggcattcccg aggaggacga ggcgcgaatc    12300
agagcggcac tgacgtcgat cccgttcccg gccttgcgcg aggcaggctt ggtgagtccg    12360
ctgctcgcac ttgccggaca cccggtcgac tccggtatct cctcggacga tgcggccgcg    12420
acctcgatcg atgcgatgga tgtagccggc ctcgtcgaag cagcgctggg cgaacgcgag    12480
tcctgagacc gccgacctgg gagatgacgg tgaccaccag ttacgaagaa gttgtcgagg    12540
cactgcgagc atcgctcaag gagaacgaac gcctccggcg cggcagggat cggttctccg    12600
cggagaagga cgatcccatc gcgatcgtgg cgatgagttg tcgttatccc ggtcaggtct    12660
cctcgccgga ggacctgtgg caactggctg ccggcggtgt ggacgcgatc tccgaagttc    12720
cgggggatcg cggatgggac ctggatgcg tgttcgttcc ggactccgat cgtcctggca     12780
cgtcgtatgc ctgcgcgggc ggttttcttc agggcgtgtc ggagttcgac gcgggtttct    12840
tcgggatttc gccgcgtgag gcgctggcga tggatccgca gcagcggttg ctgctggaag    12900
tcgcgtggga ggtcttcgag cgggctgggc tggagcagcg gtcgacacgc ggttcccgcg    12960
ttggcgtgtt cgtcggcacc aatggccagg actacgcgtc gtggttgcgg acgccgccgc    13020
ctgcggtggc aggtcatgtg ctgacgggcg gtgcggcagc ggttctttcg gccgggttg     13080 cgtattcgtt cgggttcgag ggtcctgcgg tgacggtgga tacggcgtgt tcgtcgtcgt    13140
tggtggcgtt gcacctggcg gggcaagcac tgcgggccgg tgagtgcgac cttgcccttg    13200
ccggtggcgt cacggtgatg tcgacgccga aggtgttcct ggagttctcc cgccaacggg    13260
gtctcgcgcc ggatgggcgg tgcaagtcgt tcgcggcggg tgcggatggc actggatggg    13320
gtgagggtgc cggactgttg ttgctggagc ggttgtcgga tgcccggcgg aatgggcatg    13380
aggtgctggc ggttgttcgt ggtagtgcgg tgaatcagga cggtgcgtcg aatggtttga    13440
ccgcgccgaa tggttcgtcg cagcagcggg tgattaccca ggcgttggcg agtgcggggt    13500
tgtcggtgtc cgatgtggat gctgtggagg cgcatgggac gggcacgcgg cttggtgatc    13560
cgatcgaggc gcaggcgctg atcgccacct acggccgtga tcgtgatcct ggccggccgt    13620
tgtggttggg gtcggtcaag tcgaacatcg gtcatacgca agcggcggcg ggtgtggctg    13680
gtgtgatcaa gatggtgatg gcgatgcggc acgggcagct gccacgcacg ttgcacgtgg    13740
aatcgccgtc gccggaggtg gattggtcgg cggggacggt tcaactcctt acggagaaca    13800
cgccctggcc caggagtggt cgtgttcgtc gggtgggggt gtcgtcgttc gggatcagtg    13860
gtactaacgc gcacgtcatc ctcgaacagc ccccggagt gccgagtcag tctgcggggc     13920
cgggttcggg ttctgtcgtg gatgttccgg tggtgccgtg gatggtgtcg ggcaaaacac    13980
ccgaagcgct atccgcgcag gcaacggcgt tgatgaccta tctggacgag cgacctgatg    14040
tctcctcgct ggatgttggg tactcgctgg cgttgacacg gtcggcgctg gatgagcgag    14100
cggtggtgct ggggtcggac cgtgaaacgt tgttgtgcgg tgtgaaagcg ctgtctgccg    14160
gtcatgaggc ttctgggttg gtgaccggat ctgtggggc tggggccgc atcgggtttg      14220 tgttttccgg tcagggtggt cagtggctgg ggatgggccg ggggctttac cgggcttttc    14280
cggtgttcgc tgctgccttt gacgaagctt gtgccgagct ggatgcacat ctgggccagg    14340
aaatcggggt tcgggaggtg gtgtccggtt cggatgcgca gttgctggat cggacgttgt    14400
gggcgcagtc gggtttgttc gcgttgcagg tgggcttgct gaagttgctg gattcgtggg    14460
gggttcggcc gagtgtggtg ttggggcatt cggtgggcga gttggcggcg gcgttcgcgg    14520
```

```
cgggtgtggt gtcgttgtcg ggtgcggctc ggttggtggc gggtcgtgcc cggttgatgc    14580
aggcgttgcc gtctggcggt gggatgctgg cggtgcctgc tggtgaggag ctgttgtggt    14640
cgttgttggc cgatcagggt gatcgtgtgg ggatcgccgc ggtcaacgct gcggggtcgg    14700
tggtgctctc tggtgatcgg gatgtgctcg atgaccttgc cggtcggctg gacgggcaag    14760
ggatccggtc gaggtggttg cgggtgtcgc atgcgtttca ttcgtatcgg atggatccga    14820
tgctggcgga gttcgccgaa ttggcacgaa ccgtggatta ccggcgttgt gaagtgccga    14880
tcgtgtcgac cttgaccgga gacctcgatg acgctggcag gatgagcggg cccgactact    14940
gggtgcgtca ggtgcgagag ccggtccgct tcgccgacgg tgtccaggcg ctggtcgagc    15000
acgatgtggc cactgttgtc gagctcggtc cggacggggc gttgtcggcg ctgatccagg    15060
aatgtgtcgc cgcatccgat cacgccgggc ggctgagcgc ggtcccggcg atgcgcagga    15120
accaggacga ggcgcagaag gtgatgacgg ccctggcaca cgtccacgta cgtggtggtg    15180
cggtggactg gcggtcgttc ttcgccggta cgggagcgaa acaaatcgag ctgcccacct    15240
acgccttcca acgacagcgg tactggctgg tgccatcgga ttccggtgat gtgacaggtg    15300
ccggtctggc cggggcggag catccgctgt tgggtgctgt ggtgccggtc gcgggtggtg    15360
acgaggtgtt gctgaccggc aggatttcgg tgcggacgca tccgtggctg ccgaacacc     15420 gggtgctggg tgaagtgatc gttgcgggca ccgcgttgct ggagatcgcc ttgcacgcgg    15480
gggaacgtct tggttgtgaa cgggtggaag agctcaccct ggaagcaccg ctggtcctgc    15540
cggagcgcgg ggcgatccag gttcagctgc gagtgggcgc gcccgagaat tccggacgca    15600
ggccgatggc gctgtattca cgccccgaag gggcggcgga gcatgactgg acgcggcacg    15660
ccacgggccg gttggcgcca ggccgcggcg aggcggctgg agacctggcc gactggccgg    15720
ctcctggcgc gctgccggtc gacctcgacg aattctatcg ggacctcgca gagcttgggc    15780
tggagtacgg cccgatcttc caagggctca aggcggcctg gcggcaaggg gacgaggtgt    15840
acgccgaagc cgcgctgccg ggaacggaag attctggttt cggggtgcat ccggcactgc    15900
tggacgcggc tctgcacgca acggctgtcc gagacatgga tgacgcacgc ttgccgttcc    15960
agtgggaagg tgtgtccctg cacgccaagg ccgcgccggc tttgcgggtc cgcgtggtcc    16020
cggctggtga cgatgccaag tccctgctgg tttgtgatgg caccggtcga ccggtgatct    16080
cggtggaccg actcgtattg cggtcggctg cggcccggcg gaccggtgcg cgccgacagg    16140
cccatcaagc tcggttgtac cggttgagct ggccaacggt tcaactgccg acatccgctc    16200
agccaccgtc ctgcgtgctt ctcggcacct cagaagtgtc cgctgacata caggtgtatc    16260
cggacctccg gtcgttgacg gctgcgttgg atgccggtgc cgaaccaccc ggcgtcgtca    16320
tcgcacccac gccccccggc ggtggacgaa cagcggatgt ccgggagacg actcggcatg    16380
cactcgacct ggtacaaggc tggctttccg atcagcgact caacgaatcc cgattgctcc    16440
tggtgacaca gggagcagtg gccgtggagc cgggcgaacc cgtgaccgat ctggcgcagg    16500
ccgcgctctg gggactgctg cggtcgacgc agaccgaaca ccctgatcgc ttcgtcctcg    16560
tcgatgtgcc tgagcccgcg caactcctcc ccgcgctgcc gggggtgctg gcctgcggcg    16620
aacctcagct cgcgttgcga cgtggcggcg ctcatgcgcc cagactggct ggactgggca    16680
gcgatgacgt cctgcccgtg ccggacggca ccgggtggcg attggaggcc acgcgcccgg    16740
gaagcctgga tgggttggca ttggtggacg aaccgacggc cacggcaccg ctgggtgacg    16800
gtgaggtcag gattgcgatg cgcgcggccg gggtgaactt ccgggatgcg ctcatcgcgc    16860
tcggtatgta tcccggtgtg gcatcgctgg gcagtgaggg cgccggggtc gtggtggaga    16920
```

```
ccggccccgg cgtcaccggc ctggcacccg gcgaccgcgt gatgggaatg atcccgaagg    16980
cgttcgggcc gctcgcggtc gccgaccatc gcatggtgac gaggattccc gctggttgga    17040
gcttcgcgcg ggccgcatcg gtgccgatcg tctttctcac cgcctactac gcgctggttg    17100
atctcgccgg gttgagacca ggggagtcgt tgctggttca ttcggccgcc ggtggggtgg    17160
ggatggccgc gatccaactc gccaggcacc tcggtgcaga ggtgtacgcc accgctagcg    17220
aggacaagtg gcaagccgtg gagctgagcc gagaacacct cgcttcgtcg cggacgtgcg    17280
atttcgagca gcagttcctc ggggcaaccg gcggacgcgg cgtcgacgtc gtgctcaact    17340
ccctcgccgg ggagttcgcc gatgcgtctc tgcgaatgct gccgcgcggt ggccgtttcc    17400
tggagttggg gaagacggat gttcgtgacc ccgtcgaggt cgccgatgcg catccgggcg    17460
tgtcttacca ggctttcgat accgtagagg caggcccgca gcgaatcggc gagatgcttc    17520
acgagctggt ggagttgttc gagggacgcg tgctggagcc cctgcctgtc acggcttggg    17580
acgttcggca ggcgcccgag gcgctacggc acctgagcca agcgcggcat gtgggaaagc    17640
tggtgctcac catgcctccg gtgtgggacg ccgcaggcac ggttctggtt accggcggaa    17700
cgggagcact tggcgcagag gtcgcccggc acctcgtgat cgagcgcggg gtgcgaaacc    17760
tggtcctcgt cagcaggcgc ggtcccgcag ccagtggcgc tgctgagctc gtggcgcaac    17820
tgacggccta cggtgccgag gtttccttgc aggcttgcga tgtcgccgat cgtgagacct    17880
tggcgaaggt gcttgccagc atcccggacg agcatccgtt gaccgccgtg gtgcacgcgg    17940
ctggtgttct cgacgacgga gtgtccgaat cgctcaccgt ggagcggctg gaccaggttc    18000
tgcgcccgaa ggtcgatggc gcgcggaatc tgctcgagct gatcgacccg gacgtggccc    18060
tcgtgttgtt ctcgtcggtg tcgggtgtgc tcggcagcgg tgggcagggt aactacgcgg    18120
cggccaactc cttcctcgac gcattggcgc agcaaaggca gtcgcgcggc ctaccgacga    18180
gatcattggc ctgggggccc tgggcggaac atggcatggc cagcaccttg cgcgaagccg    18240
agcaggatcg attggcgcga tctgggttgc tgccgatctc gaccgaggag gggttgtccc    18300
agttcgacgc cgcgtgcggc ggcgcgcata ccgtggtggc gccggttcga ttcagccgct    18360
tgtccgacgg gaacgcgatc aagttctccg tcctgcaagg tttggtcggg ccgcatcgcg    18420
tcaacaaagc ggcgactgcg gatgatgccg agagcctccg gaaacggttg gacgcttgc     18480 cggatgcaga acaacatcgg attctgctgg acctcgtccg catgcatgtg gcggcagtgc    18540
tcggattcgc cggttctcag gagatcaccg cggacggcac gttcaaggtg ctgggcttcg    18600
actcgttgac cgtggtcgag ttgcgcaacc ggatcaacgg ggcgacgggg ctgcgactgc    18660
ccgccaccct ggtgttcaac tacccgacgc cggatgcgct cgccgcgcac ctcgtcaccg    18720
cgctgtccgc agaccgcctg gccgggacat tcgaggaact cgacaggtgg gcggcgaacc    18780
tgcccacgct ggccagggat gaggccacgc gggcgcagat caccacccgg ctacaggcga    18840
tcttgcagag cctggcggac gtgtccgcg gaaccggcgg cggctccgtg ccggaccggc      18900
tcagatcggc cacggacgac gagctttcc aactcctcga caacgatctc gaacttccct     18960
gatgcctcag ccggagcctt cgcaacttcc tggagggaaa cgccacatgt cgaatgaaga    19020
gaagctccgg gagtacttgc ggcgtgcgct cgtggatctg caccaggcgc gcgagcggct    19080
gcacgaggcg gagtcgggag agcgggaacc catcgcgatc gtggcgatgg gctgccggta    19140
cccgggtggg gtgcaggacc cggaagggct gtggaaactg gtcgcctccg gtggcgacgc    19200
catcggtgaa ttccccgctg atcgtggttg gcacctcgac gagctctacg atcccgaccc    19260
```

```
ggatcagccc ggaacctgct acacccggca cggcggcttc ctccacgacg ccggcgagtt   19320
cgacgcggga ttcttcgaca tcagcccccg tgaggcgctc gcgatggacc cgcagcagcg   19380
gctgctgctg gaaatctcct gggagaccgt cgaatccgct gggatggacc cgaggtcctt   19440 gcggggagc cgcaccgggg tgttcgcggg attgatgtac gagggctatg acaccggcgc   19500
ccaccgggca ggagaaggtg tcgaaggcta tctcggaacc ggcaatgcgg gaagcgtcgc   19560
ctctggtcgg gttgcgtatg cgttcgggtt cgagggccca gcggtgacgg tagacacggc   19620
gtgctcgtcg tcgttggtgg cgctgcattt ggcgtgtcag tcgttgcggc agggcgagtg   19680
tgatctggcg ctggccggtg gagtgacggt gatgtcgacg ccggagaggt tcgtggagtt   19740
ctcccgtcag cgtggtctcg caccggatgg gcggtgtaag tcgttcgcgg cggctgcgga   19800
tggaaccggt tggggtgagg gtgccggttt ggtgttgctg gagcggctgt cagacgccag   19860
gcggaacggg catcgggtac tggcggttgt tcgtggtagc gcggtgaatc aggacggtgc   19920
gtcgaacgga ttgacggccc cgaacgggct ggcccaggag cgggtcattc agcaggtgct   19980
cacgagtgcg gggctgtcgg cgtccgatgt ggacgctgtg gaggcgcatg gaacgggtac   20040
gcggcttggt gatccgatcg aggcgcaggc tctgatagcc gcctatggac aggatcggga   20100
ccgggaccgg ccgctgtggt tggggtcggt caagtccaac atcggtcata cgcaggcggc   20160
tgcgggcgtc gctggtgtga tcaagatggt catggcgatg cggcacgggg agctgccgcg   20220
cacgttgcac gtgacgagc cgaattcgca cgtggactgg tcggctggtg cggtccgact   20280
cctgaccgag aacatccgct ggccagggac gggtacgcgc cgcgctggag tgtcgtcgtt   20340
cggggtaagc ggtaccaacg cacacgtcat cctcgaacac acccgctcg ccgtgaccga   20400 gaacgaggaa gcagcgcagt ccccagcacc tgggatcgtg ccctgggcgt tgtccgggcg   20460
gtcgtcgacg gcgctgcggg cccaggccga acggctgcgc gagctgtgcg agcagaccga   20520
tcccgacccc gtcgatgtcg gtttctcact ggccgccacg cgcacggctt gggagcaccg   20580
agcggtggtg cttggtcggg acagcgctac gttgcgctcc gggcttggcg ttgttgccag   20640
cggtgaacca gcggtcgatg tcgttgaggg gagcgtcctg gacggcgagg tcgtcttcgt   20700
cttccccggt cagggctggc agtgggccgg tatggcagtc gacctgctgg acgcttcgcc   20760
gacgttcgcg cgccacatgg acgagtgcgc caccgcgctg cggaggtacg tggactggtc   20820
gttggtcgac gtgctgcgcg gagcggagaa ctccccaccg ctggaccggg tggacgtgct   20880
ccagcccgcg tccttcgcgg tgatggtgtc gctcgccgag gtgtggcgtt cctacggggt   20940
gaggccggcg gccgtcgtcg gccacagtca aggcgaaatc gccgcggcct gcgcagccgg   21000
ggtgctgccg ctggaggatg cggccaggct tgtcgcattg cgcagcagag cgttgaaggg   21060
actttcgggg cggggtggca tggcgtcgct ggcctgccct gcggatgagg tcgcggcatt   21120
gttcgcggga tcgggcggcc gtctggaagt tgcggcgatc aacggcccgc gatcggtcgt   21180
ggtgtccggc gatctggaag cggtggacga actgctggca gagtgcgctg aaaaggacat   21240
gcgtgcacgc cgtatccccg tcgactacgc ctcgcattca gcgcacgtgg aggtggttcg   21300
gagcccggtg ctggcggccg ccgccggggt gcgacaccgg gacggccagg tgccgtggtg   21360
gtcgacggta atcggcgact gggtggatcc ggccaggctg gacggcgagt attggtatcg   21420
gaacctccgg cagccggtcc ggttcgaaca cgccgtgcag ggcctggtcg agcggggatt   21480
cggcctgttc atcgaaatga gtgcgcatcc ggtgctgacc acggcggtcg aggaaaccgg   21540
tgcggagtcg gagaccgccg tggccgcggt aggtaccttg cgacgtgact cgggcggcct   21600
ccggaggttg ttgcattcgc tggccgaggc gtacgtgcgc ggcgccaccg tggactgggc   21660
```

```
cgtggcgttc gggggcgcgg gccgacggct ggacctgccg acctacccgt tccagcgcca   21720
gcggtactgg ctggacaagg gagctgcctc cgacgaggct cgtgcggtct cggacccggc   21780
ggcgggctgg ttctggcaag ccgtggcgcg ccaagacctg aaaagcgtgt ccgatgccct   21840
cgatctcgac gccgacgcac cgctgagcgc aacacttcca gccctgtccg tctggcaccg   21900
tcaggaacga gaaagggtct tggcagacgg ttggcggtac cgagtcgact gggtacgggt   21960
ggccccgcag ccggtccgga gaacgcggga aacctggctc ctggtcgttc ccccgggcgg   22020
catcgaggaa gcgctggtcg aacggctgac ggatgcgttg aacacgcgag ggatcagcac   22080
cctgcgcctc gacgtgccac cggcggcgac cagtggcgaa ctcgcaaccg aactccgcgc   22140
cgcagccgac ggtgacccgg tgaaggcaat cctgtcgctc accgcgttgg acgagcgacc   22200
ccaccccgaa tgcaaggacg tcccgagcgg gattgccttg ctgctgaacc tggtcaaggc   22260
gctcggtgaa gccgacctca gaattcctct gtggaccatc acgcgtggtg cggtcaaggc   22320
aggccccgca gatcggctgc tgcgcccgat gcaggcgcaa gcatgggtc tggggcgagt   22380
agccgcactc gaacaccccg agcgctgggg tgggctgatc gacctgccgg attcgctgga   22440
cggcgacgtc ctcacgaggc tgggcgaagc gctcaccaac ggcttggcgg aagaccaact   22500
ggcgattcgc cagtcgggcg tgctggcccg gcgactggta cccgccccgg cgaatcagcc   22560
cgctggacgt aagtggcgcc cccgagggag gcgctgatc acgggcggac tcggcgcggt   22620
gggcgcacag gtggcgaggt ggttggccga aatcggagcc gagcgaatcg tgctcaccag   22680
tcgacgggc aaccaagcag caggcgccgc cgagctggaa gccgaactcc gggcccttgg   22740
agcgcaagtg tccatcgtgg cttgcgacgt gaccgatcgt gccgagatgt ccgcactact   22800
ggccgagttc gacgtcaccg cggtgttcca cgcggccgga gtcggtcggc tgctgccgtt   22860
ggcggagacc gaccagaacg gcctggccga aatatgcgcg gcgaaggtcc gcggcgctca   22920
ggtgctggac gaactgtgcg acagcaccga tctcgatgcc ttcgtcctgt tctcctcggg   22980
tgccggggta tggggcgggg gcggtcaggg cgcttacggc gcggcgaacg cattcttgga   23040
cacactcgcc gaacaacgcc gagcacgcgg tctgccggca acctcgatct cctggggcag   23100
ttgggccggc ggcggcatgg ccgacggcgc ggcgggcgaa cacctgcggc gacgcgggat   23160
acgtccgatg ccggcggcgt cggccatcct ggctctgcag gaagtacttg accaggatga   23220
gacgtgcgtg tcgatcgctg atgtggactg ggaccgattc gttcccacgt tcgccgcgac   23280
tcgcgccacc cggttgttcg acgaagtgcc ggcggcgaga aaggcgatgc ccgcgaatgg   23340
gccggcagaa ccaggcggct cgccgttcgc ccgcaatctc gcggagctgc cggaagccca   23400
acgacgccac gaactggtgg atctggtgtg cgcccaggtg gcaaccgtgc tcgggcacgg   23460
cagtcgcgag gaagtccagc ccgagcgggc gttccgcgcg ctcgggttcg actccctcat   23520
ggcggtggat ctgcgcaatc gtttgaccac cgccaccggg ttgcgcctgc cgaccacaac   23580
cgtcttcgac tacccgaatc cggccgcctt ggccgctcac ctgctcgagg agctggtggg   23640
tgatgtcgcg tcggctgcgg tgaccgctgc cagcgcgccc gcgagtgacg aaccgatcgc   23700
gatcgtcgcg atgagctgcc ggtttccggg tggcgcgcac tcgccggaag acctgtggcg   23760
gctggtcgcc gccggcacgg aggtgatcgg cgagttcccc tccgacccgg gctgggatgc   23820
ggaaggcctt tacgatccgg atgcttccag gcctggaacg acgtatgcgc ggatggcggg   23880
attcctctac gacgccggtg agttcgatgc cgacctgttc ggcatcagcc cacgtgaggc   23940
gttggcgatg gatccgcagc agcggttggt gctcgaaatc gcctgggaag ccctcgaacg   24000
```

```
ggccggaatc gatccgttgt ccttgaaggg cagtggggtc ggcacgtaca tcggcgctgg   24060
aagccgtggg tacgcgacgg atgtgcggca gtttcccgag gaggcggagg gctacctgct   24120
gacgggtacc tcggccagtg tgctgtcggg tcgggtcgcg tattcgtttg gtttcgaggg   24180
tcctgcggtg acggtggata cggcttgttc gtcgtcgttg gtggcgttgc atctggcgtg   24240
ccagtcgttg cgttcgggcg agtgtgatct ggcgttggcc ggtggtgtga ccgtgatgtc   24300
gacgccggag atgttcgtgg agttctcccg tcagcgcggt ttggcgccgg atgggcggtg   24360
caagtcgttc gcggagagcg cggacggcac cggctgggc gaaggcgcgg gcctgttgtt    24420
gctggagcgg ttgtcggacg cccaccggaa tgggcatcgg gtgttggcgg tggttcgtgg   24480
gtcagcggtg aatcaggacg gcgcctcgaa cggactggcg gcgccgaacg gtccgtcgca   24540 gcagcggtg atcaaccagg cactcgcgaa tgcggctctt tcggcgtccg atgtggatgc    24600
ggtggaggca catggcaccg ggaccaggct gggtgatccg atcgaggcgc aggcattgat   24660
cgcaacgtat gggcaggccc gggagcggga tcggcccttg tggctggggt cggtcaagtc   24720
gaacatcggt catacgcagg ccgcggcggg tgttgccggt gtgatcaaga tggtgatggc   24780
catgcggcac gggcagctgc ccgcctcgct gcacgcggat gagcccacgt cggaggtcga   24840
ttggtcgtcg ggggcggtcc ggctcctcgc cgaacaggta ccttggccgg agtctgaccg   24900
tgttcgtcgg gtgggggttt cgtcgttcgg gatcagcggc accaacgcac atgtgatcct   24960
cgaacaagct acgaatgcgc cagatagtac agcggagacg gacaaaacag aatccggatc   25020
tactgtcgat attccggtcg ttccctggtt ggtgtcggga aagacgacgg attccctgcg   25080
gggacaagcc gaacgagtct tgtctcaggt cgagtcccgg ccgagcagc gttcgctgga    25140 tgttgcctac tcgcttgctt ctggccgagc cgcgctggat gaacgcgctg tcgtgctggg   25200
tgcggaccgc ggtgagctgg ttgctggact ggcggcgttg gccgccggtc aggaggcttc   25260
tggggtgatc agcggaactc gtgcttctgc tcggttcggg ttcgtgttct cggggcaggg   25320
tggtcagtgg ttggggatgg gcagagcgct ctactcgaag tttccggtgt tcgctgctgc   25380
gtttgatgag gcttgcgccg agttggaggc acatctgggg gaagaccgcc gggttcggga   25440
tgtggtcttc ggttccgatg cgcagctgct ggatcagacg ctgtgggcgc agtcgggtct   25500
gttcgcgctg caagccggcc tcttggggct gctgggttcg tggggcgttc ggccggatgt   25560
ggtgatgggg cattcggtcg gggagttggc cgccgcgttt gcggctggcg tgttgtcgtt   25620
gcgggatgcg gctcggttgg tggccgcgcg cgcccggttg atgcaagccc tgccctctga   25680
cggcgcgatg ttggcggtgg ctgctggtga agaccttgtt cggccattgc tggccggtcg   25740
ggaggagtcc gtgagcgtcg ccgcgctcaa tgcccccggt tcggtggtgt tgtcgggcga   25800 tcggaggtg ctggccagca tcgtcggccg gctgaccgag ctccgagtcc ggacgcggcg    25860
cttgcgggtc tcccatgctt ttcattcgca ccggatggac ccgatgttgg gcgagttcgc   25920
ccagatcgcc gagtctgcgg agttcggtaa gccaacgaca ccgcttgtgt cgacgttgac   25980
gggtgagctc gacagagccg cggaaatgag cacaccaggg tattgggtgc gccaggcgcg   26040
tgaacccgtc cgtttcgccg acggtgtcca ggccctggca gcgcagggca taggcacggt   26100
cgtcgagctc ggcccggacg gaacgctggc ggcactggtt cggagtgtg cgaccgagtc    26160 cgatcgggtt gggcggattt cgtcgatccc actgatgcgc agggagcggg acgagacccg   26220
ttcggtgatg acagccctgg cgcatctcca cacccgtggt ggtgaggtgg actggcaggc   26280
gtttttcgcc ggtaccggcg ctaggcagct cgagttgcca acgtatgcct tccaacgaca   26340
gcactactgg atcgagtcca gtgcgcggcc agcacgcgac cgcgcagaca tcggcgaggt   26400
```

```
ggcggaacag ttctggaccg cggttgacca aggcgatctg caacgttgg tcgccgctct   26460 ggatcttggg gcggacgacg acacatgcgc atcgttgagc gatgtattgc cggcgttgtc   26520
ctcctggcga agcggactcc gcaaccgttc gctcgtcgat tcctgccggt accgaatcag   26580
ttggcattcc tctcgggagg tgccggcccc gaagatttcc ggtacctggc tgttggtcgt   26640
gcccggtgct gcggatgacg gattggtcac ggctttgacg agttcactgg tcggaggcgg   26700
cgccgaggtc gtccggatcg gcctgtccga agaggacccg caccgcgagg acgtcgcaca   26760
gcggctggcc aatgcgctga cggatgccgg tcaactcggt ggcgtgcttt cgctgttggg   26820
gctcgatgaa tcgcctgctc cgggattctc ctgcttgcca actggtttcg cgctgactgt   26880
gcagcttctg cgggccttgc ggaaggccga cgtcgaggcg cctttttggg cggtgacgcg   26940
cggcggcgtc gcgttggaag atgtacgcgt gtctccggag caggccctgg tctgggggct   27000
gctgcgtgtc gcgggactgg agcacccgga gttctggggt ggcttgatcg acctgccatc   27060
ggactgggac gaccgattgg gtgcccggtt ggcgggtgtg ttggcggatg gtggcgagga   27120
tcaagtcgcc attcgccgtg gtggtgtgtt cgtgcggcgg ttggaacgcg ctggtgcgtc   27180
gggtgccggg tcgtgtggc gtcctcgggg acggtgttg gtgacgggtg gtacgggcgg   27240
tttgggggcg catgttgccc ggtggttggc cggtgccggg gctgagcacg tggtgttgac   27300
cagccgtcga ggagcggacg ctccgggcgc tggggaattg cgggcggagc tggaggcgct   27360
gggtgctcgg gtgtcgattg tgccctgcga cgtggctgat cgtgacgcag tggctggagt   27420
gttggcaggg atcggtgggg agtgtccgct gactgcggtg gtacacgccg ccggggtcgg   27480
cgaggcgggc gacgtagtgg agatgggttt ggcggatttt gcagcggtgt tgtcggcgaa   27540
ggtgcgtggt gcggcgaatc tggacgagtt gctggccgac tcggagctgg atgcgtttgt   27600
gatgttctcc tcggtgtcgg gggtgtgggg agccggcgga cagggtgcgt atgcggctgc   27660
gaacgcctac ttggatgcgt tggccgagca gcgtcgggcg aggggattgg tcgggaccgc   27720
ggttgcgtgg ggaccgtggg ccggtgacgg catggccgcc ggcgaaaccg gcgcacagct   27780
gcaccggatg ggcctggcgt cgatggaacc gagcgcggcg ctgctggcac ttcagggtgc   27840
attggaccgc gatgagacct ccctcgtcgt ggccgatgtc gattgggcac ggttcgcccc   27900
agccttcacc tcggcacgtc gacgcccgct gctggacacc atcgacgagg cccgagccgc   27960
attgaaaacc accggcgaac aagcgggcac aggcaaaccc gttgagctga cgcaacgcct   28020
ggccggactg tcgcggaagg aacgcgacga tgcggtattg gatctggtgc gggcggagac   28080
ggcggctgtg ctgggacgcg acgatgccac ggccctggcg ccatcgcggc cgttccagga   28140
actcggattc gactccttga tggcggtgga gctgcgcaac cggctgaaca ccgccaccgg   28200
gatccagctg cccgccagca cgattttcga ctaccccaat gccgagtcgc tgtcgcgtca   28260
cctctgcgcc gagcttttcc aacggagac taccgtggac tcggcccttg ccgagctcga   28320
tcgaatcgag cagcagctct cgatgctcac cggcgaagcg cgggcacggg accgaatcgc   28380
gacacgactg cgagccctcc acgagaagtg gaacagcgca gctgaagtac cgaccggagc   28440
cgatgtcctg agcacgctcg attcggcgac gcacgacgag atattcgagt tcatcgacaa   28500
cgagctcgac ctgtcctgag cagttcctgc ggaacttcaa gcgccgaaat cgggtggaaa   28560
tcacaatggc caatgaagaa aagctcttcg gctatctgaa gaaggtaact gcggacctgc   28620
atcagacccg gcagcgcctg ctcgcggccg agagccggag tcaggagccg atcgcgatcg   28680
tctcggcgag ctgccgactg cccggcggcg tcgactctcc cgaagcgctc tggcaactcg   28740
```

-continued

```
tgcgcactgg caccgacgcc atctcggagt tccccgccga ccggggctgg gatctcggcc    28800
ggttgtacga tcccgacccg aaccaccagg gaacgtcgta cacgcgggcc ggcggtttcc    28860
tcgcaggagc gggcgatttc gaccccgcca tgttcgggat ttcgccgcgt gaggcgttgg    28920
cgatggaccc gcagcaacgg ttgttgctgg agctgtcctg ggaggccctc gaacgggcgg    28980
gcatagaccc gacatccctg cgcggcagca agaccggtgt cttcggtggt gtcacgcccc    29040
aggagtacgg gccgtccttg caggagatga gccgaaacgc tgggggtttt ggactcaccg    29100
ggcggatggt gagtgtggcg tcgggtcggg ttgcgtattc gtttggtttt gagggtcctg    29160
cggtgacggt ggatacgcgc tgttcgtcgt cgttggtggc cctgcatttg gcgtgtcagt    29220
cgttgcgttc cggcgaatgc gatctcgcgc tggccggcgg tgtgacggtg atggcgacac    29280
cggcgacgtt cgtggagttc tcccgtcagc gtggtttggc tccggacggg cggtgcaagt    29340
cgttcgcggc tgccgcggat ggcaccgggt gggggtgaggg tgccggtctg gtgttgctgg    29400
agcggttgtc ggatgcgcgg cggaatgggc acgaggttct ggcggtggtg cggggtagcg    29460
cggtgaacca ggacggcgcg tcgaatggtt tgactgcgcc gaatggtccg tcgcagcagc    29520
gggtgatcac ccaggcgttg gcgagtgcgg ggctgtcggt ttccgatgtg gatgcggtcg    29580
aggcacatgg gaccgggacc acgttgggtg atccgatcga ggcacaggcc ctgatcgcca    29640
cgtacgggca gggccgggag aaggatcggc cgttgtggtt ggggtcggtc aagtccaaca    29700
tcggtcacac gcaggcggcc gctggcgttg ccggcgtcat caagatggtc ttggcgatgc    29760
ggcacgggca gctgcccgcc acgttgcatg tggatgagcc cacgtcggcg gtggactggt    29820
cggcgggttc ggtccggctt ctcacggaga acacgccctg gccggacagt ggtcgtcctt    29880
gccgggtggg ggtgtcgtcg ttcgggatca gcggcaccaa cgcacatgtg attctcgaac    29940
agtctccagt cgagcagggc gaaccggccg ggccggtcga aggcgagcgg gaaccggatg    30000
tagccgtccc cgtggtgcct tgggtgctgt cgggtaagac accggaggct gcgcgggcgc    30060
aggccgaacg ggtgcattcg catatcgagg accggccggg gctgtcgccg gtggatgtgg    30120
cgtattcgct aggaatgaca cgcgcggcgc tggatgaacg cgcagtggtg ttgggctcgg    30180
accgtgccgc gctcctgacc gggttgaggg cattcgccga cggctgcgat gcgcccgaag    30240
tggtttcggg gtctgtgggg cttggtggcc gcgtcgggtt cgtgttctcg ggtcagggtg    30300
gtcagtggcc ggggatgggc cgggggctct actcggtgtt tccggtgttc gccgacgcgt    30360
tcgacgaggc ttgcgcggag ttggatgcac acctgggcca ggaactgcgg gttcgggatg    30420
tggtgttcgg ttcgcaagcg tggttgctgg atcggacggt gtgggcgcag tcgggttttgt    30480 tcgcgttgca gattggcttg ctgcggctgc tggggttcgtg gggtgttcgg ccggatgtgg    30540
tgttgggcca ctcggtgggt gagctggctg cggtgcatgc ggctggtgtg ttgtcgttgt    30600
cggaggccgc gcggttggtg gcgggtcgcg cccggttgat gcaggcgttg ccttctggtg    30660
gtgccatgct cgcggtcgct acgggtgagt ttcaggtcga tcctctgctg gatggggtgc    30720
gggaccggat cggtatcgcg gcggtgaatg gcccggaatc ggttgtgctc tctggtgacc    30780
gcgagctgct caccgagatc gctgatcggt tgcacgatca ggggtgccgg acccggtggt    30840
tgcgggtgtc gcatgctttc cattcgcccc atatggagcc gatgctggag gagttcgccc    30900
agatctcccg aggccgcgaa tatcacgcac cggaactgcc gatcatctcg accctgatcg    30960
gtgagctgga cggtggtcga gtgatgggca ctcccgagta ctgggtgcgt caggtgcgtg    31020
agcccgtccg tttcgccgag ggtgtccagg cgcttgtcgg tcagggtgtc ggcacgattg    31080
tcgaattggg tccggacggg gcgttgtcga cgttggtcga ggagtgtgtg gcggaatccg    31140
```

```
ggcgggtggc cgggatcccg ctgatgcgca aggaccgcga cgaggcgcga accgtgctgg    31200
cagctttggc gcagatccac acccgtggtg gtgaggtgga ctggcggtcg tttttcgccg    31260
gtaccggggc gaagcaagtc gacctgccca cctacgcctt ccagcggcag cggtactggc    31320
tggcatccac cgggcgtgcg ggtgacgtga ccgccgccgg attggccgag gcggaccatc    31380
cgctgctcgg tgcggtggtt gcgttggcag acggcgaagg tgtggtgctg accggtcggt    31440
tgacagcggg ttcgcatccg tggttgtccg atcaccgggt gctgggcgaa atcgtcgtcc    31500
ccggcaccgc gatcgtcgag ctggtgtggc acgtcggcga gcgcctcggt tgtggccggg    31560
tggaagaact ggctttggaa gcgcccctga tcctgccgga tcatggagcg gtccaggttc    31620
aggtgctggt gggaccgccc ggggaatccg agcccggtc ggtggcgctc tactcctgtc    31680
ctggcgaggc gatcgaaccc gagtggaaga agcacgcgac gggcgtgctt ctcccacccg    31740
tggccgccga gaaccatgag ctgaccgcat ggccccgga gaatgcgacc gaaatcgatg    31800 cagacgggg ctacgcattc cttgaagggc acggtttcgc gtacgaccg gcctttagat    31860 gtctgcgcgg tgcctggcga cgaggcgggg aggtgttcgc cgaagtcgca ttgccggatg    31920
acatgcaggc ggggtcgat cgattcggcg tccacccgc gttgctggac gcggttctgc    31980
atgccgccgc agccgagacg tcggtggtcc agagcgaagc gcgggtgccg ttctcgtggc    32040
gtggggtgga acttcgcgcc actgaaagcg cggtggtgcg ggcgcgcctc tcgttgactt    32100
cggatgacga actgtcgttg gtcgcagtgg accggctgg ccgattcgtg gccacggttg    32160
attcgctggt gacccgaccg atctcccggc agcaggtgag gtctggcgcg atcggtgatt    32220
gcctgttcga ggtggagtgg caccggaagg cgttgttggg aacaaccgcc ggcgacgacc    32280
ttgccatcgt cggtgacggt cccagttggc cggaatcggt gcgcgcaacc gcacggttcg    32340
cgaccctgga tgagttccgt gcggccgtgg actcggacgt tcctgccccg ggttcggtgt    32400
tggtcgcagc tatgtcggcc gaagaggtcg agggtggatc cctgccgtcg cgcgcccaag    32460
agtcgacctc cgatctgctg gctctcgtgc agtcgtggct tgcggacgag cggttcgccg    32520
aatcccagct cgtggtcgtc acgcgtgcag cggtgtcggc cgactcggat tcggacgtcg    32580
cggacctggt gggtgcgtcg tcgtgggggt gtttgagttc agcccagtcg gagaacccgg    32640
gtcgcttcgt gctggtggac gtggacggca cacctgagtc gtggcaggcg ttgccggccg    32700
ccgtgcgagc aggagaaccg cagctggcac ttcggcgcgg cgtggcgctg tgcctcggt    32760 tggcgcgact cacggtgcgc gaggagggct cctcccgca actcgacacg gacgggaccg    32820
tcctcatcac gggtggcacc ggtgcgttgg ggggagtggt tgcccgtcac ctggtggagg    32880
agcacgggat tcggcgtttg gtgttggcag gccggcgtgg ctggaatgcg cctggagtcc    32940
acgagttggt ggatgagctg gcgcgcgcgg gcgccgtggt tgaggtggtg gcttgcgatg    33000
tggctgaccg caccgatctg gagcacgtgc tggccgccat tccggtcgac tggccgctgc    33060 ggggggatcgt gcataccgct ggggtgctgg ccgacggagt gatc                   33104
```

<210> SEQ ID NO 19
<211> LENGTH: 33489
<212> TYPE: DNA
<213> ORGANISM: Saccharopolyspora spinosa

<400> SEQUENCE: 19

```
gatcccgacc ccgtcgatgt cggttttctca ctggccgcca cgcgcacggc ttgggagcac      60
cgagcggtgg tgcttggtcg ggacagcgct acgttgcgct ccgggcttgg cgttgttgcc     120
```

```
agcggtgaac cagcggtcga tgtcgttgag gggagcgtcc tggacggcga ggtcgtcttc    180
gtcttccccg gtcagggctg gcagtgggcc ggtatggcag tcgacctgct ggacgcttcg    240
ccgacgttcg cgcgccacat ggacgagtgc gccaccgcgc tgcggaggta cgtggactgg    300
tcgttggtcg acgtgctgcg cggagcggag aactccccac cgctggaccg ggtggacgtg    360
ctccagcccg cgtccttcgc ggtgatggtg tcgctcgccg aggtgtggcg ttcctacggg    420
gtgaggccgg cggccgtcgt cggccacagt caaggcgaaa tcgccgcggc ctgcgcagcc    480
ggggtgctgc cgctggagga tgcggccagg cttgtcgcat tgcgcagcag agcgttgaag    540
ggactttcgg ggcggggtgg catgcgtcg ctggcctgcc ctgcggatga ggtcgcggca    600
ttgttcgcgg atcgggcgg ccgtctggaa gttgcggcga tcaacggccc gcgatcggtc    660
gtggtgtccg gcgatctgga agcggtggac gaactgctgg cagagtgcgc tgaaaaggac    720
atgcgtgcac gccgtatccc cgtcgactac gcctcgcatt cagcgcacgt ggaggtggtt    780
cggagcccgg tgctggcggc cgccgccggg gtgcgacacc gggacggcca ggtgccgtgg    840
tggtcgacgg tgatcggcga ctgggtggat ccggccaggc tggacggcga gtattggtat    900
cggaacctcc ggcagccggt ccggttcgaa cacgccgtgc agggcctggt cgagcgggga    960
ttcggcctgt tcatcgaaat gagtgcgcat ccggtgctga ccacggcggt cgaggaaacc   1020
ggtgcggagt cggagaccgc cgtggccgcg gtaggtacct tgcgacgtga ctcgggcggc   1080
ctccggaggt tgttgcattc gctggccgag gcgtacgtgc gcggcgccac cgtggactgg   1140
gccgtggcgt cgggggcgc gggccgacgg ctggacctgc cgacctaccc gttccagcgc   1200
cagcggtact ggctggacaa gggagctgcc tccgacgagg ctcgtgcggt ctcggacccg   1260
gcggcgggct ggttctggca agccgtggcg cgccaagacc tgaaaagcgt gtccgatgcc   1320
ctcgatctcg acgccgacgc accgctgagc gcaacacttc cagccctgtc cgtctggcac   1380
cgtcaggaac gagaaagggt cttggcagac ggttggcggt accgagtcga ctgggtacgg   1440
gtggccccgc agccggtccg gagaacgcgg gaaacctggc tcctggtcgt tcccccgggc   1500
ggcatcgagg aagcgctggt cgaacggctg acggatgcgt tgaacacgcg agggatcagc   1560
accctgcgcc tcgacgtgcc accggcggcg accagtggcg aactcgcaac cgaactccgc   1620
gccgcagccg acggtgaccc ggtgaaggca atcctgtcgc tcaccgcgtt ggacgagcga   1680 ccccacccccg aatgcaagga cgtcccgagc gggattgcct tgctgctgaa cctggtcaag   1740
gcgctcggtg aagccgacct cagaattcct ctgtggacca tcacgcgtgg tgcggtcaag   1800
gcaggccccg cagatcggct gctgcgcccg atgcaggcgc aagcatgggg tctgggcga   1860 gtagccgcac tcgaacaccc cgagcgctgg ggtgggctga tcgacctgcc ggattcgctg   1920
gacggcgacg tcctcacgag gctgggcgaa gcgctcacca acggcttggc ggaagaccaa   1980
ctggcgattc gccagtcggg cgtgctggcc cggcgactgg tacccgcccc ggcgaatcag   2040
cccgctggac gtaagtggcg ccccccgaggg agcgcgctga tcacgggcgg actcggcgcg   2100
gtgggcgcac aggtggcgag gtggttggcc gaaatcggag ccgagcgaat cgtgctcacc   2160
agtcgacggg gcaaccaagc agcaggcgcc gccgagctgg aagccgaact ccgggccctt   2220
ggagcgcaag tgtccatcgt ggcttgcgac gtgaccgatc gtgccgagat gtccgcacta   2280
ctggccgagt tcgacgtcac cgcggtgttc cacgcggccg agtcggtcg gctgctgccg   2340 ttggcggaga ccgaccagaa cggcctggcc gaaatatgcg cggcgaaggt ccgcggcgct   2400
caggtgctga cgaactgtg cgacagcacc gatctcgatg ccttcgtcct gttctcctcg   2460
ggtgccgggg tatgggcgg gggcggtcag ggcgcttacg gcgcggcgaa cgcattcttg   2520
```

```
gacacactcg ccgaacaacg ccgagcacgc ggtctgccgg caacctcgat ctcctggggc    2580
agttgggccg gcggcggcat ggccgacggc gcggcgggcg aacacctgcg gcgacgcggg    2640
atacgtccga tgccggcggc gtcggccatc ctggctctgc aggaagtact tgaccaggat    2700
gagacgtgcg tgtcgatcgc tgatgtggac tgggaccgat tcgttcccac gttcgccgcg    2760
actcgcgcca cccggttgtt cgacgaagtg ccggcggcga aaaggcgat gcccgcgaat    2820 gggccggcag aaccaggcgg ctcgccgttc gcccgcaatc tcgcggagct gccggaagcc    2880
caacgacgcc acgaactggt ggatctggtg tgcgcccagg tggcaaccgt gctcgggcac    2940
ggcagtcgcg aggaagtcca gcccgagcgg gcgttccgcg cgctcgggtt cgactccctc    3000
atggcggtgg atctgcgcaa tcgtttgacc accgccaccg ggttgcgcct gccgaccaca    3060
accgtcttcg actacccgaa tccggccgcc ttggccgctc acctgctcga ggagctggtg    3120
ggtgatgtcg cgtcggctgc ggtgaccgct gccagcgcgc ccgcgagtga cgaaccgatc    3180
gcgatcgtcg cgatgagctg ccggtttccg ggtggcgcgc actcgccgga agacctgtgg    3240
cggctggtcg ccgccggcac ggaggtgatc ggcgagttcc cctccgaccg gggctgggat    3300
gcggaaggcc tttacgatcc ggatgcttcc aggcctggaa cgacgtatgc gcggatggcg    3360
ggattcctct acgacgccgg tgagttcgat gccgacctgt tcggcatcag cccacgtgag    3420
gcgttggcga tggatccgca gcagcggttg gtgctcgaaa tcgcctggga agccctcgaa    3480
cgggccggaa tcgatccgtt gtccttgaag gcagtgggg tcggcacgta catcggcgct    3540
ggaagccgtg ggtacgcgac ggatgtgcgg cagtttcccg aggaggcgga gggctacctg    3600
ctgacgggta cctcggccag tgtgctgtcg ggtcgggtcg cgtattcgtt tggtttcgag    3660
ggtcctgcgg tgacggtgga tacggcttgt tcgtcgtcgt tggtggcgtt gcatctggcg    3720
tgccagtcgt tgcgttcggg cgagtgtgat ctggcgttgg ccggtggtgt gaccgtgatg    3780
tcgacgccgg agatgttcgt ggagttctcc cgtcagcgcg gtttggcgcc ggatgggcgg    3840
tgcaagtcgt tcgcggagag cgcggacggc accggctggg gcgaaggcgc gggcctgttg    3900
ttgctggagc ggttgtcgga cgcccaccgg aatgggcatc gggtgttggc ggtggttcgt    3960
gggtcagcgg tgaatcagga cggcgcctcg aacggactgg cggcgccgaa cggtccgtcg    4020
cagcagcggg tgatcaacca ggcactcgcg aatgcggctc tttcggcgtc cgatgtggat    4080
gcggtggagg cacatggcac cgggaccagg ctgggtgatc cgatcgaggc gcaggcattg    4140
atcgcaacgt atgggcaggc ccgggagcgg gatcggccct tgtggctggg gtcggtcaag    4200
tcgaacatcg tcatacgca ggccgcggcg ggtgttgccg gtgtgatcaa gatggtgatg    4260
gccatgcggc acgggcagct gcccgcctcg ctgcacgcgg atgagcccac gtcggaggtc    4320
gattggtcgt cggggcggt ccggctcctc gccgaacagg taccttggcc ggagtctgac    4380
cgtgttcgtc gggtgggggt ttcgtcgttc gggatcagcg gcaccaacgc acatgtgatc    4440
ctcgaacaag ctacgaatgc gccagatagt acagcggaga cggacaaaac agaatccgga    4500
tctactgtcg atattccggt cgttccctgg ttggtgtcgg aaagacgac ggattccctg    4560 cggggacaag ccgaacgagt cttgtctcag gtcgagtccc ggccggagca gcgttcgctg    4620
gatgttgcct actcgcttgc ttctggccga ccgcgctgg atgaacgcgc tgtcgtgctg    4680
ggtgcggacc gcggtgagct ggttgctgga ctggcggcgt tggccgccgg tcaggaggct    4740
tctggggtga tcagcggaac tcgtgcttct gctcggttcg ggttcgtgtt ctcggggcag    4800
ggtggtcagt ggttggggat gggcagagcg ctctactcga agtttccggt gttcgctgct    4860
```

```
gcgtttgatg aggcttgcgc cgagttggag gcacatctgg gggaagaccg ccgggttcgg    4920
gatgtggtct tcggttccga tgcgcagctg ctggatcaga cgctgtgggc gcagtcgggt    4980
ctgttcgcgc tgcaagccgg cctcttgggg ctgctgggtt cgtggggcgt tcggccggat    5040
gtggtgatgg ggcattcggt cggggagttg gccgccgcgt ttgcggctgg cgtgttgtcg    5100
ttgcgggatg cggctcggtt ggtggccgcg cgcgcccggt tgatgcaagc cctgccctct    5160
gacggcgcga tgttggcggt ggctgctggt gaagaccttg ttcggccatt gctggccggt    5220
cgggaggagt ccgtgagcgt cgccgcgctc aatgccccg gttcggtggt gttgtcgggc     5280
gatcgggagg tgctggccag catcgtcggc cggctgaccg agctccgagt ccggacgcgg    5340
cgcttgcggg tctcccatgc tttcattcg caccggatgg acccgatgtt gggcgagttc     5400
gcccagatcg ccgagtctgc ggagttcggt aagccaacga caccgcttgt gtcgacgttg    5460
acgggtgagc tcgacagagc cgcggaaatg agcacaccag ggtattgggt gcgccaggcg    5520
cgtgaacccg tccgtttcgc cgacggtgtc caggccctgg cagcgcaggg cataggcacg    5580
gtcgtcgagc tcggcccgga cggaacgctg gcggcactgg ttcgggagtg tgcgaccgag    5640
tccgatcggg ttgggcggat ttcgtcgatc ccactgatgc gcaggagcg ggacgagacc     5700
cgttcggtga tgacagccct ggcgcatctc cacacccgtg gtggtgaggt ggactggcag    5760
gcgttttcg ccggtaccgg cgctaggcag ctcgagttgc caacgtatgc cttccaacga     5820
cagcactact ggatcgagtc cagtgcgcgg ccagcacgcg accgcgcaga catcggcgag    5880
gtggcggaac agttctggac cgcggttgac caaggcgatc tggcaacgtt ggtcgccgct    5940
ctggatcttg gggcggacga cgacacatgc gcatcgttga gcgatgtatt gccggcgttg    6000
tcctcctggc gaagcggact ccgcaaccgt cgctcgtcg attcctgccg gtaccgaatc     6060
agttggcatt cctctcggga ggtgccggcc ccgaagattt ccggtacctg gctgttggtc    6120
gtgcccggtg ctgcggatga cggattggtc acggctttga cgagttcact ggtcggaggc    6180
ggcgccgagg tcgtccggat cggcctgtcc gaagaggacc cgcaccgcga ggacgtcgca    6240
cagcggctgg ccaatgcgct gacggatgcc ggtcaactcg gtggcgtgct ttcgctgttg    6300
gggctcgatg aatcgcctgc tccgggattc tcctgcttgc caactggttt cgcgctgact    6360
gtgcagcttc tgcgggcctt gcggaaggcc gacgtcgagg cgccttttg ggcggtgacg     6420
cgcggcggcg tcgcgttgga agatgtacgc gtgtctccgg agcaggccct ggtctggggg    6480
ctgctgcgtg tcgcgggact ggagcacccg gagttctggg gtggcttgat cgacctgcca    6540
tcggactggg acgaccgatt gggtgccggg ttggcgggtg tgttggcgga tggtggcgag    6600
gatcaagtcg ccattcgccg tggtggtgtg ttcgtgcggc ggttggaacg cgctggtgcg    6660
tcgggtgccg ggtcggtgtg gcgtcctcgg gggacggtgt tggtgacggg tggtacgggc    6720
ggtttggggg cgcatgttgc ccggtggttg gccggtgccg gggctgagca cgtggtgttg    6780
accagccgtc gaggagcgga cgctccgggc gctggggaat tgcggcgga gctgaggcg     6840
ctgggtgctc gggtgtcgat tgtgcccctgc gacgtggctg atcgtgacgc agtggctgga    6900
gtgttggcag ggatcggtgg ggagtgtccg ctgactgcgg tggtacacgc cgccggggtc    6960
ggcgaggcgg cgacgtagt ggagatgggt ttggcggatt ttgcagcggt gttgtcggcg     7020
aaggtgcgtg gtgcggcgaa tctggacgag ttgctggccg actcggagct ggatgcgttt    7080
gtgatgttct cctcggtgtc gggggtgtgg ggagccggcg acagggtgc gtatgcggct     7140
gcgaacgcct acttggatgc gttggccgag cagcgtcggg cgaggggatt ggtcgggacc    7200
gcggttgcgt ggggaccgtg ggccggtgac ggcatggccg ccggcgaaac cggcgcacag    7260
```

```
ctgcaccgga tgggcctggc gtcgatggaa ccgagcgcgg cgctgctggc acttcagggt    7320
gcattggacc gcgatgagac ctccctcgtc gtggccgatg tcgattgggc acggttcgcc    7380
ccagccttca cctcggcacg tcgacgcccg ctgctggaca ccatcgacga ggcccgagcc    7440
gcattggaaa ccaccggcga acaagcgggc acaggcaaac ccgttgagct gacgcaacgc    7500
ctggccggac tgtcgcggaa ggaacgcgac gatgcggtat tggatctggt gcgggcggag    7560
acggcggctg tgctgggacg cgacgatgcc acggccctgg cgccatcgcg gccgttccag    7620
gaactcggat tcgactcctt gatggcggtg gagctgcgca accggctgaa caccgccacc    7680
gggatccagc tgcccgccag cacgattttc gactacccca atgccgagtc gctgtcgcgt    7740
cacctctgcg ccgagctttt cccaacggag actaccgtgg actcggccct tgccgagctc    7800
gatcgaatcg agcagcagct ctcgatgctc accggcgaag cgcgggcacg ggaccgaatc    7860
gcgacacgac tgcgagccct ccacgagaag tggaacagcg cagctgaagt accgaccgga    7920
gccgatgtcc tgagcacgct cgattcggcg acgcacgacg agatattcga gttcatcgac    7980
aacgagctcg acctgtcctg agcagttcct gcggaacttc aagcgccgaa atcgggtgga    8040
aatcacaatg gccaatgaag aaaagctctt cggctatctg aagaaggtaa ctgcggacct    8100
gcatcagacc cggcagcgcc tgctcgcggc cgagagccgg agtcaggagc cgatcgcgat    8160
cgtctcggcg agctgccgac tgcccggcgg cgtcgactct cccgaagcgc tctggcaact    8220
cgtgcgcact ggcaccgacg ccatctcgga gttccccgcc gaccggggct gggatctcgg    8280
ccggttgtac gatcccgacc cgaaccacca gggaacgtcg tacacgcggg ccggcggttt    8340
cctcgcagga gcgggcgatt tcgaccccgc catgttcggg atttcgccgc gtgaggcgtt    8400
ggcgatggac ccgcagcaac ggttgttgct ggagctgtcc tgggaggccc tcgaacgggc    8460
gggcatagac ccgacatccc tgcgcggcag caagaccggt gtcttcggtg gtgtcacgcc    8520
ccaggagtac gggccgtcct tgcaggagat gagccgaaac gctgggggtt ttggactcac    8580
cgggcggatg gtgagtgtgg cgtcgggtcg ggttgcgtat tcgtttggtt ttgagggtcc    8640
tgcggtgacg gtggatacgg cgtgttcgtc gtcgttggtg gccctgcatt tggcgtgtca    8700
gtcgttgcgt tccggcgaat gcgatctcgc gctggccggc ggtgtgacgg tgatggcgac    8760
accggcgacg ttcgtggagt tctcccgtca gcgtggtttg gctccggacg ggcggtgcaa    8820
gtcgttcgcg gctgccgcgg atggcaccgg gtggggtgag ggtgccggtc tggtgttgct    8880
ggagcggttg tcggatgcgc ggcggaatgg gcacgaggtt ctggcggtgg tgcggggtag    8940
cgcggtgaac caggacggcg cgtcgaatgg tttgactgcg ccgaatgtc cgtcgcagca    9000 gcgggtgatc acccaggcgt tggcgagtgc ggggctgtcg gtttccgatg tggatgcggt    9060
cgaggcacat gggaccggga ccacgttggg tgatccgatc gaggcacagg ccctgatcgc    9120
cacgtacggg cagggccggg agaaggatcg gccgttgtgg ttggggtcgg tcaagtccaa    9180
catcggtcac acgcaggcgg ccgctggcgt tgccggcgtc atcaagatgg tcttggcgat    9240
gcggcacggg cagctgcccg ccacgttgca tgtggatgag cccacgtcgg cggtggactg    9300
gtcggcgggt tcggtccggc ttctcacgga gaacacgccc tggccggaca gtggtcgtcc    9360
ttgccgggtg ggggtgtcgt cgttcgggat cagcggcacc aacgcacatg tgattctcga    9420
acagtctcca gtcgagcagg gcgaaccggc cgggccggtc gaaggcgagc gggaaccgga    9480
tgtagccgtc cccgtggtgc cttgggtgct gtcgggtaag acaccggagg ctgcgcgggc    9540
gcaggccgaa cgggtgcatt cgcatatcga ggaccggccg gggctgtcgc cggtggatgt    9600
```

```
ggcgtattcg ctaggaatga cacgcgcggc gctggatgaa cgcgcagtgg tgttgggctc    9660
ggaccgtgcc gcgctcctga ccgggttgag ggcattcgcc gacggctgcg atgcgcccga    9720
agtggtttcg gggtctgtgg ggcttggtgg ccgcgtcggg ttcgtgttct cgggtcaggg    9780
tggtcagtgg ccggggatgg gccggggggct ctactcggtg tttccggtgt cgccgacgc    9840
gttcgacgag gcttgcgcgg agttggatgc acacctgggc caggaactgc gggttcggga    9900
tgtggtgttc ggttcgcaag cgtggttgct ggatcggacg gtgtgggcgc agtcgggttt    9960
gttcgcgttg cagattggct tgctgcggct gctgggttcg tggggtgttc ggccggatgt   10020
ggtgttgggg cactcggtgg gtgagctggc tgcggtgcat gcggctggtg tgttgtcgtt   10080
gtcggaggcc gcgcggttgg tggcgggtcg cgcccggttg atgcaggcgt tgccttctgg   10140
tggtgccatg ctcgcggtcg ctacgggtga gtttcaggtc gatcctctgc tggatggggt   10200
gcgggaccgg atcggtatcg cggcggtgaa tggcccggaa tcggttgtgc tctctggtga   10260
ccgcgagctg ctcaccgaga tcgctgatcg gttgcacgat caggggtgcc ggacccggtg   10320
gttgcgggtg tcgcatgctt tccattcgcc ccatatggag ccgatgctgg aggagttcgc   10380
ccagatctcc cgaggccgcg aatatcacgc accggaactg ccgatcatct cgaccctgat   10440
cggtgagctg acggtggtc gagtgatggg cactcccgag tactgggtgc gtcaggtgcg   10500
tgagcccgtc cgtttcgccg agggtgtcca ggcgcttgtc ggtcagggtg tcggcacgat   10560
tgtcgaattg ggtccggacg gggcgttgtc gacgttggtc gaggagtgtg tggcggaatc   10620
cgggcgggtg gccgggatcc cgctgatgcg caaggaccgc gacgaggcgc gaaccgtgct   10680
ggcagctttg gcgcagatcc acacccgtgg tggtgaggtg gactggcggt cgttttcgc   10740
cggtaccggg gcgaagcaag tcgacctgcc cacctacgcc ttccagcggc agcggtactg   10800
gctggcatcc accgggcgtg cgggtgacgt gaccgccgcc ggattggccg aggcggacca   10860
tccgctgctc ggtgcggtgg ttgcgttggc agacggcgaa ggtgtggtgc tgaccggtcg   10920
gttgacagcg ggttcgcatc cgtggttgtc cgatcaccgg gtgctgggcg aaatcgtcgt   10980
ccccggcacc gcgatcgtcg agctggtgtg gcacgtcggc gagcgcctcg gttgtggccg   11040
ggtggaagaa ctggctttgg aagcgcccct gatcctgccg gatcatggag cggtccaggt   11100
tcaggtgctg gtgggaccgc ccggggaatc cggagcccgg tcggtggcgc tctactcctg   11160
tcctggcgag gcgatcgaac ccgagtggaa gaagcacgcg acgggcgtgc ttctcccacc   11220
cgtggccgcc gagaaccatg agctgaccgc atggccccg gagaatgcga ccgaaatcga   11280
tgcagacggg gtctacgcat tccttgaagg gcacggtttc gcgtacggac cggcctttag   11340
atgtctgcgc ggtgcctggc gacgaggcgg ggaggtgttc gccgaagtcg cattgccgga   11400
tgacatgcag gcggggtcg atcgattcgg cgtccacccc gcgttgctgg acgcggttct   11460
gcatgccgcc gcagccgaga cgtcggtggt ccagagcgaa gcgcgggtgc cgttctcgtg   11520
gcgtggggtg gaacttcgcg ccactgaaag cgccggtggtg cgggcgcgcc tctcgttgac   11580
ttcggatgac gaactgtcgt tggtcgcagt ggacccggct ggccgattcg tggccacggt   11640
tgattcgctg gtgacccgac cgatctcccg gcagcaggtg aggtctggcg cgatcggtga   11700
ttgcctgttc gaggtggagt ggcaccggaa ggcgttgttg ggaacaaccg ccggcgacga   11760
ccttgccatc gtcggtgacg gtcccagttg gccggaatcg gtgcgcgcaa ccgcacggtt   11820
cgcgaccctg gatgagttcc gtgcggccgt ggactcggac gttcctgccc cgggttcggt   11880
gttggtcgca gctatgtcgg ccgaagaggt cgagggtgga tccctgccgt cgcgcgccca   11940
agagtcgacc tccgatctgc tggctctcgt gcagtcgtgg cttgcggacg agcggttcgc   12000
```

```
cgaatcccag ctcgtggtcg tcacgcgtgc agcggtgtcg gccgactcgg attcggacgt   12060
cgcggacctg gtgggtgcgt cgtcgtgggg gttgttgagt tcagcccagt cggagaaccc   12120
gggtcgcttc gtgctggtgg acgtggacgg cacacctgag tcgtggcagg cgttgccggc   12180
cgccgtgcga gcaggagaac cgcagctggc acttcggcgc ggcgtggcgc tggtgcctcg   12240
gttggcgcga ctcacggtgc gcgaggaggg ctcctccccg caactcgaca cggacgggac   12300
cgtcctcatc acgggtggca ccggtgcgtt gggggggagtg gttgcccgtc acctggtgga   12360
ggagcacggg attcggcgtt tggtgttggc aggccggcgt ggctggaatg cgcctggagt   12420
ccacgagttg gtggatgagc tggcgcgcgc gggcgccgtg gttgaggtgg tggcttgcga   12480
tgtggctgac cgcaccgatc tggagcacgt gctggccgcc attccggtcg actggccgct   12540 gcggggatc gtgcataccg ctggggtgct ggccgacgga gtgatcgggt ccttgtcggc   12600
ggcggatgtg ggcacggtgt ttgccccgaa ggtgacgggg gcatggcatc tgcacgagtt   12660
gacccgcgat ctggatctgt cgttcttcgt tcttttctct tccttctccg ggattgcggg   12720
tgccgcaggg caggccaact acgcggcggc gaacacgttc ctggatgcat tggcgcgtta   12780
tcgccgggcg cgtgggctgc ctgggttgtc gttggcgtgg ggactgtggg cgcaacccag   12840
cggtatgacg agtggcttgg acgggcgtc ggtggagcgg ttggcgcgga cgggcatcgc   12900
agaactttcc acggaggatg gactccgcct gttcgatgcc gcgttcgcga aggaccgggc   12960
ttgcgtcgtt gccgctcgat tggacagggc gctgctggtc gggaacggac gatcgcacgc   13020
gattccggcg ctgttgagcg cgttggttcc tgttcgcggc ggtgtggcga ggaaaacagc   13080
caattctcag gccgcggatg aggacgcact gttgggtttg gtgcgggagc acgtttcggc   13140
cgtgctgggt tattcgggtg cggtcgaggt tgggggcgac cgtgctttcc gtgatctggg   13200
ttttgattcg ttgtctggcg tggagttgcg gaaccgcctt gccggggtgc tgggggtgcg   13260
gttgccggcg actgcggtgt tcgactatcc gacgccgcgg gcgctggcgc gtttcctgca   13320
tcaggaactg gcaggcgagg tcgcgtccac gtcgacgccg gtgaccaggg cagcgagtgc   13380
cgaagaggat cttgttgcga ttgtcgggat gggatgtcgt tttccgggtg gggtgtcgtc   13440
gccggaggag cttttggcgg ctggtggccgg cggcgtggat gcggtggctg ggttcccaga   13500
cgatcgcggc tgggatctcg cggcgttgta cgatcctgat cccgatcgtc tcgggacctc   13560
gtatgtgtgt gagggcgggt ttctgcggga cgcggcggag ttcgatgctg acatgttcgg   13620
catcagcccg cgtgaggcgt tggcgatgga tccgcagcag cggttgctgc tggaggtcgc   13680
ctgggaaacc ttggagcggg ctgggatcga tccgttctcg ttgcacggca gccggaccgg   13740
tgtgttcgcg ggcttgatgt accacgacta tggggcccga ttcattacca gagcaccgga   13800
gggcttcgaa gggcacctcg ggacgggcaa tgcggggagc gtgctgtcgg gtcgggttgc   13860
gtattcgttt ggtttcgagg gtcctgcggt gacggtggat acggcgtgtt cgtcgtcgtt   13920
ggtggcgtta cacctggcgg gtcaagcact gcgggccggt gagtgcgaat cgcccttgc   13980 cggtggcgtc acggtgatgt cgacgccgac gacgttcgtg gagttctccc gtcaacgggg   14040
tctggctccg gatgggcggt gcaagtcgtt cgcggcggcc gcggatggca ccgggtgggg   14100
cgagggtgcc ggtctggtgt tgctggagcg gttgtcggat gccgcgca atgggcacga   14160 ggttctggcg gtggtgcggg gtagcgcggt gaaccaggac ggcgcgtcga atggcttgac   14220
tgcgccaaat ggtccgtcac agcaaagggt gatcacccag gcactcacga gtgccgggct   14280
gtccgtgtcc gacgtggatg ctgtggaggc gcatgggacg ggcacgcggc ttggtgatcc   14340
```

```
gatcgaggcg caggcgttga tcgctacgta cggccgggat cgtgatcccg gtcggccgtt    14400
gtggctgggg tcggtgaagt cgaatattgg tcacacccag gcggcggcgg gtgtcgctgg    14460
tgtgatcaag atggtgatgg cgatgcggca gggggagctg ccgcgcacgt tgcacgtgga    14520
cgagccctcc gcgcaggtgg actggtctgc gggcacggtc caactcctca cggagaacac    14580
gccctggccc gacagcggtc gtcttcgccg ggcgggcgtg tcatcgttcg ggatcagtgg    14640
caccaacgcg cacctgatcc ttgaacaacc tccgcgagag tcgcagcgct caacagagcc    14700
ggattcgggt tctgtccgcg atttcccggt ggtgccgtgg atggtgtcgg gcaaaacacc    14760
cgaagcgcta tccgcccagg cagatgcatt gatgtcctac ttgagcaatc gcgttgatgc    14820
ttccccgcga gatatcggtt attcgcttgc ggtgacccgt ccggcgttgg accaccgcgc    14880
tgtcgtgctg ggtgcggatc gtgccgcgtt gctgccgggc ttgaaagcgc tggccgttag    14940
taatgacgct gccgaggtga tcaccggcac tcgtgccgct gggccggtcg gattcgtgtt    15000
ctccggtcaa ggtggtcagt ggcccgggat gggaagcggg ctccactcgg cgtttccggt    15060
gttcgccgac gcgtttgacg aagcctgctg cgagctggat gcgcatctcg ggcagatggc    15120
ccggctacga gatgtgttgt ccggttcgga tacgcaactt ctggaccaga ccttgtgggc    15180
gcagccgggc ctgttcgcgt tgcaagtcgg actctgggag ttgttgggtt cgtggggtgt    15240
ccggcccgct gtggtgctgg gccactcggt cggtgagctg gcggcggcgt tcgcggctgg    15300
agtgttgtcg ttgcgggatg cggctcggct ggtggcgggc cgtgcccggt tgatgcaagc    15360
cctgccaact ggcggtgcca tgctcgctgc ggctgctgga gaggagcagc tgcgcccgtt    15420
gctggccgac tgccggtgatc gtgtggggat cgccgcggtc aacgctcccg ggtcggtggt    15480
gctctccggt gatcgggatg tgctcgatga cattgccggt cggctggacg ggcaagggat    15540
ccggtccagg tggttgcggg tttcgcatgc gtttcattcg catcggatgg atccgatgct    15600
ggcggagttc accgaaatcg cccggagcgt ggactaccgg tcgtcagggc tgccgatcgt    15660
gtcgacgttg acgggtgagc tcgatgaggt cggcatgccg gctacgccgg agtattgggt    15720
gcgccaggtg cgagaacccg tccgcttcgc cgacggtgtt gctgcgctcg cggctcacgg    15780
tgtgagcacc gtcgtcgagg tcggtccgga tggggtgttg tcggcgctgg tgcaggagtg    15840
cgcggccgga tccgatcagg gcggacgggt ggccgcggtt ccgctcatgc gcagcaatcg    15900
cgacgaggcg cacacggtga caacggcatt ggcgcagatc catgtgcgtg gtgctgaggt    15960
ggactggcgg tcgttttttcg ccggtaccgg ggcaaagcag gtcgagctgc ccacgtatgc    16020
cttccaacga cagcggtact ggcttgactc accatccgaa ccggtcgggc aatccgccga    16080
tcccgcgcgc cagtcgggct tctgggaact cgtcgagcag gaagatgtca gcgcgctcag    16140
cgccgctctg cacattaccg gcgatcacga cgtgcaggcg tccctggaat cggtggttcc    16200
ggtcctctcc tcctggcatc gccggatccg caacgaatcc ctggtgcacc agtggcggta    16260
ccggatttcc tggcatgagc gggcagattt gccagacccc tcgttgtcgg ggacatggct    16320
cgtcgtcgtg ccggaggggt ggtcggcgag tcggcaagtt ctgcgtttca acgagatgtt    16380
cgaggaacgg ggttgcccgg cagttctgtt cgagctcgcc gggcacgacg aggaagccct    16440
ggcgcaacga ttccgctcgt tgcctgttgc gtcaggggga ataagcggcg tgttgtcctt    16500
gctggcgctg gatgaatcgc cgtcctcgcc gaacgctgct tgccgaatg gcgcgctgaa    16560 ctcgttggta ctgctgcgag ctctgcgggc gcggatgtg tcggcgccat tgtggttggc    16620
gacgtgtggt ggtgtcgcgg tcgggatgt gccggtgaac ccggggcagg cgctggtgtg    16680
gggactgggt cgcgtcgtcg gtctggagca tccggcctgg tggggtggcc tggtcgacgt    16740
```

```
gccgtgcttg ctcgatgagg acgctcgaga acgcttgtcg gtcgtgttgg caggtcttgg   16800
cgaggacgag atcgcggtac gtcccggtgg tgtgttcgtg cggcggttgg aacgcgctgg   16860
tgcggcgtcg ggtgccgggt cggtgtggcg tcctcggggg acggtgttgg tgacgggtgg   16920
tacgggcggt ttgggggcgc atgttgcccg gtggttggcg ggtgccgggg ctgagcatgt   16980
ggtgttgacc agccgtcgag gcgcggcggc tccgggcgct ggagatttgc gggcggagct   17040
ggaggcgctg ggcgctcggg tttcgatcac ggcctgcgac gtggccgatc gtgacgcttt   17100
ggccgaagtg ttggcgacca ttccggatga ttgcccgctg accgcggtga tgcatgcggc   17160
gggggtcgtt gaagtcggcg acgtggcgtc gatgtgtttg accgacttcg ttggggtgct   17220
gtcggcgaag gcaggtggtg cggcgaatct cgatgagttg ctcgccgatg tcgagctgga   17280
tgccttcgtg ctgttctcat ccgtctcggg tgtgtggggt gctggcgggc agggcgctta   17340
tgcggcggcg aatgcctact tggatgcgtt ggcgcagcag cgtcgggcaa ggggttggt    17400
ggggactgcg gttgcgtggg gcccgtgggc cggtgacgga atggccgcag gtgaaggcgg   17460
tgcacagctg cgccgggccg gcctggtgcc aatggctgcg gatcgggcgt tgctggcact   17520
tcagggcgca ttggatcgtg acgagacatc cctggtcgtg gccgatatgg cgtgggagag   17580
gttcgccccg gtgttcgcca tgtcccgtcg gcgtccgctg ctcgacgagc tgcccgaagc   17640
acagcaggcg ttggcggatg cggagaacac cactgatgct gcggactcgg ccgtcccgct   17700
accgcggctc gcgggcatgg cagccgccga acgccgccgc gcgatgctgg acctggtgct   17760
ggcggaggcc tcgattgtgt tgggacacaa cgggtctgac ccagttggtc ccgaccgggc   17820
gttccaggag ctcggatttg attcgctgat ggccgtcgaa ctgcgcaaca ggttgggcga   17880
ggcaacagga ttgagtctgc cggccacgtt gatcttcgat tatccgagcc catccgcgct   17940
ggctgagcag ctggtcggcg agctggtggg agcgcagccc gcgaccaccg tcgtggccgg   18000
ggccgatcca gtggatgatc cggttgtcgt ggtcgcgatg ggatgccggt atccgggcga   18060
cgtctgctcg cccgaggagc tgtggcagct ggtttctgcg ggacgtgatg cggtatcgac   18120
gttccccgtc gatcgggtt gggactgcaa cacgttgttc gacccggatc cggatcgggc   18180
aggcagtacc tatgtgcgag aaggtgcctt cctgaccggt gctgatcggt tcgacgccgg   18240
gttcttcggc atcagccctc gcgaggcgcg cgcaatggat ccgcagcaga ggttgttgct   18300
cgaagtggcg tgggaggttt tcgaacgagc aggaatcgct ccgctgtcgt tgcggggtag   18360
caggaccggt gtgttcgcgg ggaccaatgg gcaggaccac ggtgcgaaag tggctgccgc   18420
gccggaggcg gcgggtcacc tcctgaccgg aaacgccgcg agtgtcctgg ccggccggct   18480
ttcctacacg ttcggccttg aggggcctgc ggtggcggtg gataccgcgt gttcgtcgtc   18540
gttggtggcg ttgcatttgg cgtgccagtc gctgcgttcg ggtgagtgtg atatggcgtt   18600
ggcaggtggt gtgacggtga tgtcgacacc cctggctttc ctcgagttct ctcgtcagcg   18660
cggtttggcg ccagatggtc ggtgcaagtc gtttgcggcc gctgcggatg caccggggtg   18720
gggtgagggt gccggcctgg tgttgctgga gcggttgtcg gatgctcgtc ggaatggtca   18780
ccgggtgttg gccgtggttc gcgggtctgc ggtgaatcag gatggtgcgt cgaatggcct   18840
gactgcgccg aatggtccgt cgcagcagcg ggtgattcgg caggccctcg cgaatgcggg   18900
gctgtcggcg tccgatgtgg atgtcgtgga ggcgcacggg accggtaccg ggctcgggga   18960
tccgatcgag gcgcaggcgc tgatcgcgac atatgggcag gagcgggatc ctgagcgggc   19020
cctgtggctg gggtcgatca agtccaacat cggccacacg caggcggcgg ccggtgtggc   19080
```

```
gggggtcatc aagatggtgc aggccatgcg gcacgggag ttgcctgcga cgttgcacgt    19140
ggacaagccc actccacagg tggactggtc tgccggggcc gttcggctcc tcaccgggaa    19200
cacgccctgg cccgagagcg gccgtcctcg tcgagcgggg gtgtcgtcgt tcgggatcag    19260
cggcaccaac gcacacctca tcctcgaaca accaccgtcg gaaccagcgg agatcgacca    19320
atcggatcgg cgggtcactg cgcatccagc ggtgatcccg tggatgttgt cggctaggag    19380
tctcgcagcg ctgcaggccc aagcggctgc gctgcaggcc cggctggacc ggggtcctgg    19440
cgcttctccg ctggatttgg ggtattcact cgcgaccact cgttctgtgc tggacgaacg    19500
cgccgtcgtg tggggtgccg atcgggaggc actgctgtcc aggctggcag cgctcgccga    19560
tggccggacg gcgccggggg tgataacggg ctctgcgaat tccggtggcc gcatcggatt    19620
cgttttttcc ggtcagggca gtcagtggct ggggatggga aaggcgttgt gcgcggcttt    19680
cccggcgttc gcggacgcct tcgaggaagc ctgcgacgcg ctaagcgcac acctgggcgc    19740
ggacgttcgg ggtgtgctgt tcggtgctga tgagcagatg ctcgaccgga cgctgtgggc    19800
gcagtcgggg atcttcgcgg ttcaagtcgg cctcctggga ttgctgaggt cgtggggcgt    19860
gcggccggcc gcggtgctgg ggcactcggt cggcgagttg gctgcggcgc acgcggctgg    19920
tgtgttgtcc ttgccggacg ctgcacggtt ggttgcggct cgggcccacc tgatgcaggc    19980
attgcccacc ggcggcgcaa tgctcgcggt cgccaccagc gaggcggcgg tcggaccgct    20040
gctttccggg gtgtgcgatc gggtcagcat cgctgcgatc aacggccccg agtcggtagt    20100
gctctccggc gaccgcgatg tgctcgtgga gctcgcaggc gaattcgatg cccgagggct    20160
taggaccaaa tggttgcggg tctcccatgc tttccactcg caccggatgg aaccgattct    20220
ggacgagtac gcggaaaccg ccaggtgcgt cgagttcggt gaaccggtgg tgccgatcgt    20280
ctccgccgcg accggtgcgc tggacaccac cggactgatg tgcgcggccg actactggac    20340
gcgccaagtg cgtgatcctg tccgcttcgg agacggtgtc cgggcgctcg tcggccaagg    20400
cgtgacacat atcgtcgagt tcggcccgga cggggcgttg tcggccctgg tcgagcagtg    20460
cttggccggg tccgaccagg ctgggagggt ggcggcgatc ccgctgatgc gcagggaccg    20520
cgatgaggtc gagaccgcgg tggcggccct ggcgcacgtg cacgtccgcg gtggtgcggt    20580
ggactggtcg gcttgcttcg ccggcaccgg cgcccgcacc gtcgagttgc ccacctacgc    20640
cttccaacgc cagcggtact ggctggccgg gcaagcggac gggcgcggcg gcgatgtggt    20700
tgccgacccg gtcgacgcgc gcttctggga gttggtcgag cgcgccgatc cggaaccgtt    20760
ggtggatgaa ctctgcatcg accgggacca gcccttccgg gaggtgctgc ccgttctggc    20820
ttcctggcgc gagaaacaac gccaggaggc cctcgcggat tcctggcgct accaggtgcg    20880
ctggaggtcc gtcgaggtgc cgtccgcagc cgccctccgg ggcgtgtggc tggtggtgct    20940
tccagctgac gtgccccgag atcaaccggc ggtcgtcatc gacgcgctga tcgcgcgcgg    21000
cgccgaggtc gcggtcctgg aattgaccga gcaggacctc caacgcagtg cgcttgtgga    21060
caaggtgcgc gccgtcattg cggaccgcac cgaggtgacg ggtgtgttgt ctctgttggc    21120
gatggacggc atgccctgcg cggcgcatcc gcacctgtcc cgtggtgtcg ccgctaccgt    21180
gatcctgacg caggtgttgg gcgatgcggg tgtttccgcc ccgctgtggc tggccacgac    21240
cggtggcgtc gaggccggga ccgaggacgg tccggccgat ccggaccacg gcttgatctg    21300
ggggctcggc agggtcgtcg gccttgaaca tccgcagtgg tggggtggcc tgatcgacct    21360
tccgagacca ctggacgaga cgtcccggaa cgggttggtg gccgcactcg ccgggacggc    21420
ggccgaagat cagctcgccg tgcgttcatc cgggttgttc gttcgcagag tggtgcgcgc    21480
```

```
agcgcggaac cccggtcag agacatggcg tagccgggga acggtcctca tcacgggcgg    21540
aacaggcgcg ctcggtgccg aggtcgcacg atggctggcc cggcgggag ctgagcacct    21600 ggtgttgatc agtcgccgcg gcccggaagc tcccggcgca gcggacctag gggccgagct    21660
gactgaactc ggcgtgaaag tcacagtctt ggcctgcgat gtgacggacc gcgacgagct    21720
ggcggcggtg ctggcggccg ttcccacgga gtatccgctg tcggcggtcg tgcacaccgc    21780
cggcgtcggg acgcctgcga acctggccga gacgaccttg cgcagttcg ccgacgtgtt    21840 gtcggccaag gtcgtcggcg cggcgaacct ggaccggctg cttggcgggc aaccgttgga    21900
cgccttcgtg ctgttctcct cgatctcggg agtttgggga gccggcggcc aaggagccta    21960
ttcggccgcc aatgcgtatc tcgatgccct tgccgagcgc cgacgggctt gcgggcggcc    22020
ggcgacgtgc atcgcctggg gtccgtgggc gggtgcgggc atggccgttc aggaaggtaa    22080
cgaggcgcat ctccgccgaa ggggcctggt accgatggaa ccgcagtcgg ccctcttcgc    22140
gctgcaacag gccctgtccc aacgagaaac cgccatcacc gtcgcagatg tggactggga    22200
gcgattcgcc gcctctttca ccgcggcccg cccgcgacca ctgttggaag agatcgtgga    22260
tctacgcccc gacaccgaga ccgaggagaa gcacggtgcc ggcgagctgg ggcagcagct    22320
ggccgcactg ccgcccgctg agcgcggaca cctgctgctg gaggtggtgc tggcggaaac    22380
cgccagcacc ctggggcacg attcggcgga ggctgtgcaa cccgatcgga ccttcgccga    22440
actgggcttc gattcgctga ccgcggtaga gctgcgcaac aggttgaacg cggtgaccgg    22500
gcttcgcctg ccgccgacgc tggttttcga ccacccgacg ccgctggcgt tgtccgaaca    22560
gttggttccg gccctggtcg cggagccgga caacggcatc gaatcgctgc tcgccgagct    22620
cgacaggctg gataccacgt tggcgcaagg gccttcgatc ccactggaag accaggccaa    22680
ggtggcggag cgcttgcacg cactcctcgc caagtgggac ggggcgcgtg acggcacggc    22740
cagagcgacg tcaccccaat cgctgacggc ggccacggac gacgaaatct tcgacctcat    22800
cgaccggaag ttccggcgct gaccgcccctt tcctcgcctc agctcccctg attactggaa    22860
cggtgtattt cgatggccaa tgaagaaaag ctccgcgagt acctcaagcg tgtcgtcgtc    22920
gaactggaag aggcgcacga acgcctgcac gagttggagc gccaggagca cgaccccatc    22980
gcgatcgtgt cgatgggatg tcgttatccc ggtggcgtct ccactccgga ggagctgtgg    23040
cgactggtcg tcgacggagg agacgcgatc gcgaacttcc ccgaagaccg tggctggaat    23100
ctggacgagc tgttcgatcc tgatccgggc cgagccggga cctcctacgt ccgcgagggt    23160
ggtttcctgc gcggggtcgc ggacttcgat gccgggctct tcgggatcag tccgcgcgag    23220
gcacaggcga tggacccgca acagcggttg ctgctggaga tctcgtggga ggtgttcgag    23280
cgcgccggca ttgacccgtt ttcttgcgg ggtaccaaga ccggtgtgtt cgcgggcctg    23340
atctaccacg actacgcgtc gcggtttcgc aagaccccg cggagttcga gggttacttc    23400
gccaccggca acgcgggcag cgtcgcatcc ggcgggtgg cttacacctt cgggttagag    23460
ggcccggcgg tcaccgtgga caccgcctgc tcgtcgtccc tggtggcgct gcacctggcc    23520
tgccagtccc tgcggctggg cgaatgcgac ctggccctgg ccggtggcat ttcggtgatg    23580
gccacgccgg gagccttcgt cgagttcagc cggcaacgcg cactcgcctc ggatggccgg    23640
tgcaagccct tcgcggatgc cgccgacggc accggctggg gcgagggcgc cggaatgctg    23700
ctgctggaac ggctgtcgga cgcacgacga aacggccacc cggtgctggc ggcgtggtc    23760 ggttccgcga tcaaccagga cgggacgtcc aacggcctga ccgcgcccag cggtcccgca    23820
```

```
cagcagcgag tgatccgcca agccctggcg aacgccgggt tgtcgcccgc cgaggtcgat    23880
gtggtcgagg cgcacggcac gggcacggcc ttgggcgacc cgatcgaggc gcaggccctg    23940
atcgccacct acggggcgaa ccggtcggcg gatcatccgc tgctgctggg ttccctcaag    24000
tcgaacatcg gccacaccca ggctgccgcc ggtgtggccg gggtgatcaa gtcggtcctg    24060
gccatcaggc accgggagat gccccgcagc ctgcacatcg accagccatc gcagcacgtg    24120
gactggtcgg cgggcgcggt gcggctgctc acggacagcg ttgactggcc ggatctcggc    24180
aggccgcgcc gagcaggggt gtcctcgttc ggcatgagcg gtaccaacgc acacctgatc    24240
gtcgaggaag tatccgacga gccggtctcg ggcagtaccg agccgaccgg ggcatttccc    24300
tggccgctgt ccggcaagac ggagacggca ttgcgcgagc aggctgccga gttgctctcc    24360
gtagtgaccg agcacccgga gccgggactg ggggacgtcg ggtactcgct ggccaccggt    24420
cgcgctgcga tggagcaccg ggctgtcgtg gttgccgacg atcgggactc tttcgtcgcc    24480
ggactgacgg cgttggctgc gggcgttccg gcagccaacg tggtgcaggg cgcggccgac    24540
tgcaagggaa aggtcgcgtt cgtgttcccc ggccagggct cgcattggca ggggatggcg    24600
agggaactgt ccgaatcctc gccggtgttc cggcggaagc tggcggaatg cgcggcggct    24660
acggcccctt acgtggactg gtcgctgctc ggcgtccttc gcggtgatcc cgatgcaccc    24720
gcgctggatc gcgacgacgt gattcagctc gcgctgttcg ccatgatggt gtcgctggcc    24780
gaactgtggc gttcgtgcgg agtggagccc gccgcgtgg tcggtcattc ccagggcgag    24840
atcgccgccg cccatgtggc aggcgctttg tccttgactg atgcggtgcg catcatcgct    24900
gcccgctgcg atgcggtgtc ggcgctgacc gggaagggag gcatgctcgc gattgccttg    24960
ccggaaagcg cggtggtgaa gcgaatcgca ggcctgccgg agctgaccgt tgcggcggtc    25020 aacgacccg gctccactgt cgtttccggc gaaccgtcgg ctctggagcg tctgcagacc    25080
gaactgaccg cggaaaacgt gcagacccgg cgggtgggaa ttgattacgc ctcgcattcg    25140
ccgcagatcg cgcaggtcca gggccggctt ctggaccggc tgggcgaagt cgggtccgaa    25200
cctgctgaga tcgctttcta ctcgacggtc accggcgagc ggacggacac cggccgactc    25260
gacgccgact actggtacca gaaccttcgg cagcccgtcc gcttccagca gaccgtcgcc    25320
cggatggcag atcagggcta tcggttcttc gtcgaggtga gcccgcaccc gctgctcacc    25380
gccggaatcc aggaaacgct ggaagccgcg gacgcgggcg gggtggtggt cggttcgctg    25440
cggcgtggcg agggcggctc ccggcgctgg ctgacttcgc tggccgagtg ccaggtgcgc    25500
ggactgccgg tgaattggga acaggtattc ctcaacaccg gagcccgacg cgtgccgctg    25560
ccgacctacc cgttccagcg gcagcggtac tggttggagt ccgccgagta cgacgcgggc    25620
gatctcggtt cggtgggctt gctctccgcc gagcatcccc tgctcggggc tgcggtgacg    25680
ctggccgatg cgggcgggtt cctgctgacc ggcaagctgt cggtcaagac ccagccctgg    25740
ttggccgacc acgtggtcgg cggggcgatc ctgctgcccg gcaccgcgtt cgtgaaaatg    25800
ctgatacgcg ccgcggacca ggtcgggtgc gatctgatcg aggagttgtc cctgacgact    25860
ccgctggttt tgcccgcgac cggtgcggtg caggtgcaga tcgcggttgg cggtccggac    25920
gaggccgggc gccgctcggt ccgcgtgcat tcctgtcgag acgacgccgt gccgcaggac    25980
tcgtggacct gccacgcgac cggcacgttg acctccagcg atcaccagga cgccggccag    26040
ggccccgatg ggatttggcc gcccaacgat gctgtcgcgg ttcgctgga cagcttctac    26100 gcccgcgcag ctgagcgggg cttcgatttc ggcccggcgt tccaggggtt gcaggcggct    26160
tggaagcgcg gagacgagat cttcgccgag gtcggcctgc ccaccgcaca ccgcgaagac    26220
```

```
gccggcaggt tcggaatcca ccctgctctg ctggatgcgg cactgcaggc gctgggcgca   26280
gccgaagagg atccggacga gggatggctc ccgttcgcgt ggcaaggtgt gtccctcaaa   26340
gcgacgggcg cactttccct tcgggtgcac ctcgttccgg cgggcgcgaa tgcggtgtcg   26400
gtgttcacga ccgacacgac tggccaagcc gtgctctcca tcgattcgct ggtgctgcgc   26460
cagatttcgg acaagcagtt ggcagcggcc cgtgcgatgg aacacgagtc cctgttccgg   26520
gtcgactgga agcgaatctc gcccggcgct gccaagccgg tctcctgggc agtgatcggc   26580
aatgacgaac tcgcccgagc ctgcggctcg gcacttggca cggaactcca ccccgacctg   26640
accgggttgg ctgaccccgcc cccggacgtc gtggtggtgc catgcggtgc gtctcgccag   26700
gacttggacg ttgcttccga ggcacgtgcc gcgacacaac gcatgcttga cctgatccag   26760
gattggttgg cggcggcgcg attcgccgga tctcgcctgg tggttgtgac gtgtggtgcg   26820
gcgtcgacag gtcccgccga gggtgtttcc gacctggtgc atgctgcgtc gtggggtttg   26880
ttgcgttcgg cgcagtcgga gaacccggac cgattcgtgt tggtcgatgt ggacggaacc   26940
gccgaatcat ggcgtgcgct cgcggcggcc gtgcgttccg gagaaccgca gctggcgttg   27000
cgcgccggtg aagtccgggt gcctcgcctg cgcgcgatgtg ttgccgccga ggacagccgg   27060
atcccagtgc ccggtgcgga tgggacggtg ttgatttccg gcggtacggg cctgctgggc   27120
gggttggttg cccggcattt ggtggcggag cgcggtgtcc gccgcctggt gctcgcgggg   27180
cgacgcggct ggagcgcccc cggggtcacc gacctggtgg atgagttggt gggcctggga   27240
gctgcggtcg aggtggcgag ctgcgatgtc ggggatcggg cccagttgga ccggctgctg   27300
acgacgatct cggcagagtt cccgctgcgc ggagtggtgc atgcggccgg gcacttgcc   27360 gacggggtcg tcgagtcgct gacaccagag cacgtggcaa aggtgttcgg cccgaaggcc   27420
gccggtgcgt ggcacctgca cgagttgact cttgatctgg atctctcgtt cttcgtgctc   27480
ttctcctcgt tctccggcgt ggcggggggct gcgggtcagg gaaactacgc ggcggcgaac   27540
gcgttcctgg acggcctggc tcagcaccgg cggacggcgg ggctgcctgc ggtgtcgctg   27600
gcttggggct tgtgggagca gcccagcggg atgaccggag cgctcgatgc ggcgggccgt   27660
agccgcattg cgcgcaccaa tccgccgatg tccgcgccgg acgggttgcg gctgttcgag   27720
atggcgtttc gcgttccggg cgaatcgctt ctggttccgg tccacgtcga cctgaacgcc   27780
ctgcgcgctg atgcggccga cggcggtgtg cctgcgttgt tgcgcgacct ggtgccagcg   27840
cccgtgcggc ggagcgcggt caacgagtcg gcggacgtca acggtctggt tggtcggctg   27900
cggaggctgc cggacctgga tcaggaaacc cagctgttgg gtttggtgcg cgagcatgtt   27960
tcggcggtgc tggggcattc gggtgcggtc gaggtcgggg ccgatcgtgc tttccgggat   28020
ttgggttttg attcgttgtc cggtgtggag tttcggaacc ggcttggcgg ggtgctgggc   28080
gttcggttgc cggctactgc ggtgttcgac tatccgacac cgcgggcgtt ggttcggttc   28140
ttgctcgaca aactgattgg tggcgtggag gctccgactc ccgcaccggc ggctgtggcg   28200
gcggtgactg ctgacgatcc cgttgtgatc gtggggatgg gctgtcgtta tccgggtggg   28260
gtgtcctcgc cggaggagct ttggcgtttg gtggccgggg gcttggatgc ggtggcggag   28320
ttcccggacg atcgtggctg ggatcaggcg gggttgttcg atccggatcc cgatcgtctt   28380
gggacctcgt atgtgtgtga gggtggcttc ctgcgagatg cggcagagtt cgatgccggt   28440
ttcttcggga tttccccgcg tgaggcgttg gcgatggatc cgcagcagcg gttgctgctg   28500
gaagtcgctt gggaaaccgt ggagcgggcg gggattgatc cgctttcgtt gcggggagc   28560
```

```
cggaccggcg tgttcgcggg gctgatgcac cacgactacg gcgcgcggtt catcacgagg   28620
gcgccggagg gtttcgaggg ttatctaggt aatggcagcg cgggaggcgt gttttcgggt   28680
cgggttgcgt attcgtttgg tttcgagggt cctgcggtga cggtggatac ggcgtgttcg   28740
tcgtcgttgg tggcgctgca cctggcgggt caagcactgc ggtctggtga gtgtgatctg   28800
gctcttgcgg gtggtgtgac ggtgatggcc acgccgggga tgttcgtgga gttttcgcgt   28860
caacggggct tggcggcgga tgggcggtgc aagtcgtttg cggcggctgc ggatggcacc   28920
ggttggggag aaggcgcggg cttggtgttg ttggagcggc tgtcggatgc ccggcgcaac   28980
gggcacgcgg ttctggcggt cgtgcggggt agcgcggtga atcaggatgg tgcgtcgaat   29040
ggtttgacgg cgccgaatgg gccctcgcag cagcgggtga tcacgcaggc gttggcgagt   29100
gctggtttgt cggtgtctga tgtggacgcc gtggaggcgc atgggactgg aaccaggctt   29160
ggtgatccga ttgaggcgca ggctctgatt gccacttacg ggcaggggcg ggatagcgat   29220
cggccgttgt ggttggggtc ggtgaagtcg aatattggtc atacgcaggc ggcggcgggt   29280
gtcgctggtg tgatcaagat ggtgatggcg atgcggcacg ggcagctgcc cgcgacgttg   29340
catgtggatg aacctacgtc ggaagtggat tggtcggcgg gggatgtcca gctcctcacg   29400
gagaacaccc cctggcccgg caacagccat cctcggcggg tgggcgtgtc gtcgttcggg   29460
atcagcggca ccaacgcaca cgtcatcctc gaacaagcct cgaaaacacc agacgagact   29520
gcggacaaga gcggtcccga ttcggaatcg accgtggacc ttccagcggt cccgttgatc   29580
gtgtcgggga gaacaccggc agcgctcagc gctcaggcga gcgcattgtt gtcctatttg   29640
ggtgagcgtg gcgatatttc cacgctggat gcggcgtttt cgttggcttc ctcccgggcc   29700
gcgttggagg agcgggcggt ggtgctggga gcggaccgcg aaacgttgtt gtccgggttg   29760
gaagcgctgg cttccggtcg cgaggcttct ggggtggtgt cggatcccc ggtctctggc    29820 ggggttgggt tcgtgttcgc cggtcagggc ggacagtggt tggggatggg ccgggggctc   29880
tactcggttt ttccggtgtt cgctgacgcg tttgacgaag catgtgccgg actgacgcg    29940 catctggggc aggacgtggg ggtccgggat gtggtgtttg gttccgacgg gtccttgttg   30000
gatcggacgc tgtgggccca gtcgggtttg ttcgcgttgc aggttggttt gctgagcctg   30060
ctgggttcgt ggggtgtccg gccgggtgtg gtgctgggcc attcggtcgg cgagttcgcg   30120
gcggcggttg cggcgggagt gttgtcgttg ccggatgcgg ctcggatggt ggcgggtcgt   30180
gcccggttga tgcaggcgtt gccttctggc ggtgccatgt tggcggtggc tgctggtgag   30240
gagcagctgc ggccgttgtt ggccgatcgg gttgatggtg cgggtatcgc cgcggtcaac   30300
gctcctgagt cggtggtgct ctccggcgat cgggaggtgc ttgacgacat cgccggcgcg   30360
ctggatgggc aagggattcg gtggcggcgg ttgcgggttt cgcatgcgtt tcattcgtat   30420
cggatggacc cgatgttgca ggagttcgcc gaaatcgcac gcagcgtgga ctaccggcgt   30480
ggcgacctac cggtcgtgtc gacgttgacg ggtgagctcg acaccgcagg tgtgatggct   30540
acgccggagt attgggtgcg tcaggttcga gagcccgtcc gcttcgccga cggcgtccgg   30600
gtgctcgcgc agcaaggggt cgccacgatc ttcgaactcg gccctgatgc gacgctgtcg   30660
gccctgattc ccgattgtca ttcgtgggct gatcaggcca tgccgattcc gatgctgcgt   30720
aaagaccgta cggaaaccga aactgtggtc gccgcggtgg cgcgggcgca cacgcgtggt   30780
gttccggtcg aatggtcggc gtatttcgcc ggcaccgggg cacggcgggt cgagttgccg   30840
acgtatgcct tccagcggca gcggtactgg ctggaaacat cggattacgg cgatgtgacg   30900
ggtatcggcc tggctgcggc ggagcatccg ttgctggggg ccgtggttgc gctggccgat   30960
```

```
ggtgatggga tggtgctgac cggccggttg tcggtgggga cgcatccgtg gctggcccag   31020
catcgcgtgc tgggcgaggt cgtcgtcccc ggcaccgcca tcctggagat ggccctgcac   31080 gcagggcgc gtctcggctg tgaccgggtg gaagagctca ccctggaaac accgctggtg    31140
gtccccgaac gcgcggcggg tgccggtagt cgtggccctg cggagagggac cacagtttca   31200 attgaaactg cggaagaacg tgtgcggacg aacgacgcca tcgaaatcca gctgctggtg   31260
aacgcacccg acgaaggcgg tcggcgaagg gtgtcgctgt attcccgccc ggccggtggg   31320
tcgagaggtg ggggttggac gcgccacgcc accggcgaac tcgtcgtcgg caccaccggt   31380
ggtagggcgg ttcctgattg gtcggctgag ggtgccgagt cgattgctct cgatgagttc   31440
tacgtcgctc tggccggaaa cgggttcgag tacgggccgt tgttccaggg gcttcaggcg   31500
gcatggcgtc gtggtgacga ggttctcgcc gaaatcgccc cgccggccga ggccgatgcg   31560
atggcgtcgg gatacctgct cgacccagcg ttgctggatg ccgcgctgca ggcgtccgcg   31620
ctcggcgacc gcccggagca aggcggcgcg tggctgccgt tctcattcac cggcgtcgaa   31680 cttccgctc cggcagggac gatcagcagg gtgcggctgg agaccaggcg acccgacgcg   31740
atatcggtgg ccgtgatgga tgagagtggg cggttgctcg cctcgatcga ttctctcagg   31800
ctacgaagcg tgtcgtcggg acagctggcg aatcgggacg ctgtccgcga cgcgctgttc   31860
gaggtgacct gggagccggt ggcgacgcag tcgacggaac cgggtcgctg ggccctgctt   31920
ggtgatactg cctgcggtaa agacgatctc atcaaactcg caacggattc cgccgaccgc   31980
tgcgcggatc tggcggcgct agccgagaaa cttgattcca gcgcgctggt tcctgatgtc   32040
gtggtctact gcgccggaga acaggcggat cccggcaccg gcgcagccgc acttgcggag   32100
acccagcaga cgttggctct gctccaagcg tggttggctg agccgcggtt ggccgaggca   32160
cgtctggtgg tggtgacgtg tgcagcggtg acgacggctc cgagtgacgg tgcatcagag   32220
ctggcacatg cgccgttgtg ggggttgttg cgtgccgcgc aggtggagaa cccggggcag   32280
tttgtgctgg cggacgtcga cggaaccgcc gaatcgtggc gtgcgttgcc gagtgcgttg   32340
ggctcgatgg aaccgcagtt ggccctgcgg aagggcgcgg tgcgagcgcc ccgcttggct   32400
tcggtcgccg ggcagatcga cgtgcccgcg gttgtgcgg atcccgaccg aaccgtgctg    32460
atttcgggcg gcacgggcct gttgggggg gcggttgccc gccacctggt gaccgaacgc   32520
ggtgtccgcc gattggtgtt gacgggccgt cgtggctggg atgctcctgg aatcaccgag   32580
ttggtgggtg agctgaacgg cctcggtgcc gtggtcgacg tggtggcgtg cgacgtcgcg   32640
gatcgtgctg atctggagtc gttgctggcg gcggtcccgg cggaatttcc gttgtgcggc   32700
gtggtgcatg ccgcgggggc gctggccgac ggggtgatcg agtcgttgtc accggacgac   32760
gtgggagcgg tgttcggccc gaaggcgcg ggggcgtgga atctgcacga gctgactcgt    32820
gatacggacc tgtcgttctt cgcgttgttc tcctcgcttt ccggtgttgc cggcgctcct   32880
ggtcagggca attatgcggc ggcgaacgcg ttcctggacg cattggcgca ttaccggcgg   32940
tcacagggac tgcctgcggt gtcgctggcc tggggcctgt gggagcagcc gagcgggatg   33000
acggagacgc tcagcgaggt cgaccggagc aggatcgcgc gcgccaaccc gccgttgtcc   33060
accaaggagg gattgcggct gttcgatgcc gggctgcgcg tggaccgggc agcggtagtt   33120
ccggcgaagt tggacaggac tttcctggcc gagcaggcgc ggtcgggctc gctgcccgca   33180
ttgttgacgg cactggtacc ccccatccgt cgtaataggc gggctagcgg aaccgagctc   33240
gcggacgagg gcaccctgct cggggtggtg cgggagcatg ccgcggccgt gctggggtat   33300
```

```
tcgagcgcgg ctgacgtcgg ggtcgagcgc gctttccggg atctgggttt tgattcgttg   33360
tctggtgtgg agttgcggaa ccgccttgcc ggggtgctgg gggtgcggtt gccggcgact   33420
gcggtgttcg actatccgac gccgagggcg ctggcccggt tcctgcacca ggaactggca   33480
gacgagatc                                                            33489

<210> SEQ ID NO 20
<211> LENGTH: 27064
<212> TYPE: DNA
<213> ORGANISM: Saccharopolyspora spinosa

<400> SEQUENCE: 20
gatctggatc tctcgttctt cgtgctcttc tcctcgttct ccggcgtggc ggggggctgcg     60 ggtcagggaa actacgcggc ggcgaacgcg ttcctggacg gcctggctca gcaccggcgg    120
acggcggggc tgcctgcggt gtcgctggct tggggcttgt gggagcagcc cagcgggatg    180 accgagcgc tcgatgcggc gggccgtagc cgcattgcgc gcaccaatcc gccgatgtcc    240
gcgccggacg ggttgcggct gttcgagatg gcgtttcgcg ttccgggcga atcgcttctg    300
gttccggtcc acgtcgacct gaacgccctg cgcgctgatg cggccgacgg cggtgtgcct    360
gcgttgttgc gcgacctggt gccagcgccc gtgcggcgga gcgcggtcaa cgagtcggcg    420
gacgtcaacg gtctggttgg tcggctgcgg aggctgccgg acctggatca ggaaacccag    480
ctgttgggtt tggtgcgcga gcatgtttcg gcggtgctgg ggcattcggg tgcggtcgag    540
gtcggggccg atcgtgcttt ccgggatttg ggttttgatt cgttgtccgg tgtggagttt    600
cggaaccggc ttggcggggt gctgggcgtt cggttgccgg ctactgcggt gttcgactat    660
ccgacaccgc gggcgttggt tcggttcttg ctcgacaaac tgattggtgg cgtggaggct    720
ccgactcccg caccggcggc tgtggcggcg gtgactgctg acgatcccgt tgtgatcgtg    780
gggatgggct gtcgttatcc gggtggggtg tcctcgccgg aggagctttg gcgtttggtg    840
gccgggggct tggatgcggt ggcggagttc ccggacgatc gtggctggga tcaggcgggg    900
ttgttcgatc cggatcccga tcgtcttggg acctcgtatg tgtgtgaggg tggcttcctg    960
cgagatgcgg cagagttcga tgccggtttc ttcgggattt ccccgcgtga ggcgttggcg   1020
atggatccgc agcagcggtt gctgctggaa gtcgcttggg aaaccgtgga gcgggcgggg   1080
attgatccgc tttcgttgcg ggggagccgg accggcgtgt tcgcgggct gatgcaccac   1140 gactacggcg cgcggttcat cacgagggcg ccggagggtt tcgagggtta tctaggtaat   1200
ggcagcgcgg gaggcgtgtt ttcgggtcgg gttgcgtatt cgtttggttt cgagggtcct   1260
gcggtgacgg tggatacggc gtgttcgtcg tcgttggtgg cgctgcacct ggcgggtcaa   1320 gcactgcgt ctggtgagtg tgatctggct cttgcgggtg gtgtgacggt gatgccacg   1380 ccggggatgt tcgtggagtt ttcgcgtcaa cggggcttgg cggcggatgg gcggtgcaag   1440
tcgtttgcgg cggctgcgga tggcaccggt tggggagaag gcgcgggctt ggtgttgttg   1500
gagcggctgt cggatgcccg gcgcaacggg cacgcgttc tggcggtcgt gcggggtagc   1560
gcggtgaatc aggatggtgc gtcgaatggt ttgacggcgc gaatgggcc ctcgcagcag   1620 cgggtgatca cgcaggcgtt ggcgagtgct ggtttgtcgg tgtctgatgt ggacgccgtg   1680
gaggcgcatg ggactggaac caggcttggt gatccgattg aggcgcaggc tctgattgcc   1740
acttacgggc aggggcggga tagcgatcgg ccgttgtggt tggggtcggt gaagtcgaat   1800
attggtcata cgcaggcggc ggcggtgtc gctggtgtga tcaagatggt gatgcgatg   1860 cggcacgggc agctgcccgc gacgttgcat gtggatgaac ctacgtcgga agtggattgg   1920
```

```
tcggcggggg atgtccagct cctcacggag acacccccct ggcccggcaa cagccatcct    1980
cggcgggtgg gcgtgtcgtc gttcgggatc agcggcacca acgcacacgt catcctcgaa    2040
caagcctcga aaacaccaga cgagactgcg gacaagagcg gtcccgattc ggaatcgacc    2100
gtggaccttc cagcggtccc gttgatcgtg tcggggagaa caccggcagc gctcagcgct    2160
caggcgagcg cattgttgtc ctatttgggt gagcgtggcg atatttccac gctggatgcg    2220
gcgttttcgt tggcttcctc ccgggccgcg ttggaggagc gggcggtggt gctgggagcg    2280
gaccgcgaaa cgttgttgtc cgggttggaa gcgctggctt ccggtcgcga ggcttctggg    2340
gtggtgtcgg gatccccggt ctctggcggg gttgggttcg tgttcgccgg tcagggcgga    2400
cagtggttgg ggatgggccg ggggctctac tcggtttttc cggtgttcgc tgacgcgttt    2460
gacgaagcat gtgccggact ggacgcgcat ctggggcagg acgtgggggt ccggatgtg     2520
gtgtttggtt ccgacgggtc cttgttggat cggacgctgt gggcccagtc gggtttgttc    2580
gcgttgcagg ttggtttgct gagcctgctg ggttcgtggg gtgtccggcc gggtgtggtg    2640
ctgggccatt cggtcggcga gttcgcggcg gcggttgcgg cgggagtgtt gtcgttgccg    2700
gatgcggctc ggatggtggc gggtcgtgcc cggttgatgc aggcgttgcc ttctggcggt    2760
gccatgttgg cggtggctgc tggtgaggag cagctgcggc cgttgttggc cgatcgggtt    2820
gatggtgcgg gtatcgccgc ggtcaacgct cctgagtcgg tggtgctctc cggcgatcgg    2880
gaggtgcttg acgacatcgc cggcgcgctg gatgggcaag ggattcggtg gcggcggttg    2940
cgggtttcgc atgcgtttca ttcgtatcgg atggacccga tgttgcagga gttcgccgaa    3000
atcgcacgca gcgtggacta ccggcgtggc gacctaccgg tcgtgtcgac gttgacgggt    3060
gagctcgaca ccgcaggtgt gatggctacg ccggagtatt gggtgcgtca ggttcgagag    3120
cccgtccgct tcgccgacgg cgtccgggtg ctcgcgcagc aaggggtcgc cacgatcttc    3180
gaactcggcc ctgatgcgac gctgtcggcc ctgattcccg attgtcattc gtgggctgat    3240
caggccatgc cgattccgat gctgcgtaaa gaccgtacgg aaaccgaaac tgtggtcgcc    3300
gcggtggcgc gggcgcacac gcgtggtgtt ccggtcgaat ggtcggcgta tttcgccggc    3360
accggggcac ggcgggtcga gttgccgacg tatgccttcc agcggcagcg gtactggctg    3420
gaaacatcgg attacggcga tgtgacgggt atcggcctgg ctgcggcgga gcatccgttg    3480
ctgggggccg tggttgcgct ggccgatggt gatgggatg tgctgaccgg ccggttgtcg     3540
gtggggacgc atccgtggct ggcccagcat cgcgtgctgg gcgaggtcgt cgtccccggc    3600
accgccatcc tggagatggc cctgcacgca ggggcgcgtc tcggctgtga ccgggtggaa    3660
gagctcaccc tggaaacacc gctggtggtc cccgaacgcg cggcgggtgc cggtagtcgt    3720
ggccctgcgg gagggaccac agtttcaatt gaaactgcgg aagaacgtgt gcggacgaac    3780
gacgccatcg aaatccagct gctggtgaac gcacccgacg aaggcggtcg gcgaagggtg    3840
tcgctgtatt cccgcccggc cggtgggtcg agaggtgggg gttggacgcg ccacgccacc    3900
ggcgaactcg tcgtcggcac caccggtggt agggcggttc ctgattggtc ggctgagggt    3960
gccgagtcga ttgctctcga tgagttctac gtcgctctgg ccggaaacgg gttcgagtac    4020
gggccgttgt tccaggggct tcaggcggca tggcgtcgtg gtgacgaggt tctcgccgaa    4080
atcgccccgc cggccgaggc cgatgcgatg gcgtcgggat acctgctcga cccagcgttg    4140
ctggatgccg cgctgcaggc gtccgcgctc ggcgaccgcc cggagcaagg cggcgcgtgg    4200
ctgccgttct cattcaccgg cgtcgaactt tccgctccgg cagggacgat cagcagggtg    4260
```

```
cggctggaga ccaggcgacc cgacgcgata tcggtggccg tgatggatga gagtgggcgg      4320
ttgctcgcct cgatcgattc tctcaggcta cgaagcgtgt cgtcgggaca gctggcgaat      4380
cgggacgctg tccgcgacgc gctgttcgag gtgacctggg agccggtggc gacgcagtcg      4440
acggaaccgg gtcgctgggc cctgcttggt gatactgcct gcggtaaaga cgatctcatc      4500
aaactcgcaa cggattccgc cgaccgctgc gcggatctgg cggcgctagc cgagaaactt      4560
gattccagcg cgctggttcc tgatgtcgtg gtctactgcg ccggagaaca ggcggatccc      4620
ggcaccggcg cagccgcact tgcggagacc cagcagacgt tggctctgct ccaagcgtgg      4680
ttggctgagc cgcggttggc cgaggcacgt ctggtggtgg tgacgtgtgc agcggtgacg      4740
acggctccga gtgacggtgc atcagagctg gcacatgcgc cgttgtgggg gttgttgcgt      4800
gccgcgcagg tggagaaccc ggggcagttt gtgctggcgg acgtcgacgg aaccgccgaa      4860
tcgtggcgtg cgttgccgag tgcgttgggc tcgatggaac cgcagttggc cctgcggaag      4920
ggcgcggtgc gagcgccccg cttggcttcg gtcgccgggc agatcgacgt gcccgcggtt      4980
gtggcggatc ccgaccgaac cgtgctgatt tcggcggca cgggcctgtt ggggggcgcg      5040
gttgcccgcc acctggtgac cgaacgcggt gtccgccgat tggtgttgac gggccgtcgt      5100
ggctgggatg ctcctggaat caccgagttg gtgggtgagc tgaacggcct cggtgccgtg      5160
gtcgacgtgg tggcgtgcga cgtcgcggat cgtgctgatc tggagtcgtt gctggcggcg      5220
gtcccggcgg aatttccgtt gtgcggcgtg gtgcatgccg cggggggcgct ggccgacggg      5280 gtgatcgagt cgttgtcacc ggacgacgtg ggagcggtgt tcggcccgaa ggcggcgggg      5340
gcgtggaatc tgcacgagct gactcgtgat acggacctgt cgttcttcgc gttgttctcc      5400
tcgctttccg gtgttgccgg cgctcctggt cagggcaatt atgcggcggc gaacgcgttc      5460
ctggacgcat tggcgcatta ccggcggtca caggactgc ctgcggtgtc gctggcctgg      5520
ggcctgtggg agcagccgag cgggatgacg gagacgctca gcgaggtcga ccggagcagg      5580
atcgcgcgcg ccaacccgcc gttgtccacc aaggagggat tgcggctgtt cgatgccggg      5640
ctggcgctgg accgggcagc ggtagttccg gcgaagttgg acaggacttt cctggccgag      5700
caggcgcggt cgggctcgct gcccgcattg ttgacggcac tggtaccccc catccgtcgt      5760
aataggcggg ctagcggaac cgagctcgcg gacgagggca ccctgctcgg ggtggtgcgg      5820
gagcatgccg cggccgtgct gggggtattcg agcgcggctg acgtcggggt cgagcgcgct      5880
ttccgggatc tgggttttga ttcgttgtct ggtgtggagt tgcggaaccg ccttgccggg      5940
gtgctggggg tgcggttgcc ggcgactgcg gtgttcgact atccgacgcc gagggcgctg      6000
gcccggttcc tgcaccagga actggcagac gagatcgcta cgacgccagc gccggtgacg      6060
acgaccaggg caccggtcgc cgaagacgat ctcgtcgcga tagtcgggat gggatgccgt      6120
tttcccggtc aggtgtcctc gccggaggag ctctggcgtt tggtggccgg gggcgtggat      6180 gcggtcgcg acttcccagc cgatcgcggc tgggatctgg caggcttgtt cgatccggac      6240
ccggaacggg ctgggaagac ctacgtgcgg gaagggccct tcctcaccga cgccgatcgg      6300
ttcgatgcgg gtttcttcgg gatttccccg cgtgaggcgt tggcgatgga tccgcagcaa      6360
cggctgttgc tggagctgtc ctgggaggcc attgaacggg cagggatcga tccgggttcg      6420
ctgaggggga gtcggaccgg tgtgttcgcg gggctgatgt accacgacta tggcgcccgg      6480
ttcgccagcc gagccccgga aggttttcgag gggtatctcg gcaatggcag tgctgggagt      6540
gtcgcgtcgg gccggattgc gtactcgttt ggtttcgagg gtcctgccgt gacggtggat      6600
actgcgtgtt cgtcgtcgtt ggtggcgttg catttggcgg gtcagtcgtt gcgttccggc      6660
```

```
gaatgcgatc tcgcccttgc cggtggtgtg acggtgatgt cgacgcccgg gacgtttgtg    6720
gaattctccc gtcagcgggg cctggcaccg gacgggcggt gcaagtcgtt cgcggagagc    6780
gcggacggta ccggttgggg tgagggtgct ggtttggtgt tgttggagcg gttgtcggat    6840
gctcggcgga atgggcatcg ggtgttggcg gtggttcgtg ggtcggcggt gaatcaggat    6900
ggtgcgtcga atggcttgac cgcgccgaat ggtccctcgc agcagcgggt catccagcag    6960
gcgttggcga gtgcgggtct gtcggtgtcc gatgtggatg ccgtggaggc gcatgggacc    7020
gggaccaggt tgggtgatcc gattgaggcg caggctctga ttgctacgta tgggcgcgat    7080
cgtgatcccg gtcggccgtt gtggttgggg tcggtgaagt ccaacatcgg tcatacgcag    7140
gcggcggcgg gtgttgccgg tgtgatcaag atggtgatgg cgatgcggca cgggcaactt    7200
ccgcgcacgc tgcacgtgga tgcaccctcc tcgcaggtgg attggtcggc ggggagggtc    7260
cagctcctga cggagaacac gccctggccc gacagtggtc gcccctgtcg ggtgggggtg    7320
tcgtcgttcg ggatcagcgg caccaacgcg cacgtcatcc tggaacagtc cacggggcag    7380
atggatcagg cagcggagcc ggattcgagt cctgttctgg atgttccggt ggtgccgtgg    7440
gtggtgtcgc gcaaaacacc cgaagcgcta tccgcccagg cggcaacgtt ggcgacctat    7500
ttggaccaaa atgttgatgt ctcccctctg gacgttggga tttcgcttgc ggtgacccgt    7560
tcggcgctgg atgagcgggc ggtggtgctg ggtcggatc gtgacacgtt gttgtctggc    7620
ctgaatgcgc tggctgccgg tcatgaggct gctggcgtgg ttacgggacc tgtcgggatt    7680
ggtggccgga ccgggtttgt gttcgccggt caaggcggtc agtggttggg gatgggccgc    7740
cggttgtact cggagtttcc ggcgttcgcc ggtgctttcg acgaagcatg cgccgagctc    7800
gatgcgaacc tggggaggga agtcgggggtt cgggatgtgg tgttcggctc cgacgagtcc    7860
ttgctggatc ggactttgtg ggcgcagtcg ggtttgttcg cgttgcaggt cggtctctgg    7920
gaattgttgg gtacgtgggg tgttcggccc agcgtagtgc tggggcattc ggtcggggag    7980
ctagccgcgg cgttcgccgc aggtgtgctg tcgatggcgg aggcggctcg gctggtggcg    8040
ggtcgtgcgc ggttgatgca ggcgttgcct tctggcggtg ccatgctggc ggtgtccgcg    8100
accgaggccc gagtcggccc gctgctcgat ggggtgcggg atcgtgttgg tgtcgcagcg    8160
gttaacgctc cggggtcggt ggtgcttttcc ggtgaccggg atgtgctcga tggcattgcc    8220
ggtcggctgg acgggcaagg tatccggtcg aggtggttgc gggtttcgca cgcgtttcat    8280
tcgcatcgga tggatccgat gctggcggag ttcgccgagc tcgcacggag cgtggactac    8340
cggtctccac ggctgccgat tgtctcgacg ctgaccggaa acctcgatga cgtgggcgtg    8400
atggctacgc cggagtattg ggtgcgccag gtgcgagagc ccgtccgctt cgccgacggt    8460
gtccaggcgc ttgtggacca aggcgtcgac acgattgtgg aactcggtcc ggacggggcg    8520
ttgtcgagct tggttcaaga gtgtgtggcg gagtccgggc gggcgacggg gattccgttg    8580
gtgcggagag accgtgatga ggtccgaacg gtgctgacg cttggcgca gacccacact    8640
cgtggtggcg cggtggactg ggggtcattt ttcgctggta cgagggcaac gcaagtcgac    8700
cttcccacgt atgccttcca acgacagcgg tactggctgg agccatcgga ttccggtgat    8760
gtgaccggtg ttggcctgac cggggcggag catccgctgt gggtgccgt ggtgccggtc    8820
gcgggcggcg atgaggtgct gctgaccggc aggctgtcgg tggggacgca tccgtggctg    8880
gcggaacacc gcgtgctggg cgaagtcgtc gtccccggca ccgcgttgct ggagatggcg    8940
tggcgggccg gtagccaggt cggttgtgaa cgtgtggagg agctcaccttt ggaggcaccg    9000
```

```
ctggtcctgc cggagcgggg cgctgcggcg gtgcagttgg cggtgggggc tccggatgag   9060
gccggccggc gcagtttgca gctctattcc cgaggcgctg atgaagacgg cgactggcgg   9120
cggattgcct ccgggctgtt ggcccaggcc aatgcggtgc cgccggcgga ttcgacggca   9180
tggccgccgg acgcgccgg gcaggtcgat ctggcgagt tctacgagcg cctcgccgag    9240
cgcggcttga cctacggtcc ggtattccaa gggctccgcg ccgcatggcg gcacggcgac   9300
gatatcttcg ccgaattggc cgggtcacca gacgcctcgg gtttcggcat ccacccggcg   9360
ctgctggacg ctgcactgca cgcgatggcg cttggtgctt cgcccgactc ggaagcgcgt   9420
ctgccgtttt cctggcgtgg cgcccagctg taccgcgctg aaggagcagc gcttcgggta   9480
cggctctcgc cgctgggctc cggtgcagtc tcattgacgt tggtggatgc cacagggcga   9540
cgagtcgctg cggtggaatc gctttcgacg cgaccggtct ccaccgacca gatcggtgcc   9600
ggtcgcggcg atcaagagcg gctgctgcac gtcgagtggg taaggtcggc tgaatctgcg   9660
gggatgtctc tgacctcctg cgcggtggtc ggtttgggcg aaccggagtg gcacgctgcg   9720
ctgaagacca ctggtgtcca agtcgagtcc catgcggacc ttgcttcgtt ggccaccgag   9780
gttgccaagc ggggttcagc tcctggtgcg gtcatcgtcc cgtgcccgcg accccgagcg   9840
atgcaggagc tgccgaccgc cgcgcgaagg gcgacgcaac aggcgatggc gatgctgcag   9900
caatggcttg ccgatgaccg gttcgtcagt acgcgcctga tcctgctgac gcatcgggcg   9960
gtctccgcag ttgctggaga agacgtgctc gacctggtac acgcgccgct gtggggcttg  10020
gtccgcagcg cgcaagcgga gcacccggac cgattcgcct tgatcgatat ggacgacgag  10080
cgagcatcgc agacggcact cgccgaagcg ctgactgcgg gagaagcgca gctcgcggtg  10140
cggtcgggag ttgtgctggc gccccgcctc ggccaggtga aggtgagtgg aggtgaagcg  10200
ttcaggtggg atgaaggcac cgtgctggtc accggcggaa ccggcgggct cggggccctg  10260
ctcgcacgcc atctggtcag cgcccacggt gtgcggcacc tgttgctcgc aagtcgccgt  10320
ggtctggcgg cgcccggagc ggatgagctg gtggccgagc tggagcaggc cggcgccgac  10380
gtcgcggtcg tcgcgtgcga ctcggcagat cgggactcgc ttgcgcggct ggtggcgtcg  10440
gtgcctgcgg aaaacccgtt gcgggtggtg gtgcacgccg ccggtgtgct ggatgacggt  10500
gtgctgatgt cgatgtcgcc ggagcgcttg gacgcggtgt gcggcccaa agtggatgcc   10560 gcgtggtacc tgcacgagct gactcgggaa ctcggtctgt cggcgttcgt gttgttctcc   10620
tcggtcgcgg gcctgttcgg cggtgcgggg cagagcaatt acgctgccgg caacgctttc   10680
ctggatgcct tggcgcattg ccggcaggcc caggggctgc ccgcgctgtc gctggcctcc   10740
gggctgtggg cgagtatcga tggaatggcg ggcgacctcg ctgcggcaga tgtggagcgg   10800
ctgtcgcggg caggcattgg cccgcttcg gcaccgggag ggctggcctt gttcgacgct  10860
gccgttggct cggacgaacc gttgctggca ccggtgcgac tggatgtcga agcactgcgt  10920
gtgcaggccc gatccgtgca gacccggatt ccggaaatgc tgcatggcat ggcaatgggg  10980
ccaagccgcc gcactccgtt cacttccagg gttgagccgt tgcacgaacg gctggccgga  11040
ttgtcggagg gcgaacgtcg gcagcaagtg ctccagcgcg tccgcgccga tatcgcggtg  11100
gtactggggc acggcaggtc gagcgatgtg gacatcgaga agcctttggc cgagctgggt  11160
ttcgactcgc tgacggccat cgaactccgc aaccgtctcg ctaccgccac cggactgcgg  11220
cttcccgcga cgctgccctt cgaccacggc actgcggcgg cactcgccca gcacgtgtgc  11280
gcgcagctag gcaccgcgac cgcgccggca ccgaggcgaa ccgacgacaa cgacgccacg  11340
gagcccgtga ggtcgctctt ccaacaggcg tatgcggctg gccggatact tgacgggatg  11400
```

```
gatttggtga aggtcgctgc ccagttgcga ccggtgttcg gttcgcctgg cgagctggaa   11460
tccctgccga aacccgtcca gctttcccgt ggtcccgaag agcttgcctt ggtgtgcatg   11520
ccggcgctga tcgggatgcc gcccgcacag cagtacgcgc ggatcgccgc cgggttccgc   11580
gatgtgcggg acgtttcggt gatcccgatg cctggattca ttgcgggaga accgctgccg   11640
tccgccatcg aggtggcggt tcggacgcag gcggaggcgg tgctgcagga attcgccggg   11700
ggctcgttcg tactggtcgg gcattcctcc ggggctggc tggcgcacga ggtagccggt    11760
gagctggagc gtcgcggggt cgtcccggcc ggggtcgtac tgctggacac ctacatcccc   11820
ggtgagatca cgccgaggtt ctccgtggcg atggcccacc ggacgtatga gaagctcgcg   11880
actttcacgg acatgcagga tgtcggtatc accgcgatgg gcgggtactt ccggatgttc   11940
accgagtgga ctccgacgcc gatcggtgct ccgacgctgt tcgtgcggac cgaagattgc   12000
gtcgcagacc ctgaagggcg gccgtggaca gatgactcct ggcggccagg gtggactctc   12060
gcggatgcca cggtccaggt gccgggcgac cacttctcga tgatggacga gcacgccggg   12120
tccaccgcac aggcagtcgc gagttggctt gacaaactca accagcgcac cgctcggcaa   12180
cgctgacggg cgtccttta ggaccttctg ggcggcaccg gccacccgg cggtgccgcc     12240 ttccgtggtc caggctcgcc gatcttgacg gcgcacgatg cgcggcacgc gcgctgatcg   12300
tgattccgct gccgctcgtg gccatcggcc tggcgaatca tgtccttcg ggcaacgtca    12360 aacgaattcg tccgagcccg cattccgagg tgagggcac ccttgggtgg ctgagccgct    12420
caagggtgcc cctcacctcg aaattcgtcc gatttgggcg gtggacgcaa ccccggtggg   12480
cgtggtgcgt ctttcttgtt gacagagcgg tgagaagccg ctgacacacc tgagaggaaa   12540 agggagcat gatgctcaag cgccaccgtt tgacgaccgc catcaccggc cttctggggg    12600
gagtactgct ggtcagcggc tgcggaaccg ccgccgcact tcagtcctcg ccggcgcccg   12660
ggcatgacgc gcgcaatgtt ggtatggcct cgggcggggg cggcggggac atcggcacgt   12720
cgaactgctc ggaggccgat ttcctcgcca ccgcgacacc ggtgaaaggc gaccccggca   12780
gtttcatcgt ggcgtacggg aaccggtcgg acaagacctg cacgatcaac ggcggcgtgc   12840
cgaacctcaa gggcgtggac atgagcaact cgccgatcga ggacctgccg gtcgaggacg   12900
tgcggcttcc cgacgcgccc aaggaattca ccctccagcc cggtcagagc cgtacgccg    12960 gcattggcat ggtcctggcc gacagcggcg acccgaacgc ccatgtcctc accgggttcc   13020
agtcctcgct gccggacatg tccgaggccc agccggtcaa cgttctcggc gacggcaacg   13080
tgaagttcgc cgcgaagtac ctgcgagtca gctcgctggt gtctaccgca gacgagctgc   13140
gctaaaaccc atgtgagtcc cgcagattcg acctcgccgt gcggcgcctc cggcgaagcg   13200
tccgtacgtt tgtcgttgtg accagcgttg ttcacgtccg ggcgcagcgc tggtacatac   13260
tcaggcgtct cgggcgcctc caacggggcc tggcatccgg ggccgtcgag tgcggcggcg   13320
ctgacgcgtt ctctgtcggg cgttgtcacg ccgccgcct cgaaccggtc ccgcccgtc     13380 ggagccggtg gtccagcgcg gtgtggcggc ggccggagcc gacggtgcgc accgcctgcc   13440
cgagggcctt tttcgaaccg acgaggacca cgaccttctt ggcccgggtg accgccgtgt   13500
agagcaggtt gcgctgcagc atcatccagg cgcttgtggt caaggggatc accacgcacg   13560
ggtattcgct tccctgcgaa cgatggatgg tcaccgcgta ggcgtggacc agttcgtcga   13620
gttctgtgaa gtcgtagtcg atgtcctcgt cctcgtcggt tcgcacggtc atggtctgtg   13680
cttcgttgtc gagggcggac acgacgccct gcgtgccgtt gaacacgccg ttggcgccct   13740
```

```
tgtcgtagtt gttgcggatc tgcgtgacct tgtcgccgac gcggaagatc cgtccgccga   13800
accgccgctc tggcaggccc tccctggccg gggtgatcgc ttcctgcaac agctggttca   13860
gcgcgcctgc acctgcgggg cctcgatgca tcggggcgag gacctgcacg tcggtgcgcg   13920
ggttgaaccg gaacttccgc ggaatccggc gggcgacgac gtcgacggtg agctcggcgg   13980
tcggttcgct ttcctctacg tggaacagga agaagtcggt cagcccgtgt gtcagcggat   14040
agtccccggc gttgattcgg tgcgcgttgg tcaccacccc ggactcggcg gcctgccgga   14100
acacctcgtt gagccgcacg tgtggaatcg gggtgccagg ggcgagcaga tcgcgcagta   14160
cctcaccggc tccgaccgac gggagctggt cgacgtcgcc gaccagcagc aggtgcgcgc   14220
cgggcgcgat cgccttggcc agtttgttgg ctaacagcag gtcgagcatg gacgcctcgt   14280
cgaccacgac gaggtcggcg tccagcgggt tgtcccggtc gtaggcggcg tccccgcccg   14340
gctggagttg gagcaggcgg tgcacggtcg ccgcgtcgtg tccggtgagc tcggtcagcc   14400
gcttcgccgc tcgtcccgtc ggcgcggcga ggatcacctt ggccttttc gcctgagcta   14460 atgcgatgat cgaccgcacg gtgaagctct tgccgcagcc tggacctccg gtgagcacgg   14520
cgaccttctc ggtcagggcc agcttgacgg cgcgctcctg cgcctcggcg agttcggcac   14580
cggtagcgcg gcgcaaccag tcgagggcct tgtgccaatc gacgtcggcg aagacgggca   14640
tccggtccgc gctggtgttc agcagccggg acagctggtt ggccagggcg acttcggcgc   14700
ggtggaaggg cacgagatag atcgcgaccg tcggcacctc gtcgtcatcg gtggggatct   14760
cctcgcggac cacaccttcc tcggtgacga gttcggcgag gcattcgatc accagcccgg   14820
tgtcgacggc gaggatcttc accgcctcgg cgatcagctc gttctccggc aggtagcagt   14880
tgccgtcgcc ggtggactcc gacagcgtga actgaaggcc cgcctttacc cgctgcgggg   14940
agtcgtgcgg gattcccacc gctttggcga tggtgtcggc ggtcttgaaa ccgattcccc   15000
acacgtcgcc tgccagccgg tatggctctt ccttgacggt ccggatcgcg tcgtcgtggt   15060
actgcttgta gatcttcacc gccagcgagg tcgagacgcc gacgccttgc aggaagatca   15120
tcacctcctt gatcgccttc tgctcctccc acgcgtcggc gatcagcttc gtccgcttcg   15180
ggccgagctt ggggacctcg atcagccgcg cgggttcctg ctcgatgacg tcgagcgcgg   15240
cgacgccgaa gtggtcgacg atcttctcgg cgagtttggg gccgatgccc ttgatcaggc   15300
cagaccccag gtagcggcgg ataccttgca cggtcgcagg cagcacgtc gtgtagtcgt   15360 cgacgtggaa ctgccgcccg tactgggggt gcgaccccca ccggccgcgc atgcgcaacg   15420
cctcgccggg ctgcgcgccc agcagcgcgc cgacgaccgt caccaggtca ccgcccggc   15480 cggtgtcgat ccgcgcgacg gtgtagccgc tctcctcgtt ggcgaacgtg atccgctcca   15540
gcgtgccctc cagcaccgca gtccacgtgg ccgactcccg tccttttcc accgacaaca   15600 cgtatcacga acggctgtca agcaaaccgg cggtcaccac atgcagcggc atctcccgaa   15660
cgcctcgggc tccggcgtca gcgggtgggc gttcgcgatg ccttggtgcg gccggtggga   15720
gttgtagatt ttttcgtcct cgcgcagggc ctggagtagg tgccgctggc tccagatcga   15780
aagcgccggg ataaaccggc ttgacggagg agatggaaga gctctacgtc gaatggccag   15840
cgacccacga cgaccccgag tcatgcgtcg acgacctgcg aggccgtggc gaagcgttga   15900 caggggcac gtgggggcgt gcgatcaggt cgcggcgccg gctcagcgcc gtgtccggac   15960
gcaccagcag ccgcgacgga ctggttccgc tcctcgagcg cggtgtcctc gatcgtctt   16020 ttcgagctcg atgccggccg cgttcgcgag gtggccagtc cagtcggtcg gcagtcgtgg   16080
tcgcagtctg ccttttgaac atctggtcaa ttcagctttg aatgatcgtt cggcgagtat   16140
```

```
tgtcctgccc gccaattgtt tgctcgccgt gcgccctggg acaggagcgc ggcgttcggg    16200
gacggcgtgc tggcgaaggt gtcgattggc tcggacggcc ggaccaggat cgccgacgtc    16260
gtgatcgcca cgagcgtcgg cgatgcccgg tactatctgg agcaccagcg agtggacaac    16320
gacttccacg ggcgcggtgc gctcctgatc atgaatcaag aactgagacc gtcagggtga    16380
acgtgccgtc gtggggcact gtgaggatgt gcatcacacg gccggggtag gtgatcgagg    16440
aggccctgat cgcgggctgc cgcggctgtg cccagtcgaa tcgcagcacc acctggccgc    16500
gggtgagcgt cagcccctgc gcgtcgagtg cgactttgtc ggagtccctc accaccaacg    16560
ggatctgctc ggttgccggt gcgttcgcct gcaccgacct ggtgatccgg tcgggccgca    16620
cggtcacatc ggtgacgacc gagccattcg cggtgcggta gcggaaccgg tatggctcgc    16680
cgcccaggaa ctccgcctgc tgcggtccgt tcgcgtccgg cacctggccc gggaagaccg    16740
tcgcccagca ggcgtggtcg ttgttgttca tcgactggac gaccgtgccc gcgaccgggt    16800
gccacaggaa cgtcagaccg gtgcggccca gcgaggtcgc gcgcctcgtg ccgaagtagc    16860
cgccgaggta gaactgcggc ctgcgtagga acaggaagtc ttgcccctgg tcgctgcgga    16920
tctcggtgaa gtgcgcctgt tggtatggaa gtttcgcgat cgcggccgtg cgctgggcgc    16980
gggtcggata gcgctcgccg tagatcgcgt gggtgaggat gcgcggtgag gtgtcctgtt    17040
tgacgagtgc gggcaccggt gccgggtcct cggcccaggc cgctcgtgcg gcggcgaggt    17100
cttcgcggct ggacaggaac gcgcccaagt tcggcaccac tggcacgaac tggttgttca    17160
gcgcggtacg ttccgggtcc ggtcgcacgt cggcgtagaa ccgcgccgag gtgcgggagt    17220
tgggggcgac gttggcgaac cagccggagc cgtcgggttc gcgcagcagg ttgtagctga    17280
gccagtcggt gtacttccgc gccatcgtga cgaggttggc gttgttggac tggcgccacg    17340
cgtcggccat ctccggcagc atcacctcga agttgtagtt ggtgtccgcg ccggtcaact    17400
cgtagaagta gcccgaagga ctctgcccgt tcgcggcaag gcgcgcgaac gcctcggtca    17460
actgctgccg cagcgcgggg tcggggtcct ggttcagcgc gagcgaggag ccggcgagcc    17520
cggcggtaac ctggttcgcg tagtggattg tgggctgcca ggcgctaccg ttgcccgggt    17580
tgaggagcca cgtcatcgct ttgcgcagcg ccgaggtgat ctgcgactgg cgttgcggca    17640
ggatgttcgc cgcgcgcagc agggcgttgg tcttgctcag gtaccccaac ccgaagccgg    17700
tggcggcgag cccgtgctcg gtcggcgaat actccggcca cgagccgtca tcgtgctgca    17760
accctaggta gtgtccgagc ccggcgtcga gcgcggcgag cagagtcgcg tcgccccggt    17820
acgggttcca cgtgcgggat tgcgtggcga accaggcgag cgtgtagacg tgctcctgga    17880
cgcgggcgtt gtaggacacc gccgggctgc gccaccagcc tccggcgaag aagccgctcg    17940
agtccatgtc ggcgaccatc ggcgagaccg cggtgaggta cgacgcgaat cgctgctcct    18000
cgggtgcgaa caggcgccgg ttcggtgtgg tgggcggcgg ggcgggcagt gcgagtgcgc    18060
gggtcggcag tgcggcgagc agtccgagag cggcggcgcc ggtcatcagg ctgcgacggc    18120
tgaacgtagt cacgggccta cctccttgtg gccgatcaac cctcacccgc tgcgtagccg    18180
cacgtcaaga tgataattcg aattattatg ggcttgacga cgcgtaggcc gacgacgcag    18240
aattcctgcc aattcgtatt ggcaagcggg ggtgctcgtg gcccgacggc tcacccagca    18300
ggacatcgcc cggatggcag gagtcagcca ggccacggtg tcgctggtgc tcaacaaccg    18360
gaaggacggc aacgtccgga tcgcggcgga gacccgtgcg caggtactgg aggtgattcg    18420
gaagaccggc tacgtcgcga acccgatcgc ccgcaggatg cgcgatcggc acaaccgcat    18480
```

```
cctcggcgtg ttcacctacg aggcggtgtt cccgagcacc cacgcgaact tctaccagtc   18540
gttcctcgaa ggcatcgagg aacaggccga ggaggtcggc tgtgacctgt tgttgttcac   18600
cagcgccaag gccaccgggg agcggcggcg gattttcggc gacgacagcc gggtgcggct   18660
cgccgacggc agtctgctgc tcggtcgcac ggtcgaccgc gacgacctga cccagctgct   18720
cgccgaaagc atcccgtacg tctccatcgg acgacgcgac gacgcgggcg gtccggtgcc   18780
gcacgtcggg gccgactacc gcaccgcggt gcgagacctg gtggaccgcg cggtcgcgct   18840
cggccaccgc gggttcgcgt acgtggggtc tggtgggggc gcggagtcgt ccgcggatcg   18900
gctgcgaggc ttccgcgaag ccgttgccgc acatggcgtc caagggatgc atgtggagac   18960
cccacagctc gatcagctgc gcgaagcggg cgtcaccgct gtgctcaccg aagaggtgtc   19020
ggacggggcc gcgctcgtgc tcgccgggcg cgaacgcggg ctctccgtgc cgggcgacct   19080
cgccgtgctc tcgctcggtg ccgctacccg gtcggcaccg gacgacgacg tggcgctcac   19140
cggtttccgc atccccaggc gcgagatggg gcgccgggcg gtgcaggcgc tgaccgaggt   19200
gctcgaaaac ggcaccacac cgcaagaact gctcccgtgc gagttcgtcg agggctcgac   19260
gctgggcgca ccacgccttt gaccaggagg aactgttgct cgaccacacc acggacgttg   19320
tcgtcgttgg cggcggactc ggcggtgtcg ccgccgcact cgcgttgctg cgcgcgggcc   19380
gccgggtcgt gctcaccgag gagtacgact ggctcggcgg ccagctgacc agccaggccg   19440
tgccgcccga cgagcacagc tgggtggagc gcttcggcgt caccgcgagc taccgggcgt   19500
tacgcgacgg catccgcgac tactaccgcc gccactaccc gctgaccccg cgcgcacggg   19560
cgtggcggga gctcaacccc ggtgcgggca acgtgagcag gctctgccac gagccccgcg   19620
tcgccgtcgc ggtgatcgac gagatgctgg cgccgttccg cggcagtggc aggctgaccg   19680
tgctgcagcc gtaccggccg gtggccgcgc acaacgacgg cgaccggatc gtgtcggtga   19740
ccgttgcgca ccgcgacacc ggtgaacaga tcgagctctc cgcgccgtac atcctggacg   19800
cgacggagac gggtgaactg cttccgttgt ccagcacgga gtacgtcacc ggcttcgagt   19860
ccactctgga caccggcgag ccgagtgcgc ccgacgtcgc gcagccggcg aacatgcagg   19920
cggtgtcggt gtgcttcgtg gtcgaccacg tcgacggcga ccacaccatc gacaaaccgg   19980
cgcggtacga cttctggcgc gcgtaccagc cggacttctg gggcgaccgg atgctgtcgt   20040
tccgctcccc caaccgcgc acgctcgcga tctccgaacg tacgttcacc ccgaacccgg   20100
acgacgaccc gctcggcgtc gtgtcggacc agcggctcag tgccggtgac agcaatctgt   20160
ggacgttccg gcgcatcgcc gcgcgtcgca acttcgtcga gggtgcctac gacagcgaca   20220
tctgcctggt gaactggccg atcatcgact acttcgagtc gccggtgatc gacgtgccgg   20280
acgccgacgc gcacatcgcc gcggcgcggg aactctcacg ttcggtgctc tactggctac   20340
agaccgaggc gccgcgccca gacggcggca ccggcttccc cggcctccgc ctgcgcggcg   20400
acgtcaccgg cagcgcggac ggtctcgcgc aggcgccgta catccgcgag tccaggcgca   20460
tcagggccga gcacacgatc gtcgaacagg acctctcgct cgccgtgcgc ggcgacaagg   20520
gtgcggtgca gcacgccgac gccgtgggtg tcggcatgta ccgtatcgac ctgcaccct   20580 ccaccggtgg cgacaactac atcgacgtcg cgagctgccc gttcgagatc ccgctcggcg   20640
cgctgatccc gcaacgggtg gagaacctgc tacccgcggg caagaacatc ggcaccaccc   20700
acatcaccaa cggttcccac cggctgcacc cagtcgagtg aacgtcggc gaggtcgcgg   20760 gcgcgctcgc tgccttctgc ctggcgcacc gagtcacccc tcgcgcggtg cgcaatacc   20820 ctggcctgct cgcggacttc cagcagtgtc tggaacgcga cggggtcgag ctccgctggc   20880
```

```
cggacgtgtc cggctactga cgcagggaga cgaaaatgac aaagctgtca cgacgactca   20940
cggcactcat cgtcgcaggg ctgttcgccc tcaccggctg cggtggtgga tcaaccgcac   21000
agtccggacc gaagtcgctg cgcatgaccg tgtggactgc caacgcggcg catctcaagc   21060
tgctcaacga catcgccgcc gagtacaagg cctcgcaccc ggacatcgcc gagatcaagt   21120
tcgactcggt gcccgccgac ggctacacca ccacgctcac cacccagatc gccggcggta   21180
acgcgccgga cctggcctgg atcctggagg agtcggcacc ggacttcgtg gcgtccggtg   21240
cgctcgcccc ggtgcgcggc aagatcgaga aggccgacga gctcgtgccg tccgcgacga   21300
agctgtggga aggacggc gaactgtacg cctacccgtt ctccacctcg ccgttcggct   21360
tgttcgtcaa caccgacctg gtgaagggcg cctcggcgga ctggacctgg gaccaggcga   21420
tcgcggctgc ctctgcgtcg gcggccgcct ccggcaaggg cggcctggta ctgccggact   21480
tcaagtacca gaactgggca gtgctgtcct ctatctggcg cggctgggga gctgatgcgt   21540
ggagcgcgga cggtcgctcg tgcgggttct ccagcagcga gatgaacgac gcgatgtcct   21600
tcttgcacaa ggccatcttc accgacaagg cgattccggg ccccggcacg acggtggact   21660
tcttcgccgg cgacgcggcg atggcgatcg gccagatctc ccggtccagt gcgttgaagg   21720
acgcgaagtt cggctggacg ctgctgccgc tgccggccgg tccgaagggt gactacgcgg   21780
tgatcgggca ggccgggatc ggtgtgctga agcagtcgca caacgtcgac gccgcgacgg   21840
acttcctcgc cttcctcacc aaccagacca actccgccaa gctcgcgcag ttcttccccc   21900
cggcgcggtc gtcgctgctc aacgcggaga cgctcgccaa gagcaacccg ttgatcaagg   21960
ccgagcaact gcagtccgtc gtcgtcgacg gcatcaacaa gggcgtcgtg aagccgagcc   22020
acaagggtca ggaggagctg aaccagacga tccgcgccgc gctcgacccg ttgtggaagc   22080
cggacgcgaa cgtgcagaac gtgctgaacg acgtgtgcac caagatcaaa ccgctgctgg   22140
agaacaagtg acggcggtcg cacactccac gcgggccgta gcccgcaagg ggacgtcgta   22200
ctggacgcag cgcaggcgcg acaatctggt tggttacctg ttcgtcgcgc ccgcgctgct   22260
cggcagcatc gcgttcgtgc tggtgccgct ggccttggtc ggctggtaca gcctcaacga   22320
gtggaacgtg ctcgccggca cgttcgagtt cgtcggcgcg cagaactacc aacagctgct   22380
cgccgacgag aagctgcgcg actcgctggt ggcgaccact tggttcgccg ccggcctggt   22440
cgtgctcaac ctgtcactag cgctgctgct ggccgtgctg ctcaaccaga gctgagcgg   22500
caccacggtc ttccgcacgt tgttcttctc tcccgtcctc gtgtcgctgg tggcgtggac   22560
gctggtgtgg cagctgatac tgcagccgga gggcagcgtc aacggactgc tcgggttctt   22620
cggtgccgac gggccgaact ggctgcgcgg tgagtcgacc gcgatggtct cggtgatcgt   22680
cgtgcaggtc tcaagaacg tcggcctgaa catggtgctg ttcctcgcgg cgctgcaagg   22740
cgtgccgcag ccgttgtacg aggcggcgaa gatcgacggg gcgggtgcct ggacccggtt   22800
ccgccgcatc accttgccgt tgatcagccc gacgatcctg ctcacgtcga tcatcaccat   22860
cgtcggctcg ctgcaggtgt tcgcgcagat cgcggtgctc acgcagggcg tccgggcac   22920
gtccacgacc gtactgatct actacctgta ccagcaggcg ttccagttcc accacttcgg   22980
ctacggcgcg acgatctcgg tactgctgtt cgtcatcgtc gccgcactca ccctgctgca   23040
gtggcagatg cgccggaagt gggtgctgca tgaggcttag ggtcaagatc acgctatacg   23100
ggctgctgtg cctgctgtgc gtgccttttcg tgttcccaac ctggtggatg atcacctcgt   23160
cgatgaagcc catcagcgag atcttctcca cctcgccgct gccgtcggag tggacgttct   23220
```

```
ccacctaccg gcaggtgttc gagatgcagc cgttcgcgca gcagtactgg aacagcctct   23280
acatcgcggt gatcgtcacg acaggcacaa tggcggtggc ggcgatggcc ggatacgcgt   23340
tcgcgcgtat ccggttcccg ggccagaacg tgctgttcgt ggtcgtcctg atcggcctgc   23400
tcatcccgag cgaggtcacc atcgtgccgc tgttcaagat gttccagtcg ctcggcctga   23460
ccaacacgca ctggccgcta atcatcgtgc cgatcttcgg ggcgccctgt gtgctggcga   23520
tcttcatcat cgcgccagttc ttcatcgccc tgccgtcgga gctggaggag gccgcgcgga   23580
tggacggcct cggacgagcg ggcatcttct accgggtggc cctgccgctg tcccggcccg   23640
cgctgggcgc cgtcgcgatc ttcacgttcc tgcactcgtg gaacctctac ctggagccga   23700
tcgtctatct gtccacaccg gacatgtaca cgttgccgca agcgctcacg cagttcgtcg   23760
acaactacgg cggcccgatg tggaacgtgc agctcgccgc cgcgaccatg accgcagtgc   23820
cgattctcgt cgtgttcgtg ctggcgcagc ggcagttcat cgagggactc gcgcacaccg   23880
gggttaaggg gtgagtcccg cgatcgaccc ggagatcgcc gcgctggtag acctcgccag   23940
accaccggtg acgccagcgg gaatcgacgc ggtccgggcg ggaggacgcg tcgtcaccga   24000
tgccgagctg acgcgcggtg gcaccgtgac gttcgccgat ccgatgccg atggcgtgcc   24060 cgtgcttgtg ctgcgcccag cgggtgtgcc acgtcttccg gtgctgcacc tgcacggcgg   24120
cgggatggtc gcgggcaccc ggcgcaccga cctgcacgtg ctggccgagt gggtgtcgga   24180
gctgggtgtc gtgctggtgt cgccggagta ccggctcgca cccgagcacc cgcacccggc   24240
gccgtcgcag gactgcttcc gggtgctgga gtggatgtcc cgcaacggct tcggcccgcc   24300
tgtcgttgcg ggtacatcgg cgggcggcgg gctggcggct cgggtgacgc tgatggcccg   24360
cgacctcggc ggtccgccga tccgcggcca gctgctgatg tgcccgatgc tcgacgaccg   24420
gtgcgacacc ccgtccagcc acgagtacct cgacgggaac acgtgggtgc gcgcgtcgac   24480
gatcaccggc tgggaagccc tgctcggcga tgcgcggggc ggtcccgacg tctcaccgta   24540
cgccgcaccg gcacgtgcca ccgacctcgc caggttgcca cctacctacg tcgacatcgg   24600
ctcggccgac ctgttccgcg acgaggccat cgactacgcc ctgcggctgt ggcgcgctgg   24660
cggagacgca gaactgcacg tctgcccggg cgggtgccac ggattcgacc agctcgtgcc   24720
cgacgcggcg ctgtcgcggc gggcacgagc cgcccgcatc gactggctgc ccgcgtgct   24780 ggagactcac agctaaacgt tcggcatgg ctcgcgggcg cgcattcgga gatgaggtag   24840
cggtcgctgc ggcgttgccc gccgttactg gcctgcggag acgacgtact cgcacttgaa   24900
cctgttggcg aaggcgtagg gcctcgtggt gcgtctgacc gggttcgctg gttgtgggct   24960
ggggtttagt cgggccgtca ggctgtacgc gtcgcatccc tcagcgggag ttgtcggtgc   25020
ggggccgggt gatcaggtcg cgaagctccc cggataccgg tgggggtcgc cgggtccact   25080
tcggcctgac caggcgtcga tgccaggcga gcgaggtgcg tgtcgagaca atccggtggc   25140
cgtggagtcg ctgggggtag gagccggggg agccgcggcc gcagccccg atccggccag   25200 gccggcttcg ccgtaatagc gggagcgcat tcaatcgtcc ccgatctgtg cctctggatc   25260
acgctggggg cgcatcgtgc tgtgatcagg ggattgggc tggagacttt cgacccgcac   25320
cgctggcacc tggccttcga cgtgctgtgg cgcctcggcg gtgacgagcc gtacctgtcg   25380
gtcatcggtt gcgggctgaa atggcctgct cacatccaag atgtcagctt gcaccttgag   25440
gcaacgttca gcggtcgcgc atgccctagc acctcggaca atctggtcac gactgatgtc   25500
gctactgtgg gtgcagccgc ggtactgatc cggtgtggtg gtgcgggggt gcgtccgttg   25560
tggacgcacc cccgtttcgc tgtgccgagg aagaacgtgc tgttgtggac tatgtagttg   25620
```

```
cagccgagtt ggtccgagga gttgcctaga ccacgcgggt gctgccgggt cgcggagcgc   25680
agcagcagcg cggccaagtt caccagcggc aagcacgaac cggcggacgc tgatccgcac   25740
tacccggccc tgatgacggg cctcgccggc gacgatggtc cggccgtcgt cggaggtgat   25800
caggcagggc ggtctgcccg tgcacgtcga atagcgctcg ggcctcaccg tagaacggct   25860
cgaggtcctc gtaggacaat ggccacgcct tcgaccggcc gcccatgtgc tcgacctcgg   25920
tgaagtcgct cgcgcggaaa cgaggtatgg acgcaccgta gaagcgggtg ttgcccgccg   25980
acccagtagc acttaccagg agaaaacggg gcgccggtgc gcccccgggg ggcgcgcagt   26040
ccgtaggcgc atgtcccgca gccgcagccc ttcccggaac cgatcaccag gacatcggtg   26100
tcgatctcat ctgcgtcgtc gagatagacc agcgagtccg ggctcagccc ggggcggaag   26160
ccgctcgccg cggagcttct ggtacaggga acaggtgcgg gtgctgctcc ggggtgtgtt   26220
gagcgttggc cataagggga tcacgcgaga tctaccgcaa cggcaacctc ggcggcgtga   26280
gccaatggat cgaatcggtc aaccagaccc tgaaagggca actcggtctg gaagggcacg   26340
gcggtcgtac cccgccgggg tgtttacccg cattgcgcaa cgcctgctgg tcctggccgc   26400
cgccatctgg cacaactgga ccaccggctg atcagcaaac gatcattcat cccttacggc   26460
cattaacatc aaattcacag aatcaatcat ctagtggcct gacaatcacc acaaaagaca   26520
tcaacatcac aacatgtcgt tgttgtatta agaaccggcc gtgcccggtt ctccccctgt   26580
gcgaccatag tttgccggaa cctgcccgct cctgctgctc tcccaagaat gacacgagat   26640
gaccggttgg agggactacc gggcaatgcc cgtggggttt tcgggcagcc gtgaggcggt   26700
tgttgatctg tttcgggtta ggatgctgtg tttgagtgtg tcgagaaatg cgtctgtcgt   26760
cacgcacttt ggggcaatgg ccgtcggttt tcgggcagtc gtggcccttg ttcgtgttcg   26820
cgcctcttgt tgcgccgtca tgctggaatt attgcctcgg tcggacagcg gggtgggcag   26880
atgaccagct tggatgggaa gaatgaccgg atcaacgcgg ttttcacctc gttgcaggtc   26940
tgttggctgc gtaaacatct ggaaggttgc ttgtccaacg tggaacgggt tctcgatggc   27000
gcggtggatg atcgggtcat cacgaggctg ttcgctggca gtcccggcga gcgcagttac   27060
gcat                                                              27064
```

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
aggtgatccc gttcctgcgc                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
aagccgctcc gcgagttcgt                                                20

<210> SEQ ID NO 23
<211> LENGTH: 59
<212> TYPE: DNA

```
<213> ORGANISM: Artificial Sequence
<220> FEATURE:
<223> OTHER INFORMATION: Synthetic

<400> SEQUENCE: 23
gccgttgtcc accaaggagg gattgcggct gttcgatgca ttccggggat ccgtcgacc        59

<210> SEQ ID NO 24
<211> LENGTH: 58
<212> TYPE: DNA
<213> ORGANISM: Artificial Sequence
<220> FEATURE:
<223> OTHER INFORMATION: Synthetic

<400> SEQUENCE: 24
ccggtggtgt tatctggcag cagtgccgtc gatagtatgt gtaggctgga gctgcttc         58

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
gacgtcgcgg atcgtgctga tc                                               22

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
gcggcgctgg atgtcaca                                                    18

<210> SEQ ID NO 27
<211> LENGTH: 59
<212> TYPE: DNA
<213> ORGANISM: Artificial Sequence
<220> FEATURE:
<223> OTHER INFORMATION: Synthetic

<400> SEQUENCE: 27
tgcgaccgag tccgatcggg ttgggcggat ttcgtcgata ttccggggat ccgtcgacc        59

<210> SEQ ID NO 28
<211> LENGTH: 58
<212> TYPE: DNA
<213> ORGANISM: Artificial Sequence
<220> FEATURE:
<223> OTHER INFORMATION: Synthetic

<400> SEQUENCE: 28
caggtgctga aagcgagctt tttggcctct gtcgtttcct gtaggctgga gctgcttc        58

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ggctgaccga gctccgagtc                                                  20
```

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
cgacctcgcg ggttttcg                                              18

<210> SEQ ID NO 31
<211> LENGTH: 59
<212> TYPE: DNA
<213> ORGANISM: Artificial Sequence
<220> FEATURE:
<223> OTHER INFORMATION: Synthetic

<400> SEQUENCE: 31
cacccgtatc gccggtcctg tcgttcccgc ggatcccgga ttccggggat ccgtcgacc   59

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
gtctgctccc acagttgccg g                                          21

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
ggtcctttcc ggcgatccg                                             19

<210> SEQ ID NO 34
<211> LENGTH: 33
<212> TYPE: DNA
<213> ORGANISM: Artificial Sequence
<220> FEATURE:
<223> OTHER INFORMATION: Synthetic

<400> SEQUENCE: 34
cccaagcttg tacgaggcgg cgaagatcga cgg                             33

<210> SEQ ID NO 35
<211> LENGTH: 36
<212> TYPE: DNA
<213> ORGANISM: Artificial Sequence
<220> FEATURE:
<223> OTHER INFORMATION: Synthetic

<400> SEQUENCE: 35
cccattaatt ccagaccgag ttgcccttc agggtc                           36

<210> SEQ ID NO 36
<211> LENGTH: 34
<212> TYPE: DNA
<213> ORGANISM: Artificial Sequence
<220> FEATURE:

<223> OTHER INFORMATION: Synthetic

<400> SEQUENCE: 36
ccctctagat ctgctcctcg ggtgcgaaca ggcg                              34

<210> SEQ ID NO 37
<211> LENGTH: 32
<212> TYPE: DNA
<213> ORGANISM: Artificial Sequence
<220> FEATURE:
<223> OTHER INFORMATION: Synthetic

<400> SEQUENCE: 37
ccctctagat ggagaacccg cacgagcgac cg                                32

<210> SEQ ID NO 38
<211> LENGTH: 35
<212> TYPE: DNA
<213> ORGANISM: Artificial Sequence
<220> FEATURE:
<223> OTHER INFORMATION: Synthetic

<400> SEQUENCE: 38
gattctagaa cgtcgcgaag aagatctcca agaag                             35

<210> SEQ ID NO 39
<211> LENGTH: 32
<212> TYPE: DNA
<213> ORGANISM: Artificial Sequence
<220> FEATURE:
<223> OTHER INFORMATION: Synthetic

<400> SEQUENCE: 39
gcgtctagat cgacggtccg cgatttcaat gg                                32

<210> SEQ ID NO 40
<211> LENGTH: 36
<212> TYPE: DNA
<213> ORGANISM: Artificial Sequence
<220> FEATURE:
<223> OTHER INFORMATION: Synthetic

<400> SEQUENCE: 40
ggttctagag ggatcaacaa caacttcacc agcagg                            36

<210> SEQ ID NO 41
<211> LENGTH: 34
<212> TYPE: DNA
<213> ORGANISM: Artificial Sequence
<220> FEATURE:
<223> OTHER INFORMATION: Synthetic

<400> SEQUENCE: 41
ggatctagat cggtacgtcg agggcgacaa caac                              34

<210> SEQ ID NO 42
<211> LENGTH: 32
<212> TYPE: DNA
<213> ORGANISM: Artificial Sequence
<220> FEATURE:
<223> OTHER INFORMATION: Synthetic

<400> SEQUENCE: 42
gattctagaa gcaccagcac ggacagcagc gc                                32

```
<210> SEQ ID NO 43
<211> LENGTH: 35
<212> TYPE: DNA
<213> ORGANISM: Artificial Sequence
<220> FEATURE:
<223> OTHER INFORMATION: Synthetic

<400> SEQUENCE: 43
gattctagac gccgaagcaa ccctgaacgc atacc                                 35

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
atctggcgcg gctggggagc tgatg                                            25

<210> SEQ ID NO 45
<211> LENGTH: 25
<212> TYPE: DNA
<213> ORGANISM: Artificial Sequence
<220> FEATURE:
<223> OTHER INFORMATION: Synthetic

<400> SEQUENCE: 45
cgtcgggctg atcaacggca aggtg                                            25

<210> SEQ ID NO 46
<211> LENGTH: 2531
<212> TYPE: DNA
<213> ORGANISM: Artificial Sequence
<220> FEATURE:
<223> OTHER INFORMATION: Synthetic

<400> SEQUENCE: 46
taagcggccg caacccgccc tcgtacatcc ctgctccctc cggaggtgtg ctgtcggacg      60
gacttgtcgg tcggaaaccg ctagccggcg tggcggcgcg tgagttcctc cagtcgcggg     120
acgatctcct gcggcgtcgg gtcggacagc gcctcctcgc gaagcttcac cgcgttctcg     180
gtgtaggtgg ggtcctcgac cacctgggtg agggcgctcg ccaatgagtc ggcatcgacc     240
tcgtccggcc ggaggtagat tcccgcgccc agttccgcgg tctgctggcc gcgtagcatg     300
caatcccatt catgtgcaac tgatatttgc ggaattccgt ggtgcagtgc cgtggcccag     360
gttccggccc cgccgtggtg gatgatcgcc gcgcagttct ggagcagaac gcccatcgga     420
acgaaatcca ccaaacgaat gttgtccggt accgcggagg tatccggacc ggaacccgta     480
accacgattt cgccatcgaa tcgcgcgagc tgcgcgagcg tccgcgcgaa ctgatcggca     540
tcggcggcga gcccgagtcc ggagaaccct ccggtaatgc agatgcgtcg agtcgcactg     600
cccttcttga gccagtccgg aaccaccgac gcgccgttgt agggcagggt ccgcgcgaca     660
acggtttcca ttccggtgtc cagccggaaa ctcggcggca actggtcgac cgaccactgc     720
ccgaccgcga ggtcctcgcc gaattcgacg ccgaagcgcc ccgcgacctc ggtcagccac     780
gtgcccagcg ggtccggccg gtcctccggc ggccgtcgca ggcgttgcgc ctggaaccgg     840
ccgcggaagt agccggtgag gtcgctgccc cacagcagcc gggcgtgcgc ggctccgcag     900
gcccgggccg cgacggcgcc ggcgaaggtg aacggctccc agagcaccag gtcaggacgc     960
cagtcccggg cgaagtcgac cagctcggcg acgaaggagt cgttgttgac caccgggtat    1020
```

| | |
|---|---|
| acccaccgcg aggtggcctc ctgcatgccg agcaggaact cccacgagtg cagctcctgc | 1080 |
| tcgcggtggt agaagtccag gtagaaggag tagcggtgca cctgagcggc gacttccggg | 1140 |
| acgatgtcga acagccggtg gtcggagccg acgggtaccg cggtgagacc ggcgccgatg | 1200 |
| accgcgtcgg tgagcgcggg ctgggcggcc acgcgcacgt cgtgacccgc ggtgcgcagc | 1260 |
| gcccacgcca gcgggaccag tccctggaag tgcgtgcggt gcgcgaagga cgtcagcagt | 1320 |
| acccgcacta gtgctcctcg gtggggtca gggcggccac cgtccggtcg atgccgtcgg | 1380 |
| tgagggaaac ccgggggcgc cagccggtcc ggctgcggaa ctcggtggag tcgatgtcgt | 1440 |
| cgctgcggaa gtcgttggcc tcggcgtgct cgggcgcggg cacggtgacc acgtcgacgg | 1500 |
| cggggctgcc ggtctgccgg gcgacgctgc cggagacggc ccggaagatg tcgccgagcg | 1560 |
| gctcggatcg gtcggcgccc agcgcccacg tgccgccggc cagcgcgtcg tggtgctcca | 1620 |
| gcgcggcggc gaacgcggtg gccacgtcct cgacgtgcag caggtcgcgg cgcacgccgc | 1680 |
| cgtcgtgcca catggtgagc ggctcgccgg cgagggcacg ccggatcatc gctgcgacca | 1740 |
| cgcccccgccc catggggccg gacgggccgc tctggccgta gacggcgggc agccgcagga | 1800 |
| tcacgccgcg cacccggccc tcgtcggtgg ctttgcgcag gatgcgctcg gcctcggtct | 1860 |
| tctgctgcgc gtacctgctg gccgccgacg ggttcgcggc ctgtgcggtg ctcgcgtaga | 1920 |
| gcaacacggg cggcgtcgac ctgcggcgat cgtgcagcgc gccgacgagg tcgtgcatca | 1980 |
| ggccgacgtt gacccgctcg gcttccgggt cggaggtggc gctgcgccag gtggaaccgc | 2040 |
| ccgctgcgtg cgccaccagg tgcacgatca cgtcggcgtc ctcgatcgcg gcggcggccc | 2100 |
| ggcccggttc cagcaggtcg gcgcgcaggt cctcgacctc cgcggcgccg gcggaaccg | 2160 |
| cgggcgctcc gccgcgggac accgcgcgca gccggaccgg tggtcgcgc agctcgcgca | 2220 |
| gaaccgcgct cccgacgaag ccggaagcgc ccagaagggt gatcaattga cgcggggaat | 2280 |
| cactgatccc attcaccgga gcatttgctc gctttccagg tcggtgctac gggcgaaatt | 2340 |
| caaagaatct ccccagcgcg atgtgcggca accgtcact gggccaccac agtaggtagc | 2400 |
| cgccgttgat cttgtcaaca tgcagatgtt cacaggttcg ttggctcgac gaggcgatgt | 2460 |
| caacctcttg atccttccta tattgttcgc ccattgcgtg gtcgtcgagt aggggacgc | 2520 |
| gtggatcctt a | 2531 |

<210> SEQ ID NO 47
<211> LENGTH: 2667
<212> TYPE: DNA
<213> ORGANISM: Artificial Sequence
<220> FEATURE:
<223> OTHER INFORMATION: Synthetic
<400> SEQUENCE: 47

| | |
|---|---|
| taactgcagc cacgaccgat cgcgccgggc tgggcaggca gctccagatg atccgcggcc | 60 |
| tgcactgggg ttacggcagc aacggcgacc cttacccgat gctgctgtgc ggacacgacg | 120 |
| acgacccgca gcgccggtac cgctcgatgc gcgagtccgg tgtgcggcgc agccgcaccg | 180 |
| agacgtgggt ggtggccgac cacgccaccg cccggcaggt gctcgacgac cccgcgttca | 240 |
| cccgcgccac cggacgcaca ccggaatgga tgcgggccgc gggcgcgcca cccgccgagt | 300 |
| gggcccagcc gttccgggac gtgcacgccg cgtcctggga aggcgaggtc cccgacgtcg | 360 |
| gggaactggc ggagagcttc gccggtctgc tccccggccg gggcgcgcgg ctggacctgg | 420 |
| tcggcgactt cgcctggcag gtaccggtgc agggcatgac cgccgtgctc ggcgcagccg | 480 |
| gagtgctgcg cggcgccgcg tgggacgccc gcgtcagcct ggacgcccag ctcagcccgc | 540 |

```
agcagctcgc ggtgaccgaa gcagcggtcg cggcactgcc cgccgacccc gcactgcgcg      600
ccctgttcgc cggggccgag atgaccgcga acaccgtggt cgacgcggtc ctggccgtct      660
cggccgaacc ggggctggcc gaacggatcg ccgacgaccc cgccgccgcg cagcgaaccg      720
tcgccgaggt gctgcgcctg cacccggcat tgcacctgga gcggcgcacg gccaccgcag      780
aggtgcggct cggcgagcac gtgatcggcg aaggcgagga ggtcgtggtc gtcgtcgcgg      840
cggccaaccg cgaccggag gtcttcgccg agcccgaccg cctcgacgtg gaccgccccg       900
acgccgaccg cgcgctgtcg gcacatcgcg gccaccccgg caggctggag gagctggtca      960
ccgcgctcgc caccgccgca ctgcgggccg cggccaaggc gctgcccgga ctcacgccca     1020
gcggcccggt cgtccggcgc cgccgatcac ccgtcctgcg gggaaccaac cgctgccccg     1080
tcgagctctg aggtaaccgc gatgcgcgtc gtcttctcct ccatggccag caagagccac     1140
ctcttcggcc tcgtccccct cgcatgggcg ttccgcgcgg cggggcacga ggtccgcgtg     1200
gtcgcgtccc cggcgctcac cgaggacatc accgcgccg gctgaccgc cgtcccggtc       1260 ggcaccgacg tcgacctcgt ggacttcatg acccacgcgg ccacgacat catcgactac       1320 gtccggagcc tggacttcag cgagcgggac cccgccacct tgacctggga gcacctgctg     1380
ggcatgcaga ccgtgctcac cccgaccttc tacgccctga tgagcccgga cacgctcatc     1440
gaaggcatgg tctcgttctg ccggaagtgg cggcccgacc tggtcatctg ggagccgctc     1500
accttcgccg cgcccatcgc ggcggcggtg accggaacgc cgcacgcgcg gctgctgtgg     1560
ggacccgaca tcaccacccg ggcgcggcag aacttcctcg gcctgctgcc cgaccagccg     1620
gaggagcacc gggaggaccc gctcgccgag tggctcacct ggacgctgga gaagtacggc     1680
ggcccggcct tcgacgagga ggtggtcgtc gggcagtgga cgatcgaccc cgccccggcc     1740
gcgatcaggc tcgacaccgg cctgaagacc gtcgggatgc gctacgtcga ctacaacggg     1800
ccgtccgtgg tgccggaatg gctgcacgac gagcccgagc gccgccgcgt gtgcctcacg     1860
ctcgggatct ccagccgcga gaacagcatc gggcaggtct ccatcgagga gctgctgggt     1920
gccgtcggcg acgtcgacgc cgagatcatc gcgaccttcg acgcgcagca gctagaaggc     1980
gtcgcgaaca tcccggacaa cgtccgcacg gtcggcttcg tcccgatgca cgcgctgctg     2040
ccgacctgcg cggcgacggt gcaccacggc ggacccggga gctggcacac cgcggcgatc     2100
cacggcgtgc cgcaggtgat cctgcccgac ggctgggaca ccggcgtgcg cgcgcagcgc     2160
acgcaggaat tcggggcggg gatcgcgctg cccgtgcccg agctgacccc cgaccagctc     2220
cgggagtcgg tgaagcgggt cctcgacgac ccggcccacc gcgccggcgc ggcgcggatg     2280
cgcgacgaca tgctcgcgga ccgtcaccg gccgaggtcg tcggcatctg cgaggaactg      2340
gccgcaggaa ggagagaacc acgatgacca ccgacgccgc gacgcacgtg cggctcgggc     2400
gttccgcgct gctcaccagc aggctctggc tcggcacggt gaacttcagc ggacgcgtcg     2460
aggacgacga cgcgctgcgc ctgatggacc acgcccggga ccgcggcatc aactgcctcg     2520
acaccgccga catgtacggc tggcggctct acaagggcca caccgaggag ctggtgggca     2580
ggtggctggc ccagggcggc ggacggcgcg aggacaccgt gctggcgacc aaggtcggcg     2640
gcgagatgag cgcggccgct cgagtta                                         2667
```

<210> SEQ ID NO 48
<211> LENGTH: 3595
<212> TYPE: DNA
<213> ORGANISM: Artificial Sequence
<220> FEATURE:

<223> OTHER INFORMATION: Synthetic

<400> SEQUENCE: 48

| | | |
|---|---|---|
| cccaagcttg tacgaggcgg cgaagatcga cggggcgggt gcctggaccc ggttccgccg | 60 |
| catcaccttg ccgttgatca gcccgacgat cctgctcacg tcgatcatca ccatcgtcgg | 120 |
| ctcgctgcag gtgttcgcgc agatcgcggt gctcacgcag ggcggtccgg gcacgtccac | 180 |
| gaccgtactg atctactacc tgtaccagca ggcgttccag ttccaccact tcggctacgg | 240 |
| cgcgacgatc tcggtactgc tgttcgtcat cgtcgccgca ctcaccctgc tgcagtggca | 300 |
| gatgcgccgg aagtgggtgc tgcatgaggc ttagggtcaa gatcacgcta tacgggctgc | 360 |
| tgtgcctgct gtgcgtgcct ttcgtgttcc caacctggtg gatgatcacc tcgtcgatga | 420 |
| agcccatcag cgagatcttc tccacctcgc cgctgccgtc ggagtggacg ttctccacct | 480 |
| accggcaggt gttcgagatg cagccgttcg cgcagcagta ctggaacagc ctctacatcg | 540 |
| cggtgatcgt cacgacaggc acaatggcgg tggcggcgat ggccggatac gcgttcgcgc | 600 |
| gtatccggtt cccgggccag aacgtgctgt tcgtggtcgt cctgatcggc ctgctcatcc | 660 |
| cgagcgaggt caccatcgtg ccgctgttca agatgttcca gtcgctcggc ctgaccaaca | 720 |
| cgcactggcc gctaatcatc gtgccgatct tcggggcgcc ctgtgtgctg gcgatcttca | 780 |
| tcatgcgcca gttcttcatc gccctgccgt cggagctgga ggaggccgcg cggatggacg | 840 |
| gcctcggacg agcgggcatc ttctaccggg tggccctgcc gctgtcccgg cccgcgctgg | 900 |
| gcgccgtcgc gatcttcacg ttcctgcact cgtggaacct ctacctggag ccgatcgtct | 960 |
| atctgtccac accggacatg tacacgttgc cgcaagcgct cacgcagttc gtcgacaact | 1020 |
| acggcggccc gatgtggaac gtgcagctcg ccgccgcgac catgaccgca gtgccgattc | 1080 |
| tcgtcgtgtt cgtgctggcg cagcggcagt tcatcgaggg actcgcgcac accgggggtta | 1140 |
| aggggtgagt cccgcgatcg acccggagat cgccgcgctg gtagacctcg ccagaccacc | 1200 |
| ggtgacgcca gcgggaatcg acgcggtccg ggcgggagga cgcgtcgtca ccgatgccga | 1260 |
| gctgacgcgc ggtggcaccg tgacgttcgc cgatgccgat gccgatggcg tgcccgtgct | 1320 |
| tgtgctgcgc ccagcgggtg tgccacgtct tccggtgctg cacctgcacg gcggcgggat | 1380 |
| ggtcgcgggc acccggcgca ccgacctgca cgtgctggcc gagtgggtgt cggagctggg | 1440 |
| tgtcgtgctg gtgtcgccgg agtaccggct cgcacccgag cacccgcacc cggcgccgtc | 1500 |
| gcaggactgc ttccgggtgc tggagtggat gtcccgcaac ggcttcggcc gcctgtcgt | 1560 |
| tgcgggtaca tcggcgggcg gcgggctggc ggctgcggtg acgctgatgg cccgcgacct | 1620 |
| cggcggtccg ccgatccgcg gccagctgct gatgtgcccg atgctcgacg accggtgcga | 1680 |
| caccccgtcc agccacgagt acctcgacgg gaacacgtgg gtgcgcgcgt cgacgatcac | 1740 |
| cggctgggaa gccctgctcg gcgatgcgcg gggcggtccc gacgtctcac cgtacgccgc | 1800 |
| accggcacgt gccaccgacc tcgccaggtt gccacctacc tacgtcgaca tcggctcggc | 1860 |
| cgacctgttc cgcgacgagg ccatcgacta cgccctgcgg ctgtggcgcg ctggcggaga | 1920 |
| cgcagaactg cacgtctggc ccggcgggtg ccacggattc gaccagctcg tgcccgacgc | 1980 |
| ggcgctgtcg cggcgggcac gagccgcccg catcgactgg ctgcgccgcg tgctggagac | 2040 |
| tcacagctaa acgtttcggc atggctcgcg ggcgcgcatt cggagatgag gtagcggtcg | 2100 |
| ctgcggcgtt gcccgccgtt actggcctgc ggagacgacg tactcgcact tgaacctgtt | 2160 |
| ggcgaaggcg tagggcctcg tggtgcgtct gaccgggttc gctggttgtg ggctgggggtt | 2220 |
| tagtcgggcc gtcaggctgt acgcgtcgca tccctcagcg ggagttgtcg gtgcggggcc | 2280 |

```
gggtgatcag gtcgcgaagc tcccggata ccggtggggg tcgccgggtc cacttcggcc    2340
tgaccaggcg tcgatgccag gcgagcgagg tgcgtgtcga gacaatccgg tggccgtgga    2400
gtcgctgggg gtaggagccg ggggagcgcg gccggcagcg cccgatccgg ccaggccggc    2460
ttcgccgtaa tagcgggagc gcattcaatc gtccccgatc tgtgcctctg gatcacgctg    2520
ggggcgcatc gtgctgtgat caggggattg gggctggaga ctttcgaccc gcaccgctgg    2580
cacctggcct tcgacgtgct gtggcgcctc ggcggtgacg agccgtacct gtcggtcatc    2640
ggttgcgggc tgaaatggcc tgctcacatc caagatgtca gcttgcacct tgaggcaacg    2700
ttcagcggtc gcgcatgccc tagcacctcg gacaatctgg tcacgactga tgtcgctact    2760
gtgggtgcag ccgcggtact gatccggtgt ggtggtgcgg gggtgcgtcc gttgtggacg    2820
cacccccgtt tcgctgtgcc gaggaagaac gtgctgttgt ggactatgta gttgcagccg    2880
agttggtccg aggagttgcc tagaccacgc gggtgctgcc gggtcgcgga gcgcagcagc    2940
agcgcggcca agttcaccag cggcaagcac gaaccggcgg acgctgatcc gcactacccg    3000
gccctgatga cgggcctcgc cggcgacgat ggtccggccg tcgtcggagg tgatcaggca    3060
gggcggtctg cccgtgcacg tcgaatagcg ctcgggcctc accgtagaac ggctcgaggt    3120
cctcgtagga caatggccac gccttcgacc ggccgcccat gtgctcgacc tcggtgaagt    3180
cgctcgcgcg gaaacgaggt atggacgcac cgtagaagcg ggtgttgccc gccgacccag    3240
tagcacttac caggagaaaa cggggcgccg gtgcgccccc gggggcgcg cagtccgtag    3300 gcggatgtcc cgcagccgca gcccttcccg gaaccgatca ccaggacatc ggtgtcgatc    3360
tcatctgcgt cgtcgagata gaccagcgag tccggctca gccggggcg gaagccgctc    3420 gccgcggagc ttctggtaca gggaacaggt gcggtgctg ctccggggtg tgttgagcgt    3480
tggccataag gggatcacgc gagatctacc gcaacggcaa cctcggcggc gtgagccaat    3540
ggatcgaatc ggtcaaccag accctgaaag ggcaactcgg tctggaatta atggg          3595
```

<210> SEQ ID NO 49
<211> LENGTH: 3600
<212> TYPE: DNA
<213> ORGANISM: Artificial Sequence
<220> FEATURE:
<223> OTHER INFORMATION: Synthetic

<400> SEQUENCE: 49

```
ccctctagat ctgctcctcg ggtgcgaaca ggcgccggtt cggtgtggtg ggcggcgggg     60
cgggcagtgc gagtgcgcgg gtcggcagtg cggcgagcag tccgagagcg gcggcgccgg    120
tcatcaggct gcgacggctg aacgtagtca cgggcctacc tccttgtggc cgatcaaccc    180
tcacccgctg cgtagccgca cgtcaagatg ataattcgaa ttattatggg cttgacgacg    240
cgtaggccga cgacgcagaa ttcctgccaa ttcgtattgg caagcggggg tgctcgtggc    300
ccgacggctc acccagcagg acatcgcccg gatggcagga gtcagccagg ccacggtgtc    360
gctggtgctc aacaaccgga aggacggcaa cgtccggatc gcggcggaga cccgtgcgca    420
ggtactggag gtgattcgga agaccggcta cgtcgcgaac ccgatcgccc gcaggatgcg    480
cgatcggcac aaccgcatcc tcggcgtgtt cacctacgag gcggtgttcc cgagcaccca    540
cgcgaacttc taccagtcgt tcctcgaagg catcgaggaa caggccgagg aggtcggctg    600
tgacctgttg ttgttcacca gcgccaaggc caccggggag cggcggcgga ttttcggcga    660
cgacagccgg gtgcggctcg ccgacggcag tctgctgctc ggtcgcacgg tcgaccgcga    720
```

```
cgacctgacc cagctgctcg ccgaaagcat cccgtacgtc tccatcggac gacgcgacga    780
cgcgggcggt ccggtgccgc acgtcggggc cgactaccgc accgcggtgc gagacctggt    840
ggaccgcgcg gtcgcgctcg gccaccgcgg gttcgcgtac gtggggtctg gtggggcgc     900
ggagtcgtcc gcggatcggc tgcgaggctt ccgcgaagcc gttgccgcac atggcgtcca    960
agggatgcat gtggagaccc cacagctcga tcagctgcgc gaagcgggcg tcaccgctgt    1020
gctcaccgaa gaggtgtcgg acggggccgc gctcgtgctc gccgggcgcg aacgcgggct    1080
ctccgtgccg ggcgacctcg ccgtgctctc gctcggtgcc gctacccggt cggcaccgga    1140
cgacgacgtg gcgctcaccg gtttccgcat ccccaggcgc gagatggggc gccgggcggt    1200
gcaggcgctg accgaggtgc tcgaaaacgg caccacaccg caagaactgc tcccgtgcga    1260
gttcgtcgag ggctcgacgc tgggcgcacc acgcctttga ccaggaggaa ctgttgctcg    1320
accacaccac ggacgttgtc gtcgttggcg gcggactcgg cggtgtcgcc gccgcactcg    1380
cgttgctgcg cgcgggccgc cgggtcgtgc tcaccgagga gtacgactgg ctcggcggcc    1440
agctgaccag ccaggccgtg ccgcccgacg agcacagctg ggtggagcgc ttcggcgtca    1500
ccgcgagcta ccgggcgtta cgcgacggca tccgcgacta ctaccgccgc cactacccgc    1560
tgaccccgcg cgcacgggcg tggcgggagc tcaaccccgg tgcgggcaac gtgagcaggc    1620
tctgccacga gccccgcgtc gccgtcgcgg tgatcgacga gatgctggcg ccgttccgcg    1680
gcagtggcag gctgaccgtg ctgcagccgt accggccggt ggccgcgcac aacgacggcg    1740
accggatcgt gtcggtgacc gttgcgcacc gcgacaccgg tgaacagatc gagctctccg    1800
cgccgtacat cctggacgcg acggagacgg gtgaactgct tccgttgtcc agcacggagt    1860
acgtcaccgg cttcgagtcc actctggaca ccggcgagcc gagtgcgccc gacgtcgcgc    1920
agccggcgaa catgcaggcg gtgtcggtgt gcttcgtggt cgaccacgtc gacggcgacc    1980
acaccatcga caaaccggcg cggtacgact ctggcgcgc gtaccagccg gacttctggg    2040
gcgaccggat gctgtcgttc cgctccccca accgcgcac gctcgcgatc tccgaacgta    2100
cgttcacccc gaacccggac gacgacccgc tcggcgtcgt gtcggaccag cggctcagtg    2160
ccggtgacag caatctgtgg acgttccggc gcatcgccgc gcgtcgcaac ttcgtcgagg    2220
gtgcctacga cagcgacatc tgcctggtga actggccgat catcgactac ttcgagtcgc    2280
cggtgatcga cgtgccggac gccgacgcgc acatcgccgc ggcgcgggaa ctctcacgtt    2340
cggtgctcta ctggctacag accgaggcgc cgcgcccaga cggcggcacc ggcttccccg    2400
gcctccgcct gcgcggcgac gtcaccggca gcgcggacgg tctcgcgcag gcgccgtaca    2460
tccgcgagtc caggcgcatc agggccgagc acacgatcgt cgaacaggac ctctcgctcg    2520
ccgtgcgcgg cgacaagggt gcggtgcagc acgccgacgc cgtgggtgtc ggcatgtacc    2580
gtatcgacct gcaccccctcc accggtggcg acaactacat cgacgtcgcg agctgcccgt    2640
tcgagatccc gctcggcgcg ctgatcccgc aacgggtgga gaacctgcta cccgcgggca    2700
agaacatcgg caccacccac atcaccaacg gttcccaccg gctgcaccca gtcgagtgga    2760
acgtcggcga ggtcgcgggc gcgctcgctg ccttctgcct ggcgcaccga gtcaccccctc    2820
gcgcggtgca caatacccct ggcctgctcg cggacttcca gcagtgtctg gaacgcgacg    2880
gggtcgagct ccgctggccg acgtgtccg gctactgacg cagggagacg aaaatgacaa    2940
agctgtcacg acgactcacg gcactcatcg tcgcagggct gttcgccctc accggctgcg    3000
gtggtggatc aaccgcacag tccggaccga agtcgctgcg catgaccgtg tggactgcca    3060
acgcggcgca tctcaagctg ctcaacgaca tcgccgccga gtacaaggcc tcgcacccgg    3120
```

```
acatcgccga gatcaagttc gactcggtgc ccgccgacgg ctacaccacc acgctcacca    3180
cccagatcgc cggcggtaac gcgccggacc tggcctggat cctggaggag tcggcaccgg    3240
acttcgtggc gtccggtgcg ctcgccccgg tgcgcggcaa gatcgagaag gccgacgagc    3300
tcgtgccgtc cgcgacgaag ctgtgggaga aggacgcgca actgtacgcc tacccgttct    3360
ccacctcgcc gttcggcttg ttcgtcaaca ccgacctggt gaagggcgcc tcggcggact    3420
ggacctggga ccaggcgatc gcggctgcct ctgcgtcggc ggccgcctcc ggcaagggcg    3480
gcctggtact gccggacttc aagtaccaga actgggcagt gctgtcctct atctggcgcg    3540
gctggggagc tgatgcgtgg agcgcggacg gtcgctcgtg cgggttctcc atctagaggg    3600
```

<210> SEQ ID NO 50
<211> LENGTH: 1141
<212> TYPE: DNA
<213> ORGANISM: Artificial Sequence
<220> FEATURE:
<223> OTHER INFORMATION: Synthetic

<400> SEQUENCE: 50

```
gattctagaa cgtcgcgaag aagatctcca agaagatccg cgacgagggc ccgaagggcg      60
ttcaggccca gatccagggc gagcagctgc gggtgtccgg caagaagaag gacgacctgc     120
aggccgtgat ccagttgctg aagtcgagcg acttcgacgt cgcgctccag ttcgagaatt     180
tccggtaatc caccgctgga ggtatccggg tgaaggggat cgtgctggcg ggtggcaacg     240
ggacccggct gcatccgctg acgcaggccg tgtccaaaca gctacttccg gtgtacgaca     300
agccgatgat ctactacccg ctgtcggtgc tgatgctggc cggcatccgg gacgtgctgc     360
tgatctcgac cccggccgac atgccgttgt ccagcggct gctcgggaac gggtcgcagt     420
tcggcattcg gatcgagtac gccgagcagt cccagcccaa cgggctagcc gaggcgttcg     480
tgatcggtgc cgacttcgtc ggcgacgact cggtggcgtt ggtgctcggc gacaacatct     540
tttacgggca gggcttttcc gggatcctcc agcagtgcgt ccgggagctc gacggctgca     600
cgctgttcgg ctaccggtc cgcgaccgc agcgctacgg cgtcggtgag gtggacgacg     660
acggtcggct gttgtccatc gtggagaagc cggagcggcc gaagtccaac atggccatca     720
ccggcctgta cttctacgac aacgacgtgg tgcgcatcgc caaggggctc acgccgtcgg     780
cccgcggcga gctggagatc accgacgtca acctggccta cctgcaggag ggccgggcgc     840
acctgaccaa gctcggccgc gggttcgcct ggctggacac cgggacccac gactcgctag     900
tggaggcctc gcagttcgtg caggtgctgg agcaccggca gggcgtgcgg atcgcctgcc     960
tggaggagat cgccctgcgc atgggctaca tctcggccga cgactgtttc gcgctgggcg    1020
tgaagctggc caagtcgggc tacgcgagt acgtcatgga cgtcgcccgc aactccggcg    1080
cgcggggctg acccgagctc gtccgatttc cattgaaatc gcggaccgtc gatctagacg    1140
c                                                                    1141
```

<210> SEQ ID NO 51
<211> LENGTH: 974
<212> TYPE: DNA
<213> ORGANISM: Artificial Sequence
<220> FEATURE:
<223> OTHER INFORMATION: Synthetic

<400> SEQUENCE: 51

```
ggttctagag ggatcaacaa caacttcacc agcaggttca acaatttgtc aatcccactt      60
```

```
ggcagtacgc gcgtcctttt tggatcggga ttgcggcagt acgtgcaccc ggtttcagtg      120
ccccatttcg cagtacgtac gtccgttttg aatatggcga tcaatggctc gcatgaccca      180
tatcaactcc gccccaccga accgcattcc aaccaacgtc ataggctttc ggccgtgcag      240
gtacgtcgac ttgacatcac gggtgcatac gagttcaccc cgaaggcctt ccccgaccac      300
cggggcctgt tcgtggcccc gttccaggag gcggcgttca tcgacgccac ggggcacccg      360
ctgcgagtcg cgcagaccaa ccacagcgtc tcggcgcgca acgtcatccg cggcgtgcac      420
ttctcggacg tgccgccggg ccaagcgaag tacgtgtact gcccgcaggg cgcgctgctc      480
gacgtggtca tcgacatccg ggtcggttcc ccgaccttcg gccgctggga ggcggtccgg      540
ctcgacgaca ccgagtaccg ggccgtctac ctagccgaag gactcgggca cgcgttcgcc      600
gcgctgaccg acgacaccgt gatgacctac ctctgctcga cgcccacac cccgggcgcc      660 gagcacggca tcgacccgtt cgacccggaa ctcgcgttgc cgtggtccga cctcgacggt      720
gaaccggtcc tgtccgaaaa ggaccggacc gccccgagcc tcgcggaagc cgccgacaac      780
ggcctgcttc cggactacga aacatgcctc gcccactacg aaggcctgcg cagccccggc      840
tgaacggtca ccgcaagcgg cccggcttcg gccagaggcg ccaccggata atgccgagca      900
cctcggccgg gccgagctcc cgcgagtccg tcgagccgaa gttgttgtcg ccctcgacgt      960
accgatctag atcc                                                        974

<210> SEQ ID NO 52
<211> LENGTH: 2685
<212> TYPE: DNA
<213> ORGANISM: Artificial Sequence
<220> FEATURE:
<223> OTHER INFORMATION: Synthetic

<400> SEQUENCE: 52
gattctagaa gcaccagcac ggacagcagc gcgaacagca tccggccgaa ggtgcgcggg       60
ccccggtggt tgcgtcgtcg ttgccagacg tcgccttccg ggggaacctg cgcattcccc      120
gaacgggggg aagaacggcg acgagcgtca ctctgggcgg acctgcggcc ggggccgccg      180
ggtggtggag cggctccgcc gcgacgactg ctcggcgggg tgccgccgac cccgggccgg      240
ccgtgggcgc cgggtccgcg gggcggaacg ggtctgccgg gctgaccctg cgggccgcct      300 ggccaccctcg gccggtcctc cacgaatcct ccttggcctg ccggcggggcg ttacagtttc      360 gggaagtgat tttgctcgtg ttccgaatgc aggctagcgg tgttcctggg gcggttgggc      420
aggtcccagc aacagtggtg atatccctca taagggcgaa gcgacttcgt cacgttgcgt      480
aatgcgggat cctgcttcgt agctcggtgt gtcatgccag actgcgcacg cggacctgca      540 gcggccgcg aaatcccggc gaggaagggc gcgatgcgga ttctggtcac cggcggagcc      600
ggtttcatcg gctcgcacta cgttcggcag ttgctcggtg gtgcgtaccc cgcattcgcc      660
gacgccgacg tggtcgtgct cgacaagctc acctacgccg gcaacgaggc gaacctggcg      720
ccggtcgcgg acaaccccg gctgaagttc gtctgcggcg acatctgcga ccgcgaactg      780
gttggcggcc tgatgtccgg cgtggacgtg gtggtgcact cgccgccga aacccacgtc      840 gaccgctcga tcaccggctc ggacgccttc gtgatcacca acgtggtcgg caccaacgtg      900
ctgctgcagg ccgcgctcga cgccgagatc ggcaagttcg tgcacgtttc caccgacgag      960
gtctacggct ccatcgagga cggctcgtgg cccgaagacc acgcgctgga gccgaattcc     1020
ccgtactcgc cggcgaaagc gggctcggac ctgctggccc gcgcctacca ccgcacccac     1080
ggactgccgg tgtgcatcac ccgctgctcc aacaactacg ggccctacca gttcccggag     1140
```

```
aaggtgctgc cgctgttcat cacgaacctg atggacggca gccaggtgcc gctctacggc    1200
gacgggctca acgtgcggga ctggctgcac gtcagcgacc actgccgggg catccagctg    1260
gtggccgact ccgggcgcgc gggcgagatc tacaacatcg gcggcggcac cgagctgacc    1320
aacaacgagc tgaccgagcg gctgctggca gagctgggcc tcgactggtc ggtggtgcgg    1380
ccggtcaccg accgcaaggg ccacgaccgc cgctactcgg tggaccacag caagatcgtc    1440
gaggaactgg ggtacgcgcc gcaggtcgac ttcgagaccg gctgcgcga gacaatccgc     1500 tggtaccagg acaaccggga ctggtgggag ccgctgaagg cccgatcggc ggtggctcga    1560
tgagtcgcct cgccgtgctg gtgcccggcg gccgcggcca gctgggctcg gagctggccc    1620
ggatcctcgc cgcgcggacg ggggcgctgg tgcaccggcc gggttccggg gaactggacg    1680
tcaccgacgc cgaggaggtc gccgacgcgt tgggttcctt cgcggagacg gcgaaggacg    1740
cggagctgcg accggtggtg atcaacgccg cggcgtacac ggcggtggac gcggccgagt    1800
ccgacccgga ccgcgcggcc cggatcaacc cgaaggcgc ggcctcgctg gcgaaagcgt     1860
gccggagcag cggtctgccc ctggtgcacg tgtcgacgga ttacgtgttc cccggtgatg    1920
gggcccggcc gtacgagccg acggacccga ccgggccgcg atcggtctac gggcgcacca    1980
agctcgaagg cgaacgggcc gtgctggagt ccggcgcgcg ggcctgggtg gtgcgcacgg    2040
catgggtgta cggcgcgagc ggcaagaact tcctgaaaac gatgatccgc ctctcggggg    2100
agcgcgacac gctgtccgtt gtggacgatc agatcggctc gccgacttgg gcggcggacc    2160
tggcgagcgg cctgctggag ctggccgaac gggtcgccga acgccgtgga ccggagcaga    2220
aggtgctgca ctgcaccaat tccggccagg tgacctggta cgagttcgcg cgggcgatct    2280
tcgcggaatt cggcctggac gagaaccgcg tccacccgtg cacgacgcg gacttccccc      2340 tcccggcgca ccgcccggcc tactcggtcc tgtccgacgt ggcgtggcga gaggcgggcc    2400 tgacccgat gcgcacctgg cgggaagccc tggcggcggc cttcgagaaa gacggcgaaa     2460
ccctccgaac ccgctgacca gtcacccgga gggcgcgagt agccccggca gggccgcttc    2520
gacgcgatat cggctggcgc ggtgcgcaca atgggtgtcg ccggggcgag gaaggaaggc    2580
caggtgcccc gggggcatga ctgggagcct ggcctgatgc ctgtccgggg cgttcagcct    2640
gcggcgaggc ggtatgcgtt cagggttgct tcggcgtcta gaatc                    2685
```

```
<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
tagagcaaca cgggcggcg                                                   19

<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
ggcctgcagc gtgatcccat ac                                               22

<210> SEQ ID NO 55
```

```
<211> LENGTH: 21
<212> TYPE: DNA
<213> ORGANISM: Artificial Sequence
<220> FEATURE:
<223> OTHER INFORMATION: Synthetic

<400> SEQUENCE: 55
gtcatggaat cgggcaccg c                                              21

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
aagcatccgg gcacgaggtc                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tcgtgccctg ggcgttgtcc                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ccgcgcactg gactcgatcc                                               20

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
cgtcgagtcg ctgacaccag agc                                           23

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
gcgtcgtagc gatctcgtct gc                                            22

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
```
gagggactac cgggcaatgc c                                          21

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
agctctccgc cagttccccg                                            20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
attccgggga tccgtcgacc                                            20

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
tgtaggctgg agctgcttc                                             19

<210> SEQ ID NO 65
<211> LENGTH: 1391
<212> TYPE: DNA
<213> ORGANISM: Artificial Sequence
<220> FEATURE:
<223> OTHER INFORMATION: Synthetic

<400> SEQUENCE: 65
cgataagctt gatattccgg ggatccgtcg acctgcagtt cgaagttcct attctctaga      60
aagtatagga acttcgaagt tcccgccagc ctcgcagagc aggattcccg ttgagcaccg     120
ccaggtgcga ataagggaca gtgaagaagg aacacccgct cgcgggtggg cctacttcac     180
ctatcctgcc cggctgacgc cgttggatac accaaggaaa gtctacacga acccttggc     240 aaaatcctgt atatcgtgcg aaaaaggatg gatataccga aaaaatcgct ataatgaccc     300
cgaagcaggg ttatgcagcg gaaaatgcag ctcacggtaa ctgatgccgt atttgcagta     360
ccagcgtacg gcccacagaa tgatgtcacg ctgaaaatgc cggcctttga atgggttcat     420
gtgcagctcc atcagcaaaa ggggatgata agtttatcac caccgactat ttgcaacagt     480
gccgttgatc gtgctatgat cgactgatgt catcagcggt ggagtgcaat gtcgtgcaat     540
acgaatggcg aaaagccgag ctcatcggtc agcttctcaa ccttggggtt accccggcg      600 gtgtgctgct ggtccacagc tccttccgta gcgtccggcc cctcgaagat gggccacttg     660
gactgatcga ggccctgcgt gctgcgctgg tccgggagg acgctcgtc atgccctcgt       720 ggtcaggtct ggacgacgag ccgttcgatc ctgccacgtc gcccgttaca ccggaccttg     780
gagttgtctc tgacacattc tggcgcctgc caaatgtaaa gcgcagcgcc catccatttg     840
cctttgcggc agcggggcca caggcagagc agatcatctc tgatccattg cccctgccac     900

-continued

```
ctcactcgcc tgcaagcccg gtcgcccgtg tccatgaact cgatgggcag gtacttctcc      960
tcggcgtggg acacgatgcc aacacgacgc tgcatcttgc cgagttgatg gcaaaggttc     1020
cctatggggt gccgagacac tgcaccattc ttcaggatgg caagttggta cgcgtcgatt     1080
atctcgagaa tgaccactgc tgtgagcgct ttgccttggc ggacaggtgg ctcaaggaga     1140
agagccttca gaaggaaggt ccagtcggtc atgcctttgc tcggttgatc cgctcccgcg     1200
acattgtggc gacagccctg ggtcaactgg gccgagatcc gttgatcttc ctgcatccgc     1260
cagaggcggg atgcgaagaa tgcgatgccg ctcgccagtc gattggctga gctcataagt     1320
tcctattccg aagttcctat tctctagaaa gtataggaac ttcgaagcag ctccagccta     1380
cacatcgaat t                                                          1391
```